US008362277B2

(12) United States Patent
McKnight et al.

(10) Patent No.: US 8,362,277 B2
(45) Date of Patent: Jan. 29, 2013

(54) PRO-NEUROGENIC COMPOUNDS

(75) Inventors: Steven L. McKnight, Dallas, TX (US);
Andrew A. Pieper, Plano, TX (US);
Joseph M. Ready, Carrollton, TX (US);
Jef K. De Brabander, Flower Mound, TX (US)

(73) Assignee: Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 12/832,056

(22) Filed: Jul. 7, 2010

(65) Prior Publication Data

US 2011/0003836 A1 Jan. 6, 2011

Related U.S. Application Data

(63) Continuation-in-part of application No. 12/685,652, filed on Jan. 11, 2010.

(60) Provisional application No. 61/143,755, filed on Jan. 9, 2009.

(51) Int. Cl.
*C07D 209/82* (2006.01)
*A61K 31/403* (2006.01)

(52) U.S. Cl. ....................................... 548/444; 514/411

(58) Field of Classification Search .................. 548/444; 514/411
See application file for complete search history.

(56) References Cited

U.S. PATENT DOCUMENTS

| | | | |
|---|---|---|---|
| 3,409,628 A | 11/1968 | Berger et al. | |
| 3,518,250 A | 6/1970 | Schumaker | |
| 5,306,609 A | 4/1994 | Mihayashi et al. | |
| 6,187,785 B1 | 2/2001 | Zefirov et al. | |
| 6,468,996 B1 | 10/2002 | Jeppesen et al. | |
| 6,514,968 B1 | 2/2003 | TenBrink | |
| 6,770,656 B2 | 8/2004 | Halazy et al. | |
| 6,835,513 B2 | 12/2004 | Jubran et al. | |
| 6,849,640 B2 | 2/2005 | Ennis et al. | |
| 6,864,025 B2 | 3/2005 | Law et al. | |
| 7,018,988 B2 | 3/2006 | Halazy et al. | |
| 7,071,206 B2 | 7/2006 | Zefirov et al. | |
| 7,148,259 B1 | 12/2006 | Li et al. | |
| 7,438,916 B2 | 10/2008 | Rathore et al. | |
| 7,445,877 B2 | 11/2008 | Jubran et al. | |
| 7,449,478 B2 | 11/2008 | Hsieh et al. | |
| 7,807,704 B2 | 10/2010 | Thomas et al. | |
| 7,834,063 B2 | 11/2010 | Turnbull et al. | |
| 2003/0171309 A1 | 9/2003 | Halazy et al. | |
| 2003/0203296 A1 | 10/2003 | Law et al. | |
| 2003/0207188 A1 | 11/2003 | Jubran et al. | |
| 2003/0216427 A1 | 11/2003 | Halazy et al. | |
| 2005/0124675 A1 | 6/2005 | Hsieh et al. | |
| 2005/0277038 A1 | 12/2005 | Jubran et al. | |
| 2006/0038170 A1 | 2/2006 | Brunschwiler et al. | |
| 2007/0185152 A1 | 8/2007 | Yamashita et al. | |
| 2007/0196395 A1 | 8/2007 | Mackerell et al. | |
| 2007/0203236 A1 | 8/2007 | Smith et al. | |
| 2007/0275965 A1 | 11/2007 | Thomas et al. | |
| 2008/0058383 A1 | 3/2008 | Jernstedt et al. | |
| 2008/0255124 A1 | 10/2008 | Turnbull et al. | |
| 2009/0163545 A1 | 6/2009 | Goldfarb | |
| 2009/0236229 A1 | 9/2009 | Advincula et al. | |
| 2010/0305121 A1 | 12/2010 | Smith et al. | |
| 2011/0003836 A1 | 1/2011 | McKnight et al. | |
| 2011/0015217 A1 | 1/2011 | McKnight et al. | |
| 2012/0022096 A1 | 1/2012 | McKnight et al. | |

FOREIGN PATENT DOCUMENTS

| | | |
|---|---|---|
| CN | 101139347 | 3/2008 |
| CN | 101429198 | 5/2009 |
| EP | 1094063 | 4/2001 |
| EP | 1591511 | 11/2005 |
| FR | 1167510 | 11/1958 |
| GB | 2355659 | 5/2001 |
| WO | 92/21660 | 12/1992 |
| WO | 96/34863 | 11/1996 |
| WO | 00/23425 | 4/2000 |
| WO | WO 00/23425 | 4/2000 |
| WO | 00/78795 | 12/2000 |
| WO | 01/29028 | 4/2001 |
| WO | 01/71430 | 9/2001 |
| WO | 02/060867 | 8/2002 |
| WO | 03/007069 | 1/2003 |
| WO | 03/007070 | 1/2003 |
| WO | 03/007071 | 1/2003 |
| WO | 03/032072 | 4/2003 |
| WO | WO 03/091247 | 11/2003 |
| WO | WO 2004/052885 | 6/2004 |
| WO | 2004/106335 | 12/2004 |
| WO | 2005/055951 | 6/2005 |
| WO | 2005/056522 | 6/2005 |
| WO | 2005/074971 | 8/2005 |
| WO | 2007/008541 | 1/2007 |
| WO | 2007/041697 | 4/2007 |
| WO | WO2007062399 | 5/2007 |
| WO | 2007/079239 | 7/2007 |
| WO | 2007/081091 | 7/2007 |
| WO | 2007/087425 | 8/2007 |
| WO | 2008/021745 | 2/2008 |
| WO | 2008/060190 | 5/2008 |
| WO | 2008/115098 | 9/2008 |

(Continued)

OTHER PUBLICATIONS

Jeppesen et al. (CAPLUS Abstract of: WO 2000/023425).*
Raymond (CAPLUS Abstract of: FR 1167510 (1958)).*
Kubinyi (3D QSAR in Drug Design: Ligand-Protein Interactions and Molecular Similarity, vol. 2-3, Springer, 1998, 800 pages). TOC and pp. 243-244 provided.*
Pieper et al. (Cell, 142 (Jul. 9, 2010), p. 39-51).*
Wermuth, The Practice of Medicinal Chemsitry, 2d ed. (2003), 768 pages. Chapter 9-10 provided.*
Boekelheide, V. et al., "Curariform Activity and Chemical Structure. VII. Some 1-Skatylisoquinoline Derivatives and a Novel Method for their Synthesis," *J. Am. Chem. Soc.*, 72(5), pp. 2134-2137 (May 1950).

(Continued)

*Primary Examiner* — Robert Havlin
(74) *Attorney, Agent, or Firm* — Greenberg Traurig, LLP; David J. Dykeman; Fang Xie

(57) ABSTRACT

This invention relates generally to stimulating neurogenesis (e.g., post-natal neurogenesis, e.g., post-natal hippocampal neurogenesis) and protection from neuron cell death.

10 Claims, 43 Drawing Sheets

FOREIGN PATENT DOCUMENTS

| | | |
|---|---|---|
| WO | 2008/123796 | 10/2008 |
| WO | 2008/123800 | 10/2008 |
| WO | 2008/156105 | 12/2008 |
| WO | 2009/040517 | 4/2009 |
| WO | 2009/055828 | 4/2009 |
| WO | 2010/081115 | 7/2010 |
| WO | WO2010008115 | 7/2010 |
| WO | WO2011117668 | 9/2011 |
| WO | WO 2012/006419 | 1/2012 |

OTHER PUBLICATIONS

Jackson-Lewis, V. et al., "Protocol for the MPTP Mouse Model of Parkinson's Disease," Nature Protocols, 2, pp. 141-151 (Feb. 2007).

Tatton, N.A. et al., "In Situ Detection of Apoptotic Nuclei in the Substantia Nigra Compacta of 1-methyl-4-phenyl-1,2,3,6-tetrahydropyridine-treated Mice Using Terminal Deoxynucleotidyl Transferase Labelling and Acridine Orange Staining," Neuroscience, 77(4), pp. 1037-1048 (Apr. 1997).

Notification Concerning the Transmittal of International Preliminary Report on Patentability and Written Opinion of the International Searching Authority in counterpart PCT Application No. PCT/US2010/020681, mailed Jul. 21, 2011, 7 pages.

Abad, J. L. et al., "Internal Oxidosqualenes: Determination of Absolute Configuration and Activity as Inhibitors of Purified Pig Liver Squalene Epoxidase", J. Org. Chem., vol. 60, (1995), pp. 3648-3656.

Alexander, M. et al., "A Central Strategy for Converting Natural Products into Fluorescent Probes", ChemBioChem, vol. 7, (2006), pp. 409-416.

Altman, J. "Are new neurons formed in the brains of adult mammals?" Science, vol. 135, (1962), pp. 1127-1128.

Altman, J. "Autoradiographic Investigation of Cell Proliferation in the Brains of Rats and Cats", Anat. Rec., vol. 145, (1963), pp. 573-591.

Altman, J., "Autoradiographic and Histological Studies of Postnatal Neurogenesis IV. Cell Proliferation and Migration in the Anterior Forebrain, with Special Reference to Persisting Neurogenesis in the Olfactory Bulb", J. Comp. Neur., vol. 137, (1969), pp. 433-457.

Altman, J. et al., "Autoradiographic and Histological Evidence of Postnatal Hippocampal Neurogenesis in Rats", J. Comp. Neur., vol. 124, (1965), pp. 319-335.

Altman, J. et al., "Autoradiographic and Histological Studies of Postnatal Neurogenesis. I. A Longitudinal Investigation of the Kinetics, Migration and Transformation of Cells Incorporating Tritiated Thymidine in Neonate Rats, with Special Reference to Postnatal Neurogenesis in Some Brain Regions", J. Comp. Neur., vol. 126, (1966a), pp. 337-389.

Altman, J. et al., "Autoradiographic and Histological Studies of Postnatal Neurogenesis. II. A Longitudinal Investigation of the Kinetics, Migration and Transformation of Cells Incorporating Tritiated Thymidine in Neonate Rats, with Special Reference to Postnatal Neurogenesis in Some Brain Regions", J. Comp. Neur., vol. 128, (1966b), pp. 431-473.

Asso, V. et al., "α-Naphthylaminopropan-2-ol Derivatives as BACE1 Inhibitors", ChemMedChem, vol. 3, (2008), pp. 1530-1534.

Bachurin, S. et al., "Antihistamine agent Dimebon as a novel neuroprotector and a cognition enhancer", Ann N Y Acad Sci., vol. 939, (2001), pp. 425-435.

Bachurin, S. et al., "Mitochondria as a target for neurotoxins and neuroprotective agents" Ann N Y Acad Sci, vol. 993, (2003), pp. 334-344.

Bachurin, S. et al., "Questions and Answers, Session VII: Oxidative Stress, Mitochondria, and Approaches to Neuroprotection", Ann. N.Y. Acad. Sci., 993, (2003), pp. 345-349.

Beyer, M. et al., "Synthesis of Novel Aromatic Nitroxides as Potential DNA Intercalators. An EPR Spectroscopical and DFT Computational Study", J. Org. Chem., vol. 68, (2003), pp. 2209-2215.

Boldrini, M. et al., (2009). Antidepressants increase neural progenitor cells in the human hippocampus, Neuropsychopharmacology, vol. 34, (2009), pp. 2376-2389.

Bombrun, A. et al., "3, 6-Dibromocarbazole Piperazine Derivatives of 2-Propanol as First Inhibitors of Cytochrome c Release via Bax Channel Modulation", Journal of Medicinal Chemistry, vol. 46, No. 21, (2003), pp. 4365-4368.

Borrell-Pagès, M. et al., Human Genome & Diseases: Review, "Huntington's disease: from huntingtin function and dysfunction to therapeutic strategies", Cell. Mol. Life Sci., vol. 63, (2006), pp. 2642-2660.

Brown, J. P. et al., "Transient Expression of Doublecortin during Adult Neurogenesis", The Journal of Comparative Neurology, vol. 467, (2003), pp. 1-10.

Browne, S.E. et al., "The Energetics of Huntington's Disease[*]", Neurochemical Research, vol. 29, No. 3, (2004), pp. 531-546.

Burd, G.D. et al., "Ultrastructural Characterization of Synaptic Terminals Formed on Newly Generated Neurons in a Song Control Nucleus of the Adult canary forebrain", The Journal of Comparative Neurology, vol. 240, (1985), pp. 143-152.

Burns, A. et al., "Dimebon in Alzheimer's disease: old drug for new indication", Lancet, vol. 372, (2008), pp. 179-180.

Cattaneo, E. et al., "Normal Huntingtin Function: An Alternative Approach to Huntington's Disease", Nature Reviews, Neuroscience, vol. 6, (2005), pp. 919-930.

Carter, R. J. et al., "Characterization of Progressive Motor Deficits in Mice Transgenic for the Human Huntington's Disease Mutation", The Journal of Neuroscience, vol. 19, No. 8, (1999), pp. 3248-3257.

Cha, Jang-Ho J., Perspectives on Disease, "Transcriptional dysregulation in Huntington's disease", Trends Neurosci., vol. 23, No. 9, (2000), pp. 387-392.

Cha, Jang-Ho J. et al., "Altered brain neurotransmitter receptors in transgenic mice expressing a portion of an abnormal human Huntington disease gene", Proc. Natl. Acad. Sci. USA, Neurobiology, vol. 95, (1998), pp. 6480-6485.

Chakraborti, A. K. et al., "Lithium Bromide, and Inexpensive and Efficient Catalysis for Opening of Epoxide Rings by Amines at Room Temperature under Solvent-Free Condition", Eur. J. Org. Chem., (2004), pp. 3597-3600.

Davies, S.W. et al., "Formation of Neuronal Intranuclear Inclusions Underlies the Neurological Dysfunction in Mice Transgenic for the HD Mutation", Cell, vol. 90, (1997), pp. 537-548.

Distelmaier, F. et al., "Life cell quantification of mitochondrial membrane potential at the single organelle level", Cytometry A, vol. 73, (2008), pp. 129-138.

Di Santo, R. et al., "Design, synthesis and QSAR studies on N-aryl heteroarylisopropanolamines, a new class of non-peptidic HIV-1 protease inhibitors", Bioorganic & Medicinal Chemistry, vol. 10, No. 8, (2002), pp. 2511-2526.

Doody, R.S. et al., "Effect of dimebon on cognition, activities of daily living, behavior, and global function in patients with mild-to-moderate Alzheimer's disease: a randomized, double-blind, placebo-controlled study", Lancet, vol. 372, (2008), pp. 207-215.

Doody, R.S. et al., "Intermittent preventive antimalarial treatment in infancy", www.thelancet.com, vol. 372, (2008), pp. 1383.

Driscoll, I. et al., "The Aging Hippocampus: A Multi-level Analysis in the Rat", Neuroscience, vol. 139, (2006), pp. 1173-1185.

Eriksson, P.S. et al. "Neurogenesis in the adult human hippocampus", Nat. Med., vol. 4, (1998), pp. 1313-1317.

Fedele, V. et al., "Neurogenesis in the R6/2 Mouse Model of Huntington's Disease is Impaired at the Level of NeuroD1", Neuroscience, vol. 173, (2011), pp. 76-81.

Fernandes, H.B. et al., Neurobiology of Disease, "Mitochondrial Sensitivity and Altered Calcium Handling Underlie Enhanced NMDA-Induced Apoptosis in YAC128 Model of Huntington's Disease", The Journal of Neuroscience, vol. 27, No. 50, (2007), pp. 13614-13623.

Ferris, R.M. et al., "Rimcazole (BW 234U), a Novel Antipsychotic Agent Whose Mechanism of Action Cannot Be Explained by a Direct Blockage of Postsynaptic Dopaminergic Receptors in Brain", Drug Development Research, New York, NY US LNKD—DOI:10.1002/DDR.430090302, vol. 9, No. 3, (1986), pp. 171-188.

Freireich, E. J. et al., "Quantitative Comparison of Toxicity of Anticancer Agent in Mouse, Rat, Hamster, Dog, Monkey, and Man", Cancer Chemotherapy Reports, vol. 50, No. 4, (1966), pp. 219-244.

Gennaro, A. R. et al., "Remington's Pharmaceutical Sciences", 17th ed., Mack Publishing. Easton, PA, (1985), pp. 1418-1419.

Getautis, V. et al., "Study of the Products From Reaction of 1(2)-Aminoanthraquinones with 1-Chloro-2, 3-Expoxypropane" Chemistry of Heterocyclic Compounds, vol. 41, No. 4, (2005), pp. 426-436.

Gil, J. M.A.C. et al., "The R6 lines of transgenic mice: A model for screening new therapies for Huntington's disease", Brain Research Reviews, vol. 59, (2009), pp. 410-431.

Gil, J. M.A.C. et al., "Asialoerythropoetin is not effective in the R6/2 line of Huntington's disease mice", BMC Neuroscience, vol. 5, No. 17, (2004), pp. 1-10.

Gil, J. M.A.C. et al., "Reduced hippocampal neurogenesis in R6/2 transgenic Huntington's disease mice", Neurobiology of Disease, vol. 20, (2005), pp. 744-751.

Godin, J. D. et al., "Huntingtin is Required for Mitotic Spindle Orientation and Mammalian Neurogenesis", Neuron, vol. 67, (2010), pp. 392-406.

Goehler, H. et al., "A Protein Interaction Network Links GIT1, an Enhancer of Huntingtin Aggregation, to Huntington's Disease", Molecular Cell, vol. 15, (2004), pp. 853-865.

Goldberg, Y. P. et al., "Cleavage of huntingtin by apopain, a proapoptotic cysteine protease, is modulated by the polyglutamine tract", Nature Genetics, vol. 13, (1996), pp. 442-449.

Goldman, S. A. et al., "Neuronal production, migration, and differentiation in a vocal control nucleus of the adult female canary brain", Proc. Natl. Acad. Sci. USA, vol. 80, (1983), pp. 2390-2394.

Gross, C. G., "Neurogenesis in the adult brain: death of a dogma", Natural Reviews, vol. 1, (2000), pp. 67-73.

Harbert, C. A., et al., "Neuroleptic Activity in 5-Aryltetrahydro-γ-carbolines", J. Med. Chem. vol. 23, (1980), pp. 635-643.

Kamnasaran, D. et al., "Disruption of the neuronal PAS3 gene in a family affected with schizophrenia", J. Med. Genet, vol. 40, (2003), pp. 325-332.

Kamogawa, H. et al., "Syntheses of N-Substituted Carbazoles Involving Polymerizable Terminal Vinyl Groups", Journal of Polymer Science: Polymer Chemistry Edition, vol. 17, No. 1, (1979), pp. 9-18.

Kempermann, G., et al., "More hippocampal neurons in adult mice living in an enriched environment", Nature, vol. 386, (1997), pp. 493-495.

Kim, J. et al., "Mitochondrial loss, dysfunction and altered dynamics in Huntington's disease", Human Molecular Genetics, vol. 19, No. 20, (2010), pp. 3919-3935.

Kim, Sung-Eun et al., "Treadmill exercise prevents aging-induced failure of memory through an increase in neurogenesis and suppression of apoptosis in rat hippocampus", Experimental Gerontology, vol. 45, (2010), pp. 357-365.

Kohl, Z. et al., "Impaired adult olfactory bulb neurogenesis in the R6/2 mouse model of Huntington's disease", BMC Neuroscience, vol. 11, No. 114, (2010), pp. 1-11.

Krishnan, V. et al., "The molecular neurobiology of depression", Nature, vol. 455, (2008), pp. 894-902.

Kuhn, H. et al., "Neurogenesis in the Dentate Gyms of the Adult Rat: Age-Related Decrease of Neuronal Progenitor Proliferation", The Journal of Neuroscience, vol. 16, No. 6, (1996), pp. 2027-2033.

Lachman, L. et al., "Semi Solids", The Theory and Practice of Industrial Pharmacy, Chapter 17, (1970), pp. 491-516.

Lavedan, C. et al., "Association of the NPAS3 gene and five other loci with response to the antipsychotic iloperidone identified in a whole genome association study", Molecular Psychiatry, vol. 14, (2009), pp. 804-819.

Lavedan, C. et al., "Effect of a ciliary neurotrophic factor polymorphism on schizophrenia symptom improvement in an iloperidone clinical trial", Pharmacogenomics, vol. 9, No. 3, (2008), pp. 289-301.

Lione, L.A. et al., "Selective Discrimination Learning Impairments in Mice Expressing the Human Huntington's Disease Mutation", The Journal of Neuroscience, vol. 19, No. 23, (1999), pp. 10428-10437.

Liu, X. et al., "Induction of apoptotic program in cell-free extracts: requirement for dATP and cytochrome C", Cell, vol. 86, (1996), pp. 147-157.

Loo, D.T., et al., "Apoptosis is induced by β-amyloid in cultured central nervous system neurons", Proc. Natl. Acad. Sci. USA, vol. 90, (1993), pp. 7951-7955.

Maegawa, Y. et al., "A useful procedure for diiodination of carbazoles and subsequent efficient transformation to novel 3,6-bis(triethoxysilyl)carbazoles giving mesoporous materials", Tetrahedron Letters, vol. 47, (2006), pp. 6957-6960.

Mangialasche, F. et al., "Alzheimers's disease: clinical trials and drug development", www.thelancet.com/neurology, vol. 9, (2010), pp. 702-716.

Mangiarini, L. et al., "Exon 1 of the HD Gene with an Expanded CAG Repeat Is Sufficient to Cause a Progressive Neurological Phenotype in Transgenic Mice", Cell, vol. 87, (1996), pp. 493-506.

Martin, D. S. D. et al., "Apoptotic Changes in the Aged Brain Are Triggered by Interleukin-1β-induced Activation of p38 and Reversed by Treatment with Eicosapentaenoic Acid", The Journal of Biological Chemistry, vol. 277, No. 37, (2002), pp. 34239-34246.

Menalled, L. B. et al., "Mouse models of Huntington's disease", Trends in Pharmacological Sciences, vol. 23, No. 1, (2002), pp. 32-39.

Morcuende, A. et al., "Microwave-Promoted Transformations: Fast and Chemoselective N-Acylation of Amino Alcohols Using Catalytic Amounts of Dibutyltin Oxide. Influence of the Power Output and the Nature of the Acylating Agent of the Selectivity", J. Org. Chem., vol. 61, (1996), pp. 5264-5270.

Murphy, K. P.S.J. et al., "Abnormal Synaptic Plasticity and Impaired Spatial Cognition in Mice Transgenic for Exon 1 of the Human Huntington's Disease Mutation", The Journal of Neuroscience, vol. 20, No. 13, (2000), pp. 5115-5123.

Negrin, C.M. et al., "In vivo-in vitro study of biodegradable methadone delivery systems", Biomaterials, vol. 22, (2001), pp. 563-570.

Nucifora, Jr, F. C. et al., "Interference by Huntingtin and Atrophin-1 with CBP-Mediated Transcription Leading to Cellular Toxicity", Science, vol. 291, (2001), pp. 2423-2428.

O'Brien, J. T., A promising new treatment for Alzheimer's disease? Lancet Neurol., vol. 7, (2008), pp. 768-769.

Panov, A. V. et. al., "Early mitochondrial calcium defects in Huntington's disease are a direct effect of polyglutamines", Nature Neuroscience, vol. 5, No. 8, (2002), pp. 731-736.

Park, K. K. et al., "Promoting Axon Regeneration in the Adult CNS by Modulation of the PTEN/mTOR Pathway", Science, vol. 322, (2008), pp. 963-966.

Paton, J.A. et al., "Neurons generated in adult brain are recruited into functional circuits", Science, vol. 225, (1984), pp. 1046-1048.

Pattison, L. R. et al., "Apoptotic cascades as possible targets for inhibiting cell death in Huntington's disease", J. Neurol., vol. 253, (2006), pp. 1137-1142.

Perutz, M. F., "Glutamine repeats and neurodegenerative diseases: molecular aspects", Trends Biochem. Sci., vol. 24, (1999), pp. 58-63.

Petit, Sylvain et al., "Structure-Activity Relationship Analysis of the Peptide Deformylase Inhibitor 5-Bromo-1H-indole-3-acetohydroxamic Acid", ChemMedChem, vol. 4, (2009), pp. 261-275.

Petruska, J. et al., "Analysis of Strand Slippage in DNA Polymerase Expansions of CAG/CTG Triplet Repeats Associated with Neurodegenerative Disease", The Journal of Biological Chemistry, vol. 273, No. 9, (1998), pp. 5204-5210.

Phillips, W. et al., "Abnormalities of Neurogenesis in the R6/2 Mouse Model of Huntington's Disease Are Attributable to the In Vivo Microenvironment", The Journal of Neuroscience, vol. 25, No. 50, (2005), pp. 11564-11576.

Pickard, B. S. et al., "Disruption of a brain transcription factor, NPAS3, is associated with schizophrenia and learning disability", Am. J. Med. Genet. B. Neuropsychiatr. Genet., vol. 136B, (2005), pp. 26-32.

Pickard, B. S. et al., "The NPAS3 gene—emerging evidence for a role in psychiatric illness", Ann. Med., vol. 38, (2006), pp. 439-448.

Pickard, B. S. et al., "Interacting haplotypes at the NPAS3 locus alter risk of schizophrenia and bipolar disorder", Mol. Psychiatry, vol. 14, (2009), pp. 874-884.

Pieper, A.A. et al., "Discovery of a Proneurogenic, Neuroprotective Chemical", Cell, vol. 142, (2010), pp. 39-51.

Pieper, A. A. et al., "The neuronal PAS domain protein 3 transcription factor controls FGF-mediated adult hippocampal neurogenesis in mice", Proc. Natl. Acad. Sci. USA, vol. 102, (2005), pp. 14052-14057.

Poesen, K. et al., "Novel Role for Vascular Endothelial Growth Factor (VEGF) Receptor-1 and Its Ligand VEGF-B in Motor Neuron Degeneration", The Journal of Neuroscience, vol. 28, No. 42, pp. 10451-10459.

Ponce, M. A. et al., "Synthesis and Isolation of Bromo-β-carbolines Obtained by Bromination of β-Carboline Alkaloids", J. Heterocyclic Chem., vol. 38, (2001), pp. 1087-1095.

Rubinsztein, D. C., "Lessons from animal models of Huntington's disease", Trends in Genetics, vol. 18, No. 4, (2002), pp. 202-209.

Rubinsztein, D. C. et al., "Huntington's disease: molecular basis of neurodegeneration", Expert Review in Molecular Medicine, vol. 5, (2003), pp. 1-21.

Sadri-Vakili, G. et al., "Mechanisms of Disease: histone modifications in Huntington's disease", Nature Clinical Practice, Neurology, vol. 2, No. 6, (2006), pp. 330-338.

Schmidt, H.D. et al., "The role of neurotrophic factors in adult hippocampal neurogenesis, antidepressant treatments and animal models of depressive-like behavior", Behav. Pharmacol., vol. 18, (2007), pp. 391-418.

Stanfield, B. B. et al., "The Development of the Hippocampal Region", Cerebral Cortex (ed. Edward G. Jones and Alan Peters), vol. 7, (1988), pp. 91-131.

Sun, W. et al., "Programmed Cell Death of Adult-Generated Hippocampal Neurons Is Mediated by the Proapoptotic Gene Bax", The Journal of Neuroscience, vol. 24, No. 49, (2004), pp. 11205-11213.

Suzdalev, K.F. et al., "Synthesis of Indole 2,3-Epoxypropyl Derivatives and Their Reactions with Amines", Russian Journal of Org. Chem., (2005), 41(2), pp. 233-237.

Tang, Tie-Shan et al., "Disturbed $Ca^{2+}$ signaling and apoptosis of medium spiny neurons in Huntington's disease", Proc. Natl. Acad, Sci. USA, vol. 102, No. 7, (2005), pp. 2602-2607.

Teles, A.V.F.F. et al., "Increase in bax expression and apoptosis are associated in Huntington's disease progression", Neuroscience Letters, vol. 438, (2008), pp. 59-63.

Van Praag, H. et al., "Running increases cell proliferation and neurogenesis in the adult mouse dentate gyrus", Nat. Neurosci., vol. 2, (1999), pp. 266-270.

Wanker, E. E. et al., "HIP-I: A huntingtin interacting protein isolated by the yeast two-hybrid system", Human Molecular Genetics, vol. 6, No. 3, (1997), pp. 487-495.

Watanabe, T. et al., "Palladium-Catalyzed Direct Synthesis of Carbazoles via One-Pot N-Arylation and Oxidative Biaryl Coupling: Synthesis and Mechanistic Study", J. Org. Chem., vol. 74, (2009), pp. 4720-4726.

Weissman, S. A, et al., "Ligand-Free Palladium-Catalyzed Cyanation of Aryl Halides", J. Org. Chem., vol. 70, (2005), pp. 1508-1510.

Wermuth, C. G. "Molecular Variation Based on Isosteric Replacements", The Practice of Medicinal Chemistry, Chapter 13, (1996), pp. 204-232.

Wilen, S. H. "Tables of Resolving Agents and Optical Resolutions", E. L. Eliel,, Ed., University of Notre Dame Press, Notre Dame, IN, (1972), pp. 268-298.

Wilen, S. H. et al., "Strategies in Optical Resolutions", Tetrahedron, vol. 33, (1977), pp. 2725-2736.

Xuan, A. G. et al., "BDNF improves the effects of neural stem cells on the rat model of Alzheimer's disease with unilateral lesion of fimbria-fornix", Neuroscience Letters 440 (2008), pp. 331-335.

Yang, J. et al., "Prevention of apoptosis by Bcl-2: release of cytochrome c from mitochondria blocked", Science, vol. 275, (1997), pp. 1129-1132.

Zeron, M. M. et al., "Mutant Huntingtin Enhances Excitotoxic Cell death", Molecular and Cellular Neuroscience, vol. 17, (2001), pp. 41-53.

Zhang, H. et al., "Implantation of neural stem cells embedded in hyaluronic acid and collagen composite conduit promotes regeneration in a rabbit facial nerve injury model", Journal of Translational Medicine, 6:67, (2008), pp. 1-11.

Zoidis, G. et al., "Design and synthesis of 1,2-annulated adamantine piperidines with anti-influenza virus activity", Bioorganic & Medicinal Chemistry, vol. 17, (2009), pp. 1534-1541.

Zuccato, C. et al., "Huntingtin interacts with REST/NRSF to modulate the transcription of NRSE-controlled neuronal genes", Nature Genetics, vol. 35, No. 1, (2003), pp. 76-83.

Notification of Transmittal of the International Search Report and the Written Opinion of the International Searching Authority, or the Declaration of counterpart Application No. PCT/US2010/020681dated Jun. 17, 2010, 14 pages.

Cao, R. et al. "Synthesis, acute toxicities, and antitumor effects of novel 9-substituted β-carboline derivatives", Bioorganic & Medicinal Chemistry, vol. 12, (2004), pp. 4613-4623.

Cao, R.et al., "Design, synthesis and in vitro and in vivo antitumor activities of novel β-carboline derivatives", European Journal of Medicinal Chemistry, vol. 40, (2005), pp. 991-1001.

Cao, R. et al., "DNA binding properties of 9-substituted harmine derivatives", Biochemical and Biophysical Research Communications, vol. 338, (2005), pp. 1557-1563.

Cao, R. et al., "Synthesis and cytotoxic activities of 1-benzylidine substituted β-carboline derivatives", Bioorganic & Medicinal Chemistry Letters, vol. 18, (2008), pp. 6558-6561.

Dow, R. L. et al., "Identification of Tricyclic Analogs Related to Ellagic Acid as Potent/Selective Tyrosine Protein Kinase Inhibitors", Journal of Medicinal Chemistry, vol. 37, (1994), pp. 2224-2231.

Haggquist, G. W. et al., "Intramolecular Triplet Energy Transfer. 3. A Carbazole-Nnaphthalene System Having Short Chain Length Methylene Spacer Units", Journal of Physical Chemistry, vol. 97 (1993), pp. 9270-9273.

Hisada, K. et al., "Intramolecular Triplet Energy Transfer. 4. A Carbazole-Naphthalene System Having a Flexible Alkyl Spacer Doped in Poly(methyl methacrylate) Matrixes", Journal of Physical Chemistry B, vol. 102, (1998), pp. 2640-2645.

Jorapur, Y. R. et al., "Potassium carbonate as a base for the N-alkylation of indole and pyrrole in ionic liquids", Tetrahedron Letters, vol. 47, (2006), pp. 2435-2438.

Jun, W. G. et al., "Inorganic-organic hybrid photorefractive materials bearing the bifunctional chromophore", Journal of Nonlinear Optical Physics & Materials, vol. 14, No. 4, (2003), pp. 497-504.

Kaewtong, C. et al., "Self-Assembly and Electrochemical Oxidation of Polyamidoamine-Carbazole Dendron Surfiner Complexes: Nanoring Formation", ACS Nano, vol. 2, No. 8, (2008), pp. 1533-1542.

Kamogawa, H. et al., "Syntheses of N-substituted carbazoles involving polymerizable terminal vinyl groups", Journal of Polymer Science, Polymer Chemistry Edition, vol. 18, (1979), pp. 9-18.

Kim, T. W., "Self-quenching Mechanism: the Influence of Quencher and Spacer on Quencher-fluorescein Probes", Bulletin of the Korean Chemical Society, vol. 28, No. 7, (2007), pp. 1221-1223.

Kim, T. W., "Molecular Tripods Showing Fluorescence Enhancement upon Binding to Streptavidin", Organic Letters, vol. 7 No. 1, (2007), pp. 111-114.

Lee, H. Y. et al., "Structure-activity relationship studies of the chromosome segregation inhibitor, Incentrom A", Bioorganic & Medicinal Chemistry Letters, vol. 18, (2008), pp. 4670-4674.

Li, Z. et al., "Two Types of Nonlinear Optical Polyurethanes Containing the Same Isolation Groups: Syntheses, Optical Properties, and Influence of Binding Mode", Journal of Physical Chemistry B, vol. 113, (2009), pp. 14943-14949.

Lygaitis, R. et al., "Synthesis and photophysical properties of bipolar low-molar-mass amorphous materials", Journal of Photochemistry and Photobiology, A: Chemistry, vol. 167, (2004), pp. 163-168.

McGrath, J. E., "Novel carbazole phenoxy-based methacrylates to produce high-refractive index polymers", Polymer, vol. 47, (2006), pp. 4042-4057.

Neitzert, H. C. et al., "Monitoring of the initial degradation of oxadiazole based blue OLED's", Journal of Non-Crystalline Solids, vol. 352, (2006), pp. 1695-1699.

Okumura, H. et al., "Phenothiazine and carbazole-related compounds inhibit mitotic kinesin Eg5 and trigger apoptosis in transformed culture cells", Toxicology Letters, vol. 166, (2006), pp. 44-52.

Olla, S. et al., "Indolyl-pyrrolone as a new scaffold for Pim1 inhibitors", Bioorganic & Medicinal Chemistry Letters, vol. 19, (2009), pp. 1512-1516.

Pan, J. et al., "Synthesis of Carrier-Transporting Dendrimers with Perylenebis(dicarboximide)s as a Luminescent Core", European Journal of Organic Chemistry, vol. 4, (2006), pp. 986-1001.

Rische, T. et al., "One-pot synthesis of pharmacologically active diamines via rhodium-catalyzed carbonylative hydroaminomethylation of heterocyclic allylic amines", Tetrahedron, vol. 55, (1999), pp. 9801-9816.

Sundararajan, C. et al., "Photolytic Release of Carboxylic Acids Using Linked Donor-Acceptor Molecules: Direct versus Mediated Photoinduced Electron Transfer to N-Alkyl-4-picolinium Esters", Organic Letters, vol. 7, No. 13, (2005), pp. 2631-2634.

Thiel, M. et al., "Development of psychotropic substances. III. Diphenylamine derivatives with pyridyl and guanidyl side chains", Monatshefte fuer Chemie, vol. 93, No. 5, (1962), pp. 1080-1089.

Wilde, R. G. et al., "Acyl CoA:cholesterol acyltransferase (ACAT) inhibitors: heterocyclic bioisosteres for the urea group in DuP 128", Bioorganic & Medicinal Chemistry Letters, vol. 5, No. 2, (1995), pp. 177-180.

Yonemura, H. et al., "Effect of π-system on Long-Range Photoinduced Electron Transfer in Through-Ring α-Cyclodextrin Complexes of Carbazole-Viologen Linked Compounds" Tetrahedron Letters, vol. 39, (1998), pp. 6915-6918.

Yonemura, H. et al., "Spectroscopic Studies on Exchange Properties in Through-Ring Cyclodextrin Complexes of Carbazole-Viologen Linked Compounds: Effects of Spacer Chain Length", Journal of Physical Chemistry, vol. 96, (1992), pp. 5765-5770.

Xue, Y. et al., "Novel Hypoglycemic Compound-Synthesis of Glycine Derivatives and Research on the Role of PPARs" Jiefangjun Yaoxue Xuebao, vol. 25, No. 1, (2009), pp. 5-10.

Enyedy et al., "Discovery of Small-Molecule Inhibitors of Bcl-2 through Structure-Based Computer Screening," *J. Med. Chem.*, 44(25), pp. 4313-4324 (Dec. 6, 2001).

Mattos et al., "Multiple Binding Modes," in *3D QSAR in Drug Design: Theory, Methods and Applications*, ed. H. Kubinyi, Springer, pp. 243-244 (Dec. 31, 1993).

Ramamoorthy, "Synthesis of small molecular inhibitors targeting signal transduction pathways," *University of South Florida Thesis*, pp. 1-70 (Jun. 10, 2009).

Terfloth et al., "Electronic Screening: Lead Finding from Database Mining," in *The Practice of Medicinal Chemistry*, ed. C. Wermuth, Academic Press, pp. 131-157 (Mar. 7, 1996).

PCT International Search Report based on PCT/2011/043185 dated Apr. 10, 2012.

Kamal et al., "Carbazole-pyrrolo [2,1-c] [1, 4] benzodiazepine conjugates: design, synthesis, and biological evaluation", MedChemComm, vol. 2, No. 8, pp. 780-788, (2011).

Liu et al., "Synthesis and Spectroscopic and Electrochemical Properties of TFT-Derivatized Polycarbazole", Macromolecules, vol. 41, No. 6, pp. 2045-2048, (2008).

MacMillan, et al., "Development of Proneurogenic, Neuroprotective Small Molecules", Journal of the American Chemical Society, vol. 133, No. 5, pp. 1428-1437, (2011).

Mahapatra, et al., "A Small Molecule Which Protects Newborn Neurons", ACS Chemical Neuroscience, vol. 1, No. 9, p. 589, (2010).

International Search Report for PCT/US2012/052283 mailed Oct. 24, 2012.

U.S. Appl. No. 13/594,223, filed Aug. 24, 2012, Pro-Neurogenic Compounds.

Cimini et al., "Expression of Peroxisome Proliferator-Activated Receptors (PPARs) and Retinoic Acid Receptors (RXRs) in Rat Cortical Neurons.", Neuroscience, vol. 130, pp. 325-337, 2005.

Racke et al., PPARs in Neuroinflammation, Hindawi Publishing (Special Issue), 107 pgs., 2008.

USPTO Office Action in U.S. Appl. No. 12/685,652 mailed Jul. 19, 2012.

\* cited by examiner

Pro-Neurogenic or Neuroprotective Molecules

Pool 7 → $C_{21}H_{18}Br_2N_2O$ (MW=474.19)

Pool 14 → None Found

Pool 18 → $C_{21}H_{18}F_3N_3OS$ (MW=417.45)

Pool 19 → $C_{16}H_{19}N_5O_2S_2$ (MW=377.40)

Pool 41 → $C_{15}H_{18}N_4O_4S$ (MW=350.40)

Pool 53 → $C_{14}H_{18}IN_5O_2$ (MW=415.23)

Pool 54 → $C_{11}H_{14}BrN_3O_2S_2$ (MW=364.29)

Pool 61 → $C_{21}H_{22}N_4O_5$ (MW=410.43)

Pool 69 → None Found

Pool 70 → $C_{20}H_{18}ClFN_6O$ (MW=412.85)

FIG. 6B

Example 62 Compound Enantiomers

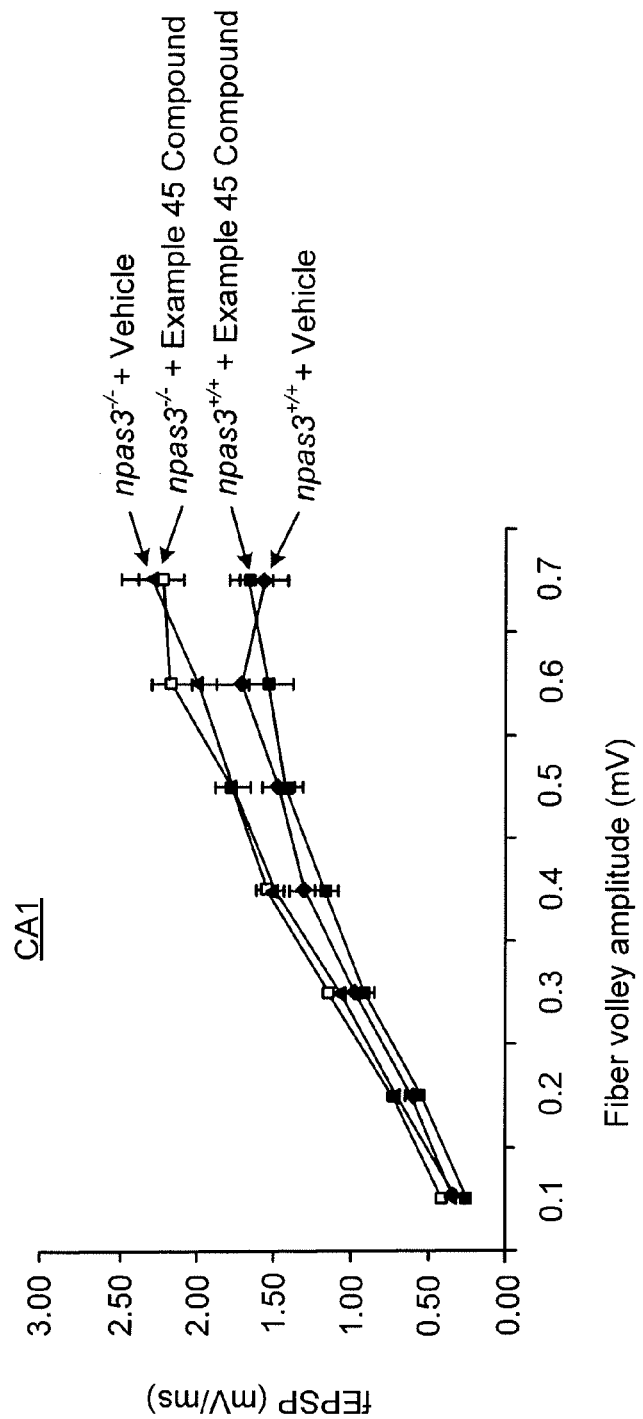

FASDP Structure

Example 45 Compound     Dimebon

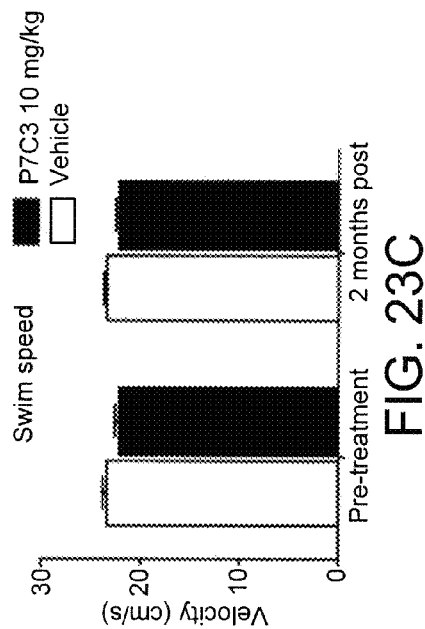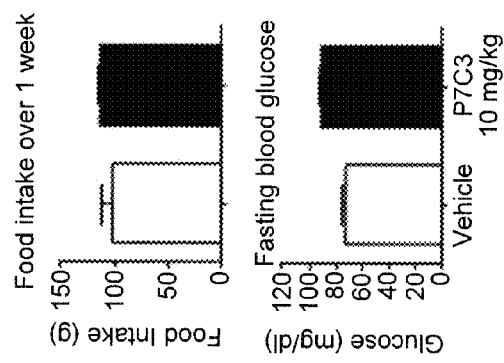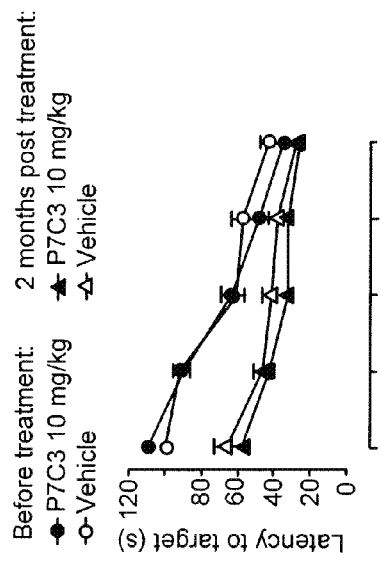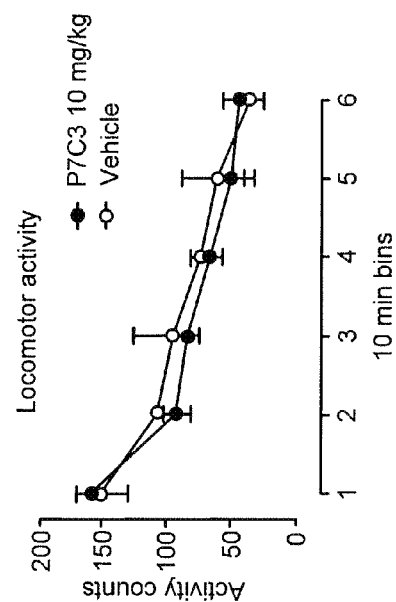

PRO-NEUROGENIC COMPOUNDS

CROSS REFERENCE TO RELATED APPLICATIONS

This application is a continuation-in-part of U.S. application Ser. No. 12/685,652, filed on Jan. 11, 2010, which claims the benefit U.S. Provisional Application No. 61/143,755, filed on Jan. 9, 2009; each of these prior applications is incorporated herein by reference in its entirety.

STATEMENT REGARDING FEDERALLY SPONSORED RESEARCH

This invention was made with government support under Grant 5DP1OD00027605, 5R37MH05938809, and 1RO1MH087986, which were awarded by the National Institute of Health; the Government has certain rights in the invention.

FIELD OF THE INVENTION

This invention relates generally to the discovery of pro-neurogenic compounds capable of promoting neurogenesis and/or reducing neuronal cell death.

BACKGROUND OF THE INVENTION

It is now accepted that the adult vertebrate brain fosters the birth and functional incorporation of newly formed neurons (Goldman and Nottebohm, 1984; Paton and Nottebohm, 1984; Burd and Nottebohm, 1985). However, it was long thought that no new neurons could be added to the adult mammalian brain. This dogma was challenged in the 1960's when autoradiographic evidence of new neuron formation in the hippocampal dentate gyrus, olfactory bulb, and cerebral cortex of the adult rat was presented (Altman, 1962, 1963; Altman and Das, 1965, 1966a,b). It is now accepted that within all mammalian species, including humans (Eriksson et al., 1998), there are two major reservoirs of neuronal stem cells, one located in the subgranular zone (SGZ) of the hippocampal dentate gyrus and another in the subventricular zone (SVZ) (Gross, 2000). Neural stem cells in the SVZ facilitate formation of new neurons that migrate rostrally to populate the olfactory bulb, while neural stem cells in the SGZ produce neurons that integrate locally in the granular layer of the dentate gyrus, a region of the hippocampus that exhibits lifelong structural and functional plasticity.

The process of new neuron formation in the adult mouse brain can be influenced by environmental, chemical and genetic variables. As demonstrated by Gage and colleagues, neurogenesis in the adult mouse brain is enhanced when animals are exposed to an enriched environment (Kempermann et al., 1998) or able to exercise voluntarily (van Praag et al., 1999). More recently, anti-depressant drugs have been shown to enhance levels of adult neurogenesis in animals, including humans (Schmidt and Duman, 2007; Boldrini et al., 2009). Among many genes reported to impact adult neurogenesis is the gene encoding neuronal PAS domain protein 3 (NPAS3), a central nervous system (CNS)-specific transcription factor that has been associated with schizophrenia and bipolar disorder (Kamnsasaran et al., 2003; Pickard et al., 2005, 2006, 2009; Lavedan et al., 2008). Animals missing both copies of the NPAS3 gene suffer a profound loss of adult hippocampal neurogenesis coupled with significant behavioral deficits (Pieper et al., 2005). Knowing that impaired post-natal neurogenesis elicits unfavorable phenotypic deficits, it is predicted that pro-neurogenic chemical compounds should exhibit favorable therapeutic benefits.

SUMMARY OF THE INVENTION

This invention relates generally to compounds that promote the generation or the survival of existing neurons in the mammalian brain. For the purpose of simplicity we refer to these compounds as being pro-neurogenic. In certain embodiments, the compounds promote the generation or survival of neurons in the post-natal mammalian brain. In certain embodiments, the compounds promote the survival, growth, development and/or function of neurons, particularly CNS, brain, cerebral, and hippocampal neurons. In certain embodiments, the compounds stimulate post-natal hippocampal neurogenesis, which while not wishing to be bound by theory, is believed to represent a therapeutic target for a variety of neuropsychiatric and neurodegenerative diseases, including (but not limited to) schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs, such as alcohol, opiates, methamphetamine, phencyclidine, and cocaine. The invention also features compositions (e.g., pharmaceutical compositions) that include such compounds as well as methods of making, identifying, and using such compounds. Other features and advantages are described in, or will be apparent from, the present specification and accompanying drawings.

Accordingly, in one aspect, methods for promoting post-natal mammalian neurogenesis and/or reducing neuronal cell death in a subject in need thereof are described, the method comprising administering an effective amount of a compound having formula (I) or a pharmaceutically acceptable salt thereof:

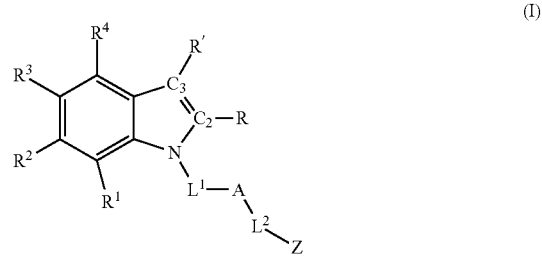

(I)

wherein:
each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro;
R and R' are defined according to (1), (2), (3), (4), or (5) below:
(1) R and R' together with $C_2$ and $C_3$, respectively, form a fused phenyl ring having formula (II):

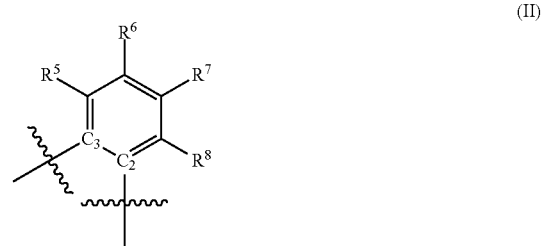

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —$NH(C_1$-$C_6$ alkyl), —$N(C_1$-$C_6$ alkyl)$_2$, —NHC(O)($C_1$-$C_6$ alkyl), and nitro; OR (2) each of R and R' is, independently, hydrogen, $C_1$-$C_6$ alkyl, or $C_1$-$C_6$ haloalkyl; OR (3) R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$; OR (4) R and R' together with $C_2$ and $C_3$, respectively, form a fused $C_5$-$C_6$ cycloalkyl ring that is optionally substituted with from 1-4 independently selected $R^a$; OR (5) R and R' together with $C_2$ and $C_3$, respectively, form a fused heteroaryl ring containing from 5-6 ring atoms, wherein from 1-2 of the ring atoms is independently selected from N, NH, N($C_1$-$C_3$ alkyl), O, and S; and wherein said heteroaryl ring is optionally substituted with from 1-3 independently selected $R^b$;

$L^1$ is:
  (i) $C_1$-$C_3$ straight chain alkylene, which is optionally substituted with from 1-2 independently selected $R^c$; or
  (ii) a bond that directly connects N in the 5-membered ring of formula (I) to A in formula (I);

$L^2$ is:
  (i) $C_1$-$C_3$ straight chain alkylene, which is optionally substituted with from 1-2 independently selected $R^c$; or
  (ii) a bond that directly connects A in formula (I) to Z in formula (I);

A is:
  (i) $CR^{A1}R^{A2}$, wherein each of $R^{A1}$ and $R^{A2}$ is independently selected from hydrogen, halo, $C_1$-$C_3$ alkyl, or $OR^9$; or
  (ii) C=O; or
  (iii) $C_3$-$C_5$ cycloalkylene that is (a) substituted with 1 oxo; and (b) optionally further substituted with from 1-4 independently selected $R^a$; or
  (iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;

Z is:
  (i) —$NR^{10}R^{11}$; or
  (ii) —C(O)$NR^{10}R^{11}$; or
  (iii) —$OR^{12}$; or
  (iv) —$S(O)_nR^{13}$, wherein n is 0, 1, or 2 or
  (v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$;
  (vi) $C_6$-$C_{10}$ aryl that is optionally substituted with from 1-4 independently selected $R^b$; or
  (vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or (viii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(ix) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(x) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(xi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^9$ is hydrogen; or $C_1$-$C_3$ alkyl that is optionally substituted with hydroxyl or $C_1$-$C_3$ alkoxy;

each of $R^{10}$ and $R^{11}$ is independently selected from the substituents delineated collectively in (a) through (k) below:
  (a) hydrogen;
  (b) $C_6$-$C_{10}$ aryl that is optionally substituted with from 1-4 $R^b$;
  (c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
  (d) $C_1$-$C_6$ alkyl or $C_1$-$C_6$ haloalkyl, each of which is optionally substituted with from 1-3 $R^d$;
  (e) —C(O)($C_1$-$C_6$ alkyl), —C(O)($C_1$-$C_6$ haloalkyl), or —C(O)O($C_1$-$C_6$ alkyl);
  (f) $C_2$-$C_6$ alkenyl or $C_2$-$C_6$ alkynyl;
  (g) $C_8$-$C_{14}$ arylcycloalkyl, wherein:
    (1) the aryl portion is optionally substituted with from 1-4 independently selected $R^b$, and
    (2) the cycloalkyl portion is optionally substituted with from 1-4 independently selected $R^a$;
  (h) arylheterocyclyl containing from 8-14 ring atoms, wherein:
    (1) the aryl portion from is optionally substituted with from 1-4 independently selected $R^b$, and
    (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

(i) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(j) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;
(k) $C_3$-$C_8$ cycloalkyl or $C_3$-$C_8$ cycloalkenyl, each of which is optionally substituted with from 1-4 independently selected $R^a$; and
(l) $C_7$-$C_{12}$ aralkyl, wherein the aryl portion is optionally the aryl portion from is optionally substituted with from 1-4 independently selected $R^b$, $R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_1$-$C_6$ alkyl or $C_1$-$C_6$ haloalkyl, each of which is optionally substituted with from 1-3 $R^d$; or
(iv) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(v) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vii) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(iii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(iv) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(v) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
(aa) $C_1$-$C_6$ alkoxy; $C_1$-$C_6$ haloalkoxy; $C_1$-$C_6$ thioalkoxy; $C_1$-$C_6$ thiohaloalkoxy; —O—($CH_2$)$_{1-3}$—[O($CH_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;
(bb) halo; hydroxyl; cyano; nitro; —$NH_2$; azido; sulfhydryl; $C_2$-$C_6$ alkenyl; $C_2$-$C_6$ alkynyl; —C(O)H; —C(O)

($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$;

(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —NH$_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —NH$_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —NH$_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; and $L^3$-($C_1$-$C_6$ alkylene)-Cy, where in $L^3$ is a —O—, —NH—, —NCH$_3$—, —C(O)—, —C(O)NH—, —C(O)NCH$_3$—, —NHC(O)—, or —NCH$_3$C(O)—, and Cy is a saturated, partially unsaturated or aromatic carbocyclic or heterocyclic ring system;

or a pharmaceutically acceptable salt thereof.

In some embodiments, one or more of (A), (B), or (C) apply.

(A) Provided that when R and R' are defined according to definition (3), then:

(i) each of $L^1$ and $L^2$ must be $C_1$-$C_3$ alkylene, which is optionally substituted with from 1-2 independently selected $R^c$ when A is CH$_2$; or (ii) Z must be other than heteroaryl containing from 5-14 (e.g., 5-6 or 6) ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; e.g., other than substituted pyridyl, e.g., other than pyridyl substituted with $C_1$-$C_3$ alkyl (e.g., CH$_3$), e.g., other than 2 or 6-methylpyridyl.

(B) Each of $R^{10}$ and $R^{11}$ cannot be optionally substituted naphthyl (e.g., each of $R^{10}$ and $R^{11}$ cannot be unsubstituted naphthyl). In embodiments, each of $R^{10}$ and $R^{11}$ is other than optionally substituted naphthyl (e.g., unsubstituted naphthyl) when R and R' are defined according to definitions (1), (2), and (4); and A is CR$^{41}$R$^{42}$ (e.g., CHOR$^9$, e.g., CHOH), and each of $L^1$ and $L^2$ is $C_1$-$C_3$ alkylene (e.g., each of $L^1$ and $L^2$ is CH$_2$).

(C) $R^{12}$ and/or $R^{13}$ cannot be substituted phenyl. In embodiments, $R^{12}$ and/or $R^{13}$ cannot be substituted phenyl when R and R' are defined according to definition (1); and A is CR$^{41}$R$^{42}$ (e.g., CHOR$^9$, e.g., CHOH), and each of $L^1$ and $L^2$ is $C_1$-$C_3$ alkylene (e.g., each of $L^1$ and $L^2$ is CH$_2$).

In some embodiments, (A), (B), or (C) applies. In other embodiments, (A) and (B); or (A) and (C); or (B) and (C) applies. In still other embodiments, (A), (B), and (C) apply.

In another aspect, methods for promoting post-natal mammalian neurogenesis in a subject in need thereof are featured. The method includes administering to the subject an effective amount of a compound having formula (I) or a pharmaceutically acceptable salt thereof.

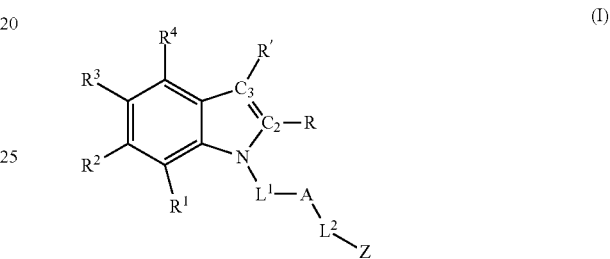

wherein:

each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —NH$_2$, —NH($C_1$-$C_6$ alkyl), —N($C_1$-$C_6$ alkyl)$_2$, —NHC(O)($C_1$-$C_6$ alkyl), and nitro;

R and R' are defined according to (1), (2), (3), (4), or (5) below:

(1) R and R' together with $C_2$ and $C_3$, respectively, form a fused phenyl ring having formula (II):

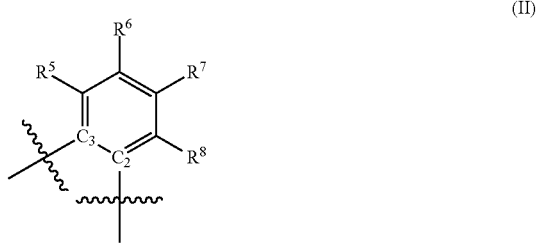

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ halothioalkoxy, $C_1$-$C_6$ alkyl, $C_1$-$C_6$ haloalkyl, cyano, —NH$_2$, —NH($C_1$-$C_6$ alkyl), N($C_1$-$C_6$ alkyl)$_2$, —NHC(O)($C_1$-$C_6$ alkyl), and nitro; OR (2) each of R and R' is, independently, hydrogen, $C_1$-$C_6$ alkyl, or $C_1$-$C_6$ haloalkyl; OR (3) R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$; OR (4) R and R' together with $C_2$ and $C_3$, respectively, form a fused $C_5$-$C_6$ cycloalkyl ring that is optionally substituted with from 1-4 independently selected $R^a$; OR (5) R and R' together with $C_2$ and $C_3$, respectively, form a fused heteroaryl ring containing from 5-6 ring atoms, wherein from 1-2 of the ring atoms is independently selected from N, NH, N($C_1$-$C_3$ alkyl), O, and S; and wherein said heteroaryl ring is optionally substituted with from 1-3 independently selected $R^b$;

$L^1$ is:
(i) $C_1$-$C_3$ straight chain alkylene, which is optionally substituted with from 1-2 independently selected $R^c$; or
(ii) a bond that directly connects N in the 5-membered ring of formula (I) to A in formula (I);

$L^2$ is:
(i) $C_1$-$C_3$ straight chain alkylene, which is optionally substituted with from 1-2 independently selected $R^c$; or
(ii) a bond that directly connects A in formula (I) to Z in formula (I);

A is:
(i) $CR^{A1}R^{A2}$, wherein each of $R^{A1}$ and $R^{A2}$ is independently selected from hydrogen, halo, $C_1$-$C_3$ alkyl, or $OR^9$; or
(ii) C=O; or
(iii) $C_3$-$C_5$ cycloalkylene that is (a) substituted with 1 oxo; and (b) optionally further substituted with from 1-4 independently selected $R^a$; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;

Z is:
(i) —$NR^{10}R^{11}$; or
(ii) —$C(O)NR^{10}R^{11}$; or
(iii) —$OR^{12}$; or
(iv) —$S(O)_nR^{13}$, wherein n is 0, 1, or 2 or
(v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$;
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or
(viii) $C_8$-$C_{14}$ arylcycloalkyl, wherein:
 (1) the aryl portion is optionally substituted with from 1-4 independently selected $R^b$, and
 (2) the cycloalkyl portion is optionally substituted with from 1-4 independently selected $R^a$;
or
(ix) arylheterocyclyl containing from 8-14 ring atoms, wherein:
 (1) the aryl portion from is optionally substituted with from 1-4 independently selected $R^b$, and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(x) heteroarylheterocyclyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(xi) heteroarylcycloalkyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) the cycloalkyl portion is optionally substituted with from 1-4 independently selected $R^a$;

$R^9$ is hydrogen; or $C_1$-$C_3$ alkyl that is optionally substituted with hydroxyl or $C_1$-$C_3$ alkoxy;

each of $R^{10}$ and $R^{11}$ is independently selected from the substituents delineated collectively in (a) through (k) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —$C(O)(C_1$-$C_6$ alkyl), —$C(O)(C_1$-$C_6$ haloalkyl), or —$C(O)O(C_1$-$C_6$ alkyl);
(f) $C_2$-$C_6$ alkenyl or $C_2$-$C_6$ alkynyl;
(g) $C_8$-$C_{14}$ arylcycloalkyl, wherein:
 (1) the aryl portion is optionally substituted with from 1-4 independently selected $R^b$, and
 (2) the cycloalkyl portion is optionally substituted with from 1-4 independently selected $R^a$;
(h) arylheterocyclyl containing from 8-14 ring atoms, wherein:
 (1) the aryl portion from is optionally substituted with from 1-4 independently selected $R^b$, and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(i) heteroarylheterocyclyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

(j) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;
(k) $C_3$-$C_8$ cycloalkyl or $C_3$-$C_8$ cycloalkenyl, each of which is optionally substituted with from 1-4 independently selected $R^a$; and
(l) $C_7$-$C_{12}$ aralkyl, wherein the aryl portion is optionally the aryl portion from is optionally substituted with from 1-4 independently selected $R^b$, $R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_1$-$C_6$ alkyl or $C_1$-$C_6$ haloalkyl, each of which is optionally substituted with from 1-3 $R^d$; or
(iv) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(v) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vii) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(iii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(iv) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(v) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
(aa) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, —NHC(O)($C_1$-$C_6$ alkyl), wherein the alkyl portion of each is optionally substituted with from 1-3 independently selected $R^e$;
(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;
(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-Cy, where in $L^3$ is a —O—, —NH—, —$NCH_3$—, —C(O)—, —C(O)NH—, —C(O)$NCH_3$—, —NHC(O)—, or —$NCH_3$C(O)—, and Cy is a saturated, partially unsaturated or aromatic carbocyclic or heterocyclic ring system;

or a salt (e.g., pharmaceutically acceptable salt) thereof.

In some embodiments, one or more of (A), (B), or (C) apply.

(A) Provided that when R and R' are defined according to definition (3), then:

(i) each of $L^1$ and $L^2$ must be $C_1$-$C_3$ alkylene, which is optionally substituted with from 1-2 independently selected $R^c$ when A is $CH_2$; or (ii) Z must be other than heteroaryl containing from 5-14 (e.g., 5-6 or 6)ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; e.g., other than substituted pyridyl, e.g., other than pyridyl substituted with $C_1$-$C_3$ alkyl (e.g., $CH_3$), e.g., other than 2 or 6-methylpyridyl.

(B) Each of $R^{10}$ and $R^{11}$ cannot be optionally substituted naphthyl (e.g., each of $R^{10}$ and $R^{11}$ cannot be unsubstituted naphthyl). In embodiments, each of $R^{10}$ and $R^{11}$ is other than optionally substituted naphthyl (e.g., unsubstituted naphthyl) when R and R' are defined according to definitions (1), (2), and (4); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

(C) $R^{12}$ and/or $R^{13}$ cannot be substituted phenyl. In embodiments, $R^{12}$ and/or $R^{13}$ cannot be substituted phenyl when R and R' are defined according to definition (1); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

In embodiments, (A), (B), or (C) applies. In other embodiments, (A) and (B); or (A) and (C); or (B) and (C) applies. In still other embodiments, (A), (B), and (C) apply.

In another aspect, methods for promoting post-natal mammalian neurogenesis in a subject in need thereof are featured. The methods include administering to the subject an effective amount of a compound having formula (I) or a pharmaceutically acceptable salt thereof, in which R and R' together with $C_2$ and $C_3$, respectively, form a fused phenyl ring having formula (II):

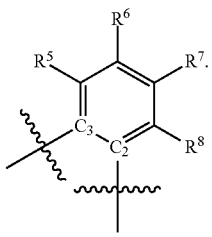

(II)

For purposes of clarification, it is understood that compounds in which R and R' together with $C_2$ and $C_3$, respectively, form a fused phenyl ring having formula (II) correspond to compounds having the following general formula:

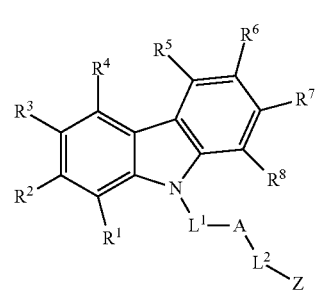

(III)

in which $R^1$, $R^2$, $R^3$, $R^4$, $L^1$, $L^2$, A, and Z can be as defined anywhere herein.

In embodiments, (A), (B), or (C) applies. In other embodiments, (A) and (B); or (A) and (C); or (B) and (C) applies. In still other embodiments, (A), (B), or (C) apply.

In another aspect, methods for promoting post-natal mammalian neurogenesis in a subject in need thereof are featured. The method includes administering to the subject an effective amount of a compound having formula (I) or a pharmaceutically acceptable salt thereof, in which:

each of $L^1$ and $L^2$ is $CH_2$;

A is $CR^{41}R^{42}$, wherein one of $R^{41}$ and $R^{42}$ is $OR^9$, and the other is hydrogen;

Z is —$NR^{10}R^{11}$; and each of $R^{10}$ and $R^{11}$ is independently selected from (a) hydrogen;

(b) $C_6$-$C_{10}$ aryl that is optionally substituted with from 1-4 $R^b$;

(d) $C_1$-$C_6$ alkyl or $C_1$-$C_6$ haloalkyl, each of which is optionally substituted with from 1-3 $R^d$;

(f) $C_2$-$C_6$ alkenyl or $C_2$-$C_6$ alkynyl.

In embodiments, (A), (B), or (C) applies. In other embodiments, (A) and (B); or (A) and (C); or (B) and (C) applies. In still other embodiments, (A), (B), and (C) apply.

In one aspect, compositions (e.g., a pharmaceutical composition) are featured, which includes a compound of formula (I) (and/or a compound of any of the other formulae described herein) or a salt (e.g., a pharmaceutically acceptable salt) thereof as defined anywhere herein and a pharmaceutically acceptable carrier. In some embodiments, the compositions can include an effective amount of the compound or salt. In some embodiments, the compositions can further include one or more additional therapeutic agents. These may include, but are not limited to, antidepressant medications (including selective serotonin reuptake inhibitors, tricyclic antidepressants, monoamine oxidase inhibitors, and other antidepressant medications including but not limited to venlafaxine, nefazadone, bupropion, mirtazapine, lithium and trazodone) and acetylcholinesterase inhibitors (including but not limited to Aricept, Reminyl, and Exelon).

In another aspect, dosage forms are featured, which includes from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of formula (I) (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

In one aspect, the compounds of formula (I) themselves (and/or a compound of any of the other formulae described herein) or a salt (e.g., a pharmaceutically acceptable salt) thereof as defined anywhere herein are featured. In another aspect, any of the formula (I) compounds specifically described herein are featured.

In one aspect, compounds having formula (I) are featured.

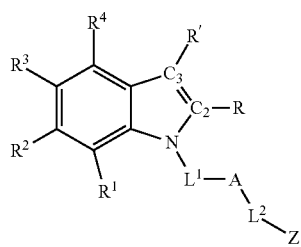

(I)

wherein:
each $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —$NH(C_1$-$C_6$ alkyl), —$N(C_1$-$C_6$ alkyl)$_2$, —$NHC(O)(C_1$-$C_6$ alkyl), and nitro;

R and R' are defined according to (1) or (2) below:
(1) R and R' together with $C_2$ and $C_3$, respectively, form a fused phenyl ring having formula (II):

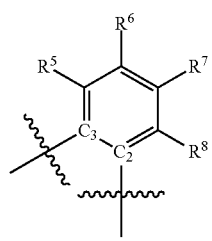

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —$NH(C_1$-$C_6$ alkyl), —$N(C_1$-$C_6$ alkyl)$_2$, —$NHC(O)(C_1$-$C_6$ alkyl), and nitro; OR (2) R and R' together with $C_2$ and $C_3$, respectively, form a fused R and R' together with $C_2$ and $C_3$, respectively, form a fused heteroaryl ring containing 6 ring atoms, wherein from 1-2 independently selected ring atoms is N; and wherein said heteroaryl ring is optionally substituted with from 1-2 independently selected $R^b$;

each of $L^1$ and $L^2$ is, independently, $C_1$-$C_3$ alkylene, which is optionally substituted with from 1-2 independently selected $R^c$;

A is:
(i) $CR^{A1}R^{A2}$, wherein each of $R^{A1}$ and $R^{A2}$ is independently selected from hydrogen, halo, $C_1$-$C_3$ alkyl, and $OR^9$, wherein $R^9$ is hydrogen or $C_1$-$C_3$ alkyl that is optionally substituted with hydroxyl or $C_1$-$C_3$ alkoxy; or
(ii) C=O; or
(iii) $C_3$-$C_5$ cycloalkylene that is (a) substituted with 1 oxo; and (b) optionally further substituted with from 1-4 independently selected $R^a$; or
(iv) heterocycloalkylene containing from 3-5 ring atoms, wherein from 1-2 of the ring atoms is independently selected from N, NH, $N(C_1$-$C_3$ alkyl), O, and S; and wherein said heterocycloalkylene is (a) substituted with 1 oxo; and (b) is optionally further substituted with from 1-4 independently selected $R^a$;

Z is:
(i) —$NR^{10}R^{11}$; or
(ii) —$C(O)NR^{10}R^{11}$, or
(iii) —$OR^{12}$; or
(iv) —$S(O)_nR^{13}$, wherein n is 0, 1, or 2 or
(v) heterocycloalkenyl containing from 5-6 ring atoms, wherein from 1-3 of the ring atoms is independently selected from N, NH, $N(C_1$-$C_6$ alkyl), $NC(O)(C_1$-$C_6$ alkyl), O, and S; and wherein said heterocycloalkenyl is optionally substituted with from 1-4 independently selected $R^a$;
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, $N(C_1$-$C_3$ alkyl), O, and S; and wherein said heteroaryl is optionally substituted with from 1-4 independently selected $R^b$; or
(viii) $C_8$-$C_{14}$ arylcycloalkyl, wherein:
(1) the aryl portion is optionally substituted with from 1-4 independently selected $R^b$, and
(2) the cycloalkyl portion is optionally substituted with from 1-4 independently selected $R^a$;
or
(ix) arylheterocyclyl containing from 8-14 ring atoms, wherein:
(1) the aryl portion from is optionally substituted with from 1-4 independently selected $R^b$, and
(2) from 1-2 of the ring atoms of the heterocyclyl portion is independently selected from N, NH, $N(C_1$-$C_6$ alkyl), $NC(O)(C_1$-$C_6$ alkyl), O, and S; and wherein said heterocyclyl portion is optionally substituted with from 1-3 independently selected $R^a$;
or
(x) heteroarylheterocyclyl containing from 8-14 ring atoms, wherein:
(1) from 1-2 of the ring atoms of the heteroaryl portion is independently selected from N, NH, $N(C_1$-$C_3$ alkyl), O, and S; and wherein said heteroaryl portion is optionally substituted with from 1-3 independently selected $R^b$; and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (xi) heteroarylcycloalkyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) the cycloalkyl portion is optionally substituted with from 1-4 independently selected $R^a$;

each of $R^{10}$ and $R^{11}$ is independently selected from the substituents delineated collectively in (a) through (k) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —C(O)($C_1$-$C_6$ alkyl), —C(O)($C_1$-$C_6$ haloalkyl), or —C(O)O($C_1$-$C_6$ alkyl);
(f) $C_2$-$C_6$ alkenyl or $C_2$-$C_6$ alkynyl;
(g) $C_8$-$C_{14}$ arylcycloalkyl, wherein:
(1) the aryl portion is optionally substituted with from 1-4 independently selected $R^b$, and
(2) the cycloalkyl portion is optionally substituted with from 1-4 independently selected $R^a$;
(h) arylheterocyclyl containing from 8-14 ring atoms, wherein:
(1) the aryl portion from is optionally substituted with from 1-4 independently selected $R^b$, and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(i) heteroarylheterocyclyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(j) heteroarylcycloalkyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) the cycloalkyl portion is optionally substituted with from 1-4 independently selected $R^a$;
(k) $C_3$-$C_8$ cycloalkyl or $C_3$-$C_8$ cycloalkenyl, each of which is optionally substituted with from 1-4 independently selected $R^a$; and
(l) $C_7$-$C_{12}$ aralkyl, wherein the aryl portion is optionally the aryl portion from is optionally substituted with from 1-4 independently selected $R^b$,
provided that one of $R^{10}$ and $R^{11}$ must be selected from (b), (c), (g), (h), (i), (j), and (k);

$R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_1$-$C_6$ alkyl or $C_1$-$C_6$ haloalkyl, each of which is substituted with from 1-3 $R^d$;
(iv) $C_8$-$C_{14}$ arylcycloalkyl, wherein:
(1) the aryl portion is optionally substituted with from 1-4 independently selected $R^b$, and
(2) the cycloalkyl portion is optionally substituted with from 1-4 independently selected $R^a$;

or (v) arylheterocyclyl containing from 8-14 ring atoms, wherein:
(1) the aryl portion from is optionally substituted with from 1-4 independently selected $R^b$, and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (vi) heteroarylheterocyclyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (vii) heteroarylcycloalkyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) the cycloalkyl portion is optionally substituted with from 1-4 independently selected $R^a$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(iii) $C_8$-$C_{14}$ arylcycloalkyl, wherein:
(1) the aryl portion is optionally substituted with from 1-4 independently selected $R^b$, and
(2) the cycloalkyl portion is optionally substituted with from 1-4 independently selected $R^a$;

or
(iv) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(v) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
  (aa) $C_1$-$C_6$ alkoxy; $C_1$-$C_6$ haloalkoxy; $C_1$-$C_6$ thioalkoxy; $C_1$-$C_6$ thiohaloalkoxy; —O—$(CH_2)_{1-3}$—[O$(CH_2)_{1-3}]_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;
  (bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;
  (cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and
  (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—;

or a pharmaceutically acceptable salt thereof.

In embodiments, 1, 2, 3, 4, 5, or 6 of the following can apply
  provided that $R^3$ and $R^6$ cannot both be hydrogen when A is $CH_2$, and R and R' are defined according to definition (1);
  provided that $R^3$ cannot be hydrogen when A is $CH_2$, and R and R' are defined according to definition (2);
  provided that $R^3$ and $R^6$ cannot both be chloro when A is $CH_2$, R and R' are defined according to definition (1), Z is —$OR^{12}$, and $R^{12}$ is unsubstituted phenyl;
  provided that $R^3$ and $R^6$ cannot both be bromo when A is $CH_2$, R and R' are defined according to definition (1), Z is —$OR^{12}$, and $R^{12}$ is phenyl that is substituted with pyridyl or alkyl that is substituted with from 1-3 $R^e$;
  provided that $R^3$ and $R^6$ cannot both be hydrogen when A is CH($CH_3$), R and R' are defined according to definition (1), Z is $NR^{10}R^{11}$, $R^{10}$ is $CH_3$, and $R^{11}$ is unsubstituted phenyl;
  provided that when A is $CR^{41}R^{42}$, and one of $R^{41}$ and $R^{42}$ is OH (i.e., $R^9$ is H), then the other of $R^{41}$ and $R^{42}$ is $C_1$-$C_3$ alkyl.

In another aspect, pharmaceutical compositions are featured that include the above-described compounds (or salts thereof as described herein) and a pharmaceutically acceptable carrier. In embodiments, 1, 2, 3, 4, 5, or 6 of the above described provisions can apply.

In one aspect, compounds having formula (I) are featured.

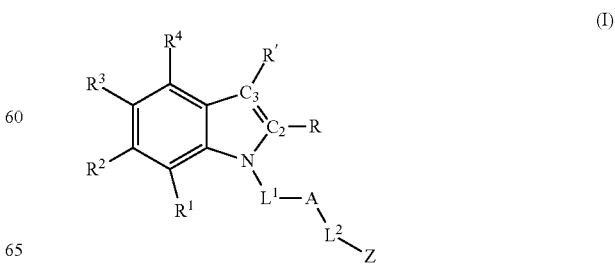

(I)

wherein:

each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro;

R and R' are defined according to (1) or (2) below:

(1) R and R' together with $C_2$ and $C_3$, respectively, form a fused phenyl ring having formula (II):

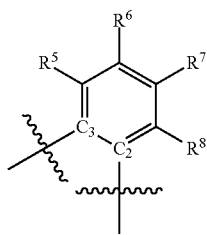

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro; OR (2) R and R' together with $C_2$ and $C_3$, respectively, form a fused R and R' together with $C_2$ and $C_3$, respectively, form a fused heteroaryl ring containing 6 ring atoms, wherein from 1-2 independently selected ring atoms is N; and wherein said heteroaryl ring is optionally substituted with from 1-2 independently selected $R^b$;

each of $L^1$ and $L^2$ is, independently, $C_1$-$C_3$ alkylene, which is optionally substituted with from 1-2 independently selected $R^c$;

A is:

(i) $CR^{A1}R^{A2}$, wherein each of $R^{A1}$ and $R^{A2}$ is independently selected from hydrogen, halo, $C_1$-$C_3$ alkyl, and $OR^9$, wherein $R^9$ is $C_1$-$C_3$ alkyl that is optionally substituted with hydroxyl or $C_1$-$C_3$ alkoxy; or (ii) C=O; or (iii) $C_3$-$C_5$ cycloalkylene that is (a) substituted with 1 oxo; and (b) optionally further substituted with from 1-4 independently selected $R^a$; or (iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;

Z is:

(i) —$NR^{10}R^{11}$; or (ii) —C(O)$NR^{10}R^{11}$; or (iii) —$OR^{12}$; or (iv) —$S(O)_nR^{13}$, wherein n is 0, 1, or 2 or (v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$;

(vi) $C_6$-$C_{10}$ aryl that is optionally substituted with from 1-4 independently selected $R^b$; or (vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or (viii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;

or (ix) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (x) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (xi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

each of R10 and $R^{11}$ is independently selected from the substituents delineated collectively in (a) through (k) below:

(a) hydrogen;

(b) $C_6$-$C_{10}$ aryl that is optionally substituted with from 1-4 $R^b$;

(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

(d) $C_1$-$C_6$ alkyl or $C_1$-$C_6$ haloalkyl, each of which is optionally substituted with from 1-3 $R^d$;

(e) —C(O)($C_1$-$C_6$ alkyl), —C(O)($C_1$-$C_6$ haloalkyl), or —C(O)O($C_1$-$C_6$ alkyl);

(f) $C_2$-$C_6$ alkenyl or $C_2$-$C_6$ alkynyl;

(g) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;

(h) arylheterocyclyl containing from 8-14 ring atoms, wherein:
  (1) the aryl portion from is optionally substituted with from 1-4 independently selected $R^b$, and (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

(i) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

(j) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

(k) $C_3$-$C_8$ cycloalkyl or $C_3$-$C_8$ cycloalkenyl, each of which is optionally substituted with from 1-4 independently selected $R^a$; and (l) $C_7$-$C_{12}$ aralkyl, wherein the aryl portion is optionally the aryl portion from is optionally substituted with from 1-4 independently selected $R^b$, provided that one of $R^{10}$ and $R^{11}$ must be selected from (b), (c), (g), (h), (i), (j), and (k);

$R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_1$-$C_6$ alkyl or $C_1$-$C_6$ haloalkyl, each of which is substituted with from 1-3 $R^d$;
(iv) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(v) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vii) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(iii) $C_3$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(iv) arylheterocyclyl containing from 8-14 ring atoms, wherein:
  (1) the aryl portion from is optionally substituted with from 1-4 independently selected $R^b$), and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(v) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
  (aa) $C_1$-$C_6$ alkoxy; $C_1$-$C_6$ haloalkoxy; $C_1$-$C_6$ thioalkoxy; $C_1$-$C_6$ thiohaloalkoxy; —O—$(CH_2)_{1-3}$—[O$(CH_2)_{1-3}]_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;
  (bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl; —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;
  (cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and
  (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—;

or a pharmaceutically acceptable salt thereof.

In embodiments, 1, 2, 3, 4, or 5 of the following can apply
  provided that $R^3$ and $R^6$ cannot both be hydrogen when A is $CH_2$, and R and R' are defined according to definition (1);
  provided that $R^3$ cannot be hydrogen when A is $CH_2$, and R and R' are defined according to definition (2);
  provided that $R^3$ and $R^6$ cannot both be chloro when A is $CH_2$, R and R' are defined according to definition (1), Z is —$OR^{12}$, and $R^{12}$ is unsubstituted phenyl;
  provided that $R^3$ and $R^6$ cannot both be bromo when A is $CH_2$, R and R' are defined according to definition (1), Z is —$OR^{12}$, and $R^{12}$ is phenyl that is substituted with pyridyl or alkyl that is substituted with from 1-3 $R^e$; and
  provided that $R^3$ and $R^6$ cannot both be hydrogen when A is $CH(CH_3)$, R and R' are defined according to definition (1), Z is $NR^{10}R^{11}$, $R^{10}$ is $CH_3$, and $R^{11}$ is unsubstituted phenyl.

In another aspect, pharmaceutical compositions are featured that include the above-described compounds (or salts thereof as described herein) and a pharmaceutically acceptable carrier. In embodiments, 1, 2, 3, 4, or 5 of the above described provisions can apply.

In another aspect, compounds having formula (I) are featured

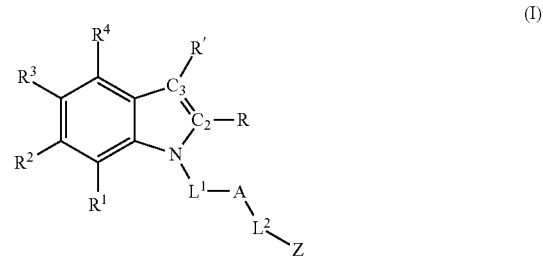

(I)

wherein:
  each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro;

R and R' are defined according to (1) or (2) below:
(1) R and R' together with $C_2$ and $C_3$, respectively, form a fused phenyl ring having formula (II):

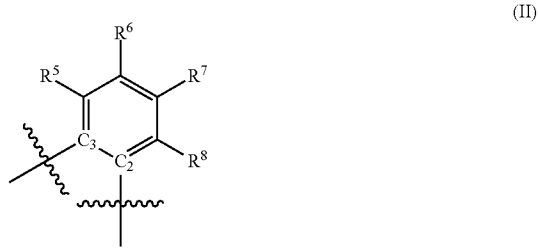

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro; OR (2) R and R' together with $C_2$ and $C_3$, respectively, form a fused R and R' together with $C_2$ and $C_3$, respectively, form a fused heteroaryl ring containing 6 ring atoms, wherein from 1-2 independently selected ring atoms is N; and wherein said heteroaryl ring is optionally substituted with from 1-2 independently selected $R^b$;

each of $L^1$ and $L^2$ is, independently, $C_1$-$C_3$ alkylene, which is optionally substituted with from 1-2 independently selected $R^c$;

A is $CR^{41}R^{42}$, wherein one of $R^{41}$ and $R^{42}$ is —OH, and the other of $R^{41}$ and $R^{42}$ is hydrogen or $C_1$-$C_3$ alkyl;

Z is —$OR^{12}$ or —$S(O)_nR^{13}$, wherein n is 0, 1, or 2;

each of $R^{12}$ and $R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(iii) $C_1$-$C_6$ alkyl or $C_1$-$C_6$ haloalkyl (e.g., $C_1$-$C_6$ alkyl), each of which is substituted with from 1-3 $R^d$; or
(iv) $C_8$-$C_{14}$ arylcycloalkyl, wherein:
(1) the aryl portion is optionally substituted with from 1-4 independently selected $R^b$, and
(2) the cycloalkyl portion is optionally substituted with from 1-4 independently selected $R^a$;
or
(v) arylheterocyclyl containing from 8-14 ring atoms, wherein:
(1) the aryl portion from is optionally substituted with from 1-4 independently selected $R^b$, and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylheterocyclyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vii) heteroarylcycloalkyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
(aa) $C_1$-$C_6$ alkoxy; $C_1$-$C_6$ haloalkoxy; $C_1$-$C_6$ thioalkoxy; $C_1$-$C_6$ thiohaloalkoxy; —O—($CH_2$)$_{1-3}$—[O($CH_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;
(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;

(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—;

or a pharmaceutically acceptable salt thereof.

In embodiments, 1, 2, 3, or 4 of the following can apply:
provided that $R^3$ and $R^6$ cannot both be hydrogen when R and R' are defined according to definition (1);
provided that $R^3$ and $R^6$ cannot both be chloro when R and R' are defined according to definition (1), Z is —$OR^{12}$, and $R^{12}$ is phenyl substituted with chloro, formyl, or —NHC(O)$CH_3$;
provided that $R^3$ and $R^6$ cannot both be bromo when R and R' are defined according to definition (1), Z is —$OR^{12}$, and $R^{12}$ is phenyl substituted with —NHC(O)$CH_3$; and
provided that $R^3$ and $R^6$ cannot both be bromo when R and R' are defined according to definition (1), Z is —$SR^{13}$, and $R^{13}$ is phenyl substituted with —OH.

In another aspect, pharmaceutical compositions are featured that include the above-described compounds (or salts thereof as described herein) and a pharmaceutically acceptable carrier. In embodiments, 1, 2, 3, 4, or 5 of the above described provisions can apply.

In another aspect, compounds having formula (I) are featured:

$$\text{(I)}$$

[Structure: benzene ring with substituents $R^1$, $R^2$, $R^3$, $R^4$ on positions, fused to a 5-membered ring containing $C_3$ (bearing $R'$), $C_2$ (bearing R), and N (bearing $L^1$—A, with $L^2$—Z branching)]

wherein:

each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro;

R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$;

each of $L^1$ and $L^2$ is, independently, $C_1$-$C_3$ alkylene, which is optionally substituted with from 1-2 independently selected $R^c$;

A is:
(i) $CR^{A1}R^{A2}$, wherein one of $R^{A1}$ and $R^{A2}$ is independently selected from hydrogen, halo, $C_1$-$C_3$ alkyl, and $OR^9$; and the other of $R^{A1}$ and $R^{A2}$ is independently selected from halo, $C_1$-$C_3$ alkyl, and $OR^9$; wherein $R^9$ is hydrogen or $C_1$-$C_3$ alkyl that is optionally substituted with hydroxyl or $C_1$-$C_3$ alkoxy; or
(ii) C=O;

Z is:
(i) —$NR^{10}R^{11}$; or
(ii) —C(O)$NR^{10}R^{11}$; or
(iii) —$OR^{12}$; or
(iv) —S(O)$_n R^{13}$, wherein n is 0, 1, or 2 or
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or each of $R^{10}$ and $R^{11}$ is independently selected from the substituents delineated collectively in (a) through (k) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —C(O)($C_1$-$C_6$ alkyl), —C(O)($C_1$-$C_6$ haloalkyl), or —C(O)O($C_1$-$C_6$ alkyl);
(f) $C_2$-$C_6$ alkenyl or $C_2$-$C_6$ alkynyl;

and
(l) $C_7$-$C_{12}$ aralkyl, wherein the aryl portion is optionally the aryl portion from is optionally substituted with from 1-4 independently selected $R^b$,
provided that one of $R^{10}$ and $R^{11}$ must be selected from (b) and (c);

$R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
(aa) $C_1$-$C_6$ alkoxy; $C_1$-$C_6$ haloalkoxy; $C_1$-$C_6$ thioalkoxy; $C_1$-$C_6$ thiohaloalkoxy; —O—(CH$_2$)$_{1-3}$—[O(CH$_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;
(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —SO$_2$($C_1$-$C_6$ alkyl); —SO$_2$$NH_2$; —SO$_2$NH($C_1$-$C_6$ alkyl); —SO$_2$N($C_1$-$C_6$ alkyl)$_2$;
(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and
(dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; and $L^3$-($C_1$-$C_6$ alkylene)-biotin, where in $L^3$ is a —O—, —NH—, —NCH$_3$—, —C(O)—, —C(O)NH—, —C(O)NCH$_3$—, —NHC(O)—, or —NCH$_3$C(O)—;

or a pharmaceutically acceptable salt thereof.

In embodiments, provision (A) described herein can apply.

In another aspect, compounds having formula (I) are featured:

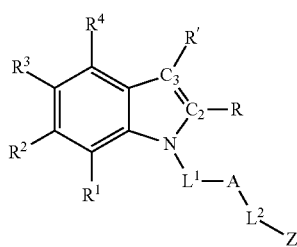

wherein:

each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —N$_3$, cyano, —NH$_2$, —NH($C_1$-$C_6$ alkyl), —N($C_1$-$C_6$ alkyl)$_2$, —NHC(O)($C_1$-$C_6$ alkyl), and nitro;

each of R and R' is, independently, hydrogen, $C_1$-$C_6$ alkyl, or $C_1$-$C_6$ haloalkyl;

each of $L^1$ and $L^2$ is, independently, $C_1$-$C_3$ alkylene, which is optionally substituted with from 1-2 independently selected $R^c$;

A is:

(i) $CR^{A1}R^{A2}$, wherein one of $R^{A1}$ and $R^{A2}$ is independently selected from hydrogen, fluoro, chloro, $C_1$-$C_3$ alkyl, and OR$^9$; and the other of $R^{A1}$ and $R^{A2}$ is independently selected from fluoro, chloro, $C_1$-$C_3$ alkyl, and OR$^9$; wherein R$^9$ is hydrogen or $C_1$-$C_3$ alkyl that is optionally substituted with hydroxyl or $C_1$-$C_3$ alkoxy; or (ii) C=O;

Z is:

(i) —NR$^{10}$R$^{11}$; or (ii) —C(O)NR$^{10}$R$^{11}$; or (iii) —OR$^{12}$; or (iv) —S(O)$_n$R$^{13}$, wherein n is 0, 1, or 2 or (vi) $C_6$-$C_{10}$ aryl that is optionally substituted with from 1-4 independently selected R$^b$; or (vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected R$^b$; or each of R$^{10}$ and R$^{11}$ is independently selected from the substituents delineated collectively in (a) through (k) below:
(a) hydrogen;
(b) $C_6$-$C_{10}$ aryl that is optionally substituted with from 1-4 R$^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 R$^b$;
(d) $C_1$-$C_6$ alkyl or $C_1$-$C_6$ haloalkyl, each of which is optionally substituted with from 1-3 R$^d$;
(e) —C(O)($C_1$-$C_6$ alkyl), —C(O)($C_1$-$C_6$ haloalkyl), or —C(O)O($C_1$-$C_6$ alkyl);
(f) $C_2$-$C_6$ alkenyl or $C_2$-$C_6$ alkynyl;
and
(l) $C_7$-$C_{12}$ aralkyl, wherein the aryl portion is optionally the aryl portion from is optionally substituted with from 1-4 independently selected R$^b$,
provided that one of R$^{10}$ and R$^{11}$ must be selected from (b) and (c);

each of R$^{12}$ and R$^{13}$ is:
(i) $C_6$-$C_{10}$ aryl that is optionally substituted with from 1-4 R$^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 R$^b$;

R$^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —NH$_2$, —NH($C_1$-$C_6$ alkyl), N($C_1$-$C_6$ alkyl)$_2$, —NHC(O)($C_1$-$C_6$ alkyl), and cyano;

R$^b$ at each occurrence is independently selected from the substituents delineated in (aa) through (dd) below:
(aa) $C_1$-$C_6$ alkoxy; $C_1$-$C_6$ haloalkoxy; $C_1$-$C_6$ thioalkoxy; $C_1$-$C_6$ thiohaloalkoxy; —O—(CH$_2$)$_{1-3}$—[O(CH$_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected R$^e$;
(bb) halo; hydroxyl; cyano; nitro; —NH$_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$;
(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected R$^a$; and
(dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

R$^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH ($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—;

or a pharmaceutically acceptable salt thereof.

In one aspect, compounds of formula (III) are featured in which:

A is $CR^{A1}R^{A2}$, in which each of $R^{A1}$ and $R^{A2}$ is, independently, hydrogen, halo, or $C_1$-$C_3$ alkyl; or A is $CR^{A1}R^{A2}$, in which one of $R^{A1}$ and $R^{A2}$ is halo (e.g., fluoro), and the other of $R^{A1}$ and $R^{A2}$ is, independently, hydrogen, halo, or $C_1$-$C_3$ alkyl (e.g., hydrogen); or A is $CR^{A1}R^{A2}$, in which one of $R^{A1}$ and $R^{A2}$ is halo (e.g., fluoro), and the other of $R^{A1}$ and $R^{A2}$ is hydrogen; and $R^1$, $R^2$, $R^3$, $R^4$, $L^1$, $L^2$, and Z can be as defined anywhere herein; or a salt (e.g., pharmaceutically acceptable salt) thereof.

In embodiments, (B) and/or (C) applies.

In one aspect, compounds of formula (III) are featured in which:

one of $R^{A1}$ and $R^{A2}$ can be $OR^9$. In embodiments, the other of $R^{A1}$ and $R^{A2}$ can be as defined anywhere herein; e.g., the other of $R^{A1}$ and $R^{A2}$ can be hydrogen or $C_1$-$C_3$ alkyl. For example, one of $R^{A1}$ and $R^{A2}$ can be $OR^9$, and the other of $R^{A1}$ and $R^{A2}$ is hydrogen or C1-C3 alkyl. In embodiments, $R^9$ can be hydrogen or C1-C3 alkyl; and $R^1$, $R^2$, $R^3$, $R^4$, $L^1$, $L^2$, and Z can be as defined anywhere herein; or a salt (e.g., pharmaceutically acceptable salt) thereof.

In embodiments, one or more of the following apply, e.g., when A is CHOH and Z is $NR^{10}R^{11}$:

each of $R^3$ and $R^6$ is $CH_3$; and/or each of $R^3$ and $R^6$ is bromo; and/or each of $R^3$ and $R^6$ is chloro; and/or one of $R^3$ and $R^6$ is $CH_3$ (e.g., $R^6$), and the other is bromo (e.g., $R^3$);

each of $R^{10}$ and $R^{11}$ is other than hydrogen;
each of $R^{10}$ and $R^{11}$ is hydrogen;
one of $R^{10}$ and $R^{11}$ is heteroaryl as defined anywhere herein;
$L^1$ and/or $L^2$ is $C_2$-$C_3$ alkylene (optionally substituted);
(B) and/or (C) applies.

In one aspect, compounds of formula (III) are featured in which Z is other than $NR^{10}R^{11}$; and $R^1$, $R^2$, $R^3$, $R^4$, $L^1$, $L^2$, Z, and A can be as defined anywhere herein; or a salt (e.g., pharmaceutically acceptable salt) thereof. In embodiments, (B) and/or (C) applies.

In one aspect, compounds of formula (III) are featured in which Z is —$OR^{12}$ and/or —$S(O)_nR^{13}$; and $R^1$, $R^2$, $R^3$, $R^4$, $L^1$, $L^2$, and A can be as defined anywhere herein; or a salt (e.g., pharmaceutically acceptable salt) thereof. In embodiments, (B) and/or (C) applies.

In one aspect, compounds of formula (III) are featured in which A is (ii) C=O; and/or (iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$; and $R^1$, $R^2$, $R^3$, $R^4$, $L^1$, $L^2$, and Z can be as defined anywhere herein; or a salt (e.g., pharmaceutically acceptable salt) thereof.

Any of the aforementioned compounds can be used in any of the methods or compositions described anywhere herein.

This invention relates generally to stimulating neurogenesis (e.g., post-natal neurogenesis, e.g., post-natal hippocampal neurogenesis) and protecting neurons from death with a compound of formula (I) (and/or a compound of any of the other formulae described herein) or a salt (e.g., a pharmaceutically acceptable salt) thereof as defined anywhere herein.

For example, methods of promoting the generation of neurons are featured. As another example, methods of promoting the survival, growth, development and/or function of neurons, particularly CNS, brain, cerebral, and hippocampal neurons are featured. As a further example, methods of stimulating post-natal hippocampal neurogenesis are featured.

In some embodiments, such methods can include in vitro methods, e.g., contacting a sample (e.g., a cell or tissue) with a compound of formula (I) (and/or a compound of any of the other formulae described herein) or a salt (e.g., a pharmaceutically acceptable salt) thereof as defined anywhere herein. In other embodiments, the methods can include administering a compound of formula (I) (and/or a compound of any of the other formulae described herein) or a salt (e.g., a pharmaceutically acceptable salt) thereof as defined anywhere herein to a subject (e.g., a mammal, such as a human).

Accordingly, in yet another aspect, this invention includes and features methods of screening for (thereby identifying) compounds that stimulate neurogenesis (e.g., post-natal neurogenesis, e.g., post-natal hippocampal neurogenesis) or protect newborn neurons from cell death. E.g., such as those described in the Examples section.

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with insufficient (e.g., aberrant) neurogenesis or unwanted neuronal cell death in a subject in need thereof are featured. The methods include administering to the subject an effective amount of a compound a compound of formula (I) (and/or a compound of any of the other formulae described herein) or a salt (e.g., a pharmaceutically acceptable salt) thereof as defined anywhere herein to the subject.

In another aspect, the use of a compound of formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions caused by, or associated with, insufficient (e.g., aberrant) neurogenesis or unwanted neuronal cell death is featured.

In embodiments, the one or more diseases, disorders, or conditions can include neuropathies, nerve trauma, and neurodegenerative diseases. In embodiments, the one or more diseases, disorders, or conditions can be diseases, disorders, or conditions caused by, or associated with insufficient neurogenesis (e.g., aberrant hippocampal neurogenesis) as is believed to occur in neuropsychiatric diseases, or aberrant neuronal cell death as is believed to occur in neurodegenerative diseases. Examples of the one or more diseases, disorders, or conditions include, but are not limited to, schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs, such as alcohol, opiates, methamphetamine, phencyclidine, and cocaine.

In some embodiments, the subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject can be a human.

In another aspect, methods of making the compounds described herein are featured. In embodiments, the methods include taking any one of the intermediate compounds described herein and reacting it with one or more chemical reagents in one or more steps to produce a compound of formula (I) (and/or a compound of any of the other formulae described herein) or a salt (e.g., a pharmaceutically acceptable salt) thereof as defined anywhere herein.

In some embodiments, compounds in which A is CHOH, and each of $L^1$ and $L^2$ is $C_1$-$C_3$ alkylene (e.g., each of $L^1$ and $L^2$ is $CH_2$) can be converted to compounds in which A is C(O), and each of $L^1$ and $L^2$ is $C_1$-$C_3$ alkylene (e.g., each of $L^1$ and $L^2$ is $CH_2$) that is substituted with $C_1$-$C_6$ thioalkoxy (e.g., —$SCH_3$). The methods include contacting the starting material with an oxidizing agent sulfur trioxide pyridine complex (see, e.g., Example 7a and 7b).

In one aspect, methods of making the pharmaceutical compositions described herein are featured. In embodiments, the methods include taking any one or more of the compounds of formula (I) (and/or compounds of any of the other formulae described herein) or a salt (e.g., a pharmaceutically acceptable salt) thereof as defined anywhere herein, and mixing said compound(s) with one or more pharmaceutically acceptable carriers.

In one aspect, kits for the treatment (e.g., controlling, relieving, ameliorating, alleviating, or slowing the progression of) or prevention (e.g., delaying the onset of or reducing the risk of developing) of one or more diseases, disorders, or conditions caused by, or associated with insufficient (e.g., aberrant) neurogenesis or unwanted neuronal cell death are featured. The kits include (i) a compound of formula (I) (and/or compounds of any of the other formulae described herein) or a salt (e.g., a pharmaceutically acceptable salt) thereof as defined anywhere herein; and (ii) instructions that include a direction to administer said compound to a subject (e.g., a patient).

Embodiments can include, for example, any one or more of the following features.

$R^3$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —$NH(C_1$-$C_6$ alkyl), —$N(C_1$-$C_6$ alkyl)$_2$, —$NHC(O)(C_1$-$C_6$ alkyl), and nitro. In embodiments, $R^3$ is halo (e.g., bromo). In embodiments, each of $R^1$, $R^2$, and $R^4$ is hydrogen.

R and R' together with $C_2$ and $C_3$, respectively, form a fused phenyl ring having formula (II):

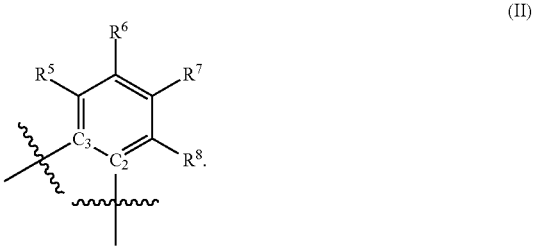

$R^6$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —$NH(C_1$-$C_6$ alkyl), —$N(C_1$-$C_6$ alkyl)$_2$, —$NHC(O)(C_1$-$C_6$ alkyl), and nitro. In embodiments, $R^6$ is halo (e.g., bromo) or $C_1$-$C_6$ alkyl (e.g., $CH_3$). In embodiments, $R^6$ is halo (e.g., bromo). In embodiments, each of $R^5$, $R^7$, and $R^8$ is hydrogen.

In embodiments, each of $R^3$ and $R^6$ is an independently selected substituent that is other than hydrogen. In certain embodiments, each of $R^3$ and $R^6$ is independently selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —$NH(C_1$-$C_6$ alkyl), —$N(C_1$-$C_6$ alkyl)$_2$, —$NHC(O)(C_1$-$C_6$ alkyl), and nitro. For example, $R^3$ can be halo (e.g., bromo); and $R^6$ can be halo (e.g., bromo) or $C_1$-$C_6$ alkyl (e.g., $CH_3$); e.g., halo (e.g., bromo). In embodiments, each of $R^1$, $R^2$, and $R^4$ is hydrogen; and each of $R^5$, $R^7$, and $R^8$ is hydrogen.

In embodiments, R and R' together with $C_2$ and $C_3$, respectively, form a fused heteroaryl ring containing from 5-6 ring atoms, wherein from 1-2 of the ring atoms is independently selected from N, NH, N($C_1$-$C_3$ alkyl), O, and S; and wherein said heteroaryl ring is optionally substituted with from 1-3 independently selected $R^b$.

For example, R and R' together with $C_2$ and $C_3$, respectively, form a fused heteroaryl ring containing-6 ring atoms, wherein from 1-2 independently selected ring atoms is N; and wherein said heteroaryl ring is optionally substituted with from 1-2 independently selected $R^b$.

In embodiments, R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$.

For example, R and R' together with $C_2$ and $C_3$, respectively, form a fused heterocyclic ring containing 6 ring atoms, wherein from 1-2 of the ring atoms is independently selected from N, NH, N($C_1$-$C_6$ alkyl), and NC(O)($C_1$-$C_6$ alkyl); and wherein said heterocyclic ring is optionally substituted with from 1-3 independently selected $R^a$.

In embodiments, R and R' is, independently, hydrogen, $C_1$-$C_6$ alkyl, or $C_1$-$C_6$ haloalkyl (e.g., $C_1$-$C_6$ alkyl, or $C_1$-$C_6$ haloalkyl; e.g., $C_1$-$C_6$ alkyl).

Each of $L^1$ and $L^2$ is, independently, $C_1$-$C_3$ straight chain alkylene, which is optionally substituted with from 1-2 independently selected $R^c$. For example, each of $L^1$ and $L^2$ is $CH_2$.

A is $CR^{A1}R^{A2}$, in which each of $R^{A1}$ and $R^{A2}$ is, independently, hydrogen, halo, $C_1$-$C_3$ alkyl, or $OR^9$.

In some embodiments, A is other than $CH_2$.

In embodiments, one of $R^{41}$ and $R^{42}$ can be independently selected from hydrogen, halo, $C_1$-$C_3$ alkyl, and $OR^9$; and the other of $R^{41}$ and $R^{42}$ can be independently selected from halo, $C_1$-$C_3$ alkyl, and $OR^9$. For example, one of $R^{41}$ and $R^{42}$ is halo, $C_1$-$C_3$ alkyl, or $OR^9$ (e.g., halo or $OR^9$); and the other is hydrogen or C1-C3 alkyl.

In embodiments, one of $R^{41}$ and $R^{42}$ is halo, and the other of $R^{41}$ and $R^{42}$ is hydrogen or halo. For example, one of $R^{41}$ and $R^{42}$ is fluoro, and the other of $R^{41}$ and $R^{42}$ is hydrogen or fluoro. In either embodiments, one of $R^{41}$ and $R^{42}$ is $OR^9$; and the other of $R^{41}$ and $R^{42}$ is $C_1$-$C_3$ alkyl. For example, one of $R^{41}$ and $R^{42}$ is OH; and the other of $R^{41}$ and $R^{42}$ is CH3.

In embodiments, the carbon attached to $R^{41}$ and $R^{42}$ is substituted with four different substituents (for purposes of clarification, these four substituents include $R^{41}$ and $R^{42}$) and is therefore a stereogenic center.

In certain embodiments, the carbon attached to $R^{41}$ and $R^{42}$ is (R) configured, meaning that the carbon attached to $R^{41}$ and $R^{42}$ has the (R) configuration (Cahn Ingold Prelog sequence rules notation). Such compounds are sometimes referred to herein as an "(R)-configured compound" (this term also includes compounds that further contain one or more stereogenic centers in addition to the (R)—$CR^{41}R^{42}$ stereogenic center).

In other embodiments, the carbon attached to $R^{41}$ and $R^{42}$ is (S) configured, meaning that the carbon attached to $R^{41}$ and $R^{42}$ has the (S) configuration (Cahn Ingold Prelog sequence rules notation). Such compounds are sometimes referred to herein as an "(S)-configured compound" (this term also includes compounds that further contain one or more stereogenic centers in addition to the (S)—$CR^{41}R^{42}$ stereogenic center).

In embodiments, the (R) configured compound (or salt, e.g., a pharmaceutically acceptable salt, thereof) is substantially free of (e.g., contains less than about 5% of; less than about 2% of, less than about 1%, less than about 0.5% of) a formula (I) compound (or salt thereof as described herein) that is (S) configured at the carbon attached to $R^{41}$ and $R^{42}$ (i.e., a formula (I) compound in which the carbon attached to $R^{41}$ and $R^{42}$ has the (S) configuration). For example, the (R) configured compound can be an (R)-enantiomer that is substantially free of its opposing (S) enantiomer. As another example, an (R) configured compound can be substantially free of a diastereomer in which the carbon attached to $R^{41}$ and $R^{42}$ has the (S) configuration. In certain embodiments, the (R) configured compound can be additionally in substantially pure form (e.g., contains less than about 5% of, less than about 2% of, less than about 1%, less than about 0.5% of other substances, including, for example, one or more of other formula (I) compounds, non-formula (I) compounds, or biological media).

In embodiments, the (S) configured compound (or salt, e.g., a pharmaceutically acceptable salt, thereof) is substantially free of (e.g., contains less than about 5% of, less than about 2% of, less than about 1%, less than about 0.5% of) a formula (I) compound (or salt thereof as described herein) that is (R) configured at the carbon attached to $R^{41}$ and $R^{42}$ (i.e., a formula (I) compound in which the carbon attached to $R^{41}$ and $R^{42}$ has the (R) configuration). For example, the (S) configured compound can be an (S)-enantiomer that is substantially free of its opposing (R) enantiomer. As another example, the (S) configured compound can be substantially free of a diastereomer in which the carbon attached to $R^{41}$ and $R^{42}$ has the (R) configuration. In certain embodiments, the (S) configured compound can be additionally in substantially pure form (e.g., contains less than about 5% of, less than about 2% of, less than about 1%, less than about 0.5% of other substances, including, for example, one or more of other formula (I) compounds, non-formula (I) compounds, or biological media).

In certain embodiments, a formula (I) compound is (+) (dextrorotatory) when in the presence of plane polarized light.

In certain embodiments, a formula (I) compound is (−) (levorotatory) when in the presence of plane polarized light.

In embodiments, the (+) (dextrorotatory) compound is substantially free of (e.g., contains less than about 5% of, less than about 2% of less than about 1%, less than about 0.5%) a formula (I) compound (or salt thereof as described herein) that is (−) (levorotatory). In certain embodiments, the (+) (dextrorotatory) compound can be additionally in substantially pure form (e.g., contains less than about 5% of, less than about 2% of, less than about 1%, less than about 0.5% of other substances, including, for example, one or more of other formula (I) compounds, non-formula (I) compounds, or biological media).

In embodiments, the (−) (levorotatory) compound is substantially free of (e.g., contains less than about 5% of, less than about 2% of, less than about 1%, less than about 0.5%) a formula (I) compound (or salt thereof as described herein) that is (+) (dextrorotatory). In certain embodiments, the (−) (levorotatory) compound can be additionally in substantially pure form (e.g., contains less than about 5% of, less than about 2% of, less than about 1%, less than about 0.5% of other substances, including, for example, one or more of other formula (I) compounds, non-formula (I) compounds, or biological media).

A is: (i) $CR^{41}R^{42}$, wherein each of $R^{41}$ and $R^{42}$ is independently selected from hydrogen, halo, $C_1$-$C_3$ alkyl, and $OR^9$, wherein $R^9$ is $C_1$-$C_3$ alkyl that is optionally substituted with hydroxyl or $C_1$-$C_3$ alkoxy; or (ii) C=O.

A is $CR^{41}R^{42}$, wherein each of $R^{41}$ and $R^{42}$ is, independently, hydrogen, halo, $C_1$-$C_3$ alkyl, or $OR^9$.

In embodiments, one of $R^{41}$ and $R^{42}$ is independently selected from hydrogen, halo, $C_1$-$C_3$ alkyl, and $OR^9$; and the other of $R^{41}$ and $R^{42}$ is independently selected from halo, $C_1$-$C_3$ alkyl, and $OR^9$.

In certain embodiments, one of $R^{41}$ and $R^{42}$ is halo, and the other of $R^{41}$ and $R^{42}$ is hydrogen, halo, or $C_1$-$C_3$ alkyl. In embodiments, one of $R^{41}$ and $R^{42}$ is halo, and the other of $R^{41}$ and $R^{42}$ is hydrogen. For example, one of $R^{41}$ and $R^{42}$ is fluoro, and the other of $R^{41}$ and $R^{42}$ is hydrogen.

In other embodiments, each of $R^{41}$ and $R^{42}$ is, independently, halo; e.g., each of $R^{41}$ and $R^{42}$ is fluoro.

In embodiments, one of $R^{41}$ and $R^{42}$ is —OH, and the other of $R^{41}$ and $R^{42}$ is hydrogen.

In embodiments, A is $CR^{41}R^{42}$, wherein one of $R^{41}$ and $R^{42}$ is independently selected from hydrogen, halo, $C_1$-$C_3$ alkyl, and $OR^9$; and the other of $R^{41}$ and $R^{42}$ is independently selected from halo, $C_1$-$C_3$ alkyl, and $OR^9$; wherein $R^9$ is hydrogen or $C_1$-$C_3$ alkyl that is optionally substituted with hydroxyl or $C_1$-$C_3$ alkoxy.

In certain embodiments, one of $R^{41}$ and $R^{42}$ is $OR^9$, and the other is hydrogen, wherein $R^9$ is hydrogen.

In embodiments, one of $R^{41}$ and $R^{42}$ is halo, and the other of $R^{41}$ and $R^{42}$ is hydrogen or halo. For example, one of $R^{41}$ and $R^{42}$ is fluoro, and the other of $R^{41}$ and $R^{42}$ is hydrogen or fluoro.

In other embodiments, one of $R^{41}$ and $R^{42}$ is $OR^9$; and the other of $R^{41}$ and $R^{42}$ is $C_1$-$C_3$ alkyl. For example, one of $R^{41}$ and $R^{42}$ is OH; and the other of $R^{41}$ and $R^{42}$ is $CH_3$.

Z is: (i) —$NR^{10}R^{11}$; or (ii) —$C(O)NR^{10}R^{11}$; or (iii) —$OR^{12}$; or (iv) —$S(O)_nR^{13}$, wherein n is 0, 1, or 2.

Z is —NR$^{10}$R$^{11}$. In embodiments, one of R$^{10}$ and R$^{11}$ is: (b) C$_6$-C$_{10}$ aryl that is optionally substituted with from 1-4 R$^b$; or (c) heteroaryl containing from 5-14 ring atoms, wherein from 1-6 of the ring atoms is independently selected from N, NH, N(C$_1$-C$_3$ alkyl), O, and S; and wherein said heteroaryl is optionally substituted with from 1-4 R$^b$; and the other of R$^{10}$ and R$^{11}$ is hydrogen or C$_1$-C$_6$ alkyl.

Z is —OR$^{12}$ or —S(O)$_n$R$^{13}$.

In embodiments, Z is —OR$^{12}$. In certain embodiments, R$^{12}$ is C$_6$-C$_{10}$ aryl that is optionally substituted with from 1-4 R$^b$.

In embodiments, R$^{12}$ is C$_1$-C$_6$ alkyl or C$_1$-C$_6$ haloalkyl (e.g., C$_1$-C$_6$ alkyl), each of which is substituted with from 1-3 R$^d$. In other embodiments, R$^{12}$ is other than C$_1$-C$_6$ alkyl or C$_1$-C$_6$ haloalkyl (e.g., C$_1$-C$_6$ alkyl), each of which is unsubstituted or substituted with from 1-3 R$^d$.

R$^3$ can be selected from halo, hydroxyl, sulfhydryl, C$_1$-C$_6$ alkoxy, C$_1$-C$_6$ thioalkoxy, C$_1$-C$_6$ haloalkoxy, C$_1$-C$_6$ thiohaloalkoxy, C$_1$-C$_6$ alkyl, C$_1$-C$_6$ haloalkyl, cyano, —NH$_2$, —NH(C$_1$-C$_6$ alkyl), N(C$_1$-C$_6$ alkyl)$_2$, —NHC(O)(C$_1$-C$_6$ alkyl), and nitro. E.g., R$^3$ can be halo (e.g., bromo). In embodiments, each of R$^1$, R$^2$, and R$^4$ can be hydrogen.

L$^1$ can be C$_1$-C$_3$ straight chain alkylene, which is optionally substituted with from 1-2 independently selected R$^c$. E.g., L$^1$ can be CH$_2$.

L$^2$ can be C$_1$-C$_3$ straight chain alkylene, which is optionally substituted with from 1-2 independently selected R$^c$. E.g., L$^2$ can be CH$_2$.

Each of L$^1$ and L$^2$ can be, independently, C$_1$-C$_3$ straight chain alkylene, which is optionally substituted with from 1-2 independently selected R$^c$. E.g., each of L$^1$ and L$^2$ can be CH$_2$.

A can be CR$^{A1}$R$^{A2}$, in which each of R$^{A1}$ and R$^{A2}$ is, independently, hydrogen, halo, C$_1$-C$_3$ alkyl, or OR$^9$.

A can be CR$^{A1}$R$^{A2}$, in which each of R$^{A1}$ and R$^{A2}$ is, independently, hydrogen, halo, or C$_1$-C$_3$ alkyl.

A can be CR$^{A1}$R$^{A2}$, in which one of R$^{A1}$ and R$^{A2}$ is halo (e.g., fluoro), and the other of R$^{A1}$ and R$^{A2}$ is, independently, hydrogen, halo, or C$_1$-C$_3$ alkyl (e.g., hydrogen).

A can be CR$^{A1}$R$^{A2}$, in which one of R$^{A1}$ and R$^{A2}$ is halo (e.g., fluoro), and the other of R$^{A1}$ and R$^{A2}$ is hydrogen.

One of R$^{A1}$ and R$^{A2}$ can be halo or OR$^9$, and the other is hydrogen.

One of R$^{A1}$ and R$^{A2}$ can be OR$^9$. In embodiments, the other of R$^{A1}$ and R$^{A2}$ can be as defined anywhere herein; e.g., the other of R$^{A1}$ and R$^{A2}$ can be hydrogen or C$_1$-C$_3$ alkyl. For example, one of R$^{A1}$ and R$^{A2}$ can be OR$^9$, and the other of R$^{A1}$ and R$^{A2}$ is hydrogen. In embodiments, R$^9$ can be hydrogen.

One of R$^{A1}$ and R$^{A2}$ can be halo. In embodiments, the other of R$^{A1}$ and R$^{A2}$ can be as defined anywhere herein; e.g., the other of R$^{A1}$ and R$^{A2}$ can be hydrogen, C$_1$-C$_3$ alkyl, or halo. For example, one of R$^{A1}$ and R$^{A2}$ can be halo (e.g., fluoro), and the other of R$^{A1}$ and R$^{A2}$ is hydrogen.

The carbon attached to R$^{A1}$ and R$^{A2}$ can have the R configuration.

The carbon attached to R$^{A1}$ and R$^{A2}$ can have the S configuration.

Each of L$^1$ and L$^2$ is, independently, C$_1$-C$_3$ alkylene, which is optionally substituted with from 1-2 independently selected R$^c$. E.g., each of L$^1$ and L$^2$ can be CH$_2$.

Z can be —NR$^{10}$R$^{11}$.

One of R$^{10}$ and R$^{11}$ can be C$_6$-C$_{10}$ aryl that is optionally substituted with from 1-4 R$^b$.

One of R$^{10}$ and R$^{11}$ can be C$_6$-C$_{10}$ aryl that is optionally substituted with from 1-4 R$^b$, and the other is hydrogen or C$_1$-C$_6$ alkyl.

One of R$^{10}$ and R$^{11}$ can be C$_6$-C$_{10}$ aryl that is optionally substituted with from 1-4 R$^b$, and the other is hydrogen. For example, one of R$^{10}$ and R$^{11}$ can be unsubstituted phenyl, and the other is hydrogen. As another example, one of R$^{10}$ and R$^{11}$ can be phenyl that is substituted with 1 R$^b$, and the other is hydrogen. In embodiments, R$^b$ can be C$_1$-C$_6$ alkoxy (e.g., OCH$_3$). For example, one of R$^{10}$ and R$^{11}$ can be 3-methoxyphenyl, and the other is hydrogen.

Z can be —OR$^{12}$. In embodiments, R$^{12}$ can be C$_1$-C$_6$ alkyl or C$_1$-C$_6$ haloalkyl, each of which is optionally substituted with from 1-3 R$^c$. In other embodiments, R$^{12}$ can be C$_6$-C$_{10}$ aryl that is optionally substituted with from 1-4 R$^b$. For example, R$^{12}$ can be unsubstituted phenyl.

Z can be —S(O)$_n$R$^{13}$, in which n can be 0, 1, or 2. In other embodiments, R$^{13}$ can be C$_6$-C$_{10}$ aryl that is optionally substituted with from 1-4 R$^b$. For example, R$^{13}$ can be unsubstituted phenyl.

Z can be heterocycloalkenyl containing from 5-6 ring atoms, wherein from 1-3 of the ring atoms is independently selected from N, NH, N(C$_1$-C$_6$ alkyl), NC(O)(C$_1$-C$_6$ alkyl), O, and S; and wherein said heterocycloalkenyl is optionally substituted with from 1-4 independently selected R$^a$.

R and R' together with C$_2$ and C$_3$, respectively, form a fused phenyl ring having formula (II):

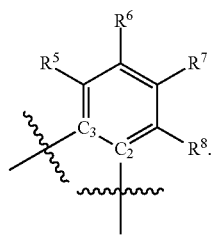

(II)

R$^6$ can be selected from halo, hydroxyl, sulfhydryl, C$_1$-C$_6$ alkoxy, C$_1$-C$_6$ thioalkoxy, C$_1$-C$_6$ haloalkoxy, C$_1$-C$_6$ thiohaloalkoxy, C$_1$-C$_6$ alkyl, C$_1$-C$_6$ haloalkyl, cyano, —NH$_2$, —NH(C$_1$-C$_6$ alkyl), N(C$_1$-C$_6$ alkyl)$_2$, —NHC(O)(C$_1$-C$_6$ alkyl), and nitro. E.g., R$^6$ can be halo (e.g., bromo). In embodiments, each of R$^5$, R$^7$, and R$^8$ can be hydrogen. Any one or more of the R$^1$, R$^2$, R$^3$, R$^4$, L$^1$, L$^2$, A, and Z embodiments described herein can be combined with any one or more of the R$^5$, R$^6$, R$^7$, and R$^8$ embodiments described herein.

Each of L$^1$ and L$^2$ can be CH$_2$; A can be CR$^{A1}$R$^{A2}$, wherein one of R$^{A1}$ and R$^{A2}$ is OR$^9$, and the other is hydrogen; Z is —NR$^{10}$R$^{11}$; and each of R$^{10}$ and R$^{11}$ can be independently selected from: (a) hydrogen; (b) C$_6$-C$_{10}$ aryl that is optionally substituted with from 1-4 R$^b$; (d) C$_1$-C$_6$ alkyl or C$_1$-C$_6$ haloalkyl, each of which is optionally substituted with from 1-3 R$^d$; and (f) C$_2$-C$_6$ alkenyl or C$_2$-C$_6$ alkynyl.

Each of R$^3$ and R$^6$ can be halo (e.g., bromo); and each of R$^1$, R$^2$, R$^4$, R$^5$, R$^7$, and R$^8$ can be hydrogen. R$^9$ can be hydrogen. One of R$^{10}$ and R$^{11}$ can be C$_6$-C$_{10}$ aryl that is optionally substituted with from 1-4 R$^b$, and the other is hydrogen. One of R$^{10}$ and R$^{11}$ can be unsubstituted phenyl, and the other is hydrogen. One of R$^{10}$ and R$^{11}$ can be phenyl that is substituted with 1 R$^b$, and the other is hydrogen. R$^b$ can be C$_1$-C$_6$ alkoxy (e.g., OCH$_3$). One of R$^{10}$ and R$^{11}$ can be 3-methoxyphenyl, and the other is hydrogen.

Each of L$^1$ and L$^2$ is CH$_2$; A is CR$^{A1}$R$^{A2}$, wherein one of R$^{A1}$ and R$^{A2}$ is OR$^9$, and the other is hydrogen; Z is —NR$^{10}$R$^{11}$; and each of R$^{10}$ and R$^{11}$ is independently selected from: (a) hydrogen; (b) C$_6$-C$_{10}$ aryl that is optionally substituted with from 1-4 R$^b$; (d) C$_1$-C$_6$ alkyl or C$_1$-C$_6$ haloalkyl, each of which is optionally substituted with from 1-3 R$^d$; and (f) C$_2$-C$_6$ alkenyl or C$_2$-C$_6$ alkynyl. Embodiment can include one or more of the following features.

Each of R$^3$ and R$^6$ is halo (e.g., bromo); and each of R$^1$, R$^2$, R$^4$, R$^5$, R$^7$, and R$^8$ is hydrogen. R$^9$ can be hydrogen. One of R$^{10}$ and R$^{11}$ can be C$_6$-C$_{10}$ aryl that is optionally substituted with from 1-4 R$^b$, and the other is hydrogen. One of R$^{10}$ and R$^{11}$ can be unsubstituted phenyl, and the other is hydrogen. One of R$^{10}$ and R$^{11}$ can be phenyl that is substituted with 1 R$^b$, and the other is hydrogen. R$^b$ can be C$_1$-C$_6$ alkoxy (e.g., OCH$_3$). One of R$^{10}$ and R$^{11}$ can be 3-methoxyphenyl, and the other is hydrogen.

In embodiments, (A), (B), or (C) applies. In other embodiments, (A) and (B); or (A) and (C); or (B) and (C) applies. In still other embodiments, (A), (B), or (C) apply.

Each of R and R' can be, independently, hydrogen, C$_1$-C$_6$ alkyl, or C$_1$-C$_6$ haloalkyl. Each of R and R' can be, independently, C$_1$-C$_6$ alkyl (e.g., each of R and R' can be CH$_3$). Each of R and R' can be hydrogen.

The compound having formula (I) can include any one or more of or be selected from:

R-1-(3,6-Dibromo-9H-carbazol-9-yl)-3-(3-methoxyphenylamino)-propan-2-ol;
S-1-(3,6-Dibromo-9H-carbazol-9-yl)-3-(3-methoxyphenylamino)-propan-2-ol;
1-(3,6-dibromo-9H-carbazol-9-yl)-3-(2-iminopyridin-1(2H)-yl)propan-2-ol;
1-(3,6-dibromo-9H-carbazol-9-yl)-3-(phenylthio)propan-2-ol;
N-(3-(3,6-dibromo-9H-carbazol-9-yl)-2-hydroxypropyl)-N-(3-methoxyphenyl)acetamide;
5-((3,6-dibromo-9H-carbazol-9-yl)methyl)-3-(3-methoxyphenyl)-oxazolidin-2-one;
N-(3-(3,6-dibromo-9H-carbazol-9-yl)-2-fluoropropyl)-3-methoxyaniline;
1-(3,6-dibromo-9H-carbazol-9-yl)-3-(3-methoxyphenylamino)-propan-2-one;
N-(3-(3,6-dibromo-9H-carbazol-9-yl)-2-methoxypropyl)-3-methoxyaniline;
1-(3,6-Dimethyl-9H-carbazol-9-yl)-3-(3-methoxyphenylamino)propan-2-ol;
1-(3-Bromo-6-methyl-9H-carbazol-9-yl)-3-(3-methoxyphenylamino)-propan-2-ol;
1-(3,6-Dichloro-9H-carbazol-9-yl)-3-(3-methoxyphenylamino)-propan-2-ol;
1-(5-bromo-2,3-dimethyl-1H-indol-1-yl)-3-(phenylamino) propan-2-ol;
1-(3,6-Dibromo-9H-pyrido[3,4-b]indol-9-yl)-3-(phenylamino)propan-2-ol;
1-(3-Azidophenylamino)-3-(3,6-dibromo-9H-carbazol-9-yl)propan-2-ol;
1,3-Bis(3,6-dibromo-9H-carbazol-9-yl)propan-2-ol;
1-(9H-Carbazol-9-yl)-3-(3,6-dibromo-9H-carbazol-9-yl) propan-2-ol;
3-(3,6-Dibromo-9H-carbazol-9-yl)-2-hydroxy-N-(3-methoxyphenyl)-propanamide;
Ethyl 5-(2-Hydroxy-3-(3-methoxyphenylamino)propyl)-8-methyl-3,4-dihydro-1H-pyrido[4,3-b]indole-2(5H)-carboxylate;
4-(3,6-dibromo-9H-carbazol-9-yl)-1-(phenylamino)butan-2-ol;
N-(3-(3,6-dibromo-9H-carbazol-9-yl)propyl)aniline;
1-(3,6-dibromo-9H-carbazol-9-yl)-4-(phenylamino)butan-2-ol;
1-(3,6-dibromo-9H-carbazol-9-yl)-3-(pyridin-2-ylamino) propan-2-ol;
1-(3,6-dibromo-9H-carbazol-9-yl)-3-(3-methoxyphenyl) (methyl)-amino)propan-2-ol;
3-(3,6-dibromo-9H-carbazol-9-yl)-1-(3-methoxyphenylamino)-1-(methylthio)propan-2-one;
3-amino-1-(3-(3,6-dibromo-9H-carbazol-9-yl)-2-hydroxypropyl)pyridinium;
1-(3,6-dibromo-9H-carbazol-9-yl)-3-(pyrimidin-2-ylamino) propan-2-ol;
N-(3-(3,6-dibromo-9H-carbazol-9-yl)-2-fluoropropyl)-3-methoxy-N-methylaniline;
1-(3,6-dibromo-9H-carbazol-9-yl)-3-methoxypropan-2-ol;
1-(3,6-dibromo-9H-carbazol-9-yl)-4-phenylbutan-2-ol;
1-(3,6-dibromo-9H-carbazol-9-yl)-3-(1H-indol-1-yl)propan-2-ol;
3-(1-(3-(3,6-dibromo-9H-carbazol-9-yl)-2-hydroxypropyl)-1H-1,2,3-triazol-4-yl)propan-1-ol;
1-(3,6-dibromo-9H-carbazol-9-yl)-3-(3-ethoxyphenylamino)propan-2-ol;
1-(3,6-dibromo-9H-carbazol-9-yl)-3-(3,5-dimethyl-1H-pyrazol-1-yl)propan-2-ol;
1-(3,6-dibromo-9H-carbazol-9-yl)-3-(phenylsulfinyl)propan-2-ol;
1-(3,6-dibromo-9H-carbazol-9-yl)-3-(phenylsulfonyl)propan-2-ol;
1-(3-bromo-9H-carbazol-9-yl)-3-(3-methoxyphenylamino) propan-2-ol;
N-(5-(3-(3-(3,6-dibromo-9H-carbazol-9-yl)-2-hydroxypropylamino)phenoxy)pentyl)-2-(7-(dimethylamino)-2-oxo-2H-chromen-4-yl)acetamide;
1-(3,6-dibromo-9H-carbazol-9-yl)-3-phenoxypropan-2-ol;
N-(2-(3-(3,6-dibromo-9H-carbazol-9-yl)-2-hydroxypropoxy)ethyl)-acetamide;
1-(3,6-dibromo-9H-carbazol-9-yl)-3-(pyridin-3-ylamino) propan-2-ol;
1-(3,6-dibromo-9H-carbazol-9-yl)-3-(pyridin-4-ylamino) propan-2-ol;
1-(2,8-dimethyl-3,4-dihydro-1H-pyrido[4,3-b]indol-5(2H)-yl)-3-(phenylamino)propan-2-ol;
N-(3-(3,6-dibromo-9H-carbazol-9-yl)-2,2-difluoropropyl)-3-methoxyaniline;
1-(3,6-dibromo-9H-carbazol-9-yl)-3-phenoxypropan-2-ol;
1-(3,6-dibromo-9H-carbazol-9-yl)-3-(phenylamino)propan-2-ol;
1-(3,6-dibromo-9H-carbazol-9-yl)-3-(o-tolylamino)propan-2-ol;
1-(3,6-dibromo-9H-carbazol-9-yl)-3-(m-tolylamino)propan-2-ol;
1-(3,6-dibromo-9H-carbazol-9-yl)-3-(2-methoxyphenylamino)propan-2-ol;
1-(3,6-dibromo-9H-carbazol-9-yl)-3-(naphthalen-1-ylamino)propan-2-ol;
1-(4-bromophenylamino)-3-(3,6-dichloro-9H-carbazol-9-yl)propan-2-ol;
1-(4-bromophenylamino)-3-(3,6-dibromo-9H-carbazol-9-yl)propan-2-ol;
1-(3,6-dibromo-9H-carbazol-9-yl)-3-(4-ethoxyphenylamino)propan-2-ol;
1-(4-chlorophenylamino)-3-(3,6-dibromo-9H-carbazol-9-yl)propan-2-ol;
1-(3,6-dibromo-9H-carbazol-9-yl)-3-(phenethylamino)propan-2-ol;
1-(3,6-dibromo-9H-carbazol-9-yl)-3-(2-hydroxyethylamino)propan-2-ol;
1-(3,6-dibromo-9H-carbazol-9-yl)-3-(2,4-dimethoxyphenylamino)propan-2-ol;
1-(3,6-dibromo-9H-carbazol-9-yl)-3-(2,3-dimethylphenylamino)propan-2-ol;
1-(2-chlorophenylamino)-3-(3,6-dibromo-9H-carbazol-9-yl)propan-2-ol;

1-(tert-butylamino)-3-(3,6-dibromo-9H-carbazol-9-yl)propan-2-ol;
1-(3,6-dibromo-9H-carbazol-9-yl)-3-(isopropylamino)propan-2-ol;
1-(3,6-dibromo-9H-carbazol-9-yl)-3-(4-methoxyphenylamino)propan-2-ol;
1-(3,6-dibromo-9H-carbazol-9-yl)-3-(3-methoxyphenylamino)propan-2-ol;
1-(3,6-dibromo-9H-carbazol-9-yl)-3-(m-tolylamino)propan-2-ol;
1-(3,6-dibromo-9H-carbazol-9-yl)-3-(3,5-dimethylphenylamino)propan-2-ol;
1-(3,6-dibromo-9H-carbazol-9-yl)-3-(3,4-dimethylphenylamino)propan-2-ol;
1-(3,6-dibromo-9H-carbazol-9-yl)-3-(3,4-dimethylphenylamino)propan-2-ol;
1-(3,6-dibromo-9H-carbazol-9-yl)-3-(2,5-dimethylphenylamino)propan-2-ol;
1-(4-bromophenylamino)-3-(2,3-dimethyl-1H-indol-1-yl)propan-2-ol;
1-(2,3-dimethyl-1H-indol-1-yl)-3-(4-methoxyphenylamino)propan-2-ol;
1-(2,3-dimethyl-1H-indol-1-yl)-3-(4-ethoxyphenylamino)propan-2-ol;
1-(2,3-dimethyl-1H-indol-1-yl)-3-(p-tolylamino)propan-2-ol;
1-(2,3-dimethyl-1H-indol-1-yl)-3-(phenylamino)propan-2-ol oxalate;
1-(1H-indol-1-yl)-3-(4-methoxyphenylamino)propan-2-ol hydrochloride;
1-(1H-indol-1-yl)-3-(phenylamino)propan-2-ol oxalate;
1-(3,4-dihydro-1H-carbazol-9(2H)-yl)-3-(m-tolylamino)propan-2-ol;
1-(9H-carbazol-9-yl)-3-(phenylamino)propan-2-ol;
1-(3,6-dichloro-9H-carbazol-9-yl)-3-(phenylamino)propan-2-ol;
1-(9H-carbazol-9-yl)-3-(p-tolylamino)propan-2-ol;
1-(3,6-dichloro-9H-carbazol-9-yl)-3-(p-tolylamino)propan-2-ol;
1-(3,6-dibromo-9H-carbazol-9-yl)-3-(p-tolylamino)propan-2-ol;
N-(4-(3-(9H-carbazol-9-yl)-2-hydroxypropoxy)phenyl)acetamide;
1-(9H-carbazol-9-yl)-3-phenoxypropan-2-ol;
1-(9H-carbazol-9-yl)-3-(4-methoxyphenylamino)propan-2-ol;
1-(benzylamino)-3-(9H-carbazol-9-yl)propan-2-ol;
methyl 4-(3-(9H-carbazol-9-yl)-2-hydroxypropoxy)benzoate;
1-(9H-carbazol-9-yl)-3-(4-methoxyphenoxy)propan-2-ol;
1-amino-3-(3,6-dibromo-9H-carbazol-9-yl)propan-2-ol;
(S)-1-(3,6-dibromo-9H-carbazol-9-yl)-3-phenoxypropan-2-ol;
(R)-1-(3,6-dibromo-9H-carbazol-9-yl)-3-phenoxypropan-2-ol;
3,6-dibromo-9-(2-fluoro-3-phenoxypropyl)-9H-carbazole;
1-(3,6-dibromo-9H-carbazol-9-yl)-3-(3-methoxyphenylamino)-2-methylpropan-2-ol;
1-(2,8-dimethyl-3,4-dihydro-1H-pyrido[4,3-b]indol-5(2H)-yl)-3-(3-methoxyphenylamino)propan-2-ol;
1-(4-azidophenylamino)-3-(3,6-dibromo-9H-carbazol-9-yl)propan-2-ol;
1-(3-azido-6-bromo-9H-carbazol-9-yl)-3-(3-methoxyphenylamino)propan-2-ol;
1-(3,6-dibromo-9H-carbazol-9-yl)-3-(4-methoxyphenoxy)propan-2-ol;
1-(3,6-dichloro-9H-carbazol-9-yl)-3-(phenylsulfonyl)propan-2-ol;
3,6-dibromo-9-(2-fluoro-3-(phenylsulfonyl)propyl)-9H-carbazole;
S)-1-(3,6-dibromo-9H-carbazol-9-yl)-3-(phenylsulfonyl)propan-2-ol;
(R)-1-(3,6-dibromo-9H-carbazol-9-yl)-3-(phenylsulfonyl)propan-2-ol;
1-(3,6-dicyclopropyl-9H-carbazol-9-yl)-3-(phenylamino)propan-2-ol;
1-(3,6-diiodo-9H-carbazol-9-yl)-3-(phenylamino)propan-2-ol;
1-(3,6-diethynyl-9H-carbazol-9-yl)-3-(3-methoxyphenylamino)propan-2-ol;
9-(2-hydroxy-3-(3-methoxyphenylamino)propyl)-9H-carbazole-3,6-dicarbonitrile;
N-(3-(3,6-dibromo-9H-carbazol-9-yl)-2-fluoropropyl)aniline;
3,6-dibromo-9-(2,2-difluoro-3-phenoxypropyl)-9H-carbazole;
N-(3-(3,6-dibromo-9H-carbazol-9-yl)-2-fluoropropyl)-4-methoxyaniline;
N-(2-bromo-3-(3,6-dibromo-9H-carbazol-9-yl)propyl)-N-(4-methoxyphenyl)-4-nitrobenzenesulfonamide;
Ethyl 2-(4-(3-(3,6-dibromo-9H-carbazol-9-yl)-2-fluoropropylamino)phenoxy)acetate; and
N-(3-(3,6-dibromo-9H-carbazol-9-yl)-2-fluoropropyl)-4-(2-(2-methoxyethoxy)ethoxy)aniline;
or a salt (e.g., a pharmaceutically acceptable salt) thereof (or any one or a subset thereof, e.g., as delineated in the claims).

In certain embodiments, the compound having formula (I) can be 1-(3,6-dibromo-9H-carbazol-9-yl)-3-(phenylamino)propan-2-ol; or a salt (e.g., a pharmaceutically acceptable salt) thereof.

In certain embodiments, the compound having formula (I) can be R-1-(3,6-Dibromo-9H-carbazol-9-yl)-3-(3-methoxyphenylamino)-propan-2-ol; or a salt (e.g., a pharmaceutically acceptable salt) thereof. In embodiments, R-1-(3,6-Dibromo-9H-carbazol-9-yl)-3-(3-methoxyphenylamino)-propan-2-ol or a salt (e.g., a pharmaceutically acceptable salt) thereof can be substantially free of (e.g., contains less than about 5% of, less than about 2% of, less than about 1%, less than about 0.5% of) S-1-(3,6-Dibromo-9H-carbazol-9-yl)-3-(3-methoxyphenylamino)-propan-2-ol or a salt (e.g., a pharmaceutically acceptable salt) thereof.

In certain embodiments, the compound having formula (I) can be S-1-(3,6-Dibromo-9H-carbazol-9-yl)-3-(3-methoxyphenylamino)-propan-2-ol; or a salt (e.g., a pharmaceutically acceptable salt) thereof. In embodiments, S-1-(3,6-Dibromo-9H-carbazol-9-yl)-3-(3-methoxyphenylamino)-propan-2-ol or a salt (e.g., a pharmaceutically acceptable salt) thereof can be substantially free of (e.g., contains less than about 5% of, less than about 2% of, less than about 1%, less than about 0.5% of) R-1-(3,6-Dibromo-9H-carbazol-9-yl)-3-(3-methoxyphenylamino)-propan-2-ol or a salt (e.g., a pharmaceutically acceptable salt) thereof.

In certain embodiments, the compound having formula (I) can be the (+) (dextrorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof. See, e.g., Example 1a and 1b. In embodiments, the (+) (dextrorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof can be substantially free of (e.g., contains less than about 5% of, less than about 2% of, less than about 1%, less than about 0.5% of) the (−) (levorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof.

In certain embodiments, the compound having formula (I) can be the (−) (levorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof. See, e.g., Example 1a and 1b. In embodiments, the (−) (levorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof can be substantially free of (e.g., contains less than about 5% of, less than about 2% of, less than about 1%, less than about 0.5% of) the (+) (dextrorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof.

The methods can further include detecting a resultant neurotrophism (e.g., neurogenesis; and/or determining that the patient has aberrant neurotrophism, particularly aberrant neurogenesis, particularly aberrant hippocampal neurogenesis, or a disease or disorder associated therewith, particularly by detecting and/or diagnosing the same.

The methods can further include detecting a resultant neurotrophism.

The methods can further include detecting determining that the subject has aberrant neurogenesis or death of neurons or a disease or disorder associated therewith, by detecting the same in said subject.

The methods can further include detecting a resultant hippocampal neurogenesis.

The disease, disorder, or condition can be a neuropsychiatric and neurodegenerative disease, including (but not limited to) schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs, such as alcohol, opiates, methamphetamine, phencyclidine, and cocaine.

In some embodiments, the compounds having formula (I) or a salt (e.g., a pharmaceutically acceptable salt) thereof provide at least about 27 ($\times 10^{-06}$) BrdU+ cells/mm$^3$ dentate gyrus when evaluated in the assay described in conjunction with Table 1 (i.e., evaluated for pro-neurogenic efficacy/neuroprotection in our standard in vivo assay at 10 μM concentration in four 12 week old adult male C57/Bl6 mice.

In some embodiments, the compounds having formula (I) or a salt (e.g., a pharmaceutically acceptable salt) thereof provide at least about 19 ($\times 10^{-6}$) BrdU+ cells/mm$^3$ dentate gyrus when evaluated in the assay described in conjunction with Table 1.

In some embodiments, the compounds having formula (I) or a salt (e.g., a pharmaceutically acceptable salt) thereof provide from about 18 to about 30 (e.g., 18-27, 19-26, 20-25, 27-30, 27-29) ($\times 10^{-06}$) BrdU+ cells/mm$^3$ dentate gyrus when evaluated in the assay described in conjunction with Table 1.

In some embodiments, the compounds having formula (I) or a salt (e.g., a pharmaceutically acceptable salt) thereof provide from about 18 to about 26 (e.g., 19-26, 20-25) ($\times 10^{-06}$) BrdU+ cells/mm$^3$ dentate gyrus when evaluated in the assay described in conjunction with Table 1.

In some embodiments, the compounds having formula (I) or a salt (e.g., a pharmaceutically acceptable salt) thereof provide from about 27 to about 30 (e.g., 27-29) ($\times 10^{-06}$) BrdU+ cells/mm$^3$ dentate gyrus when evaluated in the assay described in conjunction with Table 1.

In embodiments, a composition (e.g., a pharmaceutical composition) can include an amount effective to achieve the levels described above.

In embodiments, any compound, composition, or method described herein can also include any one or more of the other features delineated in the detailed description and/or in the claims.

DEFINITIONS

The term "mammal" includes organisms, which include mice, rats, cows, sheep, pigs, rabbits, goats, horses, monkeys, dogs, cats, and humans.

"An effective amount" refers to an amount of a compound that confers a therapeutic effect (e.g., treats, e.g., controls, relieves, ameliorates, alleviates, or slows the progression of or prevents, e.g., delays the onset of or reduces the risk of developing, a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffixes "yl," "diyl," "triyl," "tetrayl," etc; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

The following definitions are used, unless otherwise described. Specific and general values listed below for radicals, substituents, and ranges, are for illustration only; they do not exclude other defined values or other values within defined ranges for the radicals and substituents. Unless otherwise indicated, alkyl, alkoxy, alkenyl, and the like denote both straight and branched groups.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more substitutents. Examples of alkyl groups include without limitation methyl, ethyl, n-propyl, isopropyl, and tert-butyl.

As used herein, the term "straight chain $C_{n-m}$ alkylene," employed alone or in combination with other terms, refers to a non-branched divalent alkyl linking group having n to m carbon atoms. Any atom can be optionally substituted, e.g., by one or more substitutents. Examples include methylene (i.e., —$CH_2$—).

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy (—OCH$_3$), ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S(alkyl). Finally, the terms "haloalkoxy" and "thioalkoxy" refer to —O(haloalkyl) and —S(haloalkyl), respectively. The term "sulfhydryl" refers to —SH. As used herein, the term "hydroxyl," employed alone or in combination with other terms, refers to a group of formula —OH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein from 1-2 of the ring atoms is independently selected from N, NH, N(C$_1$-C$_6$ alkyl), NC(O)(C$_1$-C$_6$ alkyl), O, and S; and wherein said heterocyclic ring is optionally substituted with from 1-3 independently selected R$^{a}$" would include (but not be limited to) tetrahydrofuryl, tetrahydropyranyl, piperidyl (piperidino), piperazinyl, morpholinyl (morpholino), pyrrolinyl, and pyrrolidinyl.

The term "heterocycloalkenyl" refers to partially unsaturated monocyclic, bicyclic, tricyclic, or other polycyclic hydrocarbon groups having one or more (e.g., 1-4) heteroatom ring atoms independently selected from O, N (it is understood that one or two additional groups may be present to complete the nitrogen valence and/or form a salt), or S. A ring carbon (e.g., saturated or unsaturated) or heteroatom can be the point of attachment of the heterocycloalkenyl substituent. Any atom can be optionally substituted, e.g., by one or more substituents. Heterocycloalkenyl groups can include, e.g., dihydropyridyl, tetrahydropyridyl, dihydropyranyl, 4,5-dihydrooxazolyl, 4,5-dihydro-1H-imidazolyl, 1,2,5,6-tetrahydropyrimidinyl, and 5,6-dihydro-2H-[1,3]oxazinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclohexenyl, cyclohexadienyl, or norbornenyl.

As used herein, the term "cycloalkylene" refers to a divalent monocyclic cycloalkyl group having the indicated number of ring atoms.

As used herein, the term "heterocycloalkylene" refers to a divalent monocyclic heterocyclyl group having the indicated number of ring atoms.

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The terms "arylcycloalkyl" and "arylheterocyclyl" refer to bicyclic, tricyclic, or other polycyclic ring systems that include an aryl ring fused to a cycloalkyl and heterocyclyl, respectively. Similarly, the terms "heteroarylheterocyclyl," and "heteroarylcycloalkyl" refer to bicyclic, tricyclic, or other polycyclic ring systems that include a heteroaryl ring fused to a heterocyclyl and cycloalkyl, respectively. Any atom can be substituted, e.g., by one or more substituents. For example, arylcycloalkyl can include indanyl; arylheterocyclyl can include 2,3-dihydrobenzofuryl, 1,2,3,4-tetrahydroisoquinolyl, and 2,2-dimethylchromanyl.

The descriptors "C=O" or "C(O)" refers to a carbon atom that is doubly bonded to an oxygen atom.

The term "oxo" refers to double bonded oxygen when a substituent on carbon. When oxo is a substituent on nitrogen or sulfur, it is understood that the resultant groups has the structures N→O⁻ and S(O) and $SO_2$, respectively.

As used herein, the term "cyano," employed alone or in combination with other terms, refers to a group of formula —CN, wherein the carbon and nitrogen atoms are bound together by a triple bond.

In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group. In one aspect, the substituent(s) on a group are independently any one single, or any combination of two or more of the permissible atoms or groups of atoms delineated for that substituent. In another aspect, a substituent may itself be substituted with any one of the above substituents.

Further, as used herein, the phrase "optionally substituted" means unsubstituted (e.g., substituted with a H) or substituted. As used herein, the term "substituted" means that a hydrogen atom is removed and replaced by a substitutent. It is understood that substitution at a given atom is limited by valency.

Descriptors such as "$C_6$-$C_{10}$ aryl that is optionally substituted with from 1-4 independently selected $R^b$" (and the like) is intended to include both an unsubstituted $C_6$-$C_{10}$ aryl group and a $C_6$-$C_{10}$ aryl group that is substituted with from 1-4 independently selected $R^b$. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

In some embodiments, $R^b$ can be as defined in any one, two, three, or all of (aa) through (dd). For example, $R^b$ can be as defined in (aa) and (bb) or combinations thereof.

The phrase "Cy is a saturated, partially unsaturated or aromatic carbocyclic or heterocyclic ring system" in the definition of $R^e$ is understood to include each of the rings systems defined above (e.g., Cy can be coumarinyl or the ring component of biotin optionally substituted as defined anywhere herein).

The details of one or more embodiments of the invention are set forth in the description below. Other features and advantages of the invention will be apparent from the description and from the claims.

DETAILED DESCRIPTION

Figure 1:
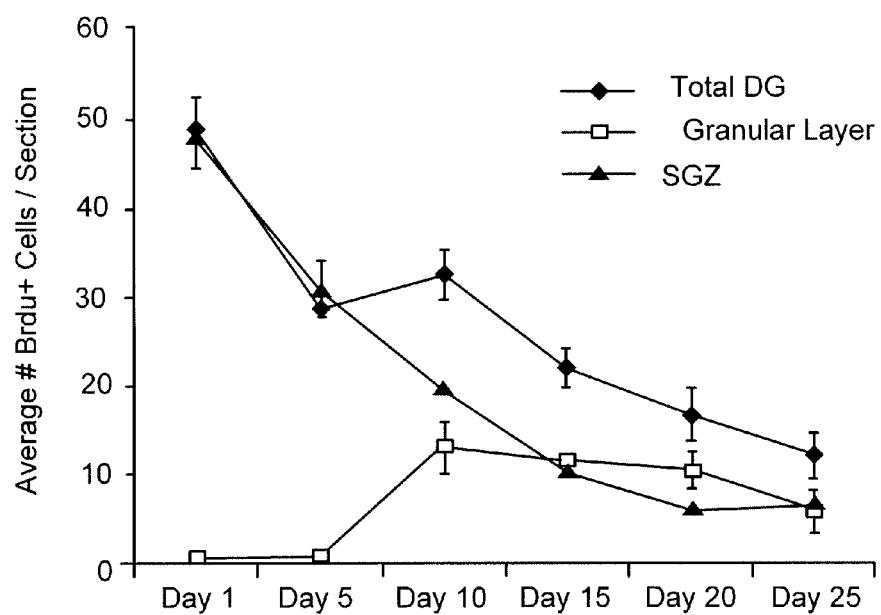
FIG. 1: Pulse-chase analysis of BrdU-labeling identified magnitude and timing of cell death following birth of new neurons in the dentate gyrus. 12 week old wild type male C57/B6 mice were individually housed without access to running wheels and injected on day 0 with BrdU (50 mg/kg, i.p.). Neural precursor cell proliferation in the dentate gyrus (DG) subgranular zone (SGZ) and granular layer (GL) was subsequently monitored through immunohistochemistry for BrdU on days 1, 5, 10, 15, 20, and 25 days post-injection. Four mice were evaluated at each time point, and 25-30 adjacent coronal sections through the hippocampus (progressing posteriorly from the point where the suprapyramidal and infrapyramidal blades are joined at the crest region and the dentate gyrus is oriented horizontally beneath the corpus callosum) from each mouse were examined. On days 1 and 5, almost 100% of BrdU-positive cells within the DG were localized in the SGZ. The total number of cells decreased approximately 40% between days 1 and 5, in accordance with the appearance of apoptotic cell bodies in the SGZ. By day 10, some BrdU positive cells had migrated into the GL, with no significant change in total number of BrdU-positive cells in the DG. By day 15, BrdU-positive cells in the SGZ declined as the number of BrdU-positive cells in the GL stayed constant, suggesting that some of the cells migrating out of the SGZ and into the GL between days 10 and 15 underwent apoptosis. This trend continued through days 20-25. These results indicated that daily injection of BrdU over a one week period of continuous molecule infusion, a time period during which 40% of newborn cells in the SGZ normally die, would allow detection of compounds that enhance either proliferation or survival of newborn cells in the dentate gyrus.

This invention relates generally to stimulating neurogenesis (e.g., post-natal neurogenesis, e.g., post-natal hippocampal neurogenesis) and/or promoting the survival of existing neurons by reducing neuronal cell death.

Compounds

In one aspect, this invention features compounds having general formula (I):

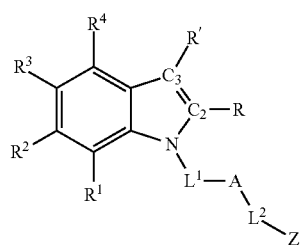

Here and throughout this specification, $R^1$, $R^2$, $R^3$, $R^4$, R, R', $L^1$, $L^2$, A, and Z can be as defined anywhere herein.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Thus, for ease of exposition, it is also understood that where in this specification, a variable (e.g., $R^1$) is defined by "as defined anywhere herein" (or the like), the definitions for that particular variable include the first occurring and broadest generic definition as well as any sub-generic and specific definitions delineated anywhere in this specification.

Variables $R^1$, $R^2$, $R^3$, $R^4$

In some embodiments, one or two of $R^1$, $R^2$, $R^3$, and $R^4$ (e.g., one of, e.g., $R^3$) is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —NH($C_1$-$C_6$ alkyl), N($C_1$-$C_6$ alkyl)$_2$, —NHC(O)($C_1$-$C_6$ alkyl), and nitro; and the others are hydrogen.

In certain embodiments, one or two of $R^1$, $R^2$, $R^3$, and $R^4$ (e.g., one of, e.g., $R^3$) is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and the others are hydrogen.

In certain embodiments, one or two of $R^1$, $R^2$, $R^3$, and $R^4$ (e.g., one of, e.g., $R^3$) is selected from halo, $C_1$-$C_6$ alkyl, and $C_1$-$C_6$ haloalkyl; and the others are hydrogen.

In certain embodiments, one or two of $R^1$, $R^2$, $R^3$, and $R^4$ (e.g., one of, e.g., $R^3$) is selected from halo and $C_1$-$C_6$ alkyl; and the others are hydrogen.

In certain embodiments, one or two of $R^1$, $R^2$, $R^3$, and $R^4$ (e.g., one of, e.g., $R^3$) is halo (e.g., bromo or chloro) and $C_1$-$C_6$ alkyl; and the others are hydrogen.

In certain embodiments, one or two of $R^1$, $R^2$, $R^3$, and $R^4$ (e.g., one of, e.g., $R^3$) is bromo; and the others are hydrogen.

In some embodiments, $R^3$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —NH$_2$, —NH($C_1$-$C_6$ alkyl), N($C_1$-$C_6$ alkyl)$_2$, —NHC(O)($C_1$-$C_6$ alkyl), and nitro; and each of $R^1$, $R^2$, and $R^4$ can be as defined anywhere herein.

In certain embodiments, $R^3$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —NH$_2$, —NH($C_1$-$C_6$ alkyl), N($C_1$-$C_6$ alkyl)$_2$, —NHC(O)($C_1$-$C_6$ alkyl), and nitro; and each of $R^1$, $R^2$, and $R^4$ is hydrogen.

In some embodiments, $R^3$ is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and each of $R^1$, $R^2$, and $R^4$ can be as defined anywhere herein.

In certain embodiments, $R^3$ is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and each of $R^1$, $R^2$, and $R^4$ is hydrogen.

In some embodiments, $R^3$ is selected from halo, $C_1$-$C_6$ alkyl, and $C_1$-$C_6$ haloalkyl; and each of $R^1$, $R^2$, and $R^4$ can be as defined anywhere herein.

In certain embodiments, $R^3$ is selected from halo, $C_1$-$C_6$ alkyl, and $C_1$-$C_6$ haloalkyl; and each of $R^1$, $R^2$, and $R^4$ is hydrogen.

In some embodiments, $R^3$ is selected from halo and $C_1$-$C_6$ alkyl; and each of $R^1$, $R^2$, and $R^4$ can be as defined anywhere herein.

In certain embodiments, $R^3$ is selected from halo and $C_1$-$C_6$ alkyl; and each of $R^1$, $R^2$, and $R^4$ is hydrogen.

In some embodiments, $R^3$ is halo (e.g., bromo or chloro); and each of $R^1$, $R^2$, and $R^4$ can be as defined anywhere herein.

In certain embodiments, $R^3$ is halo (e.g., bromo or chloro); and each of $R^1$, $R^2$, and $R^4$ is hydrogen.

In some embodiments, $R^3$ is bromo; and each of $R^1$, $R^2$, and $R^4$ can be as defined anywhere herein.

In certain embodiments, $R^3$ is bromo; and each of $R^1$, $R^2$, and $R^4$ is hydrogen.

In some embodiments, each of $R^1$, $R^2$, $R^3$, and $R^4$ is independently selected from hydrogen, halo, and $C_1$-$C_6$ alkyl.

In certain embodiments, each of $R^1$, $R^2$, $R^3$, and $R^4$ is independently selected from hydrogen and halo (e.g., bromo or chloro).

In some embodiments, each of $R^1$, $R^2$, $R^3$, and $R^4$ is hydrogen.

In some embodiments, when any one or more of $R^1$, $R^2$, $R^3$, and $R^4$ can be a substituent other than hydrogen, said substituent, or each of said substituents, is other than $C_1$-$C_6$ alkyl (e.g., other than $C_1$-$C_3$ alkyl, e.g., other than $CH_3$).

Variable $L^1$

In some embodiments, $L^1$ is $C_1$-$C_3$ (e.g., $C_1$-$C_2$) straight chain alkylene, which is optionally substituted with from 1-2 independently selected $R^c$.

In certain embodiments, $L^1$ is methylene (i.e., —$CH_2$—). In other embodiments, $L^1$ is methylene that is substituted with 1 or 2 (e.g., 1) independently selected $R^c$. In embodiments, $R^c$ is $C_1$-$C_6$ alkyl (e.g., $C_1$-$C_3$ alkyl, e.g., $CH_3$).

In certain embodiments, $L^1$ is ethylene (i.e., —$CH_2CH_2$—). In other embodiments, $L^1$ is ethylene that is substituted with 1 or 2 (e.g., 1) independently selected $R^c$. In embodiments, $R^c$ is $C_1$-$C_6$ alkyl (e.g., $C_1$-$C_3$ alkyl, e.g., $CH_3$).

Variable $L^2$

In some embodiments, $L^2$ is $C_1$-$C_3$ (e.g., $C_1$-$C_2$) straight chain alkylene, which is optionally substituted with from 1-2 independently selected $R^c$.

In certain embodiments, $L^2$ is methylene (i.e., —$CH_2$—). In other embodiments, $L^1$ is methylene that is substituted with 1 or 2 (e.g., 1) independently selected $R^c$. In embodiments, $R^c$ is $C_1$-$C_6$ alkyl (e.g., $C_1$-$C_3$ alkyl, e.g., $CH_3$). In embodiments, $R^c$ is $C_1$-$C_6$ alkoxy, $C_1$-$C_6$ thioalkoxy, $C_1$-$C_6$ haloalkoxy, or $C_1$-$C_6$ thiohaloalkoxy. For example, $R^c$ can be $C_1$-$C_6$ (e.g., $C_1$-$C_3$) thioalkoxy, such as —$SCH_3$.

In certain embodiments, $L^2$ is ethylene (i.e., —$CH_2CH_2$—). In other embodiments, $L^2$ is ethylene that is substituted with 1 or 2 (e.g., 1) independently selected $R^c$. For example, the ethylene carbon more proximal to Z in formula (I) can be substituted as described in the preceding paragraph.

In certain embodiments, $L^2$ is a bond that directly connects A in formula (I) to Z in formula (I).

Non-Limiting Combinations of Variables $L^1$ and $L^2$

In some embodiments, each of $L^1$ and $L^2$ is, independently, $C_1$-$C_3$ alkylene, which is optionally substituted with from 1-2 independently selected $R^c$.

In certain embodiments, each of $L^1$ and $L^2$ is $CH_2$.

In certain embodiments, one of $L^1$ and $L^2$ is $CH_2$ (e.g., $L^1$), and the other (e.g., $L^2$) is methylene that is substituted with 1 or 2 (e.g., 1) independently selected $R^c$, in which $R^c$ can be as defined anywhere herein.

In certain embodiments, each of $L^1$ and $L^2$ is methylene that is substituted with 1 or 2 (e.g., 1) independently selected $R^c$, in which $R^c$ can be as defined anywhere herein.

In some embodiments, $L^1$ is $C_1$-$C_3$ (e.g., $C_1$-$C_2$) straight chain alkylene, which is optionally substituted with from 1-2 independently selected $R^c$, and $L^2$ is a bond that directly connects A in formula (I) to Z in formula (I). In embodiments, $L^1$ can be, for example, methylene (i.e., —$CH_2$—) or methylene that is substituted with 1 or 2 (e.g., 1) independently selected $R^c$ (e.g., $C_1$-$C_6$ alkyl, e.g., $C_1$-$C_3$ alkyl, e.g., $CH_3$).

Variable A

[I] In some embodiments, A is:
(i) $CR^{41}R^{42}$, wherein each of $R^{41}$ and $R^{42}$ is independently selected from hydrogen, halo, $C_1$-$C_3$ alkyl, or $OR^9$; or
(ii) C=O; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$.

In some embodiments, A is $CR^{41}R^{42}$, in which each of $R^{41}$ and $R^{42}$ is, independently, hydrogen, halo, $C_1$-$C_3$ alkyl, or $OR^9$ (e.g., hydrogen, halo, or $OR^9$).

In certain embodiments, A can be $CR^{41}R^{42}$, in which each of $R^{41}$ and $R^{42}$ is, independently, hydrogen, halo, or $C_1$-$C_3$ alkyl.

In certain embodiments, A can be $CR^{41}R^{42}$, in which one of $R^{41}$ and $R^{42}$ is halo (e.g., fluoro), and the other of $R^{41}$ and $R^{42}$ is, independently, hydrogen, halo, or $C_1$-$C_3$ alkyl (e.g., hydrogen).

In certain embodiments, one of $R^{41}$ and $R^{42}$ is hydrogen. In embodiments, one of $R^{41}$ and $R^{42}$ is halo or $OR^9$, and the other is hydrogen.

In certain embodiments, one of $R^{41}$ and $R^{42}$ can be $OR^9$. In embodiments, the other of $R^{41}$ and $R^{42}$ can be as defined anywhere herein; e.g., the other of $R^{41}$ and $R^{42}$ can be hydrogen or $C_1$-$C_3$ alkyl. For example, one of $R^{41}$ and $R^{42}$ can be $OR^9$, and the other of $R^{41}$ and $R^{42}$ is hydrogen. In embodiments, $R^9$ can be hydrogen or $R^9$ can be $C_1$-$C_3$ alkyl (e.g., $CH_3$).

In certain embodiments, one of $R^{41}$ and $R^{42}$ can be halo. In embodiments, the other of $R^{41}$ and $R^{42}$ can be as defined anywhere herein; e.g., the other of $R^{41}$ and $R^{42}$ can be hydrogen, $C_1$-$C_3$ alkyl, or halo. For example, one of $R^{41}$ and $R^{42}$ can be halo (e.g., fluoro), and the other of $R^{41}$ and $R^{42}$ is hydrogen.

In embodiments, one of $R^{41}$ and $R^{42}$ is halo or $OR^9$, and the other is hydrogen.

For example, one of $R^{41}$ and $R^{42}$ can be $OR^9$, and the other is hydrogen. In embodiments, $R^9$ can be hydrogen. $R^9$ can be $C_1$-$C_3$ alkyl (e.g., $CH_3$).

As another example, one of $R^{41}$ and $R^{42}$ can be halo (e.g., fluoro), and the other is hydrogen.

In other embodiments, each of $R^{41}$ and $R^{42}$ is a substituent other than hydrogen.

For example, each of $R^{41}$ and $R^{42}$ can be halo (e.g., fluoro).

As another example, one of $R^{41}$ and $R^{42}$ can be $OR^9$ (e.g., in which $R^9$ is hydrogen), and the other is $C_1$-$C_3$ alkyl (e.g., $CH_3$).

As a further example, each of $R^{41}$ and $R^{42}$ can be $C_1$-$C_3$ alkyl (e.g., $CH_3$).

In still other embodiments, each of $R^{41}$ and $R^{42}$ is hydrogen.

Embodiments can further include any one or more of the following features.

When the carbon attached to $R^{41}$ and $R^{42}$ is substituted with four different substituents, the carbon attached to $R^{41}$ and $R^{42}$ can have the R configuration.

When the carbon attached to $R^{41}$ and $R^{42}$ is substituted with four different substituents, the carbon attached to $R^{41}$ and $R^{42}$ can have the S configuration.

[II] In some embodiments, A is C=O.

[III] In some embodiments, A is heterocycloalkylene containing from 3-5 ring atoms, in which from 1-2 of the ring atoms is independently selected from N, NH, N($C_1$-$C_3$ alkyl), O, and S; and wherein said heterocycloalkylene is (a) substituted with 1 oxo (e.g., 1 oxo on a ring carbon); and (b) is optionally further substituted with from 1-4 independently selected $R^a$.

In certain embodiments, A is heterocycloalkylene containing 5 ring atoms, in which from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$. For example, A can be:

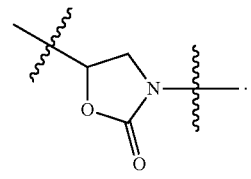 [SMILES: *C1CN(*)C(=O)O1]

Non-Limiting Combinations of Variables $L^1$, $L^2$, and A

In some embodiments:

A is (i) $CR^{41}R^{42}$, wherein each of $R^{41}$ and $R^{42}$ is independently selected from hydrogen, halo, $C_1$-$C_3$ alkyl, or $OR^9$; or (ii) C=O; and each of $L^1$ and $L^2$ is, independently, $C_1$-$C_3$ alkylene, which is optionally substituted with from 1-2 independently selected $R^c$.

In some embodiments:

A is $CR^{A1}R^{A2}$, wherein each of $R^{A1}$ and $R^{A2}$ is independently selected from hydrogen, halo, $C_1$-$C_3$ alkyl, or $OR^9$; and
each of $L^1$ and $L^2$ is, independently, $C_1$-$C_3$ alkylene, which is optionally substituted with from 1-2 independently selected $R^c$.

Embodiments can include one or more of the following features

Each of $R^{A1}$ and $R^{A2}$ can be as defined anywhere herein.
Each of $L^1$ and $L^2$ is $CH_2$.
One of $L^1$ and $L^2$ is $CH_2$ (e.g., $L^1$), and the other (e.g., $L^2$) is methylene that is substituted with 1 or 2 (e.g., 1) independently selected $R^c$, in which $R^c$ can be as defined anywhere herein. For example:
- $L^1$ can be $CH_2$; and
- One of $R^{A1}$ and $R^{A2}$ is hydrogen; and
- $L^2$ can be methylene that is substituted with 1 or 2 (e.g., 1) independently selected $R^c$ (e.g., $C_1$-$C_6$ (e.g., $C_1$-$C_3$) alkyl, such as $CH_3$; or $C_1$-$C_6$ (e.g., $C_1$-$C_3$) thioalkoxy, such as —$SCH_3$);

Each of $L^1$ and $L^2$ is methylene that is substituted with 1 or 2 (e.g., 1) independently selected $R^c$, in which $R^c$ can be as defined anywhere herein. For example:
- each of $R^{A1}$ and $R^{A2}$ can be a substituent other than hydrogen (e.g., one of which is $CH_3$), and
- each of $L^1$ and $L^2$ is methylene that is substituted with $C_1$-$C_3$ alkyl, such as $CH_3$).

In some embodiments:

A is heterocycloalkylene containing from 3-5 (e.g., 5) ring atoms, in which from 1-2 of the ring atoms is independently selected from N, NH, $N(C_1$-$C_3$ alkyl), O, and S; and wherein said heterocycloalkylene is (a) substituted with 1 oxo; and (b) is optionally further substituted with from 1-4 independently selected $R^a$; and
$L^1$ is $C_1$-$C_3$ (e.g., $C_1$-$C_2$) straight chain alkylene, which is optionally substituted with from 1-2 independently selected $R^c$, and
$L^2$ is a bond that directly connects A in formula (I) to Z in formula (I).

Variable Z

[I] In some embodiments, Z is:
(i) —$NR^{10}R^{11}$; or
(ii) —$C(O)NR^{10}R^{11}$; or
(iii) —$OR^{12}$; or
(iv) —$S(O)_nR^{13}$, wherein n is 0, 1, or 2; or
(v) heterocycloalkenyl containing from 5-6 ring atoms, wherein from 1-3 of the ring atoms is independently selected from N, NH, $N(C_1$-$C_6$ alkyl), $NHC(O)(C_1$-$C_6$ alkyl), O, and S; and wherein said heterocycloalkenyl is optionally substituted with from 1-4 independently selected $R^a$;
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, $N(C_1$-$C_3$ alkyl), O, and S; and wherein said heteroaryl is optionally substituted with from 1-4 independently selected $R^b$.

In certain embodiments, Z is as defined in (i), (iii), (iv), (v), (vi), or (vii) in the preceding paragraph.

In certain embodiments, Z is as defined in (i), (iii), (iv), (v), or (vii) in the preceding paragraph.

In certain embodiments, Z is as defined in (i), (iii), (v), or (vii) in the preceding paragraph.

In certain embodiments, Z is as defined in (i), (iii), or (iv) in the preceding paragraph.

In certain embodiments, Z is:
(i) —$NR^{10}R^{11}$; or
(iii) —$OR^{12}$; or
(v) heterocycloalkenyl containing from 5-6 ring atoms, wherein from 1-3 of the ring atoms is independently selected from N, NH, $N(C_1$-$C_6$ alkyl), $NC(O)(C_1$-$C_6$ alkyl), O, and S; and wherein said heterocycloalkenyl is optionally substituted with from 1-4 independently selected $R^a$.

In certain embodiments, Z is: (i) —$NR^{10}R^{11}$; or (iii) —$OR^{12}$.

In certain embodiments, Z is: (i) —$NR^{10}R^{11}$; or (iv) —$S(O)_nR^{13}$, wherein n is 0, 1, or 2.

In certain embodiments, Z is: (iii) —$OR^{12}$; or (iv) —$S(O)_nR^{13}$, wherein n is 0, 1, or 2.

In certain embodiments, Z does not include heterocyclyl (e.g., a nitrogenous heterocyclyl, e.g., piperazinyl or piperidinyl) as part of its structure (e.g., as a fused ring or attached to another ring by a bond).

In certain embodiments, Z is other than heterocycloalkenyl containing from 5-6 ring atoms, wherein from 1-3 of the ring atoms is independently selected from N, NH, $N(C_1$-$C_6$ alkyl), $NC(O)(C_1$-$C_6$ alkyl), O, and S; and wherein said heterocycloalkenyl is optionally substituted with from 1-4 independently selected $R^a$.

In certain embodiments, Z is other than heteroaryl containing from 5-14 ring atoms, wherein from 1-6 of the ring atoms is independently selected from N, NH, $N(C_1$-$C_3$ alkyl), O, and S; and wherein said heteroaryl is optionally substituted with from 1-4 independently selected $R^b$ (e.g., other than pyridyl).

[II] In some embodiments, Z is —$NR^{10}R^{11}$.

[A] In some embodiments, one of $R^{10}$ and $R^{11}$ is hydrogen, and the other of $R^{10}$ and $R^{11}$ is a substituent other than hydrogen.

In some embodiments, one of $R^{10}$ and $R^{11}$ is hydrogen or a substituent other than hydrogen, and the other of $R^{10}$ and $R^{11}$ is a substituent other than hydrogen.

In some embodiments, each of $R^{10}$ and $R^{11}$ is a substituent other than hydrogen.

In some embodiments, each of $R^{10}$ and $R^{11}$ is hydrogen.

[B] In some embodiments, one of $R^{10}$ and $R^{11}$ is independently selected from the substituents delineated collectively in (b), (c), (g) through (k), and (l) below:

(b) $C_6$-$C_{10}$ aryl that is optionally substituted with from 1-4 $R^b$;

(c) heteroaryl containing from 5-14 ring atoms, wherein from 1-6 of the ring atoms is independently selected from N, NH, $N(C_1$-$C_3$ alkyl), O, and S; and wherein said heteroaryl is optionally substituted with from 1-4 $R^b$;

(g) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;

(h) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, $N(C_1$-$C_6$ alkyl), $NC(O)(C_1$-$C_6$ alkyl), O, and S; and wherein said heterocyclyl portion is optionally substituted with from 1-3 independently selected $R^a$;

(i) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(j) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;
(k) $C_3$-$C_8$ cycloalkyl or $C_3$-$C_8$ cycloalkenyl, each of which is optionally substituted with from 1-4 independently selected $R^a$; and
(l) $C_7$-$C_{12}$ aralkyl, wherein the aryl portion is optionally the aryl portion from is optionally substituted with from 1-4 independently selected $R^b$,
and the other of $R^{10}$ and $R^{11}$ can be as defined anywhere herein.

In some embodiments, $R^{10}$ and $R^{11}$ cannot be $C_3$-$C_8$ cycloalkyl or $C_3$-$C_8$ cycloalkenyl, each of which is optionally substituted with from 1-4 independently selected $R^a$.

In some embodiments, one of $R^{10}$ and $R^{11}$ is independently selected from the substituents delineated collectively in (b), (c), (g) through (j), and (l) above; and the other of $R^{10}$ and $R^{11}$ can be as defined anywhere herein.

In some embodiments, one of $R^{10}$ and $R^{11}$ is independently selected from the substituents delineated collectively in (b), (c), and (g) through (j); and the other of $R^{10}$ and $R^{11}$ can be as defined anywhere herein.

In some embodiments, one of $R^{10}$ and $R^{11}$ is independently selected from:
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
and the other of $R^{10}$ and $R^{11}$ can be as defined anywhere herein.

In some embodiments, one of $R^{10}$ and $R^{11}$ is $C_6$-$C_{10}$ aryl (e.g., $C_6$) that is optionally substituted with from 1-4 (e.g., 1-3, 1-2, or 1) $R^b$; and the other of $R^{10}$ and $R^{11}$ can be as defined anywhere herein.

In certain embodiments, $R^b$ at each occurrence is independently selected from halo; or $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, and —NHC(O)($C_1$-$C_6$ alkyl), each of which is optionally substituted with from 1-3 independently selected $R^e$.

In certain embodiments, $R^b$ at each occurrence is independently selected from $C_1$-$C_6$ alkoxy; $C_1$-$C_6$ haloalkoxy; $C_1$-$C_6$ thioalkoxy; and $C_1$-$C_6$ thiohaloalkoxy, each of which is optionally substituted with from 1-3 independently selected $R^e$. In embodiments, $R^b$ can further include halo.

In certain embodiments, $R^b$ at each occurrence is independently selected from $C_1$-$C_6$ alkoxy and $C_1$-$C_6$ haloalkoxy, each of which is optionally substituted with from 1-3 independently selected $R^e$. In embodiments, $R^b$ can further include halo.

In certain embodiments, $R^b$ at each occurrence is independently selected from $C_1$-$C_6$ alkoxy, each of which is optionally substituted with from 1-3 independently selected $R^e$. In embodiments, $R^b$ is $C_1$-$C_6$ alkoxy (e.g., $OCH_3$). In embodiments, $R^b$ can further include halo.

In certain embodiments, one of $R^{10}$ and $R^{11}$ is unsubstituted phenyl, and the other of $R^{10}$ and $R^{11}$ can be as defined anywhere herein.

In certain embodiments, one of $R^{10}$ and $R^{11}$ is phenyl that is substituted with 1 $R^b$, and the other of $R^{10}$ and $R^{11}$ can be as defined anywhere herein. $R^b$ can be as defined anywhere herein (e.g., $R^b$ can be $C_1$-$C_6$ alkoxy, e.g., $OCH_3$). For example, one of $R^{10}$ and $R^{11}$ can be 3-methoxyphenyl. In embodiments, $R^b$ can further include halo.

[C] In some embodiments, when one of $R^{10}$ and $R^{11}$ is independently selected from the substituents delineated collectively in (b), (c), (g) through (k), and (l) above, the other of $R^{10}$ and $R^{11}$ can be:
  (a) hydrogen; or
  (d) $C_1$-$C_6$ alkyl or $C_1$-$C_6$ haloalkyl (e.g., $C_1$-$C_6$ alkyl), each of which is optionally substituted with from 1-3 $R^d$; or
  (e) —C(O)($C_1$-$C_6$ alkyl), —C(O)($C_1$-$C_6$ haloalkyl), or —C(O)O($C_1$-$C_6$ alkyl); or
  (f) $C_2$-$C_6$ alkenyl or $C_2$-$C_6$ alkynyl.

In certain embodiments, the other of $R^{10}$ and $R^{11}$ is:
  (a) hydrogen; or
  (d) $C_1$-$C_6$ alkyl or $C_1$-$C_6$ haloalkyl (e.g., $C_1$-$C_6$ alkyl), each of which is optionally substituted with from 1-3 $R^d$; or
  (e) —C(O)($C_1$-$C_6$ alkyl), —C(O)($C_1$-$C_6$ haloalkyl), or —C(O)O($C_1$-$C_6$ alkyl).

In certain embodiments, the other of $R^{10}$ and $R^{11}$ is:
  (a) hydrogen; or
  (d) $C_1$-$C_6$ alkyl or $C_1$-$C_6$ haloalkyl (e.g., $C_1$-$C_6$ alkyl), each of which is optionally substituted with from 1-3 $R^d$; or
  (e) —C(O)($C_1$-$C_6$ alkyl), or —C(O)($C_1$-$C_6$ haloalkyl).

In certain embodiments, the other of $R^{10}$ and $R^{11}$ can be:
  (a) hydrogen; or
  (d) $C_1$-$C_6$ alkyl (e.g., $C_1$-$C_3$ alkyl, e.g., $CH_3$), which is optionally substituted with from 1-3 $R^d$; or
  (e) —C(O)($C_1$-$C_6$ alkyl), e.g., $C_1$-$C_3$ alkyl, e.g., $CH_3$.

In certain embodiments, the other of $R^{10}$ and $R^{11}$ can be:
  (a) hydrogen; or
  (d) $C_1$-$C_6$ alkyl (e.g., $C_1$-$C_3$ alkyl, e.g., $CH_3$), which is optionally substituted with from 1-3 $R^d$.

In certain embodiments, the other of $R^{10}$ and $R^{11}$ can be hydrogen.

In certain embodiments, the other of $R^{10}$ and $R^{11}$ can be (d) or (e) or any subset thereof.

[E] In some embodiments, one of $R^{10}$ and $R^{11}$ is $C_6$-$C_{10}$ (e.g., $C_6$) aryl that is optionally substituted with from 1-4 $R^b$, and the other is hydrogen or $C_1$-$C_6$ alkyl (e.g., $C_1$-$C_3$ alkyl, e.g., $CH_3$).

In some embodiments, one of $R^{10}$ and $R^{11}$ is $C_6$-$C_{10}$ (e.g., $C_6$) aryl that is optionally substituted with from 1-4 $R^b$, and the other is hydrogen.

In certain embodiments, one of $R^{10}$ and $R^{11}$ is unsubstituted phenyl, and the other is hydrogen.

In certain embodiments, one of $R^{10}$ and $R^{11}$ is phenyl that is substituted with 1 $R^b$, and the other is hydrogen. In embodiments, $R^b$ is $C_1$-$C_6$ alkoxy (e.g., $C_1$-$C_3$ alkoxy, e.g., $OCH_3$). For example, one of $R^{10}$ and $R^{11}$ is 3-methoxyphenyl, and the other is hydrogen.

[F] In some embodiments, each of $R^{10}$ and $R^{11}$ cannot be optionally substituted naphthyl (e.g., each of $R^{10}$ and $R^{11}$ cannot be unsubstituted naphthyl). In embodiments, each of $R^{10}$ and $R^{11}$ is other than optionally substituted naphthyl (e.g., unsubstituted naphthyl) when R and R' are defined according to definitions (1), (2), and (4); and A is $CR^{A1}R^{A2}$ (e.g., $CHOR^9$, e.g., CHOH), and each of $L^1$ and $L^2$ is $C_1$-$C_3$ alkylene (e.g., each of $L^1$ and $L^2$ is $CH_2$).

[G] In some embodiments, one of $R^{10}$ and $R^{11}$ is hydrogen, and the other is heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$.

In certain embodiments, one of $R^{10}$ and $R^{11}$ is hydrogen, and the other is heteroaryl containing from 5-6 ring atoms, wherein from 1-2 of the ring atoms is independently selected from N, NH, N($C_1$-$C_3$ alkyl), O, and S; and wherein said heteroaryl is optionally substituted with from 1-2 $R^b$.

[III] In some embodiments, Z is —$OR^{12}$.

In some embodiments, $R^{12}$ is $C_1$-$C_6$ alkyl or $C_1$-$C_6$ haloalkyl, each of which is optionally substituted with from 1-3 $R^e$.

In some embodiments, $R^{12}$ is $C_1$-$C_6$ alkyl, which is optionally substituted with from 1-3 $R^e$.

In certain embodiments, $R^{12}$ is $C_1$-$C_6$ alkyl (e.g., $C_1$-$C_3$ alkyl, e.g., $CH_3$).

In certain embodiments, $R^{12}$ is $C_1$-$C_6$ alkyl (e.g., $C_1$-$C_3$ alkyl, e.g., $CH_3$), which is optionally substituted with from 1-3 (e.g., 1 or 2, e.g., 1) $R^e$. In embodiments, each occurrence of $R^e$ can be independently selected from —$NH_2$, —NH($C_1$-$C_6$ alkyl), N($C_1$-$C_6$ alkyl)$_2$, and —NHC(O)($C_1$-$C_6$ alkyl).

In some embodiments, $R^{12}$ is $C_6$-$C_{10}$ aryl that is optionally substituted with from 1-4 (e.g., 1-3, 1-2, or 1) $R^b$.

In certain embodiments, $R^b$ at each occurrence is independently selected from halo; or $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, and —NHC(O)($C_1$-$C_6$ alkyl), each of which is optionally substituted with from 1-3 independently selected $R^e$.

In certain embodiments, $R^b$ at each occurrence is independently selected from $C_1$-$C_6$ alkoxy; $C_1$-$C_6$ haloalkoxy; $C_1$-$C_6$ thioalkoxy; and $C_1$-$C_6$ thiohaloalkoxy, each of which is optionally substituted with from 1-3 independently selected $R^e$.

In certain embodiments, $R^b$ at each occurrence is independently selected from $C_1$-$C_6$ alkoxy and $C_1$-$C_6$ haloalkoxy, each of which is optionally substituted with from 1-3 independently selected $R^e$.

In certain embodiments, $R^b$ at each occurrence is independently selected from $C_1$-$C_6$ alkoxy, each of which is optionally substituted with from 1-3 independently selected $R^e$. In embodiments, $R^b$ is $C_1$-$C_6$ alkoxy (e.g., $OCH_3$).

In embodiments, $R^b$ can further include halo.

In certain embodiments, $R^{12}$ is unsubstituted phenyl.

In certain embodiments, $R^{12}$ is phenyl that is substituted with 1 $R^b$. $R^b$ can be as defined anywhere herein (e.g., $R^b$ can be $C_1$-$C_6$ alkoxy, e.g., $OCH_3$). For example, $R^{12}$ can be 3-methoxyphenyl.

[IV] In some embodiments, Z is —S(O)$_n R^{13}$, in which n can be 0, 1, or 2.

In some embodiments, $R^{13}$ is $C_6$-$C_{10}$ aryl that is optionally substituted with from 1-4 (e.g., 1-3, 1-2, or 1) $R^b$.

In certain embodiments, $R^b$ at each occurrence is independently selected from halo; or $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, and —NHC(O)($C_1$-$C_6$ alkyl), each of which is optionally substituted with from 1-3 independently selected $R^e$.

In certain embodiments, $R^b$ at each occurrence is independently selected from $C_1$-$C_6$ alkoxy; $C_1$-$C_6$ haloalkoxy; $C_1$-$C_6$ thioalkoxy; and $C_1$-$C_6$ thiohaloalkoxy, each of which is optionally substituted with from 1-3 independently selected $R^e$.

In certain embodiments, $R^b$ at each occurrence is independently selected from $C_1$-$C_6$ alkoxy and $C_1$-$C_6$ haloalkoxy, each of which is optionally substituted with from 1-3 independently selected $R^e$.

In certain embodiments, $R^b$ at each occurrence is independently selected from $C_1$-$C_6$ alkoxy, each of which is optionally substituted with from 1-3 independently selected $R^e$. In embodiments, $R^b$ is $C_1$-$C_6$ alkoxy (e.g., $OCH_3$).

In embodiments, $R^b$ can further include halo.

In certain embodiments, $R^{13}$ is unsubstituted phenyl.

In certain embodiments, $R^{13}$ is phenyl that is substituted with 1 $R^b$. $R^b$ can be as defined anywhere herein (e.g., $R^b$ can be $C_1$-$C_6$ alkoxy, e.g., $OCH_3$). For example, $R^{13}$ can be 3-methoxyphenyl.

In embodiments, $R^{12}$ and/or $R^{13}$ cannot be substituted phenyl. In embodiments, $R^{12}$ and/or $R^{13}$ cannot be substituted phenyl when R and R' are defined according to definition (1); and A is $CR^{A1}R^{A2}$ (e.g., $CHOR^9$, e.g., CHOH), and each of $L^1$ and $L^2$ is $C_1$-$C_3$ alkylene (e.g., each of $L^1$ and $L^2$ is $CH_2$).

[V] In some embodiments, Z is heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$.

In certain embodiments, Z is heterocycloalkenyl containing 6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$.

In certain embodiments, from 1-3 of the ring atoms is independently selected from N, NH, N($C_1$-$C_6$ alkyl), and NC(O)($C_1$-$C_6$ alkyl).

In certain embodiments, $R^a$ at each occurrence is, independently selected from oxo, thioxo, =NH, and =N($C_1$-$C_6$ alkyl), e.g., =NH.

For example, Z can be:

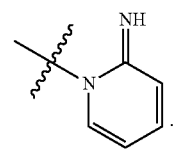 [SMILES: *n1ccccc1=N]

[V] In some embodiments, Z is heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$.

In certain embodiments, Z is heteroaryl containing from 5-10 ring atoms, wherein from 1-4 of the ring atoms is independently selected from N, NH, and N($C_1$-$C_3$ alkyl); and wherein said heteroaryl is optionally substituted with from 1-2 $R^b$.

Variables R and R'

[I] In some embodiments, R and R' together with $C_2$ and $C_3$, respectively, form a fused phenyl ring having formula (II):

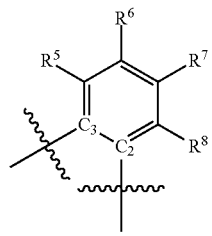

(II)

in which each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ halothioalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro.

For purposes of clarification, it is understood that compounds in which R and R' together with $C_2$ and $C_3$, respectively, form a fused phenyl ring having formula (II) correspond to compounds having the following general formula:

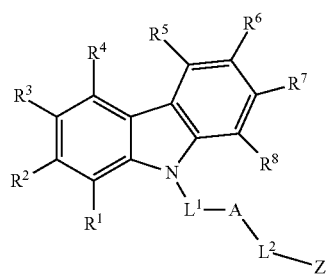

(III)

in which $R^1$, $R^2$, $R^3$, $R^4$, $L^1$, $L^2$, A, and Z can be as defined anywhere herein.

In some embodiments, one or two of $R^5$, $R^6$, $R^7$, and $R^8$ (e.g., one of, e.g., $R^6$) is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro; and the others are hydrogen.

In certain embodiments, one or two of $R^5$, $R^6$, $R^7$, and $R^8$ (e.g., one of, e.g., $R^6$) is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and the others are hydrogen.

In certain embodiments, one or two of $R^5$, $R^6$, $R^7$, and $R^8$ (e.g., one of, e.g., $R^6$) is selected from halo, $C_1$-$C_6$ alkyl, and $C_1$-$C_6$ haloalkyl; and the others are hydrogen.

In certain embodiments, one or two of $R^5$, $R^6$, $R^7$, and $R^8$ (e.g., one of, e.g., $R^6$) is selected from halo and $C_1$-$C_6$ alkyl; and the others are hydrogen.

In certain embodiments, one or two of $R^5$, $R^6$, $R^7$, and $R^8$ (e.g., one of, e.g., $R^6$) is halo (e.g., bromo or chloro) and $C_1$-$C_6$ alkyl; and the others are hydrogen.

In certain embodiments, one or two of $R^5$, $R^6$, $R^7$, and $R^8$ (e.g., one of, e.g., $R^6$) is bromo; and the others are hydrogen.

In some embodiments, $R^6$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro; and each of $R^5$, $R^7$, and $R^8$ can be as defined anywhere herein.

In certain embodiments, $R^6$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro; and each of $R^5$, $R^7$, and $R^8$ is hydrogen.

In some embodiments, $R^6$ is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and each of $R^1$, $R^2$, and $R^4$ can be as defined anywhere herein.

In certain embodiments, $R^6$ is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and each of $R^5$, $R^7$, and $R^8$ is hydrogen.

In some embodiments, $R^6$ is selected from halo, $C_1$-$C_6$ alkyl, and $C_1$-$C_6$ haloalkyl; and each of $R^5$, $R^7$, and $R^8$ can be as defined anywhere herein.

In certain embodiments, $R^6$ is selected from halo, $C_1$-$C_6$ alkyl, and $C_1$-$C_6$ haloalkyl; and each of $R^5$, $R^7$, and $R^8$ is hydrogen.

In some embodiments, $R^6$ is selected from halo and $C_1$-$C_6$ alkyl; and each of $R^5$, $R^7$, and $R^8$ can be as defined anywhere herein.

In certain embodiments, $R^6$ is selected from halo and $C_1$-$C_6$ alkyl; and each of $R^5$, $R^7$, and $R^8$ is hydrogen.

In some embodiments, $R^6$ is halo (e.g., bromo or chloro); and each of $R^5$, $R^7$, and $R^8$ can be as defined anywhere herein.

In certain embodiments, $R^6$ is halo (e.g., bromo or chloro); and each of $R^5$, $R^7$, and $R^8$ is hydrogen.

In some embodiments, $R^6$ is bromo; and each of $R^5$, $R^7$, and $R^8$ can be as defined anywhere herein.

In certain embodiments, $R^6$ is bromo; and each of $R^5$, $R^7$, and $R^8$ is hydrogen.

In some embodiments, each of $R^5$, $R^6$, $R^7$, and $R^8$ is independently selected from hydrogen, halo, and $C_1$-$C_6$ alkyl.

In certain embodiments, each of $R^5$, $R^6$, $R^7$, and $R^8$ is independently selected from hydrogen and halo(e.g., bromo or chloro).

In some embodiments, each of $R^5$, $R^6$, $R^7$, and $R^8$ is hydrogen.

In some embodiments, when any one or more of $R^5$, $R^6$, $R^7$, and $R^8$ can be a substituent other than hydrogen, said substituent, or each of said substituents, is other than $C_1$-$C_6$ alkyl (e.g., $C_1$-$C_3$ alkyl, e.g., $CH_3$).

Embodiments can include any one or more of the features described anywhere herein, including (but not limited to) those described below.

{A}

Each of $R^1$, $R^2$, $R^3$, and $R^4$ can be as defined anywhere herein.

$R^3$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro; and each of $R^1$, $R^2$, and $R^4$ can be as defined anywhere herein (e.g., each of $R^1$, $R^2$, and $R^4$ is hydrogen).

$R^3$ is selected from halo and $C_1$-$C_6$ alkyl; and each of $R^1$, $R^2$, and $R^4$ can be as defined anywhere herein (e.g., each of $R^1$, $R^2$, and $R^4$ is hydrogen).

$R^3$ is halo (e.g., bromo or chloro); and each of $R^1$, $R^2$, and $R^4$ can be as defined anywhere herein (e.g., each of $R^1$, $R^2$, and $R^4$ is hydrogen).

$R^3$ is bromo; and each of $R^1$, $R^2$, and $R^4$ can be as defined anywhere herein (e.g., each of $R^1$, $R^2$, and $R^4$ is hydrogen).

Each of $R^1$, $R^2$, $R^3$, and $R^4$ is independently selected from hydrogen and halo (e.g., bromo or chloro).

Each of $R^1$, $R^2$, $R^3$, and $R^4$ is hydrogen.

{B}

Each of $L^1$ and $L^2$ is, independently, $C_1$-$C_3$ alkylene, which is optionally substituted with from 1-2 independently selected $R^c$.

Each of $L^1$ and $L^2$ is $CH_2$.

One of $L^1$ and $L^2$ is $CH_2$ (e.g., $L^1$), and the other (e.g., $L^2$) is methylene that is substituted with 1 or 2 (e.g., 1) independently selected $R^c$, in which $R^c$ can be as defined anywhere herein.

Each of $L^1$ and $L^2$ is methylene that is substituted with 1 or 2 (e.g., 1) independently selected $R^c$, in which $R^c$ can be as defined anywhere herein.

$L^1$ is $C_1$-$C_3$ (e.g., $C_1$-$C_2$) straight chain alkylene, which is optionally substituted with from 1-2 independently selected $R^c$, and $L^2$ is a bond that directly connects A in formula (I) to Z in formula (I).

{C}

One of $R^{A1}$ and $R^{A2}$ is $OR^9$, and the other is hydrogen. In embodiments, $R^9$ can be hydrogen. $R^9$ can be $C_1$-$C_3$ alkyl (e.g., $CH_3$).

One of $R^{A1}$ and $R^{A2}$ can be halo (e.g., fluoro), and the other is hydrogen.

Each of $R^{A1}$ and $R^{A2}$ can be a substituent other than hydrogen. For example, each of $R^{A1}$ and $R^{A2}$ can be halo (e.g., fluoro). As another example, one of $R^{A1}$ and $R^{A2}$ can be $OR^9$ (e.g., in which $R^9$ is hydrogen), and the other is $C_1$-$C_3$ alkyl (e.g., $CH_3$).

Each of $R^{A1}$ and $R^{A2}$ is hydrogen.

A is $CR^{A1}R^{A2}$, wherein each of $R^{A1}$ and $R^{A2}$ is independently selected from hydrogen, halo, $C_1$-$C_3$ alkyl, or $OR^9$; and each of $L^1$ and $L^2$ is, independently, $C_1$-$C_3$ alkylene, which is optionally substituted with from 1-2 independently selected $R^c$.

{D}

Z is —$NR^{10}R^{11}$, in which $R^{10}$ and $R^{11}$ can be as defined anywhere herein.

One of $R^{10}$ and $R^{11}$ is $C_6$-$C_{10}$ aryl that is optionally substituted with from 1-4 $R^b$. In embodiments, the other of $R^{10}$ and $R^{11}$ is hydrogen or $C_1$-$C_3$ alkyl (e.g., $CH_3$). In embodiments, the other of $R^{10}$ and $R^{11}$ is hydrogen.

In certain embodiments, one of $R^{10}$ and $R^{11}$ is unsubstituted phenyl, and the other is hydrogen.

In certain embodiments, one of $R^{10}$ and $R^{11}$ is phenyl that is substituted with 1 $R^b$, and the other is hydrogen. In embodiments, $R^b$ is $C_1$-$C_6$ alkoxy (e.g., $C_1$-$C_3$ alkoxy, e.g., $OCH_3$). For example, one of $R^{10}$ and $R^{11}$ is 3-methoxyphenyl, and the other is hydrogen.

Z is —$OR^{12}$ or —$S(O)_nR^{13}$, in which $R^{12}$ and $R^{13}$ can be as defined anywhere herein.

Embodiments can include features from any one, two, three, or four of {A}, {B}, {C}, and {D}; or any combinations thereof.

In some embodiments:

$R^3$ is a substituent other than hydrogen (e.g., halo and $C_1$-$C_6$ alkyl; e.g., halo, e.g., bromo); and each of $R^1$, $R^2$, and $R^4$ can be as defined anywhere herein (e.g., each of $R^1$, $R^2$, and $R^4$ is hydrogen); and $R^6$ is a substituent other than hydrogen (e.g., halo and $C_1$-$C_6$ alkyl; e.g., halo, e.g., bromo); and each of $R^5$, $R^7$, and $R^8$ can be as defined anywhere herein (e.g., each of $R^5$, $R^7$, and $R^8$ is hydrogen).

In some embodiments:

$R^3$ is a substituent other than hydrogen (e.g., halo and $C_1$-$C_6$ alkyl; e.g., halo, e.g., bromo); and each of $R^1$, $R^2$, and $R^4$ can be as defined anywhere herein (e.g., each of $R^1$, $R^2$, and $R^4$ is hydrogen); and $R^6$ is a substituent other than hydrogen (e.g., halo and $C_1$-$C_6$ alkyl; e.g., halo, e.g., bromo); and each of $R^5$, $R^7$, and $R^8$ can be as defined anywhere herein (e.g., each of $R^5$, $R^7$, and $R^8$ is hydrogen); and A is $CR^{A1}R^{A2}$, wherein each of $R^{A1}$ and $R^{A2}$ is independently selected from hydrogen, halo, $C_1$-$C_3$ alkyl, or $OR^9$; and each of $L^1$ and $L^2$ is, independently, $C_1$-$C_3$ alkylene, which is optionally substituted with from 1-2 independently selected $R^c$.

Embodiments can include any one or more features described herein (e.g., as described under {B} and {C} above).

In some embodiments:

$R^3$ is a substituent other than hydrogen (e.g., halo and $C_1$-$C_6$ alkyl; e.g., halo, e.g., bromo); and each of $R^1$, $R^2$, and $R^4$ can be as defined anywhere herein (e.g., each of $R^1$, $R^2$, and $R^4$ is hydrogen); and $R^6$ is a substituent other than hydrogen (e.g., halo and $C_1$-$C_6$ alkyl; e.g., halo, e.g., bromo); and each of $R^5$, $R^7$, and $R^8$ can be as defined anywhere herein (e.g., each of $R^5$, $R^7$, and $R^8$ is hydrogen); and A is $CR^{A1}R^{A2}$, wherein each of $R^{A1}$ and $R^{A2}$ is independently selected from hydrogen, halo, $C_1$-$C_3$ alkyl, or $OR^9$; and each of $L^1$ and $L^2$ is, independently, $C_1$-$C_3$ alkylene, which is optionally substituted with from 1-2 independently selected $R^c$; and Z is —$NR^{10}R^{11}$, in which $R^{10}$ and $R^{11}$ can be as defined anywhere herein.

Embodiments can include any one or more features described herein (e.g., as described under {B}, {C}, and {D} above).

In some embodiments:

each of $L^1$ and $L^2$ is $CH_2$;

A is $CR^{A1}R^{A2}$, wherein one of $R^{A1}$ and $R^{A2}$ is $OR^9$, and the other is hydrogen;

Z is —$NR^{10}R^{11}$; and each of $R^{10}$ and $R^{11}$ is independently selected from (a) hydrogen;

(b) $C_6$-$C_{10}$ aryl that is optionally substituted with from 1-4 $R^b$;

(d) $C_1$-$C_6$ alkyl or $C_1$-$C_6$ haloalkyl, each of which is optionally substituted with from 1-3 $R^d$;

(f) $C_2$-$C_6$ alkenyl or $C_2$-$C_6$ alkynyl.

Embodiments can include any one or more features described herein (e.g., as described under {A}, {C}, and {D} above).

In some embodiments:

A is $CR^{A1}R^{A2}$, in which each of $R^{A1}$ and $R^{A2}$ is, independently, hydrogen, halo, or $C_1$-$C_3$ alkyl; or A is $CR^{A1}R^{A2}$, in which one of $R^{A1}$ and $R^{A2}$ is halo (e.g., fluoro), and the other of $R^{A1}$ and $R^{A2}$ is, independently, hydrogen, halo, or $C_1$-$C_3$ alkyl (e.g., hydrogen); or A is $CR^{A1}R^{A2}$, in which one of $R^{A1}$ and $R^{A2}$ is halo (e.g., fluoro), and the other of $R^{A1}$ and $R^{A2}$ is hydrogen; and $R^1$, $R^2$, $R^3$, $R^4$, $L^1$, $L^2$, and Z can be as defined anywhere herein; or a salt (e.g., pharmaceutically acceptable salt) thereof.

Embodiments can include features from any one, two, three, or four of {A}, {B}, {C}, and {D}; or any combinations thereof.

In some embodiments:
one of $R^{A1}$ and $R^{A2}$ can be $OR^9$. In embodiments, the other of $R^{A1}$ and $R^{A2}$ can be as defined anywhere herein; e.g., the other of $R^{A1}$ and $R^{A2}$ can be hydrogen or $C_1$-$C_3$ alkyl. For example, one of $R^{A1}$ and $R^{A2}$ can be $OR^9$, and the other of $R^{A1}$ and $R^{A2}$ is hydrogen. In embodiments, $R^9$ can be hydrogen; and $R^1$, $R^2$, $R^3$, $R^4$, $L^1$, $L^2$, and Z can be as defined anywhere herein; or a salt (e.g., pharmaceutically acceptable salt) thereof.

In embodiments, one or more of the following apply, e.g., when A is CHOH and Z is $NR^{10}R^{11}$:
each of $R^3$ and $R^6$ is $CH_3$; and/or each of $R^3$ and $R^6$ is bromo; and/or each of $R^3$ and $R^6$ is chloro; and/or one of $R^3$ and $R^6$ is $CH_3$ (e.g., $R^6$), and the other is bromo (e.g., $R^3$);
each of $R^{10}$ and $R^{11}$ is other than hydrogen;
each of $R^{10}$ and $R^{11}$ is hydrogen;
one of $R^{10}$ and $R^{11}$ is heteroaryl as defined anywhere herein;
$L^1$ and/or $L^2$ is $C_2$-$C_3$ alkylene (optionally substituted);
(B) and/or (C) applies.

Embodiments can include features from any one, two, three, or four of {A}, {B}, {C}, and {D}; or any combinations thereof.

In some embodiments, Z is other than $NR^{10}R^{11}$; and $R^1$, $R^2$, $R^3$, $R^4$, $L^1$, $L^2$, Z, and A can be as defined anywhere herein; or a salt (e.g., pharmaceutically acceptable salt) thereof. In embodiments, (B) and/or (C) applies. Embodiments can include features from any one, two, three, or four of {A}, {B}, {C}, and {D}; or any combinations thereof.

In some embodiments, Z is $-OR^{12}$ and/or $-S(O)_nR^{13}$; and $R^1$, $R^2$, $R^3$, $R^4$, $L^1$, $L^2$, and A can be as defined anywhere herein; or a salt (e.g., pharmaceutically acceptable salt) thereof. In embodiments, (B) and/or (C) applies. Embodiments can include features from any one, two, three, or four of {A}, {B}, {C}, and {D}; or any combinations thereof.

In some embodiments, A is (ii) C=O; and/or (iv) heterocycloalkylene containing from 3-5 ring atoms, wherein from 1-2 of the ring atoms is independently selected from N, NH, $N(C_1$-$C_3$ alkyl), O, and S; and wherein said heterocycloalkylene is (a) substituted with 1 oxo; and (b) is optionally further substituted with from 1-4 independently selected $R^a$; and $R^1$, $R^2$, $R^3$, $R^4$, $L^1$, $L^2$, and Z can be as defined anywhere herein; or a salt (e.g., pharmaceutically acceptable salt) thereof. Embodiments can include features from any one, two, three, or four of {A}, {B}, {C}, and {D}; or any combinations thereof.

[II] In some embodiments, each of R and R' is, independently, hydrogen, $C_1$-$C_6$ alkyl, or $C_1$-$C_6$ haloalkyl.

In embodiments, R and R' can each be the same or different.

In certain embodiments, each of R and R' is, independently, $C_1$-$C_6$ alkyl, e.g., each of R and R' is $CH_3$.

In other embodiments, each of R and R' is hydrogen.

Embodiments can include any one or more of the features described anywhere herein, including (but not limited to) those described in conjunction with Formula (III).

[III] In some embodiments, R and R' together with $C_2$ and $C_3$, respectively, form a fused heterocyclic ring containing from 5-6 ring atoms, wherein from 1-2 of the ring atoms is independently selected from N, NH, $N(C_1$-$C_6$ alkyl), NC(O)($C_1$-$C_6$ alkyl), O, and S; and wherein said heterocyclic ring is optionally substituted with from 1-3 independently selected $R^a$. For purposes of clarification and illustration, a non-limiting example of these compounds is provided below (formula (IV)):

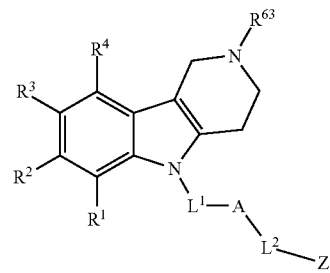

(IV)

in which $R^1$, $R^2$, $R^3$, $R^4$, $L^1$, $L^2$, A, and Z can be as defined anywhere herein. Here, R and R' together with $C_2$ and $C_3$, respectively, form a fused heterocyclic ring containing 5-6 ring atoms.

Embodiments can include any one or more of the features described anywhere herein, including (but not limited to) those described in conjunction with Formula (III). In certain embodiments, $R^{63}$ can be hydrogen or $C_1$-$C_3$ alkyl (e.g., $CH_3$).

In some embodiments, it is provided:
(i) each of $L^1$ and $L^2$ must be $C_1$-$C_3$ alkylene, which is optionally substituted with from 1-2 independently selected $R^c$ when A is $CH_2$; or
(ii) Z must be other than heteroaryl containing from 5-14 (e.g., 5-6 or 6)ring atoms, wherein from 1-6 of the ring atoms is independently selected from N, NH, $N(C_1$-$C_3$ alkyl), O, and S; and wherein said heteroaryl is optionally substituted with from 1-4 independently selected $R^b$; e.g., other than substituted pyridyl, e.g., other than pyridyl substituted with $C_1$-$C_3$ alkyl (e.g., $CH_3$), e.g., other than 2 or 6-methylpyridyl.

[IV] In some embodiments, R and R' together with $C_2$ and $C_3$, respectively, form a fused $C_5$-$C_6$ cycloalkyl ring that is optionally substituted with from 1-4 independently selected $R^a$. For purposes of clarification and illustration, a non-limiting example of such compounds is provided below (formula (V)):

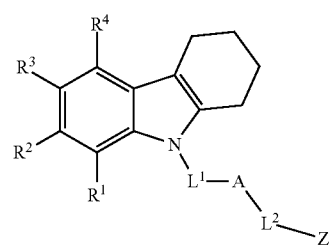

(V)

in which $R^1$, $R^2$, $R^3$, $R^4$, $L^1$, $L^2$, A, and Z can be as defined anywhere herein. Here, R and R' together with $C_2$ and $C_3$, respectively, form a fused $C_6$ cycloalkyl ring. Embodiments can include any one or more of the features described anywhere herein, including (but not limited to) those described in conjunction with Formula (III).

[V] In some embodiments, R and R' together with $C_2$ and $C_3$, respectively, form a fused heteroaryl ring containing from 5-6 ring atoms, wherein from 1-2 of the ring atoms is independently selected from N, NH, $N(C_1$-$C_3$ alkyl), O, and S; and wherein said heteroaryl ring is optionally substituted with from 1-3 independently selected $R^b$. See, e.g., the title compound of Example 13. Embodiments can include any one or more of the features described anywhere herein, including (but not limited to) those described in conjunction with Formula (III).

Any genus, subgenus, or specific compound described herein can include one or more of the stereochemistry features described herein (e.g., as delineated in the Summary).

Compound Forms and Salts

The compounds of this invention may contain one or more asymmetric centers and thus occur as racemates and racemic mixtures, enantiomerically enriched mixtures, single enantiomers, individual diastereomers and diastereomeric mixtures. All such isomeric forms of these compounds are expressly included in the present invention. The compounds of this invention may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present invention. The compounds of this invention may also be represented in multiple tautomeric forms, in such instances, the invention expressly includes all tautomeric forms of the compounds described herein, even though only a single tautomeric form may be represented. All such isomeric forms of such compounds are expressly included in the present invention.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of this invention include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

The invention also includes various hydrate and solvate forms of the compounds.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

Synthesis

The compounds of present invention can be conveniently prepared in accordance with the procedures outlined in the Examples section, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations,* 2d. ed., Wiley-VCH Publishers (1999); P. G. M. Wuts and T. W. Greene, *Protective Groups in Organic Synthesis,* 4th Ed., John Wiley and Sons (2007); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy (FT-IR), spectrophotometry (e.g., UV-visible), or mass spectrometry (MS), or by chromatography such as high performance liquid chromatograpy (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvents. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}$F NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

The compounds of the invention can be prepared, for example, using the reaction pathways and techniques as described below.

A series of carbazole 1,2-aminoalcohol compounds of formula 3 may be prepared by the method outlined in Scheme 1. The 9-oxiranylmethyl-9H-carbazole of formula 2 may be prepared from an appropriately substituted carbazole of formula 1 and epichlorohydrin in the presence of a strong base such as sodium hydride.

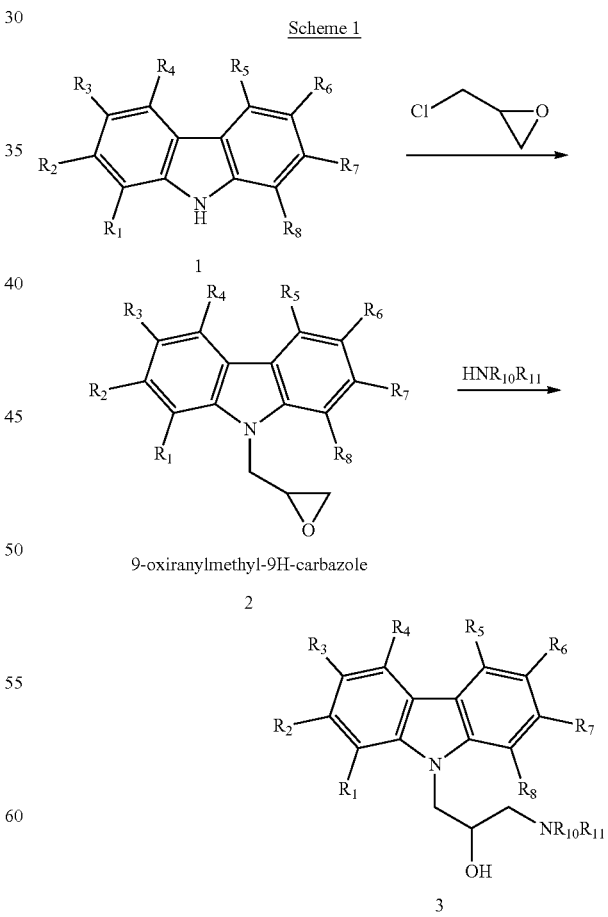

The oxiranyl ring of formula 2 may be opened in the presence of a primary or secondary amine to produce the 1,2-amino alcohol of formula 3. Such reactive primary or secondary amines can be, but are not limited to, phenethylamine, 3-phenylallyl amine, and N-substituted piperazines and the like.

Alternatively, a variety of carbazole 1,2-aminoalcohol compounds of formula 8 may be prepared by the method outlined in Scheme 2. The epoxide of 9-oxiranylmethyl-9H-carbazole of formula 2 may be opened with a primary amine, $H_2NR^{10}$, to produce the secondary aminoalcohol of formula 4 and then protected with an amine protecting group (P) such as tert-butoxycarbonyl (Boc) to afford the protected aminoalcohol of formula 5. Next, the hydroxyl group of formula 5 may be alkylated with a strong base such as sodium hydride and an alkylating agent (RX) such as an alkyl halide, tosylate, triflate or mesylate to produce the ether of formula 6. Removal of the amine protecting group in the presence of a suitable acid can provide the desired OR ether compounds of formula 7. Finally, reductive alkylation of the secondary amine of formula 7 may be achieved in the presence of an aldehyde and a reducing agent such as sodium cyano borohydride (NaCNBH$_3$) to provide the tertiary 1,2-aminoalcohol of formula 8.

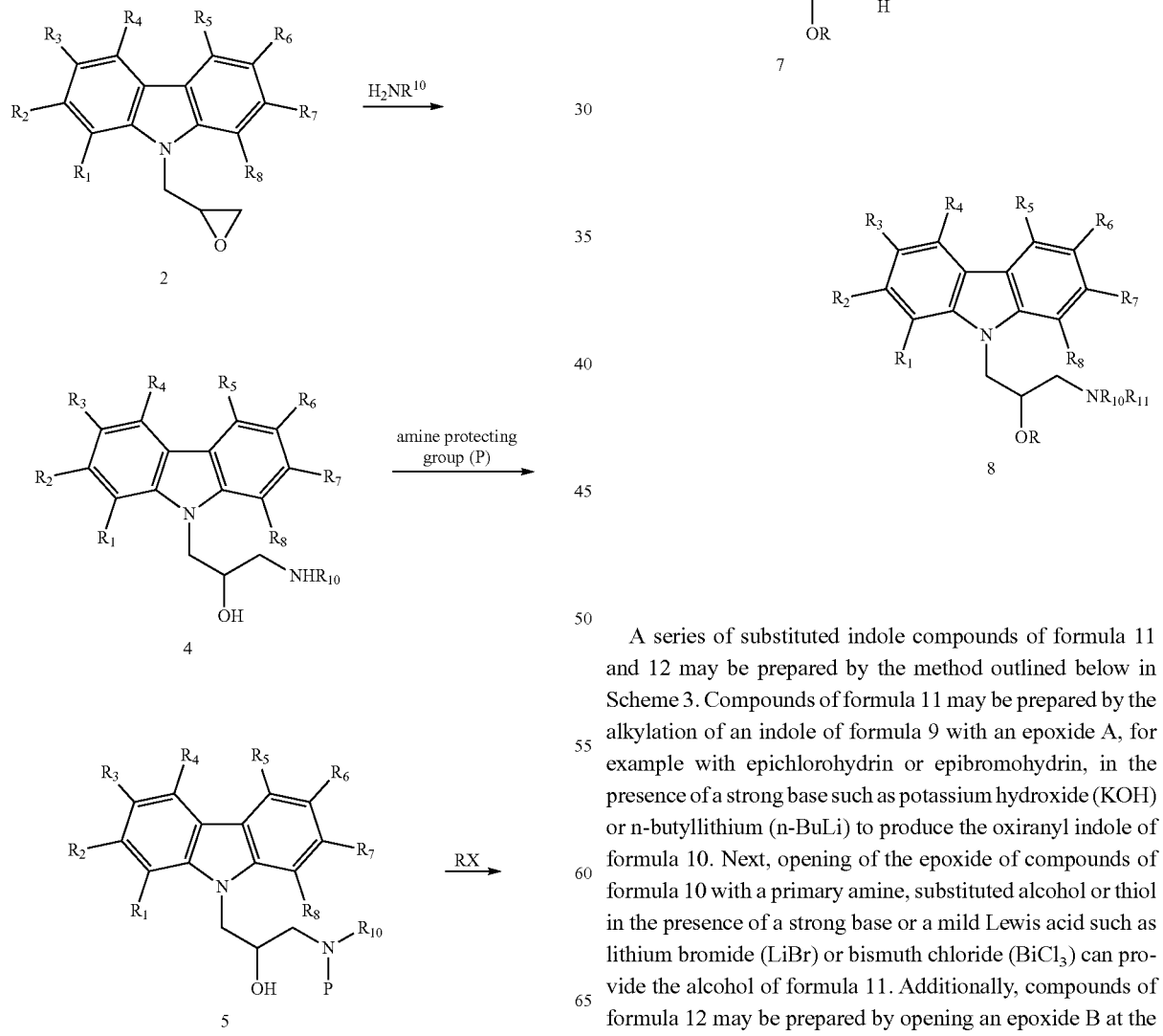

A series of substituted indole compounds of formula 11 and 12 may be prepared by the method outlined below in Scheme 3. Compounds of formula 11 may be prepared by the alkylation of an indole of formula 9 with an epoxide A, for example with epichlorohydrin or epibromohydrin, in the presence of a strong base such as potassium hydroxide (KOH) or n-butyllithium (n-BuLi) to produce the oxiranyl indole of formula 10. Next, opening of the epoxide of compounds of formula 10 with a primary amine, substituted alcohol or thiol in the presence of a strong base or a mild Lewis acid such as lithium bromide (LiBr) or bismuth chloride (BiCl$_3$) can provide the alcohol of formula 11. Additionally, compounds of formula 12 may be prepared by opening an epoxide B at the less hindered position with the indole nitrogen of formula 9.

Scheme 3

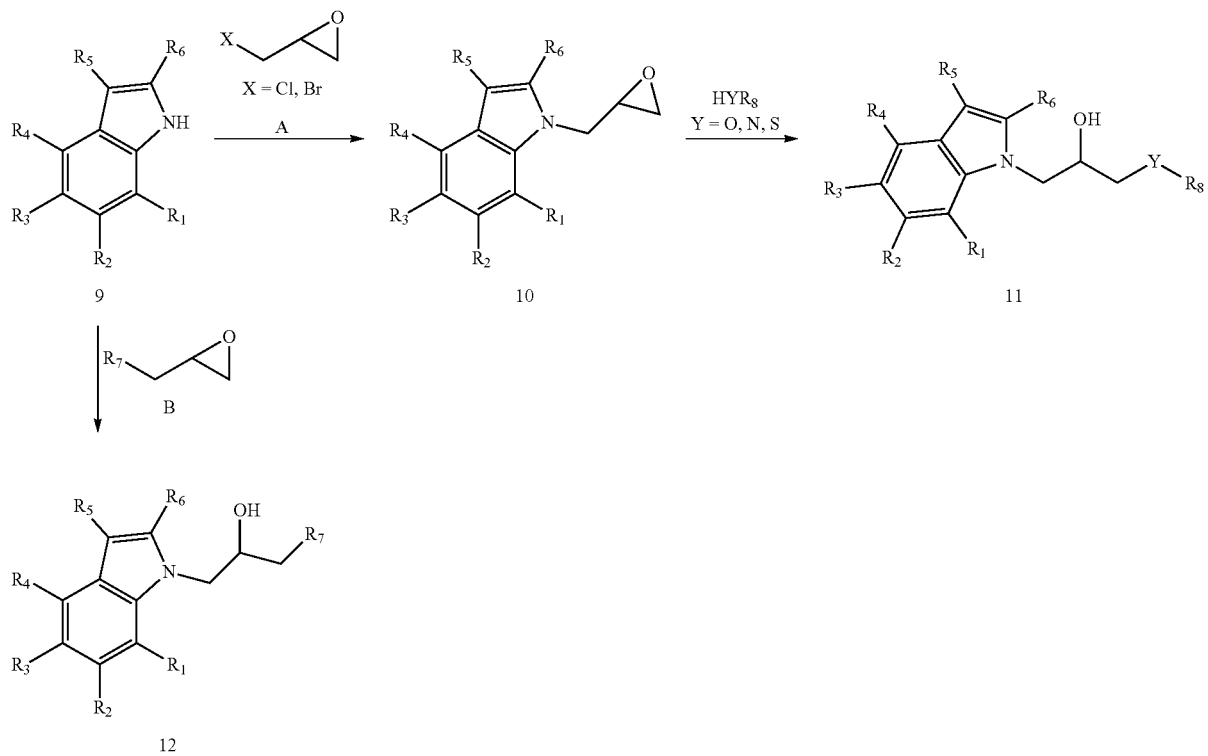

In addition, a variety of epoxide derivatives may be prepared by following the methods outlined in Scheme 4. The secondary alcohol of compounds of formula 11 may be oxidized using an oxidizing agent or under Swern-like oxidation conditions to provide the ketone of formula 13 which can further undergo reductive amination to provide the amine of compound 14. Alternatively, the secondary alcohol may be converted into an ester using a carboxylic acid anhydride (where Z=R"C(O)) or an ether (where Z=alklyl) using standard alkylation conditions to produce compounds of formula 15. Fluorine compounds of formula 16 may be prepared by reaction of the alcohol of formula 11 with a fluorinating agent such as diethylaminosulfur trifluoride (DAST). Nitrogen-heteroarylated compounds of formula 17 may be prepared in the presence of a catalytic amount of copper iodide and a heteroaryl iodide starting from compounds of formula 11 (where Y=N). Finally, sulfoxides and sulfones of formula 18 may be prepared under oxidative conditions, for example in the presence of m-chloroperoxybenzoic acid (m-CPBA), starting from sulfides of formula 11 (where Y=S).

Scheme 4

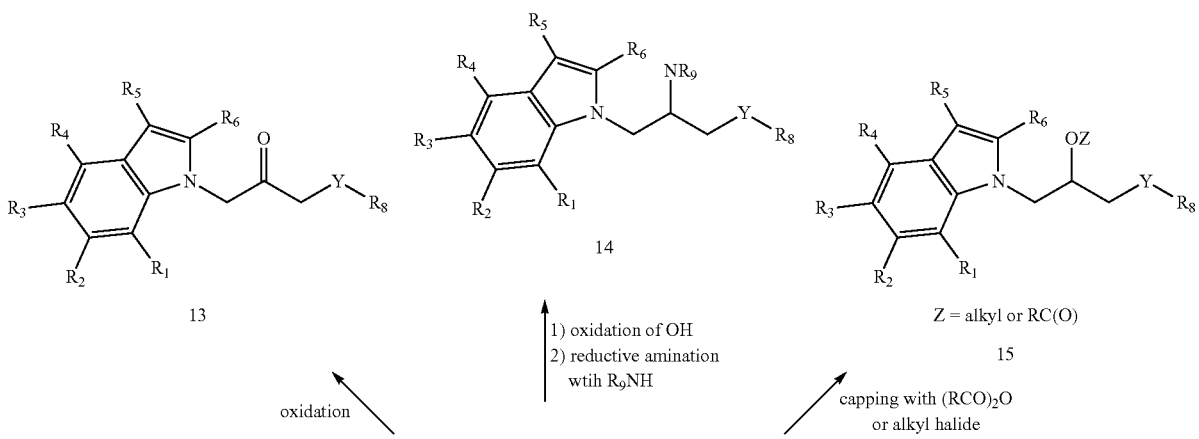

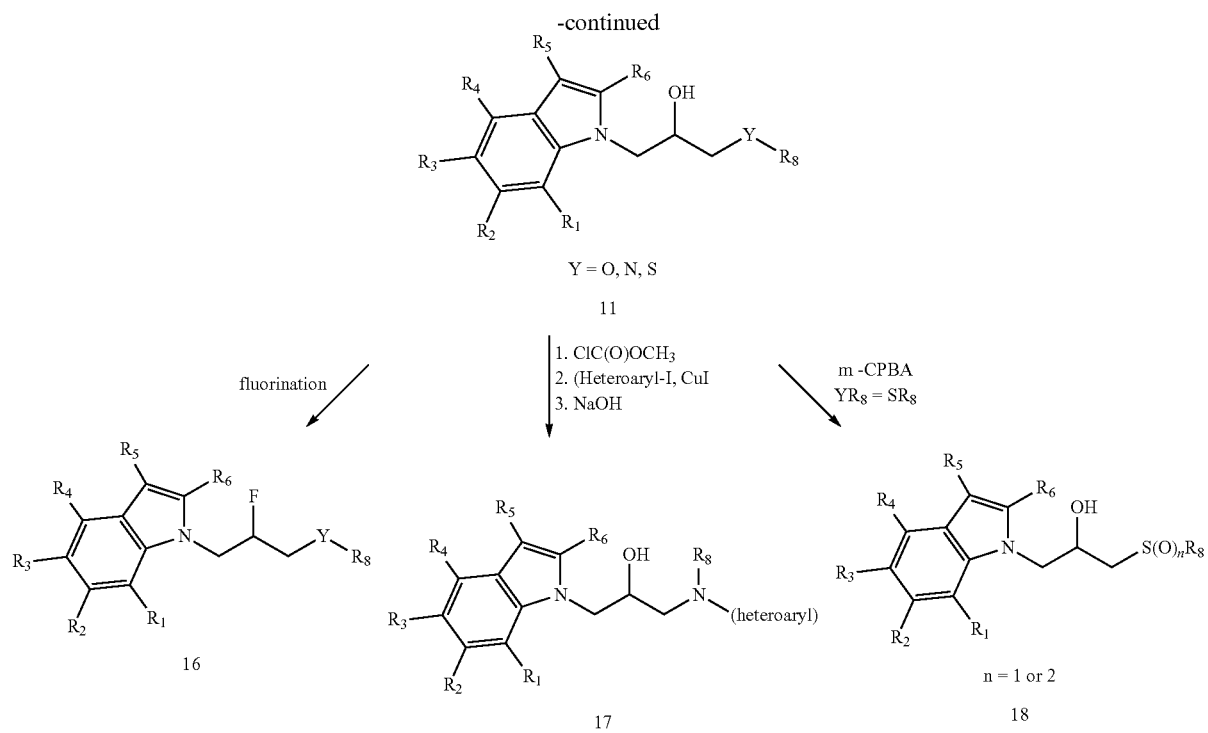

Pharmaceutical Compositions

The term "pharmaceutically acceptable carrier" refers to a carrier or adjuvant that may be administered to a subject (e.g., a patient), together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multi-pack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The following are examples (Formulations 1-4) of capsule formulations.

Capsule Formulations

| | Capsule Formulation | | | |
|---|---|---|---|---|
| | Formulatn1; mg/capsule | Formulatn2; mg/capsule | Formulatn3; mg/capsule | Formulatn4; mg/capsule |
| Carbazole (solid solution) | 100 | 400 | 400 | 200 |
| Silicon Dioxide | 0.625 | 2.5 | 3.75 | 1.875 |
| Magnesium Stearate NF2 | 0.125 | 0.5 | 0.125 | 0.625 |
| Croscarmellose Sodium NF | 11.000 | 44.0 | 40.0 | 20.0 |
| Pluronic F68 NF | 6.250 | 25.0 | 50.0 | 25.0 |
| Silicon Dioxide NF | 0.625 | 2.5 | 3.75 | 1.875 |
| Magnesium Stearate NF | 0.125 | 0.5 | 1.25 | 0.625 |
| Total | 118.750 | 475.00 | 475.00 | 475.00 |
| Capsule Size | No. 4 | No. 0 | No. 0 | No. 2 |

Preparation of Solid Solution

Crystalline carbazole (80 g/batch) and the povidone (NF K29/32 at 160 g/batch) are dissolved in methylene chloride (5000 mL). The solution is dried using a suitable solvent spray dryer and the residue reduced to fine particles by grinding. The powder is then passed through a 30 mesh screen and confirmed to be amorphous by x-ray analysis.

The solid solution, silicon dioxide and magnesium stearate are mixed in a suitable mixer for 10 minutes. The mixture is compacted using a suitable roller compactor and milled using a suitable mill fitted with 30 mesh screen. Croscarmellose sodium, Pluronic F68 and silicon dioxide are added to the milled mixture and mixed further for 10 minutes. A premix is made with magnesium stearate and equal portions of the mixture. The premix is added to the remainder of the mixture, mixed for 5 minutes and the mixture encapsulated in hard shell gelatin capsule shells.

Use

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with, aberrant (e.g., insufficient) neurogenesis or accelerated neuron cell death in a subject in need thereof are featured. The methods include administering to the subject an effective amount of a compound of formula (I) (and/or a compound of any of the other formulae described herein) or a salt (e.g., a pharmaceutically acceptable salt) thereof as defined anywhere herein to the subject.

In another aspect, the use of a compound of formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions caused by, or associated with, aberrant (e.g., insufficient) neurogenesis or exacerbated neuronal cell death is featured.

In embodiments, the one or more diseases, disorders, or conditions can include neuropathies, nerve trauma, and neurodegenerative diseases. In embodiments, the one or more diseases, disorders, or conditions can be diseases, disorders, or conditions caused by, or associated with aberrant (e.g., insufficient) neurogenesis (e.g., aberrant hippocampal neurogenesis as is believed to occur in neuropsychiatric diseases) or accelerated death of existing neurons. Examples of the one or more neuropsychiatric and neurodegenerative diseases include, but are not limited to, schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuroactive drugs, such as alcohol, opiates, methamphetamine, phencyclidine, and cocaine. The resultant promotion of neurogenesis or survival of existing neurons (i.e. a resultant promotion of survival, growth, development, function and/or generation of neurons) may be detected directly, indirectly or inferentially from an improvement in, or an amelioration of one or more symptoms of the disease or disorder caused by or associated with aberrant neurogenesis or survival of existing neurons. Suitable assays which directly or indirectly detect neural survival, growth, development, function and/or generation are known in the art, including axon regeneration in rat models (e.g. Park et al., Science. 2008 Nov. 7; 322:963-6), nerve regeneration in a rabbit facial nerve injury models (e.g. Zhang et al., J Transl Med. 2008 Nov. 5; 6(1):67); sciatic nerve regeneration in rat models (e.g. Sun et al., Cell Mol Neurobiol. 2008 Nov. 6); protection against motor neuron degeneration in mice (e.g. Poesen et al. J. Neurosci. 2008 Oct. 15; 28(42):10451-9); rat model of Alzheimer's disease, (e.g. Xuan et al., Neurosci Lett. 2008 Aug. 8; 440(3):331-5); animal models of depression (e.g. Schmidt et al., e.g. Behav Pharmacol. 2007 September; 18(5-6):391-418; Krishnan et al. Nature 2008, 455, 894-902); and/or exemplified herein.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In some embodiments, the compounds described herein can be coadministered with one or more other therapeutic agents. In certain embodiments, the additional agents may be administered separately, as part of a multiple dose regimen, from the compounds of this invention (e.g., sequentially, e.g., on different overlapping schedules with the administration of one or more compounds of formula (I) (including any subgenera or specific compounds thereof)). In other embodiments, these agents may be part of a single dosage form, mixed together with the compounds of this invention in a single composition. In still another embodiment, these agents can be given as a separate dose that is administered at about the same time that one or more compounds of formula (I) (including any subgenera or specific compounds thereof) are administered (e.g., simultaneously with the administration of one or more compounds of formula (I) (including any subgenera or specific compounds thereof)). When the compositions of this invention include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of this invention is useful when the desired treatment involves areas or organs readily accessible by topical application. For application topically to the skin, the composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of this invention may also be topically applied to the lower intestinal tract by rectal suppository formulation or in a suitable enema formulation.

In some embodiments, topical administration of the compounds and compositions described herein may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Remington's Pharmaceutical Sciences, 21st Edition (2005) published by Mack Publishing Company, which is incorporated herein by reference in its entirety.

Topically-transdermal patches are also included in this invention. Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing) on the adhesive or device.

The compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

The invention will be further described in the following examples. It should be understood that these examples are for illustrative purposes only and are not to be construed as limiting this invention in any manner.

EXAMPLES

Example 1a and 1b

S- and R-1-(3,6-Dibromo-9H-carbazol-9-yl)-3-(3-methoxyphenylamino)-propan-2-ol

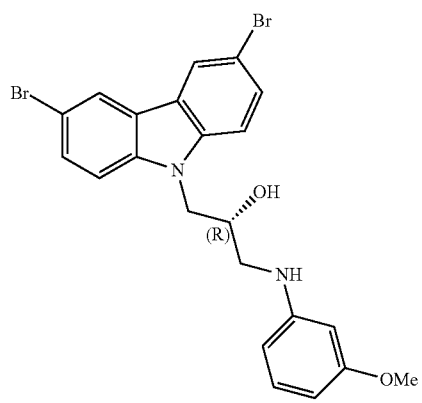

and

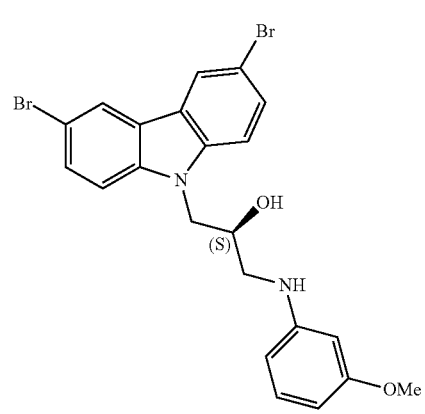

Representative Procedure 1

Step 1. Synthesis of 3,6-Dibromo-9-(oxiran-2-ylmethyl)-9H-carbazole (Epoxide 2-A)

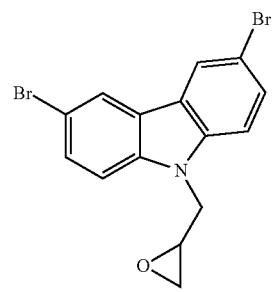 [SMILES: Brc1ccc2c(c1)c1cc(Br)ccc1n2CC1CO1]

Following a literature procedure (Asso, V; Ghilardi, E; Bertini, S; Digiacomo, M; Granchi, C; Minutolo, F; Rapposelli, S; Bortolatoi, A; Moro, S. Macchia, M. ChemMedChem, 2008, 3, 1530-1534) powdered KOH (0.103 g, 1.85 mmol) was added to a solution of 3,6-dibromocarbazole (0.500 g, 1.54 mmol) in DMF (1.5 mL) at ambient temperature and stirred for 30 min until dissolved. Epibromohydrin (0.32 mL, 3.8 mmol) was added via syringe and the reaction was stirred at room temperature overnight. Upon completion, the solution was partitioned between EtOAc and H$_2$O. The aqueous layer was washed 3× with EtOAc, and the combined organics were washed with saturated aqueous NaCl, dried over Na$_2$SO$_4$, filtered, and concentrated in vacuo. The crude residue was recrystallized from EtOAc/Hexane to afford the desired product (389 mg, 66%).

$^1$H NMR (CDCl$_3$, 500 MHz) δ 8.10 (d, 2H, J=2.0 Hz), 7.54 (dd, 2H, J=2.0, 8.5 Hz), 7.31 (d, 2H, J=8.5 Hz), 4.62 (dd, 1H, J=2.5, 16.0 Hz), 4.25 (dd, 1H, J=5.5, 16.0 Hz), 3.29 (m, 1H), 2.79 (dd, 1H, J=4.0, 4.5 Hz), 2.46 (dd, 1H, J=2.5, 5.0 Hz).

ESI m/z 381.0 ([M+H]$^+$, C$_{15}$H$_{12}$Br$_2$NO requires 379.9)

Representative Procedure 2

Step 2. Synthesis of 1-(3,6-dibromo-9H-carbazol-9-yl)-3-(3-methoxyphenylamino)propan-2-ol

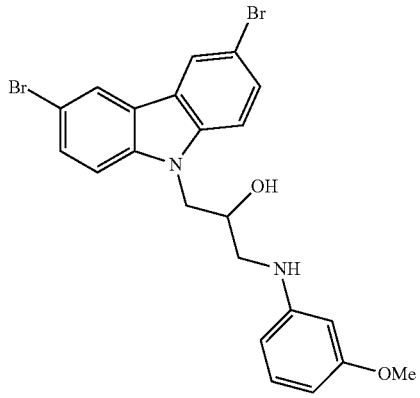 [SMILES: COc1cccc(NCC(O)Cn2c3ccc(Br)cc3c3cc(Br)ccc32)c1]

Following a literature procedure (Asso, V; Ghilardi, E; Bertini, S; Digiacomo, M; Granchi, C; Minutolo, F; Rapposelli, S; Bortolato, A; Moro, S. Macchia, M. *ChemMedChem*, 2008, 3, 1530-1534) m-Anisidine (1.0 mL, 8.95 mmol) was added to a suspension of epoxide 2-A (3.02 g, 7.92 mmol) in cyclohexane (73 mL). BiCl$_3$ (0.657 g, 2.08 mmol) was added and the mixture was heated to reflux overnight. Upon completion, the reaction was partitioned between EtOAc and H$_2$O. The aqueous layer was washed 3× with EtOAc, and the combined organics were washed with saturated aqueous NaCl, dried over Na$_2$SO$_4$, filtered, and concentrated in vacuo. The crude residue was purified by chromatography (SiO$_2$, 0-50% EtOAc/Hexane) to afford the desired alcohol as an opaque yellow solid (998 mg, 25%).

$^1$H NMR (CDCl$_3$, 400 MHz) δ 8.12 (d, 2H, J=1.6 Hz), 7.52 (dd, 2H, J=2.0, 8.8 Hz), 7.32 (d, 2H, J=8.8 Hz), 7.07 (dd, 1H, J=8.0 Hz), 6.31 (dd, 1H, J=2.4, 8.0 Hz), 6.21 (dd, 1H, J=2.0, 8.0 Hz), 6.12 (dd, 1H, J=2.0, 2.4 Hz), 4.34-4.39 (m, 3H), 4.00 (br s, 1H), 3.71 (s, 3H), 3.30 (dd, 1H, J=3.6, 13.2 Hz), 3.16 (dd, 1H, J=6.4, 13.2 Hz), 2.16 (br s, 1H).

$^{13}$C NMR (CDCl$_3$, 100 MHz) δ 161.0, 149.2, 139.9 (2C), 130.4 (2C), 129.5 (2C), 123.8 (2C), 123.5 (2C), 112.8, 111.0 (2C), 106.7, 103.8, 99.8, 69.5, 55.3, 48.0, 47.4

ESI m/z 502.9 ([M+H]$^+$, C$_{22}$H$_{21}$Br$_2$N$_2$O$_2$ requires 503.0)

Step 3. Synthesis of 1-(3,6-Dibromo-9H-carbazol-9-yl)-3-(3-methoxyphenylamino)propan-2-yl 3,3,3-trifluoro-2-methoxy-2-phenylpropanoate

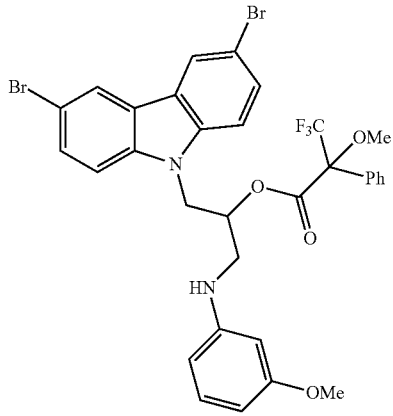 [SMILES: COc1cccc(NCC(Cn2c3ccc(Br)cc3c3cc(Br)ccc32)OC(=O)C(OC)(c2ccccc2)C(F)(F)F)c1]

1-(3,6-dibromo-9H-carbazol-9-yl)-3-(3-methoxyphenylamino)propan-2-ol (0.150 g, 0.298 mmol) was dissolved in anhydrous dichloromethane (6 mL) and cooled to 0° C. Pyridine (0.053 mL, 0.655 mmol) was added, followed by S-(+)-α-methoxy-α-trifluoromethylphenylacetyl chloride (S-Mosher's acid chloride, 0.083 mL, 0.446 mmol) and dimethylaminopyridine (0.004 g, 0.030 mmol). The reaction was allowed to warm to room temperature over 4 hours, after which it was quenched by addition of saturated aqueous NaHCO$_3$. The mixture was extracted 3× with EtOAc, and the combined organics were washed with saturated aqueous NaCl, dried over Na$_2$SO$_4$, filtered, and concentrated in vacuo. The crude residue was purified by chromatography (SiO$_2$, 0-50% EtOAc/Hexane) to afford a mixture of both possible esters and both possible amides (~5:1 ester:amide ratio by $^1$H NMR, 132 mg, 64%). Separation of the mixture was achieved using HPLC (Phenomenex SiO$_2$ Luna, 21×250 mm, 15% EtOAc/Hexane, 16 mL/min; HPLC Retention time: 25.6 min (ester 1) and 41.2 min (ester 2).

Ester 1: $^1$H NMR (CDCl$_3$, 500 MHz) δ 8.11 (d, 2H, J=2.0 Hz), 7.45 (dd, 2H, J=8.5 Hz), 7.24 (m, 2H), 7.22 (m, 4H), 7.05 (t, 1H, J=8.0 Hz), 6.32 (dd, 1H, J=2.0, 8.0 Hz), 6.12 (dd, 1H, J=2.0, 8.0 Hz), 6.05 (dd, 1H, J=2.0, 2.5 Hz), 5.59 (m, 1H), 4.54 (d, 2H, J=6.5 Hz), 3.71 (br s, 1H), 3.69 (s, 3H), 3.43 (m, 1H), 3.29 (ddd, 1H, J=5.5, 13.5 Hz), 3.19 (s, 3H).

Ester 2: $^1$H NMR (CDCl$_3$, 500 MHz) δ 8.08 (d, 2H, J=2.0 Hz), 7.42 (dd, 2H, J=2.0, 9.0 Hz), 7.28 (m, 2H), 7.24 (m, 4H), 7.04 (t, 1H, J=8.0 Hz), 6.31 (dd, 1H, J=2.0, 8.5 Hz), 6.11 (dd, 1H, J=2.0, 8.0 Hz), 6.01 (dd, 1H, J=2.0, 2.5 Hz), 5.63 (m, 1H), 4.49 (d, 2H, J=6.5 Hz), 3.82 (dd, 1H, J=5.5, 6.0 Hz), 3.66 (s, 3H), 3.42 (s, 3H), 3.39 (m, 1H), 3.28 (dd, 1H, J=5.0, 13.5 Hz)

Step 4. Synthesis of S- and R-1-(3,6-Dibromo-9H-carbazol-9-yl)-3-(3-methoxyphenylamino)-propan-2-ol

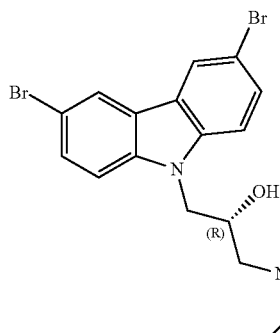

1a and

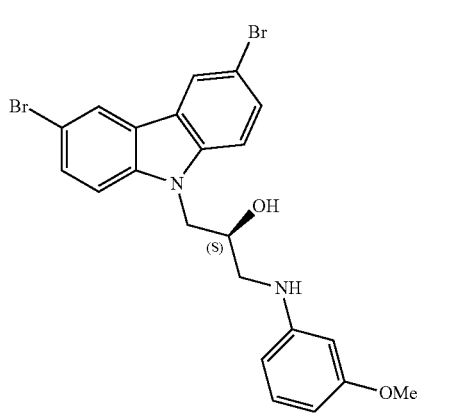

1b

Following a literature procedure (Abad, J-L; Casas, J; Sanchez-Baeza, F; Messeguer, A. *J. Org. Chem.* 1995, 60, 3648-3656) ester 1 from example 3 (0.011 g, 0.015 mmol) was dissolved in degassed Et$_2$O (0.150 mL) and cooled to 0° C. Lithium aluminum hydride (1M in THF, 0.018 mL, 0.018 mmol) was added via syringe and the reaction was stirred for 20 min. Upon completion by TLC the reaction was quenched by the addition of MeOH and stirred for 45 min. The mixture was partitioned between EtOAc and H$_2$O. The aqueous layer was extracted 3× with EtOAc, and the combined organics were washed with saturated aqueous NaCl, dried over Na$_2$SO$_4$, filtered, and concentrated in vacuo. The crude residue was purified by chromatography (SiO$_2$, 0-30% EtOAc/Hexane) to afford the desired alcohol (4.7 mg, 64%).

(From Ester 1): $[\alpha]_D$=+10° (c=0.1, CH$_2$Cl$_2$); Example 1a
(From Ester 2): $[\alpha]_D$=+14° (c=0.1, CH$_2$Cl$_2$); Example 1b Example 2

1-(3,6-dibromo-9H-carbazol-9-yl)-3-(2-iminopyridin-1(2H)-yl)propan-2-ol

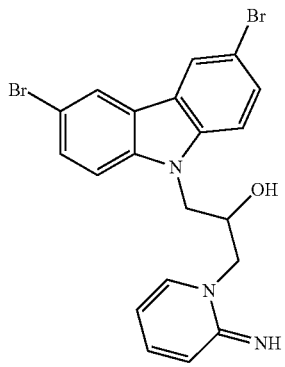 [SMILES: N=c1ccccn1CC(O)Cn1c2ccc(Br)cc2c2cc(Br)ccc21]

Example 2 was prepared following Representative Procedure 2, except with a reaction time of 2 days at 80° C. The crude product was used without further purification.

$^1$H NMR (CDCl$_3$, 400 MHz) d=8.14 (2H, J=1.9 Hz), 7.55 (dd, 2H, J=1.9, 8.8 Hz), 7.35 (d, 2H, J=8.7 Hz), 6.83 (t, 1H, J=7.6 Hz), 6.37 (d, 1H, J=6.8), 6.32 (d, 1H, J=9.1 Hz), 5.65 (t, 1H, J=6.7 Hz), 4.39 (dm, 5H), 3.54 (d, 1H, J=13.9 Hz)

MS (ESI), m/z: found 473.9 (M+1)$^+$ ([M+1]+ for C$_{20}$H$_{18}$Br$_2$N$_3$O requires 474.0)

Example 3a 1-(3,6-dibromo-9H-carbazol-9-yl)-3-(phenylthio)propan-2-ol

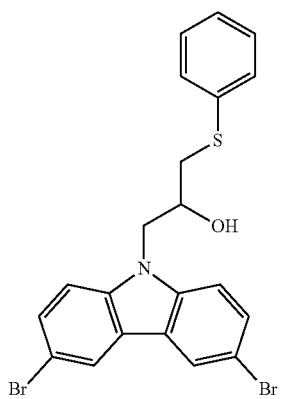 [SMILES: OC(CSc1ccccc1)Cn1c2ccc(Br)cc2c2cc(Br)ccc21]

Benzenethiol (30 μl, 0.29 mmol) was added to a solution of 3,6-dibromo-9-(oxiran-2-ylmethyl)-9H-carbazole (epoxide 2-A, 101.6 mg, 0.27 mmol) in 5.0 ml MeOH at r.t. The reaction mixture was heated to 80° C. and stirred overnight at the same temperature. The reaction was monitored by lc/ms for the consumption of SM. The reaction was cooled, diluted with ethyl acetate and washed with water and brine. The organic layer was dried over Na$_2$SO$_4$, filtered and condensed.

$^1$H NMR (CDCl$_3$, 400 MHz) δ 8.03 (d, 2H, J=2.1 Hz), 7.48 (dd, 2H, J=2.0, 8.7 Hz), 7.33-7.20 (m, 7H), 4.33 (dd, 1H, J=4.3, 14.9 Hz), 4.20 (dd, 1H, J=6.9, 14.9 Hz), 4.00-4.12 (m, 1H), 3.05 (dd, 1H, J=5.3, 13.9 Hz), 2.93 (dd, 1H, J=7.2, 13.9 Hz), 2.51 (bs, 1H);

$^{13}$C NMR (CDCl$_3$, 126 MHz) δ 139.9, 134.5, 130.4, 129.6, 129.4, 127.4, 123.8, 123.4, 112.7, 111.1, 69.3, 48.1, 39.4;

MS (ESI), m/z: found: 505.9 [M+O-1]$^-$ ([M+O-1]- for C$_{21}$H$_{17}$Br$_2$NOS requires 504.9; (oxidation occurred under MS conditions; NMR not consistent with sulfoxide)

Example 3b 1-(3,6-dibromo-9H-carbazol-9-yl)-3-phenoxypropan-2-ol

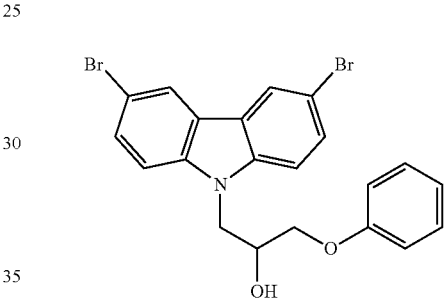

Following Representative Procedure 1, the title compound of Example 3b was prepared from dibromocarbazole and phenoxymethyloxirane in 61% yield.

$^1$H NMR (CDCl$_3$, 400 MHz) δ 8.14 (d, 2H, J=1.9 Hz), 7.51 (dd, 2H, J=1.9, 8.7 Hz), 7.36 (d, 2H, J=8.8 Hz), 7.127-7.32 (m, 2H), 7.00 (t, 1H, J=7.3 Hz), 6.87 (dd, 2H, J=0.8, 8.9 Hz), 4.58 (dd, 1H, J=7.9, 16.7 Hz), 4.41-4.49 (m, 2H), 4.00 (dd, 1H, J-4.4, 9.6 Hz), 3.89 (dd, 1H, J=4.5, 9.5 Hz), 2.38 (d=1H, J=5.7 Hz)

MS (ESI), m/z: 517.9 [M+HCOO]$^-$ ([M+HCOO]- for C21H17Br2NO2 requires 518.0

Example 3c 1-(3,6-dibromo-9H-carbazol-9-yl)-3-(phenylsulfinyl)propan-2-ol

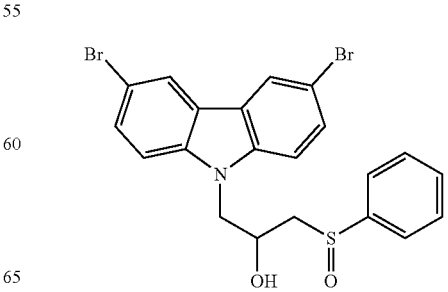

An aqueous solution of NaIO₄ (5.14 g) was added to silica gel (20 g) and shaken until a free-flowing solid was obtained. Thio-ether (1-(3,6-dibromo-9H-carbazol-9-yl)-3-(phenylthio)propan-2-ol, (0.0120 g, 0.0244 mmol) and NaIO₄/silica gel (0.1018 g NaIO4, 0.122 mmol) were suspended in CH₂Cl₂ (1 mL). The white suspension was heated to 50° C. in a sealed vial for 4 hours until TLC showed complete disappearance of starting material. The reaction mixture was subjected to silica gel chromatography using Hexanes/EtOAc (1:9) to afford 0.0081 g white solid as product, yield 65.4% as a 1:1 mixture of diastereomers.

¹H NMR (CDCl₃, 400 MHz) δppm=2.39 (dd, J=13.7, 1.7 Hz, 1H diastereomer A) 2.83 (dd, J=13.2, 2.9 Hz, 1 Dias. B) 2.97 (dd, J=13.2, 8.6 Hz, 1H Diast. B) 3.15 (dd, J=13.7, 9.3 Hz, 1H Diast. A) 3.90 (d, J=1.7 Hz, 1H Dias. B) 3.96 (d, J=2.6 Hz, 1H Diast. A), 4.24 (dd, J=15.0, 6.3 Hz, 1H Dias A), 4.30 (dd, J=15.2, 6.7, 1H Diast. B), 4.35 (dd, J=15.2, 6.0 Hz, 1H Diast. B), 4.45 (dd, J=15.1, 6.4 Hz, 1H Diast. B), 4.65-4.55 (m, 1H Diast. A) 4.87-4.76 (m, 1H Diast. B) 7.16 (d, J=8.7 Hz, 2H Diast. A) 7.34 (d, J=8.8 Hz, 2H Diast B) 7.60-7.30 (m, 7H Diast A+7H Diast. B) 8.08 (d, J=1.9 Hz, 2H Diast. A) 8.13 (d, J=1.9 Hz, 2H Diast B)

MS (ESI) m/z: 549.9 [M+HCOO]⁻ ([M+CHOO]⁻ for C₂₁H₁₇Br₂NO₂S requires 549.9).

Example 3d 1-(3,6-dibromo-9H-carbazol-9-yl)-3-(phenylsulfonyl)propan-2-ol

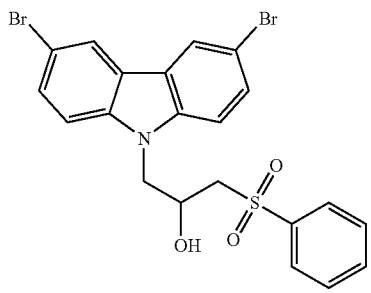 [SMILES: O=S(=O)(CC(O)Cn1c2ccc(Br)cc2c2cc(Br)ccc21)c1ccccc1]

To a solution of thio-ether (1-(3,6-dibromo-9H-carbazol-9-yl)-3-(phenylthio)propan-2-ol, (0.0113 g, 0.0230 mmol) in 0.5 mL CH₂Cl₂, a solution of mCPBA (ca. 77% pure, 0.0129 g, 0.0575 mmol) in 0.5 mL CH₂Cl₂ was added dropwise. The mixture was stirred at room temperature overnight. The crude reaction mixture was neutralized by 9 mL Et₃N and stirred for 30 min then diluted with 30 mL EtOAc and washed with saturated NaHCO₃ 3×30 mL and brine 1×30 mL. The organic layer was dried over anhydrous Na₂SO₄ and evaporated to afford the crude product, which was subjected to silica gel chromatography using Hexanes/EtOAc (3:7) to afford white solid as product (0.0120 g, yield 99.7%).

¹H NMR (CDCl₃, 400 MHz) δppm 3.15 (dd, J=14.2, 3.0 Hz, 1H) 3.21-3.31 (m, 2H) 4.38 (d, J=6.3 Hz, 2H) 4.60-4.76 (m, 1H) 7.25-7.31 (m, 2H) 7.47-7.56 (m, 4H) 7.60-7.70 (m, 1H) 7.79 (d, J=8.4, 1.2 Hz, 2H) 8.11 (d, J=1.9 Hz, 2H); MS (ESI) m/z: 565.9 [M+HCOO]; 543.7 [M+Na]⁺ ([M+HCOO]⁻ for C21H17Br2NO3S requires 595.9; [M+Na]+ requires 543.9).

Example 4

N-(3-(3,6-dibromo-9H-carbazol-9-yl)-2-hydroxypropyl)-N-(3-methoxyphenyl)acetamide

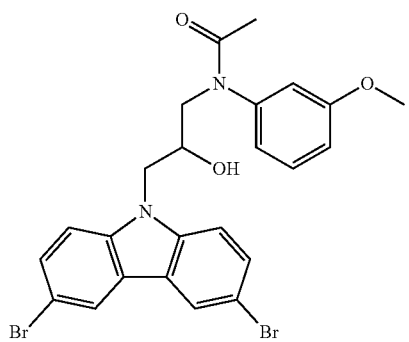 [SMILES: COc1cccc(N(CC(O)Cn2c3ccc(Br)cc3c3cc(Br)ccc32)C(C)=O)c1]

Following a literature procedure (Morcuende, A; Ors, M; Valverde, S; Herradón, B. *J. Org. Chem.* 1996, 5264-5270) triethylamine (14 μl, 0.10 mmol) and acetyl chloride (8 μl, 0.11 mmol) were added to a heterogeneous mixture of 1-(3,6-dibromo-9H-carbazol-9-yl)-3-(3-methoxyphenylamino)propan-2-ol (53 mg, 0.11 mmol) and dibutyltin oxide (5.5 mg, 0.022 mmol) in anhydrous toluene (1.5 ml). The reaction vessel was purged with nitrogen, sealed and heated under microwave radiation to 150° C. for 9 minutes. The reaction was monitored by lc/ms and all SM had been consumed. The heterogeneous solution was filtered under vacuum to yield a white solid. The crude product was used without purification.

¹H NMR (CDCl₃, 500 MHz) δ 8.09 (2H, J=1.6 Hz), 7.52 (dd, 2H, J=1.8, 8.7 Hz), 7.29 (d, 2H, J=8.8 Hz), 7.26 (t, 1H, J=8.2 Hz), 6.86 (dd, 1H, J=2.5, 8.4 Hz), 6.68 (dd, 1H, J=1.3, 7.7 Hz), 6.62 (s, 1H), 4.33-4.40 (m, 1H), 4.29 (dd, 2H, J=2.6, 6.0 Hz), 3.94 (d, 1H, J=4.1 Hz), 3.76 (s, 3H), 3.51 (dd, 1H, J=2.3, 14.0 Hz), 1.9 (s, 3H);

¹³C NMR (CDCl₃, 126 MHz) δ 173.6, 160.9, 144.5, 139.9, 131.0, 129.4, 123.8, 123.4, 119.7, 113.9, 113.5, 112.6, 111.1, 70.9, 55.7, 55.2, 46.0, 22.8.

MS (ESI), m/z: 544.9 (M+1)⁺ ([M+1]⁺ for C₂₄H₂₂Br₂N₂O₃ requires 545.0)

Example 5

5-((3,6-dibromo-9H-carbazol-9-yl)methyl)-3-(3-methoxyphenyl)-oxazolidin-2-one

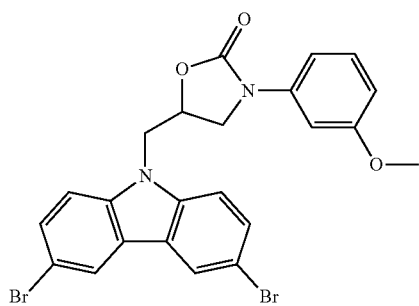 [SMILES: COc1cccc(N2CC(Cn3c4ccc(Br)cc4c4cc(Br)ccc43)OC2=O)c1]

Methyl chloroformate (10 μl, 0.13 mmol) was added to a stirring solution of jn-128-186 (55.0 mg, 0.11 mmol) and indium powder (3.5 mg, 0.030 mmol) in acetonitrile (3.0 ml), and the reaction mixture was stirred overnight at r.t. An additional 3.1 mg (0.027 mmol) of indium and 20 μl (2.6 eq.) of methyl chloroformate were added. After several hours, the reaction was diluted with ethyl acetate, and washed with water and then brine. The organic layer was dried over $Na_2SO_4$, filtered and concentrated. The methyl carbonate was purified via flash chromatography in 20-40% ethyl acetate/hexanes. Sodium methoxide (3.0 ml) was added to a solution of carbonate (21.3 mg, 0.038 mmol) and methanol (1.0 ml). After an hour at ambient temperature the solution was diluted with water and extracted with ethyl acetate. The organic layer was washed with water and brine and condensed.

$^1$H NMR (CD$_3$COCD$_3$, 500 MHz) δ 8.40 (s, 2H), 7.78 (d, 2H, J=8.5 Hz), 7.64 (d, 2H, J=8.9 Hz), 7.23-7.28 (m, 2H), 7.05 (d, 1H, J=8.3 Hz), 6.70 (d, 1H, J=8.3 Hz), 5.24-5.31 (m, 1H), 5.00 (dd, 1H, J=7.9, 15.7 Hz), 4.91 (dd, 1H, J=3.2, 15.8 Hz), 4.38 (t, 1H, J=9.3 Hz), 4.05 (m, 1H), 3.78 (s, 3H);

$^{13}$C NMR (CDCl$_3$, 126 MHz) δ 160.4, 153.9, 140.3, 140.2, 129.8, 129.4, 124.0, 123.5, 112.4, 112.1, 110.3, 109.0, 104.4, 71.9, 54.9, 47.9, 46.6.

MS (ESI), m/z: 528.9 (M+1)$^+$. ([M+1]+ for $C_{23}H_{19}Br_2N_2O_3$ calculated 529.0)

Example 6a

N-(3-(3,6-dibromo-9H-carbazol-9-yl)-2-fluoropropyl)-3-methoxyaniline

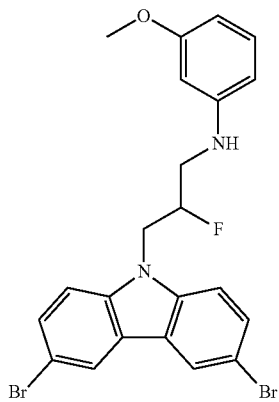 [SMILES: COc1cccc(NCC(F)Cn2c3ccc(Br)cc3c3cc(Br)ccc32)c1]

Representative Procedure 3

Epoxide Opening with Ns-Protected Anilines

N-(3-(3,6-dibromo-9H-carbazol-9-yl)-2-hydroxypropyl)-N-(3-methoxyphenyl)-4-nitrobenzenesulfonamide

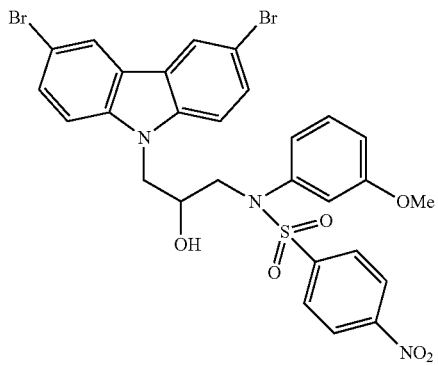 [SMILES: COc1cccc(N(CC(O)Cn2c3ccc(Br)cc3c3cc(Br)ccc32)S(=O)(=O)c2ccc([N+](=O)[O-])cc2)c1]

A heterogeneous mixture of N-(4-methoxyphenyl)-4-nitrobenzenesulfonamide (100.2 mg, 0.32 mmol) in toluene (2.5 ml, 0.13 M) under a N$_2$ atmosphere was cooled in a dry ice/acetone bath before dropwise addition of n-butyllithium (200 ul of 1.78 M in hexanes, 0.36 mmol). The reaction was stirred at −78° C. for 10 minutes before addition of carbazole epoxide 2-A. The heterogeneous mixture was stirred at room temperature for 5 minutes before heating at 100° C. for 48 hours. The cooled reaction was diluted with EtOAc and washed three times with 5% acetic acid solution, followed by a brine wash. The organic layer was dried over Na$_2$SO$_4$, filtered and condensed. The crude mixture was purified in 100% dichloromethane. Yield=88%

$^1$H NMR (CDCl$_3$, 400 MHz) δ 8.23 (d, 2H, J=8.5 Hz), 8.06 (d, 2H, J=1.9 Hz), 7.65 (d, 2H, J=8.5 Hz), 7.46, (dd, 2H, J=8.6, 1.9 Hz), 7.22 (d, 2H, J=8.8 Hz), 6.94 (d, 2H, 8.8 Hz), 6.83 (d, 2H, 9.1 Hz), 4.44 (dd, 1H, J=14.9, 3.6 Hz), 4.26-4.34 (m, 1H), 4.17-4.24 (bs, 1H), 3.81 (s, 3H), 3.62-3.75 (m, 2H).

MS (ESI), m/z: 732.0 [(M+HCOO$^-$); C28H23Br2N3O6S (M) requires 687]

Representative Procedure 4

Fluorination of Secondary Alcohol

N-(3-(3,6-dibromo-9H-carbazol-9-yl)-2-fluoropropyl)-N-(3-methoxyphenyl)-4-nitrobenzenesulfonamide

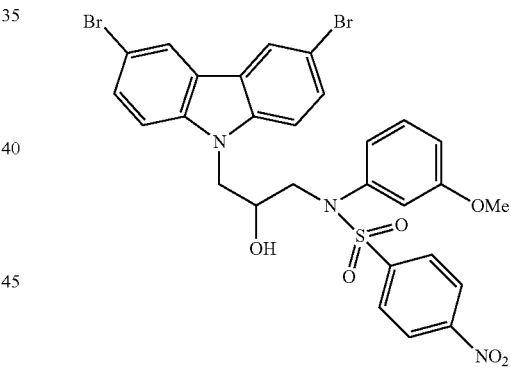

An oven dried 20 ml scintillation vial containing N-(3-(3,6-dibromo-9H-carbazol-9-yl)-2-hydroxypropyl)-N-(3-methoxyphenyl)-4-nitrobenzenesulfonamide (18.3 mg, 0.027 mmol; see representative procedure 3 above) was purged with N$_2$ and charged with anhydrous dichloromethane (1.5 ml, 0.018 M). The sealed vial was cooled in a dry ice acetone bath before the dropwise addition of diethylaminosulfur trifluoride (DAST, 7 ul, 0.053 mmol). The reaction temperature was maintained at −78° C. for an hour and then slowly warmed to room temperature and stirred overnight. The reaction was quenched with 2.0 ml of saturated NaHCO$_3$ solution and diluted with 6 ml CH$_2$Cl$_2$ and extracted three times. The combined organics were dried over Na$_2$SO$_4$, filtered and condensed. Crude product carried forward. Quantitative yield.

Alternatively, morpholinosulfur trifluoride (MORPHO-DAST) can be used at rt.

¹H NMR (CDCl₃, 400 MHz) δ 8.28 (d, 2H, J=8.0 Hz), 8.13 (s, 2H), 7.72 (d, 2H, J=8.7 Hz), 7.54, (d, 2H, J=8.0 Hz), 7.21 (d, 3H, J=8.1 Hz), 6.89 (dd, 1H, 8.3, 2.4 Hz), 6.67 (t, 1H, J=2.0 Hz), 6.55 (d, 1H, J=8.0 Hz) 4.93 (m, 1H), 4.43-4.68 (m, 2H), 4.20 (t, 1H, J=6.2 Hz), 3.81-3.99 (m, 2H), 3.75 (s, 3H).

MS (ESI), m/z: calculated 688.96, found 733.9 (M+HCOO⁻).

Representative Procedure 5

Nosyl Group Deprotection (See Fukuyama, T; Jow, C.-K; Cheung, M. *Tetrahedron Lett.* 1995, 36, 6373-6374)

N-(3-(3,6-dibromo-9H-carbazol-9-yl)-2-fluoropropyl)-3-methoxyaniline

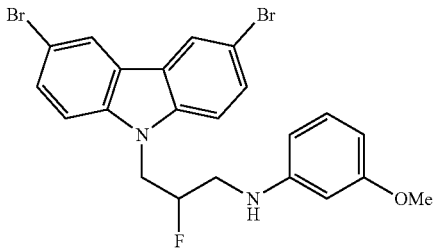 [SMILES: COc1cccc(NCC(F)Cn2c3ccc(Br)cc3c3cc(Br)ccc32)c1]

To a vial containing N-(3-(3,6-dibromo-9H-carbazol-9-yl)-2-fluoropropyl)-N-(3-methoxyphenyl)-4-nitrobenzenesulfonamide (21.0 mg, 0.030 mmol; see representative procedure 4) was added lithium hydroxide (3.2 mg, 0.134 mmol), dimethylformamide (0.5 ml, 0.06 M) and mercaptoacetic acid (4.2 ul 0.060 mmol). After stirring at rt for 1 h the reaction mixture was diluted with EtOAc and washed sequentially with water, saturated sodium bicarbonate solution, water (3×) and brine. The organic layer was dried over Na₂SO₄, filtered and condensed. The crude reaction mixture was purified in 30% EtOAc/hexanes (+0.2% TEA), with 13.6 mg isolated. Yield=88%

Additional Representative Procedure

DAST [(Et₂NSF₃) 0.12 ml, 0.916 mmol] was added dropwise to a solution of 1-(3,6-dibromo-9H-carbazol-9-yl)-3-(3-methoxyphenylamino)propan-2-ol (0.102 g, 0.203 mmol) in 6.0 ml of anhydrous DCM at −78° C. The reaction was stirred at −78° C. for one hour before being slowly warmed to 0° C. over 5 hours. The reaction was quenched by addition of phosphate buffer (pH=8) and extracted with DCM. The aqueous phase was extracted twice with 10 ml DCM. The combined organics were dried over Na₂SO4, filtered and concentrated. The crude reaction material was purified by flash chromatography on SiO2 (20% EtOAc/hexanes/0.2% TEA). Fractions containing the desired fluorinated product were further purified with 40% EtOAc/hexanes (+0.1% TEA). Isolated 5.7 mg desired product.

Analytical Data for the Title Compound of Example 6a

¹H NMR (CDCl₃, 500 MHz) δ 8.16 (2H, J=2.0 Hz), 7.56 (dd, 2H, J=1.9, 8.7 Hz), 7.31 (d, 2H, J=8.6 Hz), 7.11 (t, 1H, J=8.1 Hz), 6.36 (dd, 1H, J=2.2, 8.1 Hz), 6.23 (dd, 1H, J=2.0, 8.0 Hz), 6.15 (t, 1H, J=2.3 Hz), 5.11 (dddd, 1H, J=4.6, 5.8, 10.4, 47.7 Hz), 4.60 (m, 2H), 4.39 (dm, 2H), 3.95 (t, 1H, J=6.3 Hz), 3.75 (s, 3H)

MS (ESI), m/z: 504.9 (M+1)⁺. ([M+1]+ for C₂₂H₁₉Br₂FN₂O calculated 505.0)

Example 6b

N-(3-(3,6-dibromo-9H-carbazol-9-yl)-2-fluoropropyl)-3-methoxy-N-methylaniline

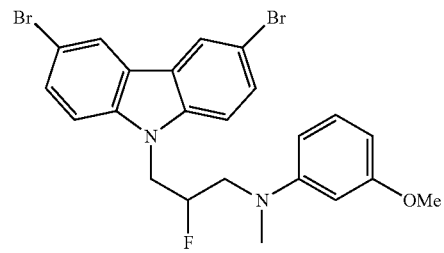 [SMILES: COc1cccc(N(C)CC(F)Cn2c3ccc(Br)cc3c3cc(Br)ccc32)c1]

The title compound of Example 6b was prepared according to the procedure described in Representative Procedure 4 except using 1-(3,6-dibromo-9H-carbazol-9-yl)-3-((3-methoxyphenyl)(methyl)-amino)propan-2-ol (see Example 23)

¹H NMR (CDCl₃, 500 MHz) δ 8.13 (d, 2H, J=1.9 Hz), 7.54 (dd, 2H, J=1.9, 8.8 Hz), 7.23 (d, 2H, J=8.7 Hz), 7.12 (t, 1H, J=8.2 Hz), 6.32 (dd, 1H, J=2.2, 8.1 Hz), 6.26 (dd, 1H, J=2.3, 8.0 Hz), 6.17 (t, 1H, J=2.4 Hz), 5.10 (dddd, 1H, J=4.6, 6.4, 10.7, 48.5 Hz), 4.37-4.48 (m, 2H), 3.72 (s, 3H), 3.60-3.71 (m, 1H), 3.53 (td, 1H, J=6.9, 15.9 Hz), 2.99 (s, 3H).

MS (ESI), m/z: 518.9 [M+1]⁺ ([M+H]+ for C23H21Br2FN2O requires 519.0.)

Example 7a 1-(3,6-dibromo-9H-carbazol-9-yl)-3-(3-methoxyphenylamino)-propan-2-one

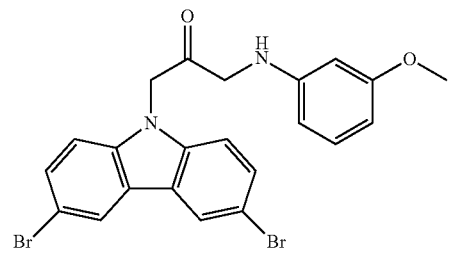 [SMILES: COc1cccc(NCC(=O)Cn2c3ccc(Br)cc3c3cc(Br)ccc32)c1]

Trietheylamine (1.65 ml, 11.8 mmol) was added to a stirring solution of 1-(3,6-dibromo-9H-carbazol-9-yl)-3-(3-methoxyphenylamino)propan-2-ol (1.02 g, 2.02 mmol) in DMSO (21 ml). The solution was stirred for 30 minutes before addition of sulfur trioxide pyridine complex (0.659 g, 4.14 mmol). After stirring overnight, additional triethylamine (1.0 ml, 7.17 mmol) was added, followed by sulfur trioxide pyridine complex (0.663 mg, 4.17 mmol) an hour later. After stirring for 1 h, the orange solution was diluted with ~150 ml ethyl acetate and washed several times with water and then brine. The organic layer was dried over Na₂SO4, filtered and concentrated to yield brown foam. Flash chromatography on SiO₂ 100% (CH₂Cl₂+0.2% TEA) provided a higher R_f ketone (thioether, 18%) and a lower R_f ketone (Yield=40%).

Major product: ¹H NMR (CDCl₃, 400 MHz) δ 8.18 (2H, J=1.9 Hz), 7.56 (dd, 2H, J=1.9, 8.7 Hz), 7.11 (d, 2H, J=8.8

Hz), 7.06 (t, 1H, J=8.1 Hz), 6.30 (dd, 1H, J=2.3, 8.2 Hz), 6.07 (dd, 1H, J=2.0, 8.0 Hz), 6.11 (t, 1H, J=2.2 Hz), 5.08 (s, 2H), 4.41 (t, 1H, J=4.8 Hz), 3.90 (d, 2H, J=5.1 Hz), 3.72 (s, 3H)
$^{13}$C NMR (CDCl$_3$, 126 MHz) δ=202.9, 161.1, 147.9 (2C), 139.5, 130.6 (2C), 129.9 (2C), 124.1 (2C), 123.9 (2C), 113.5, 110.1 (2C), 103.7, 99.3, 55.4, 51.9, 51.0.
MS (ESI), m/z: 500.9 (M+1)$^+$ ([M+1]+ for C22H18Br2N2O2 requires 501.0)

Example 7b 3-(3,6-dibromo-9H-carbazol-9-yl)-1-(3-methoxyphenylamino)-1-(methylthio)propan-2-one

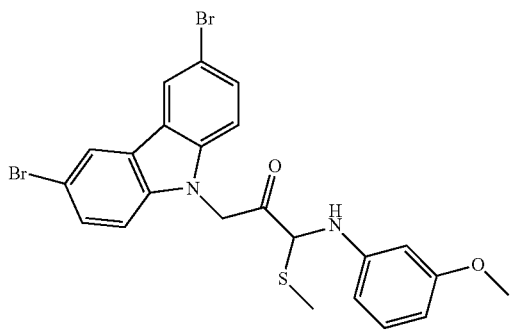 [SMILES: COc1cccc(NC(SC)C(=O)Cn2c3ccc(Br)cc3c3cc(Br)ccc32)c1]

The title compound of Example 7b was obtained as a minor product in the preparation of the title compound of Example 7a.
$^1$H NMR (CDCl$_3$, 400 MHz): δ 8.16 (d, 2H, J=2.0 Hz), 7.55 (dd, 2H, J=1.7, 8.8 Hz), 7.25 (d, J=8.8 Hz, 2H), 7.12 (t, 1H, J=8.4 Hz), 6.39 (dd, 1H, J=2.2, 8.2 Hz), 6.33 (dd, 1H, J=2.2, 8.0 Hz), 6.29 (t, 1H, J=2.2 Hz), 5.50 (d, 1H, J=18.0 Hz), 5.22 (d, 1H, J=18.4 Hz), 5.25 (d, J=8.0 Hz, 1H), 4.50 (d, J=8.0 Hz, 1H, exchangeable), 3.76 (s, 3H), 1.74 (s, 3H)
$^{13}$C NMR (CDCl$_3$, 126 MHz) δ=193.2, 160.9, 143.9 (2C), 139.8 (2C), 130.4, 129.8 (2C), 124.1, 123.7 (2C), 113.4 (2C), 110.3 (2C), 107.8, 104.7, 101.0, 60.3, 55.4, 48.9, 9.0
ESI m/z 498.9 [M–SMe+H]$^+$ ([M–SMe+H]+ for C$_{23}$H$_{20}$Br$_2$N$_2$O$_2$S requires 499.0.
HRMS m/z: 546.9675 [M+H]+ ([M+H]+ for C$_{23}$H$_{20}$Br$_2$N$_2$O$_2$S requires 545.9612.

Example 8

N-(3-(3,6-dibromo-9H-carbazol-9-yl)-2-methoxypropyl)-3-methoxyaniline

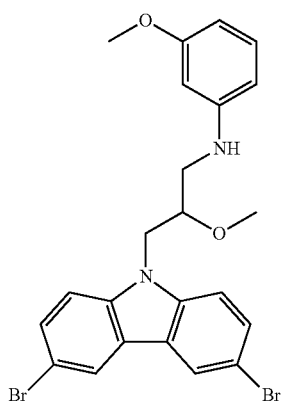 [SMILES: COc1cccc(NCC(Cn2c3ccc(Br)cc3c3cc(Br)ccc32)OC)c1]

Sodium hydride (9.0 mg, 0.23 mmol) was added to a stirring solution of 1-(3,6-dibromo-9H-carbazol-9-yl)-3-(3-methoxyphenylamino)propan-2-ol (99.3 mg, 0.20 mmol) in DMF 0.5 ml, 0.39 M). The solution was stirred at room temperature for about 70 minutes before the dropwise addition of a solution of methyl iodide (14 ml. 0.22 mol) in DMF (1.0 ml). The reaction was monitored by lc/ms for the consumption of SM and the appearance of O and N-methyl products. After 2.5 hours of stirring at r.t, conversion was about 30% and about 5% N-methyl product had formed. The reaction was stopped when an increase of N-Me to O-Me had been observed and conversion was about 50%. The brown solution was diluted with ethyl acetate and washed several times with water and finally brine. The organic layer was dried over Na$_2$SO$_4$, filtered and condensed. The mixture was purified by preparative TLC 30% EtOAc/hexanes.
$^1$H NMR (CDCl$_3$, 400 MHz) δ 8.13 (s, 2H), 7.51 (dd, 2H, J=1.8, 8.8 Hz), 7.31 (d, 2H, J=8.7 Hz), 7.09 (t, 1H, J=8.2 Hz), 6.33 (dd, 1H, J=2.3, 8.3 Hz), 6.21 (dd, 1H, J=2.1, 8.0 Hz), 6.12 (m, 1H), 4.42 (m, 1H), 4.03 (bs, 1H), 3.85 (m, 1H), 3.74 (s, 3H), 3.29 (s, 3H), 3.09 (m, 2H)
$^{13}$C NMR (CDCl$_3$, 126 MHz) δ 161.0, 149.4, 139.8, 130.4, 129.5, 123.8, 123.5, 112.7, 110.9, 106.7, 103.6, 99.7, 78.2, 58.3, 55.3, 45.3, 44.3.
MS (ESI), m/z: 516.9 (M+1)$^+$ ([M+1]+ for C$_{23}$H$_{22}$Br$_2$N$_2$O$_2$ requires 517.0).

Example 9

1-(3,6-Dimethyl-9H-carbazol-9-yl)-3-(3-methoxyphenylamino)propan-2-ol

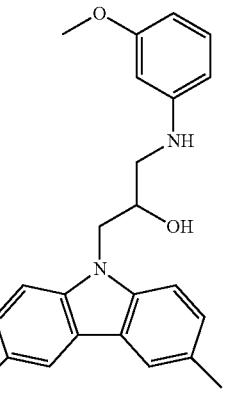

Step 1. Synthesis of
3,6-Dimethyl-9-(oxiran-2-ylmethyl)-9H-carbazole

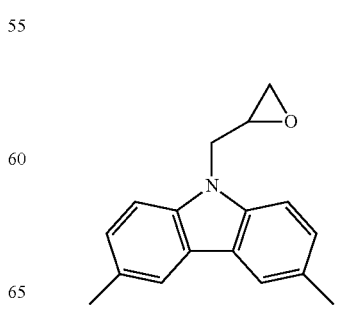

Following Representative Procedure 1, 3,6-dimethyl carbazole (Beyer, M; Fritscher, J; Feresin, E; Schiemann, O. *J. Org. Chem.* 2003, 68, 2209-2215) was added to epichlorohydrin in 69% yield.

$^1$H NMR (CDCl$_3$, 500 MHz) δ 7.84 (d, 2H, J=1.0 Hz), 7.30 (d, 2H, J=8.5 Hz), 7.26 (dd, 2H, J=1.0, 8.5 Hz), 4.54 (dd, 1H, J=3.5, 16.0 Hz), 4.35 (dd, 1H, J=4.5, 16.0 Hz), 3.30 (m, 1H), 2.76 (dd, 1H, J=4.0, 5.0 Hz), 2.52 (s, 6H), 2.51 (m, 1H)

Step 2. Synthesis of 1-(3,6-Dimethyl-9H-carbazol-9-yl)-3-(3-methoxyphenylamino)propan-2-ol

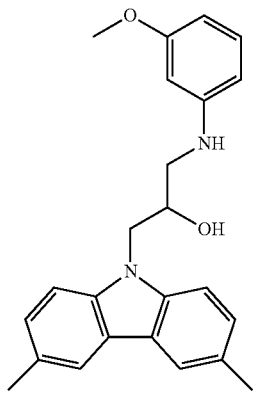

Following Representative procedure 2, 1-(3,6-Dimethyl-9H-carbazol-9-yl)-3-(3-methoxyphenylamino)propan-2-ol was prepared from 3,6-Dimethyl-9-(oxiran-2-ylmethyl)-9H-carbazole in 22% following purification by preparative TLC.

$^1$H NMR (CDCl$_3$, 500 MHz) δ 7.84 (d, 2H, J=0.5 Hz), 7.30 (d, 2H, J=8.0 Hz), 7.23 (d, 2H, J=8.0 Hz), 7.05 (t, 1H, J=8.0 Hz), 6.28 (dd, 1H, J=2.5, 8.0 Hz), 6.21 (dd, 1H, J=2.5, 8.0 Hz), 6.12 (dd, 1H, J=2.0, 2.5 Hz), 4.39 (m, 3H), 4.01 (br s, 1H), 3.68 (s, 3H), 3.31 (dd, 1H, J=3.0, 11.5 Hz), 3.17 (dd, 1H, J=6.5, 13.0 Hz), 2.51 (s, 6H), 2.13 (br s, 1H)

$^{13}$C NMR (CDCl$_3$, 125 MHz) δ 161.0, 149.5, 139.5 (2C), 130.3 (2C), 128.7, 127.3 (2C), 123.2 (2C), 120.5 (2C), 108.7 (2C), 106.7, 103.7, 99.5, 69.7, 55.2, 48.0, 47.4, 21.6 (2C).

ESI m/z 375.2 ([M+H]$^+$, C$_{24}$H$_{27}$N$_2$O$_2$ requires 375.2)

Example 10

1-(3-Bromo-6-methyl-9H-carbazol-9-yl)-3-(3-methoxyphenylamino)-propan-2-ol

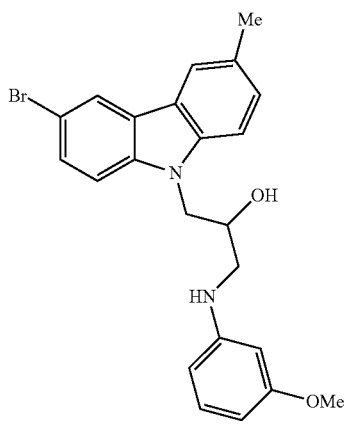 [SMILES: COc1cccc(NCC(O)Cn2c3ccc(C)cc3c3cc(Br)ccc32)c1]

Step 1. Synthesis of 3-Bromo-6-methyl-9-(oxiran-2-ylmethyl)-9H-carbazole

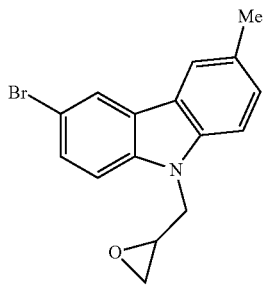

Following Representative Procedure 2, Example 14 was prepared in 74% yield.

$^1$H NMR (CDCl$_3$, 500 MHz) δ 8.13 (d, 1H, J=1.5 Hz), 7.80 (d, 1H, J=1.0 Hz), 7.50 (dd, 1H, J=2.0, 8.5 Hz), 7.33-7.28 (m, 3H), 4.57 (dd, 1H, J=3.0, 15.5 Hz), 4.29 (dd, 1H, J=5.0, 15.5 Hz), 3.29 (m, 1H), 2.77 (dd, 1H, J=4.0, 4.5 Hz), 2.51 (s, 3H), 2.48 (dd, 1H, J=2.5, 4.5 Hz)

Step 2. Synthesis of 1-(3-Bromo-6-methyl-9H-carbazol-9-yl)-3-(3-methoxyphenylamino)-propan-2-ol

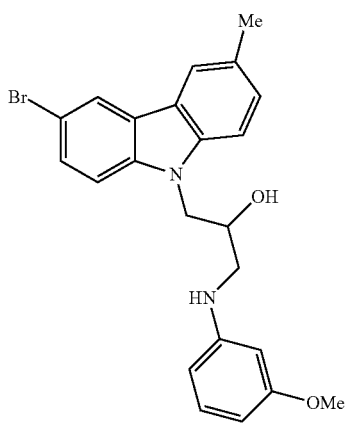 [SMILES: COc1cccc(NCC(O)Cn2c3ccc(C)cc3c3cc(Br)ccc32)c1]

Following Representative Procedure 2, Example 15 was prepared from 3-Bromo-6-methyl-9-(oxiran-2-ylmethyl)-9H-carbazole in 41% yield.

$^1$H NMR (CDCl$_3$, 500 MHz) δ 8.14 (d, 1H, J=2.0 Hz), 7.81 (s, 1H), 7.48 (dd, 1H, J=2.0, 8.5 Hz), 7.31 (d, 1H, J=5.0 Hz), 7.29 (br s, 1H), 7.06 (t, 1H, J=8.5 Hz), 6.29 (dd, 1H, J=2.0, 8.0 Hz), 6.21 (dd, 1H, J=2.0, 8.0 Hz), 6.11 (t, 1H, J=2.0 Hz), 4.37 (m, 3H), 3.99 (br s, 1H), 3.70 (s, 3H), 3.30 (dd, 1H, J=3.5, 13.5 Hz), 3.16 (dd, 1H, J=6.5, 13.5 Hz), 2.51 (s, 3H), 2.14 (br s, 1H)

$^{13}$C NMR (CDCl$_3$, 125 MHz) δ 161.0, 149.4, 139.8, 139.5, 130.3, 129.4, 128.5, 128.2, 124.7, 123.2, 122.3 120.7, 112.1, 110.6, 109.0, 106.7, 103.7, 99.6, 69.5, 55.3, 47.9, 47.4, 21.5.

ESI m/z 439.1 ([M+H]$^+$, C$_{23}$H$_{24}$BrN$_2$O$_2$ requires 439.1)

Example 11

1-(3,6-Dichloro-9H-carbazol-9-yl)-3-(3-methoxyphenylamino)propan-2-ol

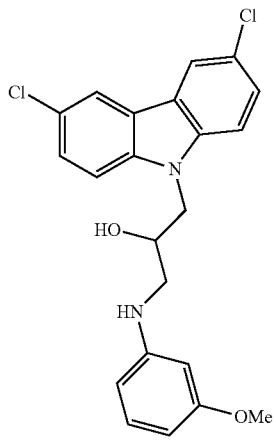 [SMILES: COc1cccc(NCC(O)Cn2c3ccc(Cl)cc3c3cc(Cl)ccc32)c1]

Step 1. Synthesis of 3,6-Dichloro-9-(oxiran-2-ylmethyl)-9H-carbazole

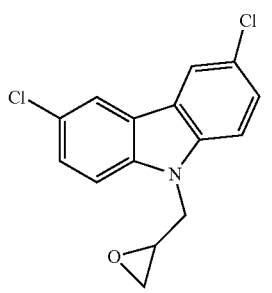 [SMILES: Clc1ccc2c(c1)c1cc(Cl)ccc1n2CC1CO1]

Following Representative Procedure 1, 3,6-Dichloro-9-(oxiran-2-ylmethyl)-9H-carbazole was prepared in 23% yield.

$^1$H NMR (CDCl$_3$, 600 MHz) δ 7.92 (d, 2H, J=1.8 Hz), 7.40 (dd, 2H, J=1.8, 9.0 Hz), 7.32 (d, 2H, J=9.0 Hz), 4.59 (dd, 1H, J=3.0, 16.2 Hz), 4.22 (dd, 1H, J=5.4, 16.2 Hz), 3.27 (m, 1H), 2.78 (dd, 1H, J=4.2, 4.8 Hz), 2.46 (dd, 1H, J=2.4, 4.8 Hz)

Step 2. Synthesis of 1-(3,6-Dichloro-9H-carbazol-9-yl)-3-(3-methoxyphenylamino)propan-2-ol

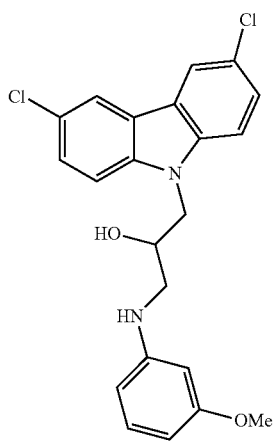 [SMILES: COc1cccc(NCC(O)Cn2c3ccc(Cl)cc3c3cc(Cl)ccc32)c1]

Following Representative Procedure 2, 1-(3,6-dichloro-9H-carbazol-9-yl)-3-(3-methoxyphenylamino)propan-2-ol was prepared from 3,6-Dichloro-9-(oxiran-2-ylmethyl)-9H-carbazole in 37% yield.

$^1$H NMR (CDCl$_3$, 500 MHz) δ 7.95 (d, 2H, J=2.0 Hz), 7.38 (dd, 2H, J=2.0, 8.5 Hz), 7.33 (d, 2H, J=9.0 Hz), 7.06 (t, 1H, J=8.0 Hz), 6.30 (dd, 1H, J=2.0, 8.0 Hz), 6.20 (dd, 1H, J=2.0, 8.0 Hz), 6.11 (dd, 1H, J=2.0, 2.5 Hz), 4.30-4.35 (m, 3H), 3.70 (s, 3H), 3.28 (dd, 1H, J=3.5, 13.0 Hz), 3.13 (dd, 1H, J=6.5, 13.0 Hz)

$^{13}$C NMR (CDCl$_3$, 150 MHz) δ 161.0, 149.3, 139.7, 130.4 (2C), 126.9 (2C), 125.5 (2C), 123.4 (2C), 120.4 (2C), 110.5 (2C), 106.7, 103.8, 99.8, 69.6, 55.3, 48.0, 47.5.

ESI m/z 415.0 ([M+H]$^+$, C$_{22}$H$_{20}$Cl$_2$N$_2$O$_2$ requires 415.1)

Example 12

1-(5-bromo-2,3-dimethyl-1H-indol-1-yl)-3-(phenylamino)propan-2-ol

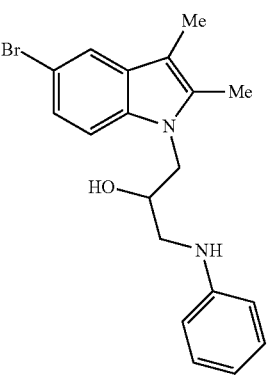 [SMILES: Cc1c(C)n(CC(O)CNc2ccccc2)c2ccc(Br)cc12]

Step 1. Synthesis of 5-Bromo-2,3-dimethyl-1H-indole

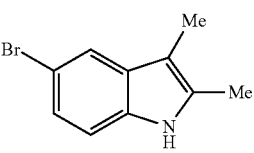 [SMILES: Cc1[nH]c2ccc(Br)cc2c1C]

Following a published procedure (Gundersen, E. G. U.S. Patent App. Publ. US 2005/070592) 2-Butanone (0.11 mL, 1.278 mmol) was added to a solution of 4-bromophenylhydrazine hydrochloride (0.300 g, 1.342 mmol in EtOH (3.8 mL). The mixture was heated to reflux for 22 h, concentrated in vacuo, and partitioned between EtOAC and 1N HCl. The organic layer was washed with H$_2$O and saturated aqueous NaHCO$_3$, dried over Na$_2$SO$_4$, filtered, and concentrated. The crude residue was purified by chromatography (SiO$_2$, 0-20% EtOAc/Hexane) to afford the desired indole as a pink powder (200 mg, 67%).

$^1$H NMR (CDCl$_3$, 500 MHz) δ 7.69 (br s, 1H), 7.55 (d, 1H, J=2.0 Hz), 7.15 (dd, 1H, J=2.0, 8.5 Hz), 7.09 (dd, 1H, J=0.5, 8.5 Hz), 2.34 (s, 3H), 2.15 (d, 3H, J=0.5 Hz)

ESI m/z 224.0 ([M+H]$^+$, C$_{10}$H$_{11}$BrN requires 224.0)

Step 2. Synthesis of 5-Bromo-2,3-dimethyl-1-(oxiran-2-ylmethyl)-1H-indole

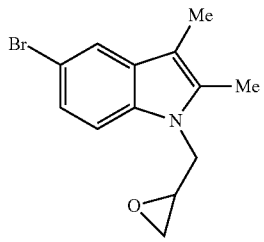 [SMILES: Cc1c(C)n(CC2CO2)c2ccc(Br)cc12]

Following Representative Procedure 1, 5-bromo-2,3-dimethyl-1-(oxiran-2-ylmethyl)-1H-indole was prepared from 5-Bromo-2,3-dimethyl-1H-indole in 48% yield.

$^1$H NMR (CDCl$_3$, 500 MHz) δ 7.58 (d, 1H, J=2.0 Hz), 7.20 (dd, 1H, J=2.0, 8.5 Hz), 7.10 (d, 1H, J=8.5 Hz), 4.35 (dd, 1H, J=3.0, 16.0 Hz), 4.09 (dd, 1H, J=4.5, 16.0 Hz), 3.17 (m, 1H), 2.72 (t, 1H, J=4.5 Hz), 2.35 (dd, 1H, J=3.0, 5.0 Hz), 2.33 (s, 3H), 2.19 (s, 3H).

ESI m/z 280.0 ([M+H]$^+$, C$_{13}$H$_{15}$BrNO requires 280.0)

Step 3. Synthesis of 1-(5-bromo-2,3-dimethyl-1H-indol-1-yl)-3-(phenylamino)propan-2-ol

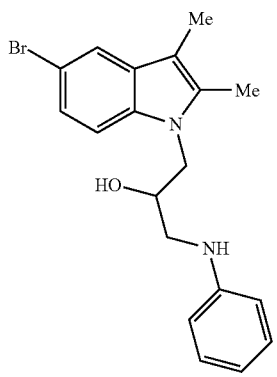 [SMILES: Cc1c(C)n(CC(O)CNc2ccccc2)c2ccc(Br)cc12]

Following Representative Procedure 2, 1-(5-bromo-2,3-dimethyl-1H-indol-1-yl)-3-(phenylamino)propan-2-ol was prepared from 5-Bromo-2,3-dimethyl-1-(oxiran-2-ylmethyl)-1H-indole in 39% yield.

$^1$H NMR (CDCl$_3$, 500 MHz) δ 7.58 (d, 1H, J=2.0 Hz), 7.17 (dd, 2H, J=7.0, 8.5

Hz), 7.11 (d, 1H, J=8.5 Hz), 6.75 (t, 1H, J=7.0 Hz), 6.60 (d, 2H, J=8.5 Hz), 4.17 (m, 1H), 4.15 (m, 2H), 3.27 (dd, 1H, J=3.0, 8.5 Hz), 3.12 (dd, 1H, J=7.0, 13.0 Hz), 2.34 (s, 3H), 2.19 (s, 3H)

$^{13}$C NMR (CDCl$_3$, 125 MHz) δ 147.9, 135.1, 134.3, 130.6, 129.6 (2C), 123.6, 120.9, 118.6, 113.7 (2C), 112.5, 110.5, 107.1, 69.9, 47.7, 47.4, 10.7, 9.0

ESI m/z 373.0 ([M+H]$^+$, C$_{19}$H$_{22}$BrN$_2$O requires 373.1).

Example 13

1-(3,6-Dibromo-9H-pyrido[3,4-b]indol-9-yl)-3-(phenylamino)propan-2-ol

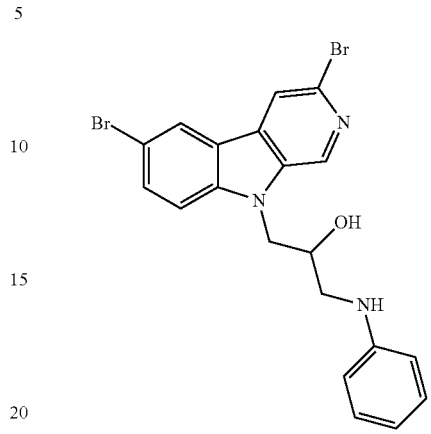

Step 1. Synthesis of 3,6-Dibromo-β-carboline

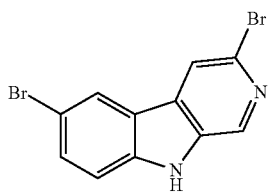 [SMILES: Brc1ccc2[nH]c3cnc(Br)cc3c2c1]

Following a literature procedure (Ponce, M. A; Erra-Balsells, R. *J. Heterocyclic Chem.* 2001, 38, 1087) β-Carboline (0.100 g, 0.595 mmol) and SiO$_2$ (1.00 g) were suspended in CH$_2$Cl$_2$ (15 mL). N-Bromosuccinimide (0.212 g, 1.189 mmol) was dissolved in CH$_2$Cl$_2$ (15 mL) and the solution was added to the carboline mixture slowly via syringe in the absence of light. The reaction was stirred at ambient temperature for 2.5 h, after which the silica gel was filtered off and washed 3×CH$_2$Cl$_2$. The combined organic layer was extracted with 0.1 M NaOH and saturated aqueous NaCl, dried over Na$_2$SO$_4$, filtered, and concentrated in vacuo. The crude product was purified by chromatography (SiO$_2$, 0-100% EtOAc/Hexane) to afford the desired 3,6-dibrominated carboline (25 mg, 13%) as well as 6,8-dibrominated carboline (15 mg, 8%) and the tribrominated carboline (36 mg, 19%).

$^1$H NMR (d$_6$-DMSO, 500 MHz) δ 8.72 (s, 1H), 8.58 (d, 1H, J=1.5 Hz), 8.48 (s, 1H), 7.70 (dd, 1H, J=1.5, 9.0 Hz), 7.58 (d, 1H, J=9.0 Hz).

ESI m/z 326.9 ([M+H]$^+$, C$_{11}$H$_7$Br$_2$N$_2$ requires 326.9).

Step 2. Synthesis of 3,6-Dibromo-9-(oxiran-2-ylmethyl)-9H-pyrido[3,4-b]indole

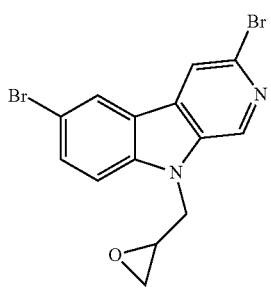 [SMILES: Brc1ccc2c(c1)c1cc(Br)ncc1n2CC1CO1]

Following Representative Procedure 1, 3,6-dibromo-9-(oxiran-2-ylmethyl)-9H-pyrido[3,4-b]indole was prepared from 3,6-dibromo-β-carboline in 73% yield.

$^1$H NMR (CDCl$_3$, 400 MHz) δ 8.62 (d, 1H, J=0.8 Hz), 8.17 (d, 1H, J=2.0 Hz), 8.02 (d, 1H, J=1.2 Hz), 7.69 (dd, 1H, J=2.0, 8.8 Hz), 7.41 (d, 1H, J=8.8 Hz), 5.34 (br s, 1H), 4.73 (dd, 1H, J=2.4, 16.0 Hz), 4.27 (dd, 1H, J=5.2, 16.0 Hz), 3.32 (m, 1H), 2.83 (dd, 1H, J=4.0, 4.4 Hz), 2.49 (dd, 1H, J=2.4, 4.4 Hz).

ESI m/z 382.9 ([M+H]$^+$, C$_{14}$H$_{11}$Br$_2$N$_2$O requires 382.9).

Step 3. Synthesis of 1-(3,6-Dibromo-9H-pyrido[3,4-b]indol-9-yl)-3-(phenylamino)propan-2-ol

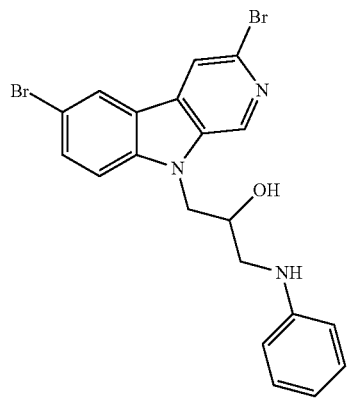 [SMILES: OC(CNc1ccccc1)Cn1c2ccc(Br)cc2c2cc(Br)ncc21]

Following Representative Procedure 2, 1-(3,6-dibromo-9H-pyrido[3,4-b]indol-9-yl)-3-(phenylamino)propan-2-ol was prepared from 3,6-dibromo-9-(oxiran-2-ylmethyl)-9H-pyrido[3,4-b]indole in 14% yield after purification by preparative TLC.

$^1$H NMR (CDCl$_3$, 500 MHz) δ 8.64 (s, 1H), 8.18 (d, 1H, J=2.0 Hz), 7.99 (s, 1H), 7.66 (dd, 1H, J=1.5, 9.0 Hz), 7.40 (d, 1H, J=9.0 Hz), 7.18 (dd, 2H, J=7.5 Hz), 6.76 (t, 1H, J=7.5 Hz), 6.63 (d, 2H, J=8.5 Hz), 5.33 (br s, 1H), 4.38-4.49 (m, 3H), 3.37 (dd, 1H, J=4.0, 13.0 Hz), 3.21 (dd, 1H, J=7.0, 13.0 Hz)

$^{13}$C NMR (CDCl$_3$, 125 MHz) δ 147.7, 141.2, 137.0, 132.6, 132.5, 130.9, 130.1, 129.7 (2C), 125.0, 122.0, 119.0, 118.6, 113.8 (2C), 113.4, 111.9, 69.6, 48.1, 47.9

ESI m/z 475.9 ([M+H]$^+$, C$_{20}$H$_{18}$Br$_2$N$_3$O requires 476.0)

Example 14

1-(3-Azidophenylamino)-3-(3,6-dibromo-9H-carbazol-9-yl)propan-2-ol

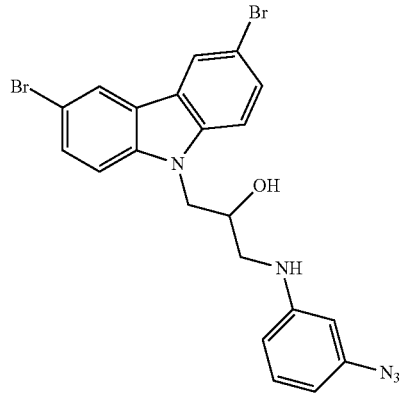 [SMILES: [N-]=[N+]=Nc1cccc(NCC(O)Cn2c3ccc(Br)cc3c3cc(Br)ccc32)c1]

Following Representative Procedure 2, Example 14 was prepared in 14% yield.

$^1$H NMR (CDCl$_3$, 500 MHz) δ 8.13 (d, 2H, J=2.0 Hz), 7.53 (dd, 2H, J=2.0, 8.5 Hz), 7.31 (d, 2H, J=8.5 Hz), 7.12 (t, 1H, J=8.0 Hz), 6.44 (dd, 1H, J=1.5, 8.0 Hz), 6.36 (dd, 1H, J=1.5, 8.0 Hz), 6.20 (dd, 1H, J=2.0 Hz), 4.35-4.41 (m, 3H), 4.10 (br s, 1H), 3.31 (dd, 1H, J=3.0, 13.0 Hz), 3.17 (dd, 1H, J=6.5, 13.0 Hz), 2.11 (br s, 1H)

ESI m/z 513.9 ([M+H]$^+$, C$_{21}$H$_{18}$Br$_2$N$_5$O requires 514.0)

Example 15

1,3-Bis(3,6-dibromo-9H-carbazol-9-yl)propan-2-ol

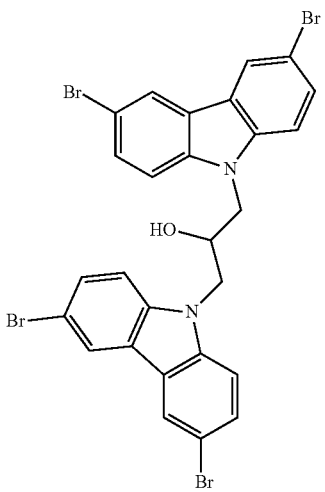 [SMILES: OC(Cn1c2ccc(Br)cc2c2cc(Br)ccc21)Cn1c2ccc(Br)cc2c2cc(Br)ccc21]

3,6-Dibromocarbazole (0.050 g, 0.154 mmol) was dissolved in DMF (1.5 mL) and cooled to 0° C. NaH (60% dispersion in mineral oil, 0.007 g, 0.169 mmol) was added and the reaction was stirred for 45 min at 0° C. 3,6-Dibromo-9-(oxiran-2-ylmethyl)-9H-carbazole (0.059 g, 0.154 mmol) was added and the reaction was stirred at ambient temperature for 24 h. Upon consumption of the starting material by TLC, the reaction was partitioned between EtOAc and H$_2$O. The aqueous layer was washed 3× with EtOAc, and the combined organics were washed with saturated aqueous NaCl, dried over Na$_2$SO$_4$, filtered, and concentrated in vacuo. The crude residue was purified by chromatography (SiO$_2$, 0-50% EtOAc/Hexane) to afford the desired product (37 mg, 34%).

$^1$H NMR (acetone-d$_6$, 400 MHz) δ 8.36 (d, 4H, J=2.0 Hz), 7.64 (d, 4H, J=8.8 Hz), 7.56 (dd, 4H, J=2.0, 8.8 Hz), 4.72 (m, 5H), 2.78 (br s, 1H)

$^{13}$C NMR (acetone-d$_6$, 100 MHz) δ 141.2 (4C), 129.8 (4C), 124.6 (4C), 124.1 (4C), 112.9 (4C), 112.7 (4C), 70.3, 48.3 (2C).

ESI m/z 747.0 ([M+CO$_2$H]$^-$, C$_{28}$H$_{19}$Br$_4$N$_2$O$_3$ requires 746.8)

Example 16

1-(9H-Carbazol-9-yl)-3-(3,6-dibromo-9H-carbazol-9-yl)propan-2-ol

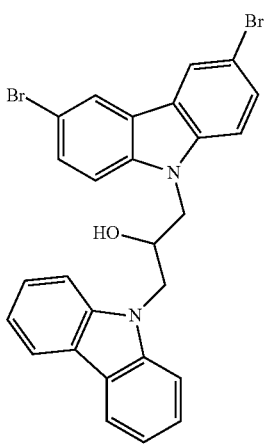 [SMILES: OC(Cn1c2ccccc2c2ccccc21)Cn1c2ccc(Br)cc2c2cc(Br)ccc21]

Following a procedure analogous to that used to prepare Example 15, Example 16 was prepared in 48% yield.

$^1$H NMR (acetone-$d_6$, 400 MHz) δ 8.36 (m, 2H), 8.14 (d, 2H, J=8.0 Hz), 7.63 (d, 2H, J=8.4 Hz), 7.55 (s, 2H), 7.42 (dt, 2H, J=1.2, 7.2 Hz), 7.20 (dt, 2H, J=0.8, 7.2 Hz), 4.76 (m, 1H), 4.64-4.72 (m, 4H), 2.77 (br s, 1H).

$^{13}$C NMR (acetone-$d_6$, 100 MHz) δ 142.0 (2C), 141.0 (2C), 129.8 (2C), 126.6 (2C), 124.5 (2C), 124.1 (2C), 123.8 (2C), 121.0 (2C), 119.9 (2C), 112.7 (2C), 112.6 (2C), 110.5 (2C), 70.3, 48.4, 48.1.

ESI m/z 591.0 ([M+CO$_2$H]$^-$, C$_{28}$H$_{21}$Br$_2$N$_2$O$_3$ requires 591.0).

Example 17

3-(3,6-Dibromo-9H-carbazol-9-yl)-2-hydroxy-N-(3-methoxyphenyl)-propanamide

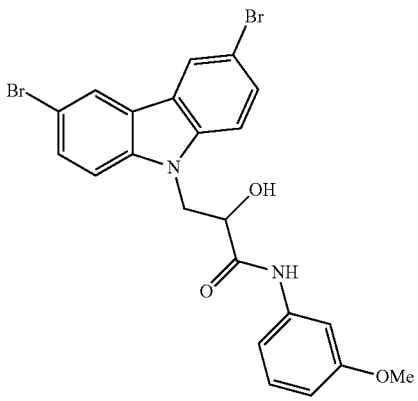 [SMILES: COc1cccc(NC(=O)C(O)Cn2c3ccc(Br)cc3c3cc(Br)ccc32)c1]

Step 1. Synthesis of Methyl 3-(3,6-Dibromo-9H-carbazol-9-yl)-2-hydroxypropanoate

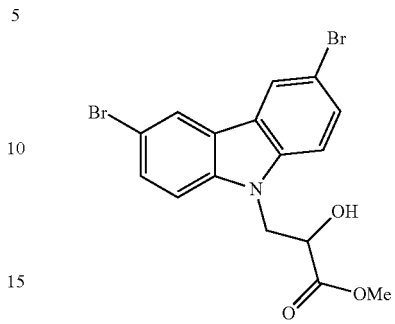

3,6-Dibromocarbazole (0.300 g, 0.923 mmol) was dissolved in DMF (1.2 mL) and cooled to 0° C. NaH (60% dispersion in mineral oil, 0.074 g, 1.846 mmol) was added and the reaction stirred for 1 h at 0° C. Methyl glycidate (0.471 g, 4.615 mmol) was added and the reaction was stirred and warmed to ambient temperature over 3.5 h. Upon completion by TLC the reaction mixture was partitioned between EtOAc and H$_2$O. The aqueous layer was extracted 3× with EtOAc, and the combined organics were washed with saturated aqueous NaCl, dried over Na$_2$SO$_4$, filtered, and concentrated in vacuo. The crude residue was purified by chromatography (SiO$_2$, 0-30% EtOAc/Hexane) to afford the desired product (125 mg, 32%).

$^1$H NMR (CDCl$_3$, 500 MHz) δ 8.10 (d, 2H, J=2.0 Hz), 7.53 (dd, 2H, J=2.0, 9.0 Hz), 7.36 (d, 2H, J=9.0 Hz), 4.63-4.55 (m, 3H), 3.69 (s, 3H), 2.94 (d, 1H, J=5.5 Hz).

ESI m/z 425.8 ([M+H]$^+$, C$_{16}$H$_{14}$Br$_2$NO$_3$ requires 425.9)

Step 2. Synthesis of 3-(3,6-Dibromo-9H-carbazol-9-yl)-2-hydroxypropanoic acid

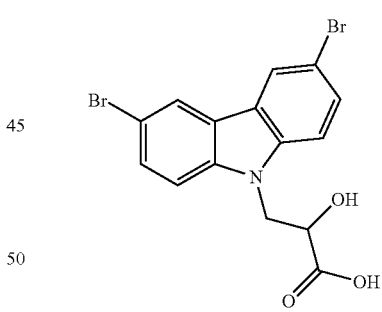

NaOH (0.64 mL, 1M solution in H$_2$O) was added to a suspension of methyl 3-(3,6-dibromo-9H-carbazol-9-yl)-2-hydroxypropanoate (0.055 g, 0.129 mmol) in EtOH (2.6 mL) and the reaction was stirred at ambient temperature for 2.5 h. The reaction was concentrated in vacuo and the residue was acidified with 1N aqueous HCl. The mixture was extracted with EtOAc (3×), and the combined organics were washed with saturated aqueous NaCl, dried over Na$_2$SO$_4$, filtered, and concentrated in vacuo to afford the desired product as a white solid (53 mg, 99%).

$^1$H NMR (CDCl$_3$, 500 MHz) δ 8.10 (d, 2H, J=1.5 Hz), 7.52 (dd, 2H, J=1.5, 8.5 Hz), 7.40 (d, 2H, J=9.0 Hz), 4.68 (m, 2H), 4.60 (dd, 1H, J=6.5, 15.5 Hz).

ESI m/z 411.9 ([M+H]$^+$, C$_{15}$H$_{12}$Br$_2$NO$_3$ requires 411.9)

Step 3. Synthesis of 3-(3,6-Dibromo-9H-carbazol-9-yl)-2-hydroxy-N-(3-methoxyphenyl)-propanamide

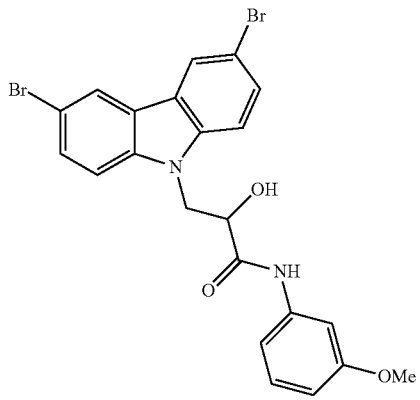 [SMILES: COc1cccc(NC(=O)C(O)Cn2c3ccc(Br)cc3c3cc(Br)ccc32)c1]

3-(3,6-Dibromo-9H-carbazol-9-yl)-2-hydroxypropanoic acid (0.025 g, 0.061 mmol) was suspended in anhydrous CH₂Cl₂ and cooled to 0° C. Thionyl chloride (0.005 mL, 0.073 mmol) was added dropwise and the reaction was stirred at 0° C. for 1 h. m-Anisidine (0.008 mL, 0.073 mmol) and Et₃N (0.010 mL, 0.073 mmol) were added and the reaction was allowed to warm to ambient temperature over 2.5 h. Upon completion, the solution was partitioned between EtOAc and H₂O. The aqueous layer was washed 3× with EtOAc, and the combined organics were washed with saturated aqueous NaCl, dried over Na₂SO₄, filtered, and concentrated in vacuo. The crude residue was purified by chromatography (SiO₂, 0-30% EtOAc/Hexane) to afford the desired product (15 mg, 48%).

$^1$H NMR (acetone-d$_6$, 500 MHz) δ 9.22 (br s, 1H), 8.34 (d, 2H, J=1.5 Hz), 7.65 (d, 2H, J=8.5 Hz), 7.59 (dd, 2H, J=4.0, 8.5 Hz), 7.42 (dd, 1H, J=2.0 Hz), 7.24 (m, 1H), 7.20 (dd, 1H, J=8.0 Hz), 6.67 (dd, 1H, J=2.0, 8.0 Hz), 5.56 (br s, 1H), 4.82 (m, 1H), 4.73 (m, 2H), 3.77 (s, 3H)

$^{13}$C NMR (CDCl₃, 100 MHz) δ 170.9, 161.1, 141.1, 140.3, 130.3 (2C), 129.8 (2C), 124.6 (2C), 124.0 (2C), 113.1 (2C), 112.8 (2C), 112.7, 110.5, 106.4, 72.7, 55.6, 48.4.

ESI m/z 514.9 ([M−H]⁻, C₂₂H₁₇Br₂N₂O₃ requires 515.0)

Example 18

Ethyl 5-(2-Hydroxy-3-(3-methoxyphenylamino)propyl)-8-methyl-3,4-dihydro-1H-pyrido[4,3-b]indole-2(5H)-carboxylate

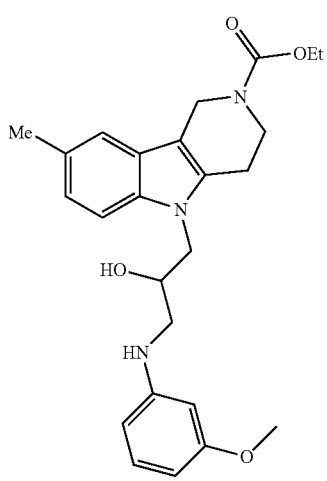 [SMILES: CCOC(=O)N1CCc2c(c3cc(C)ccc3n2CC(O)CNc2cccc(OC)c2)C1]

Step 1. Synthesis of Ethyl 8-Methyl-3,4-dihydro-1H-pyrido[4,3-b]indole-2(5H)-carboxylate

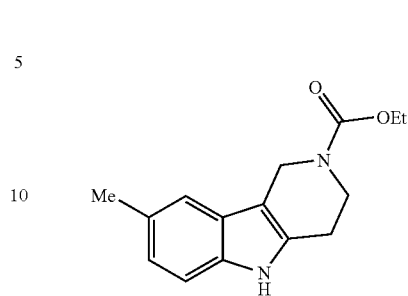

Following a literature procedure (Harbert, C. A; Plattner, J. J; Welch, W. M; Weissman, A; Koe, B. K. *J. Med. Chem.* 1980, 23, 635-643) p-tolylhydrazine hydrochloride (0.500 g, 3.15 mmol) and 1-carbethoxy-4-piperidone (0.18 mL, 1.17 mmol) were suspended in EtOH (0.880 mL) and heated to reflux for 2 hours. The reaction mixture was removed from heat and allowed to stand overnight at ambient temperature. The resulting mixture was filtered and washed with 50% aqueous EtOH to afford the desired product as a beige powder (259 mg, 86%).

$^1$H NMR (CDCl₃, 500 MHz) δ 7.73 (br s, 1H), 7.23 (s, 1H), 7.18 (d, 1H, J=8.0 Hz), 6.96 (d, 1H, J=8.0 Hz), 4.64 (br s, 2H), 4.18 (q, 2H, J=7.0 Hz), 3.85 (m, 2H), 2.81 (br s, 2H), 2.42 (s, 3H), 1.28 (t, 31-1, J=7.0 Hz).

Step 2. Synthesis of Ethyl 8-Methyl-5-(oxiran-2-ylmethyl)-3,4-dihydro-1H-pyrido[4,3-b]indole-2(5H)-carboxylate

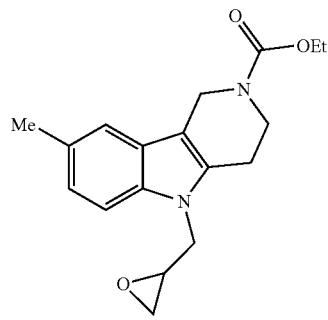 [SMILES: CCOC(=O)N1CCc2c(c3cc(C)ccc3n2CC2CO2)C1]

Ethyl 8-methyl-3,4-dihydro-1H-pyrido[4,3-b]indole-2(5H)-carboxylate (0.025 g, 0.097 mmol) was dissolved in anhydrous degassed THF and was cooled to −78° C. A solution of n-BuLi (0.082 mL, 1.78 M in hexanes) was added dropwise and the reaction was stirred at −78° C. for 30 min. Epibromohydrin (0.016 mL, 0.194 mmol) was added and the reaction was allowed to warm slowly to ambient temperature. After 3.5 h, epibromohydrin (0.008 mL, 0.097 mmol) was added and the reaction was stirred overnight at ambient temperature. Upon completion, saturated aqueous NH₄Cl was added to quench the reaction and the mixture was extracted with EtOAc (3×). The combined organic layers were washed with brine, dried over Na₂SO₄, filtered, and concentrated. The crude residue was purified by chromatography (SiO₂, 0-50% EtOAc/Hexane) to afford the desired product (15 mg, 49%).

$^1$H NMR (CDCl₃, 500 MHz) δ 7.19 (m, 1H), 7.00 (d, 1H, J=8.5 Hz), 4.65 (br s, 2H), 4.32 (dd, 1H, J=3.0, 15.5 Hz), 4.18 (q, 2H, J=7.0 Hz), 4.08 (dd, 1H, J=5.0, 15.5 Hz), 3.85 (m, 2H), 3.18 (m, 1H), 2.81 (br s, 2H), 2.73 (dd, 1H, J=4.0, 4.5 Hz), 2.44 (s, 3H), 2.38 (br s, 1H), 1.29 (t, 3H, J=7.0 Hz)

Step 3. Synthesis of Ethyl 5-(2-Hydroxy-3-(3-methoxyphenylamino)propyl)-8-methyl-3,4-dihydro-1H-pyrido[4,3-b]indole-2(5H)-carboxylate

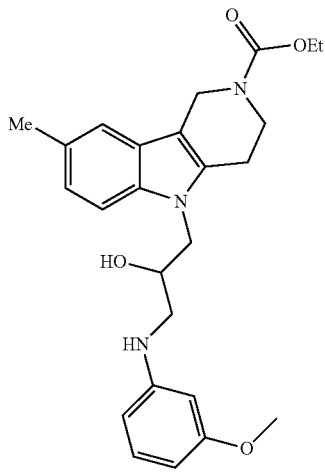 [SMILES: CCOC(=O)N1CCc2c(c3cc(C)ccc3n2CC(O)CNc2cccc(OC)c2)C1]

Following a literature procedure (Chakraborti, A. K; Rudrawar, S; Kondaskar, A. *Eur. J. Org. Chem.* 2004, 3597-3600) LiBr (0.001 g, 0.010 mmol) and m-anisidine (0.011 mL, 0.102 mmol) were added to ethyl 8-Methyl-5-(oxiran-2-ylmethyl)-3,4-dihydro-1H-pyrido[4,3-b]indole-2(5H)-carboxylate (0.032 g, 0.102 mmol) and stirred vigorously at ambient temperature overnight. Upon completion the reaction was partitioned between EtOAc/H$_2$O, and the organic layer was concentrated to an orange oil. The crude residue was purified by chromatography (SiO$_2$, 0-50% EtOAc/Hexane) to afford the desired product (30 mg, 67%).

$^1$H NMR (CDCl$_3$, 500 MHz) δ 7.23 (br s, 1H), 7.17 (d, 1H, J=8.0 Hz), 7.05 (dd, 1H, J=8.0 Hz), 6.97 (d, 1H, J=8.5 Hz), 6.28 (dd, 1H, J=1.5, 8.0 Hz), 6.19 (d, 1H, J=8.0 Hz), 6.11 (br s, 1H), 4.64 (br s, 2H), 4.18 (m, 1H), 4.16 (q, 2H, J=7.5 Hz), 4.12 (m, 1H), 3.80 (br s, 2H), 3.71 (s, 3H), 3.23 (dd, 1H, J=3.5, 13.0 Hz), 3.07 (dd, 1H, J=7.5, 13.0 Hz), 2.83 (m, 1H), 2.76 (m, 1H), 2.42 (s, 3H), 1.27 (t, 3H, J=7.0 Hz).

ESI m/z 438.2 ([M+H]$^+$, C$_{25}$H$_{32}$N$_3$O$_4$ requires 438.2).

Example 19

4-(3,6-dibromo-9H-carbazol-9-yl)-1-(phenylamino)butan-2-ol

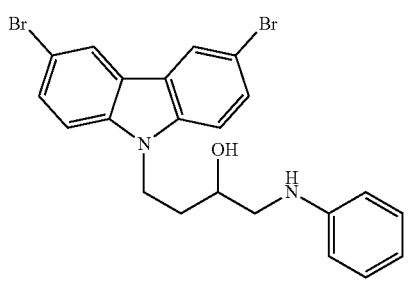 [SMILES: OC(CCn1c2ccc(Br)cc2c2cc(Br)ccc21)CNc1ccccc1]

Step 1. Synthesis of 3,6-dibromo-9-(2-(oxiran-2-yl)ethyl)-9H-carbazole

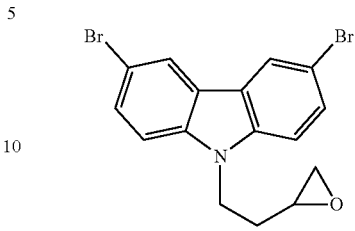

Crushed KOH (0.0054 g, 0.0954 mmol, 1.2 equiv) was added to 3,6-dibromocarbazole (0.0258 g, 0.0795 mmol, 1 equiv.) in 0.5 mL DMF solution and the mixture was stirred for 30 min. 1-Bromo-3,4-epoxybutane (0.0300 g, 0.199 mmol) in 0.5 mL DMF solution was dropwise added into the mixture and it was stirred at room temperature for overnight. Reaction crude was diluted with 20 mL EtOAc and washed with water 5×10 mL. The organic layer was dried over anhydrous Na$_2$SO$_4$ and evaporated to afford 31.2 mg white solid as product, yield 97.9%.

$^1$H NMR (CDCl$_3$, 400 MHz) δ ppm 1.65-1.81 (m, 1H) 2.13-2.27 (m, 1H) 2.34 (dd, J=4.88, 2.64 Hz, 1H) 2.64 (dd, J=4.78, 4.05 Hz, 1H) 2.69-2.80 (m, 1H) 4.26-4.54 (m, 2H) 7.27 (d, J=8.69 Hz, 2H) 7.50 (dd, J=8.69, 1.90 Hz, 2H) 8.08 (d, J=1.90 Hz, 2H)

Step 2. Synthesis of 4-(3,6-dibromo-9H-carbazol-9-yl)-1-(phenylamino)butan-2-ol

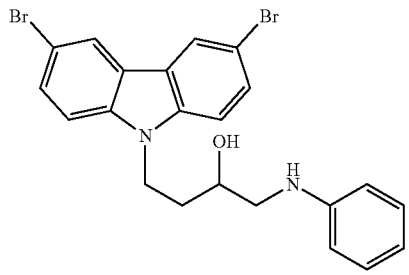 [SMILES: OC(CCn1c2ccc(Br)cc2c2cc(Br)ccc21)CNc1ccccc1]

According to Representative Procedure 2, Example 19 was isolated as a white solid in 31% yield.

$^1$H NMR (CDCl$_3$, 400 MHz) δppm 1.87-1.98 (m, 1H) 2.05-2.14 (m, 1H) 2.99-3.07 (dd, J=13.24, 3.43 Hz, 1H) 3.09-3.17 (dd, J=13.24, 8.27 Hz, 1H) 3.60-3.74 (m, 1H) 4.39-4.48 (m, 1H) 4.51-4.60 (m, 1H) 6.57 (d, J=7.71 Hz, 2H) 6.74 (t, J=7.34 Hz, 1H) 7.15 (dd, J=8.27, 7.59 Hz, 2H) 7.38 (d, J=8.69 Hz, 2H) 7.56 (dd, J=8.69, 1.90 Hz, 2H) 8.14 (d, J=1.85 Hz, 2H)

$^{13}$C NMR (CDCl$_3$, 500 MHz) δ=148.1, 139.6, 129.6, 129.4, 123.8, 123.6, 118.7, 113.6, 112.4, 110.8, 67.7, 51.0, 39.9, 33.7.

m/z (ESI): 486.9 (M+H$^+$) ([M+1] for C22H20Br2N2O requires 467.0)

Example 20

N-(3-(3,6-dibromo-9H-carbazol-9-yl)propyl)aniline

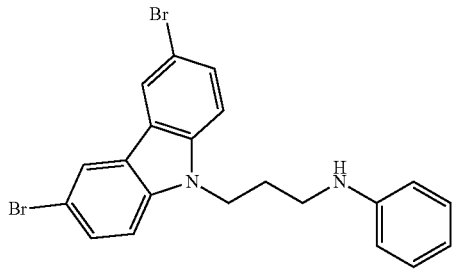 [SMILES: Brc1ccc2c(c1)c1cc(Br)ccc1n2CCCNc1ccccc1]

Step 1. Synthesis of
3,6-dibromo-9-(3-bromopropyl)-9H-carbazole

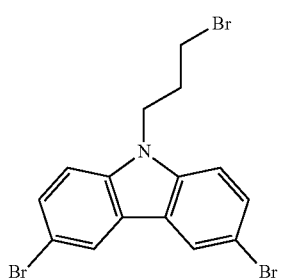 [SMILES: BrCCCn1c2ccc(Br)cc2c2cc(Br)ccc21]

Crushed KOH (0.0673 g, 1.20 mmol, 1.2 equiv) was added to 3,6-dibromocarbazole (0.3250 g, 1.00 mmol) in 2 mL DMF solution and the mixture was stirred for 30 min. 1,3-dibromopropane (0.5047 g, 2.50 mmol, 2.5 equiv) in 3 mL DMF solution was added dropwise into the mixture and it was stirred at room temperature overnight. The crude reaction mixture was diluted with 30 mL EtOAc and washed with 1M HCl 2×10 mL and water 3×10 mL. The organic layer was dried over anhydrous $Na_2SO_4$ and evaporated to afford the crude product, which was subjected to silica gel chromatography using Hexanes/EtOAc to afford 0.1275 g colorless oil as product, yield 28.6%.

$^1$H NMR (CDCl$_3$, 400 MHz) δppm 2.24-2.44 (m, 2H) 3.29 (t, J=6.05 Hz, 2H) 4.33 (t, J=6.59 Hz, 2H) 7.26 (d, J=8.83 Hz, 2H) 7.51 (dd, J=8.69, 1.95 Hz, 2H) 8.02 (d, J=1.71 Hz, 2H)

Step 2. Synthesis of N-(3-(3,6-dibromo-9H-carbazol-9-yl)propyl)-2-nitro-N-phenylbenzenesulfonamide

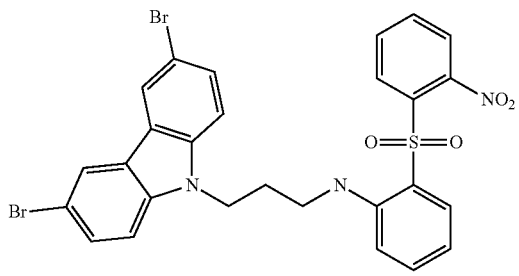 [SMILES: O=[N+]([O-])c1ccccc1S(=O)(=O)c1ccccc1NCCCn1c2ccc(Br)cc2c2cc(Br)ccc21]

Crushed KOH (0.0024 g, 0.0431 mmol) was added to 2-nitro-N-phenylbenzenesulfonamide (0.0100 g, 0.0359 mmol) in 0.2 mL DMF solution and the mixture was stirred for 30 min. 3,6-dibromo-9-(3-bromopropyl)-9H-carbazole (Example 35, 0.0240 g, 0.0538 mmol) in 0.3 mL DMF solution was added dropwise into the mixture and it was stirred at room temperature overnight. The crude reaction mixture was diluted with 20 mL EtOAc and washed with water 5×10 mL. The organic layer was dried over anhydrous $Na_2SO_4$ and evaporated to afford the crude product, which was subjected to silica gel chromatography using Hexanes/EtOAc to afford 0.0082 g white solid as impure product, purity 66.9% (impurity is starting Ns-aniline; used without additional purification), yield 35.5%.

$^1$H NMR (CDCl$_3$, 400 MHz) δppm 1.89-2.01 (m, 2H) 3.95 (t, J=6.61 Hz, 2H) 4.32-4.38 (m, 2H) 7.15 (s, 1H) 7.17 (s, 1H) 7.18-7.25 (m, 3H) 7.32 (d, J=3.66 Hz, 2H) 7.41-7.44 (m, 2H) 7.51 (dd, J=8.69, 1.95 Hz, 2H) 7.59-7.71 (m, 2H) 8.09 (d, J=1.90 Hz, 2H)

Step 3. Synthesis of N-(3-(3,6-dibromo-9H-carbazol-9-yl)propyl)aniline

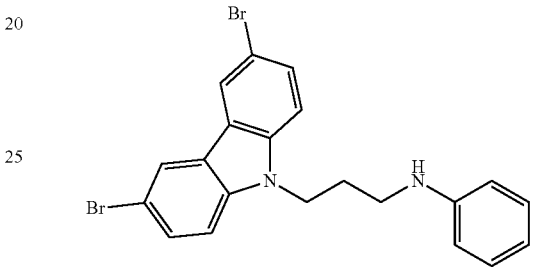

N-(3-(3,6-dibromo-9H-carbazol-9-yl)propyl)-2-nitro-N-phenylbenzenesulfonamide (0.0378 g, 0.0588 mmol, 1 equiv), cesium carbonate (0.0574 g, 0.176 mmol, 3 equiv) and benzenethiol (0.0194 g, 0.176 mmol) were mixed in 1 mL anhydrous THF. The mixture was stirred at room temperature for 3 hours. THF was removed under vacuum and the residue was purified by silica gel chromatography using Hexanes/EtOAc to afford 0.0164 g colorless oil as product, yield 60.9%.

$^1$H NMR (CDCl$_3$, 400 MHz) δppm 2.08-2.29 (m, 2H) 3.09 (t, J=6.56 Hz, 2H) 3.55 (br. s., 1H) 4.37 (t, J=6.69 Hz, 2H) 6.53 (dd, J=8.56, 0.95 Hz, 2H) 6.73 (t, J=7.32 Hz, 1H) 7.16 (dd, J=8.49, 7.37 Hz, 2H) 7.25 (d, J=8.69 Hz, 2H) 7.51 (dd, J=8.69, 1.95 Hz, 2H) 8.12 (d, J=1.85 Hz, 2H)

$^{13}$C NMR (CDCl$_3$, 400 MHz) δ=148.0, 139.5, 129.6, 129.4, 123.7, 123.6, 118.2, 113.3, 112.4, 110.5, 41.4, 40.9, 28.9

MS (ESI), m/z: 456.9 [M+H]+ ([M+H]+ for C21H18Br2N2 requires 457.0)

Example 21

1-(3,6-dibromo-9H-carbazol-9-yl)-4-(phenylamino)butan-2-ol

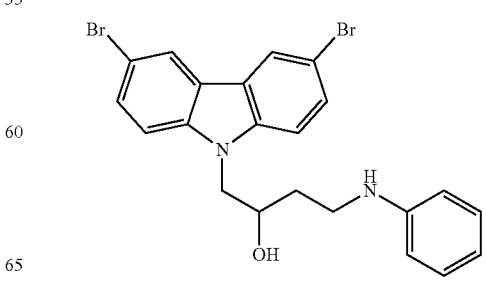

Step 1. Synthesis of N-(but-3-enyl)-2-nitro-N-phenylbenzenesulfonamide

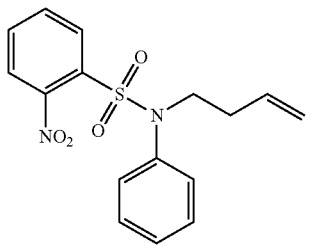 [SMILES: C=CCCN(c1ccccc1)S(=O)(=O)c1ccccc1[N+](=O)[O-]]

Crushed KOH (0.0484 g, 0.862 mmol, 1.2 equiv) was added to 2-nitro-N-phenylbenzenesulfonamide (0.200 g, 0.719 mmol) in 1 mL DMF, and the mixture was stirred for 30 min. 4-Bromo-1-butene (0.2426 g, 1.80 mmol) in 2 mL DMF solution was added dropwise into the mixture and it was stirred at room temperature overnight. The reaction mixture was diluted with 30 mL EtOAc and washed with 1M HCl 2×10 mL and water 3×10 mL. The organic layer was dried over anhydrous $Na_2SO_4$ and evaporated to afford the crude product, which was subjected to silica gel chromatography using Hexanes/EtOAc to afford 0.1546 g white solid, yield 63.5%.

$^1$H NMR (CDCl$_3$, 400 MHz) δppm 2.20 (q, J=6.90 Hz, 2H) 3.83 (t, J=7.15 Hz, 2H) 5.00 (d, J=4.39 Hz, 1H) 5.03 (s, 1H) 5.64-5.83 (m, 1H) 7.14-7.21 (m, 3H) 7.30 (d, J=1.85 Hz, 2H) 7.42-7.46 (m, 2H) 7.52-7.58 (m, 1H) 7.60-7.66 (m, 1H)

Step 2. Synthesis of 2-nitro-N-(2-(oxiran-2-yl)ethyl)-N-phenylbenzenesulfonamide

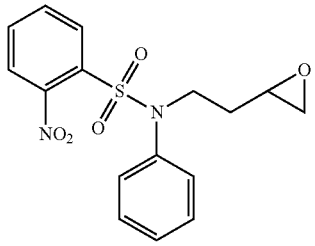 [SMILES: O=[N+]([O-])c1ccccc1S(=O)(=O)N(CCC1CO1)c1ccccc1]

mCPBA (77%, 0.0550 g, 0.246 mmol) was added to N-(but-3-enyl)-2-nitro-N-phenylbenzenesulfonamide (0.0653 g, 0.196 mmol) in 1 mL CHCl$_3$ at 0° C. The mixture was stirred at 0° C. for 30 min, then gradually warmed up to room temperature and continued to stir for 18 hr. After TLC showed the disappearance of starting material, the reaction mixture was diluted with a 1:1 mixture of water and saturated NaHCO$_3$ (2×10 mL) and water (10 mL). The organic layer was dried over anhydrous Na$_2$SO$_4$ and evaporated to afford the crude product, which was subjected to silica gel chromatography using Hexanes/EtOAc to afford 0.0662 g colorless oil as product, yield 96.9%.

$^1$H NMR (CDCl$_3$, 400 MHz) δppm 1.66-1.79 (m, 2H) 2.46 (dd, J=4.95, 2.66 Hz, 1H) 2.70-2.80 (m, 1H) 2.93-3.03 (m, 1H) 3.87-4.07 (m, 2H) 7.19-7.23 (m, 2H) 7.28-7.34 (m, 3H) 7.43-7.47 (m, 2H) 7.57-7.66 (m, 2H).

MS (ESI) m/z: 371.0 (M+Na$^+$) ([M+Na]+ for C$_{16}$H$_{16}$N$_2$O$_5$S requires 371.1)

Step 3. Synthesis of N-(2-(oxiran-2-yl)ethyl)aniline

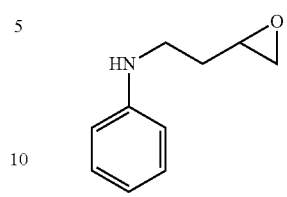

Prepared from 2-nitro-N-(2-(oxiran-2-yl)ethyl)-N-phenyl-benzenesulfonamide using an analogous procedure as used to prepare the compound of Example 20.

$^1$H NMR (CDCl$_3$, 400 MHz) δppm 1.64-1.79 (m, 1H) 1.98-2.15 (m, 1H) 2.55 (dd, J=4.90, 2.71 Hz, 1H) 2.79 (t, J=4.44 Hz, 1H) 3.00-3.10 (m, 1H) 3.31 (t, J=6.64 Hz, 2H) 3.87 (br. s., 1H) 6.62 (d, J=7.71 Hz, 2H) 6.71 (t, J=7.32 Hz, 1H) 7.18 (dd, J=8.49, 7.37 Hz, 2H)

MS (ESI) m/z: 164.1 (M+H$^+$) ([M+1]+ for C$_{10}$H$_{13}$NO requires 164.1)

Step 4. Synthesis of 1-(3,6-dibromo-9H-carbazol-9-yl)-4-(phenylamino)butan-2-ol

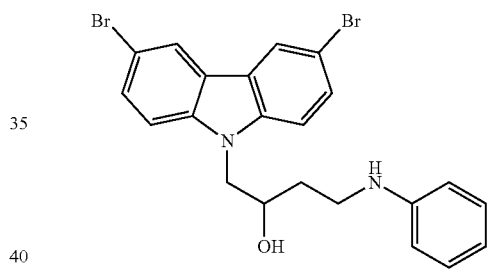

NaH (60% dispersed in mineral oil, 0.0018 g, 0.0452 mmol) was added to a solution of 3,6-dibromocarbazole (0.0147 g, 0.0452 mmol) in 0.5 mL anhydrous THF and the mixture was stirred for 15 min. N-(2-(oxiran-2-yl)ethyl) aniline (0.0067 g, 0.0410 mmol) in 1.5 mL anhydrous THF solution was added dropwise and the resulting mixture was stirred at 60° C. overnight. THF was removed under vacuum and the residue was dissolved in 10 mL EtOAc and washed with water 2×5 mL. The organic layer was dried over anhydrous Na$_2$SO$_4$ and evaporated to afford the crude product, which was subjected to silica gel chromatography using Hexanes/EtOAc to afford 0.0115 g colorless oil; yield 57.5%.

$^1$H NMR (CDCl$_3$, 400 MHz) δ ppm 1.76-1.95 (m, 2H) 3.22-3.41 (m, 2H) 4.20-4.38 (m, 3H) 6.63 (d, J=8.49 Hz, 2H) 6.76 (t, J=7.32 Hz, 1H) 7.18 (t, J=7.95 Hz, 2H) 7.31 (d, J=8.74 Hz, 2H) 7.54 (dd, J=8.69, 1.95 Hz, 2H) 8.12 (d, J=1.95 Hz, 2H)

$^{13}$C NMR (CDCl$_3$, 400 MHz) δ=148.1, 139.9, 129.6, 129.5, 123.8, 123.5, 118.7, 113.9, 112.7, 111.1, 70.7, 50.0, 42.2, 34.1.

MS (ESI) m/z: 531.0 [M+HCOO]$^-$ 486.9 [M+H]$^+$ ([M+H]+ for C$_{22}$H$_{20}$Br$_2$N$_2$O requires 487.0)

Example 22

1-(3,6-dibromo-9H-carbazol-9-yl)-3-(pyridin-2-ylamino)propan-2-ol

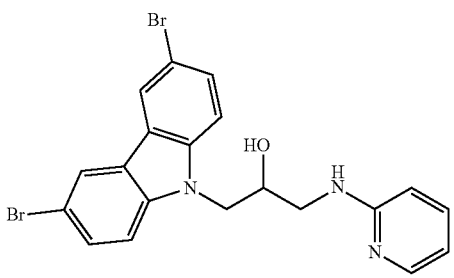 [SMILES: OC(CNc1ccccn1)Cn1c2ccc(Br)cc2c2cc(Br)ccc21]

Step 1. Synthesis of 1-amino-3-(3,6-dibromo-9H-carbazol-9-yl)propan-2-ol

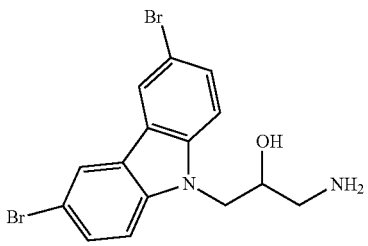 [SMILES: NCC(O)Cn1c2ccc(Br)cc2c2cc(Br)ccc21]

A solution of $NH_3$ (9.4 mL of 7M in MeOH, 65.6 mmol) was added to 3,6-dibromo-9-(oxiran-2-ylmethyl)-9H-carbazole (0.500 g, 1.31 mmol). The vial was tightly sealed and the reaction mixture was heated to 100° C. and stirred for 1 hour. Volatile components were removed under vacuum. The residue was suspended in $CH_2Cl_2$ and the white precipitate was filtered. The filtrate was saved and $CH_2Cl_2$ was removed under vacuum to afford 0.3413 g white solid as crude product, which contained about 50% unidentified side-product. This crude product was used as is in next step without any further purification. Purification by flash chromatography on silica gel provided pure material.

$^1$H NMR (CDCl$_3$, 400 MHz) δ ppm 2.61 (dd, J=12.66, 7.78 Hz, 1H) 2.90 (dd, J=12.52, 4.03 Hz, 1H) 3.96-4.06 (m, 1H) 4.32 (d, J=5.81 Hz, 2H) 7.36 (d, J=8.74 Hz, 2H) 7.55 (dd, J=8.69, 1.95 Hz, 2H) 8.13 (d, J=1.90 Hz, 2H)

MS (ESI) m/z: 396.9 (M+H$^+$) ([M+H]+ for C15H14Br2N2O requires 397.0)

Step 2. Synthesis of 5-((3,6-dibromo-9H-carbazol-9-yl)methyl)oxazolidin-2-one

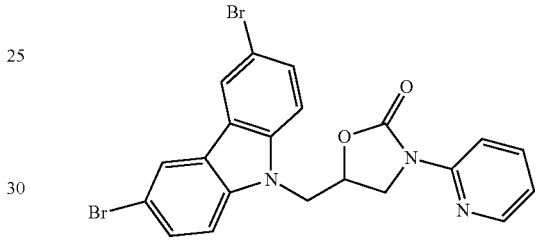

A solution of triphosgene (0.0890 g, 0.300 mmol, 0.35 equiv) in 2 mL anhydrous $CH_2Cl_2$ was added dropwise to a solution of 1-amino-3-(3,6-dibromo-9H-carbazol-9-yl)propan-2-ol (0.3413 g, 0.857 mmol) and Et$_3$N (0.1909 g, 1.886 mmol) in 1 mL $CH_2Cl_2$ under N$_2$ atmosphere at 4° C. The reaction mixture was stirred for 15 min at 4° C. and then warmed to room temperature and stirred for 1 hour. $CH_2Cl_2$ was removed under vacuum. Saturated NH$_4$Cl (5 mL) and 10 mL EtOAc was added to the residue and stirred for 20 min. Then the aqueous layer was separated and the organic layer was washed with water 2×10 mL. The combined aqueous layers were extracted with EtOAc, dried over anhydrous Na$_2$SO$_4$ and evaporated to afford the crude product, which was subjected to silica gel chromatography using $CH_2Cl_2$/EtOAc to afford 0.1173 g white solid, yield 20.0% over 2 steps.

$^1$H NMR (CDCl$_3$, 400 MHz) δ ppm 3.37 (dd, J=8.98, 6.34 Hz, 1H) 3.67 (t, J=8.49 Hz, 1H) 4.54 (dd, J=5.22, 1.81 Hz, 2H) 5.02 (br. s., 1H) 5.05-5.14 (m, 1H) 7.31 (d, J=8.69 Hz, 2H) 7.58 (dd, J=8.69, 1.85 Hz, 2H) 8.14 (d, J=1.85 Hz, 2H)

MS (ESI) m/z: 466.9 [M+HCOO]$^-$ ([M+HCOO]− for C$_{16}$H$_{12}$Br$_2$N$_2$O$_2$ requires 466.9.

Step 3. Synthesis of 5-((3,6-dibromo-9H-carbazol-9-yl)methyl)-3-(pyridin-2-yl)oxazolidin-2-one A mixture of 5-((3,6-dibromo-9H-carbazol-9-yl)methyl)oxazolidin-2-one (0.0195 g, 0.0460 mmol), 2-iodopyridine (0.0209 g, 0.102 mmol), CuI (0.0009 g, 0.00460 mmol), and K$_2$CO$_3$ (0.0058 g, 0.0418 mmol) in 0.5 mL of DMSO was sealed tightly in a vial and heated at 130° C. for 12 hours. The reaction mixture was cooled and diluted with 20 mL EtOAc and washed with water 5×10 mL. The organic layer was dried over anhydrous Na$_2$SO$_4$ and evaporated to afford the crude product, which was subjected to silica gel chromatography using $CH_2Cl_2$/EtOAc as elute to afford 0.0183 g white solid as product, yield 79.4%.

$^1$H NMR (CDCl$_3$, 400 MHz) δppm 4.04 (dd, J=10.79, 7.08 Hz, 1H) 4.36 (dd, J=10.69, 8.74 Hz, 1H) 4.60 (d, J=5.03 Hz, 2H) 5.02-5.16 (m, 1H) 7.02 (t, J=6.08 Hz, 1H) 7.35 (d, J=8.69 Hz, 2H) 7.59 (dd, J=8.66, 1.73 Hz, 2H) 7.68 (t, J=7.88 Hz, 1H) 8.11 (s, 1H) 8.13 (d, J=1.32 Hz, 2H) 8.25 (d, J=4.93 Hz, 1H)

MS (ESI) m/z: 543.9 [M+HCOO]$^-$ ([M+HCOO]− for C$_{21}$H$_{15}$Br$_2$N$_3$O$_2$ requires 544.0)

Step 4. Synthesis of 1-(3,6-dibromo-9H-carbazol-9-yl)-3-(pyridin-2-ylamino)propan-2-ol

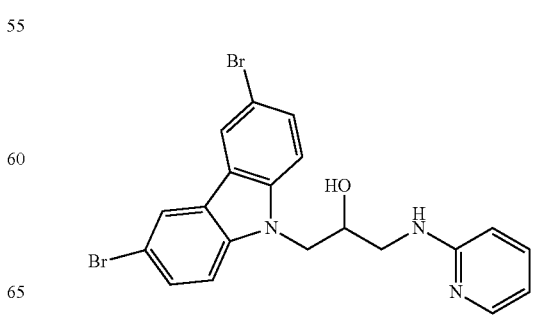

LiOH.H$_2$O (0.0076 g, 0.182 mmol, 10 equiv) was added to 5-((3,6-dibromo-9H-carbazol-9-yl)methyl)-3-(pyridin-2-yl)oxazolidin-2-one (0.0091 g, 0.0182 mmol) in a mixture of 208 μL, THF and 23 μL, H$_2$O (v/v=9:1). The mixture was stirred at room temperature for 7 days. The reaction mixture was purified by silica gel chromatography using CH$_2$Cl$_2$/EtOAc as elute to afford 0.0071 g white solid as product, yield 41.0%.

$^1$H NMR (CDCl$_3$, 400 MHz) δ ppm 2.27-2.44 (m, 1H) 3.15-3.32 (m, 1H) 3.44 (dd, J=15.23, 5.03 Hz, 1H) 4.26-4.41 (m, 31-1) 4.52 (t, J=5.00 Hz, 1H) 6.46 (d, J=8.00 Hz, 1H) 6.66 (t, J=6.20 Hz, 1H) 7.37 (d, J=8.74 Hz, 2H) 7.40-7.48 (m, 1H) 7.56 (dd, J=8.69, 1.90 Hz, 2H) 8.04 (d, J=4.49 Hz, 1H) 8.14 (d, J=1.85 Hz, 2H)

$^{13}$C NMR (CDCl$_3$, 400 MHz) δ=158.6, 146.7, 139.5, 138.1, 129.2, 123.6, 123.3, 113.9, 112.3, 110.9, 109.6, 70.5, 47.4, 46.8

MS (ESI) m/z: 518.0 [M+HCOO]$^-$ ([M+HCOO]– for C$_{20}$H$_{17}$Br$_2$N$_3$O requires 518.0.

Example 23

1-(3,6-dibromo-9H-carbazol-9-yl)-3((3-methoxyphenyl)(methyl)-amino)propan-2-ol

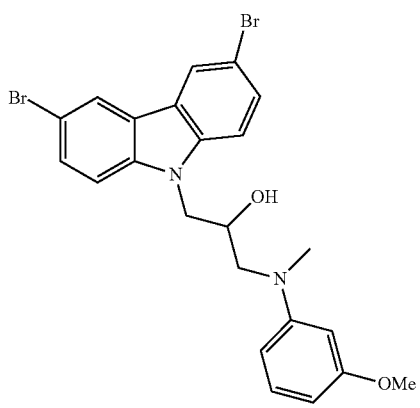 [SMILES: COc1cccc(N(C)CC(O)Cn2c3ccc(Br)cc3c3cc(Br)ccc32)c1]

Synthesized using a similar synthetic procedure analogous to Representative Procedure 2.

Example 25

3-amino-1-(3-(3,6-dibromo-9H-carbazol-9-yl)-2-hydroxypropyl)pyridinium

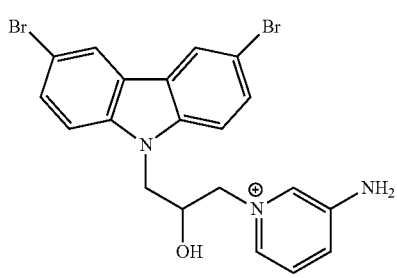 [SMILES: Nc1ccc[n+](CC(O)Cn2c3ccc(Br)cc3c3cc(Br)ccc32)c1]

Example 25 was synthesized using a similar synthetic procedure analogous to Representative Procedure 2.

Example 26

1-(3,6-dibromo-9H-carbazol-9-yl)-3-(pyrimidin-2-ylamino)propan-2-ol

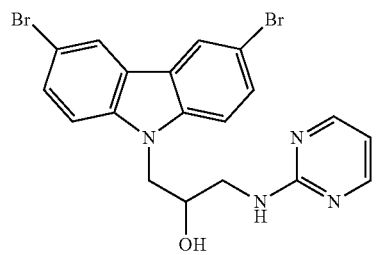 [SMILES: OC(CNc1ncccn1)Cn1c2ccc(Br)cc2c2cc(Br)ccc21]

To a 4 ml vial was added the corresponding primary amine (34.8 mg, 0.087 mmol), 2-chloropyrimidine (10.3 mg, 0.090 mmol) and dimethylformamide (1.5 ml, 0.058 M). The reaction was heated at 100° C. overnight. The cooled reaction mixture was diluted with EtOAc and washed several times with water and brine. The organic layer was dried over Na$_2$SO$_4$, filtered and condensed. The crude mixture was subjected to chromatography on silica gel (20% MeOH/CH$_2$Cl$_2$).

$^1$H NMR (CDCl$_3$, 400 MHz) δ 8.26 (d, 2H, J=4.94 Hz), 8.14 (d, 2H, J=1.88 Hz), 7.56 (dd, 2H, J=6.7, 1.9 Hz), 7.37 (d, 2H, J=8.7 Hz), 6.63 (t, 1H, J=4.9 Hz), 5.43 (t, 1H, J=5.71 Hz), 4.36 (s, 3H), 3.56 (m, 1H), 3.30-3.38 (m, 1H).

$^{13}$C NMR (CDCl$_3$, 126 MHz) §139.4, 29.5 (2C), 129.3 (2C), 123.7 (2C), 123.4 (2C), 118.6 (2) (2C), 113.5 (2C), 112.3, 110.7 (2C), 67.6, 50.9, 33.6.

MS (ESI) m/z: 474.9 [(M+1)$^+$; C19H16Br2N4O (M) requires 474)].

The title compound of Example 26 can also be synthesized using a procedure analogous to that described in Representative Procedure 2.

Example 28

1-(3,6-dibromo-9H-carbazol-9-yl)-3-methoxypropan-2-ol

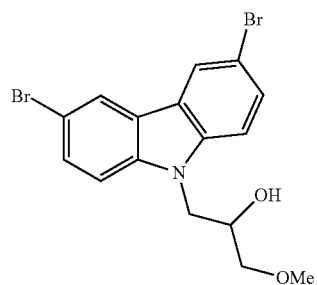 [SMILES: COCC(O)Cn1c2ccc(Br)cc2c2cc(Br)ccc21]

Following Representative Procedure 1, Example 28 was prepared from dibromocarbazole and methoxymethyloxirane

Example 29

1-(3,6-dibromo-9H-carbazol-9-yl)-4-phenylbutan-2-ol

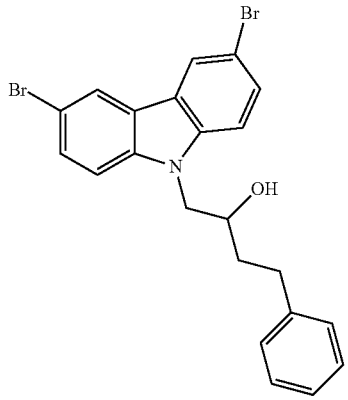 [SMILES: OC(CCc1ccccc1)Cn1c2ccc(Br)cc2c2cc(Br)ccc21]

Following Representative Procedure 1, Example 29 was prepared from dibromocarbazole and 2-phenethyloxirane.

Example 30

1-(3,6-dibromo-9H-carbazol-9-yl)-3-(1H-indol-1-yl)propan-2-ol

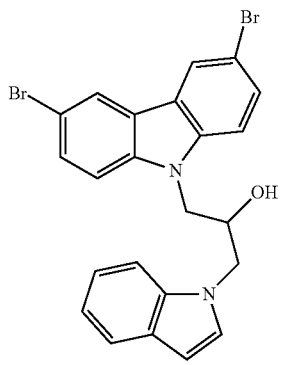 [SMILES: OC(Cn1ccc2ccccc21)Cn1c2ccc(Br)cc2c2cc(Br)ccc21]

Following Representative Procedure 1, Example 30 was prepared from dibromocarbazole and 1-(oxiran-2-ylmethyl)-1H-indole.

Example 31

3-(1-(3-(3,6-dibromo-9H-carbazol-9-yl)-2-hydroxypropyl)-1H-1,2,3-triazol-4-yl)propan-1-ol

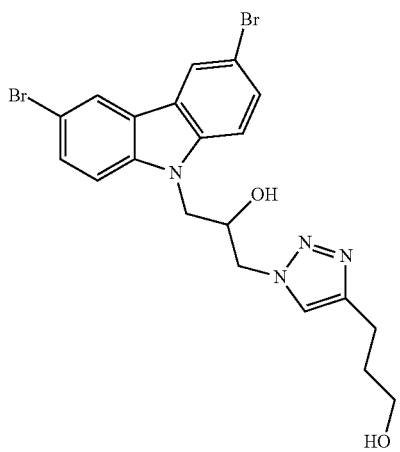 [SMILES: OCCCc1cn(CC(O)Cn2c3ccc(Br)cc3c3cc(Br)ccc32)nn1]

Example 31 was synthesized using a similar synthetic procedure analogous to Representative Procedure 2.

Example 32

1-(3,6-dibromo-9H-carbazol-9-yl)-3-(3-ethoxyphenylamino)propan-2-ol

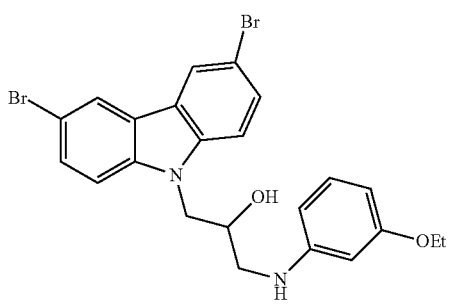 [SMILES: CCOc1cccc(NCC(O)Cn2c3ccc(Br)cc3c3cc(Br)ccc32)c1]

Example 32 was synthesized using a similar synthetic procedure analogous to Representative Procedure 2.

Example 33

1-(3,6-dibromo-9H-carbazol-9-yl)-3-(3,5-dimethyl-1H-pyrazol-1-yl)propan-2-ol

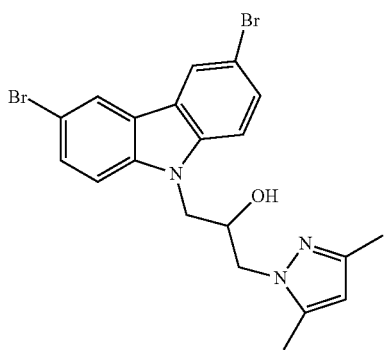 [SMILES: Cc1cc(C)n(CC(O)Cn2c3ccc(Br)cc3c3cc(Br)ccc32)n1]

Example 33 was synthesized using a similar synthetic procedure analogous to Representative Procedure 2.

Example 36

1-(3-bromo-9H-carbazol-9-yl)-3-(3-methoxyphenylamino)propan-2-ol

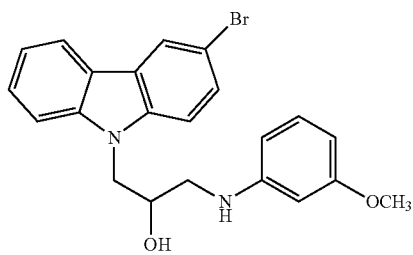 [SMILES: COc1cccc(NCC(O)Cn2c3ccccc3c3cc(Br)ccc32)c1]

Step 1. 3-bromo-9-(oxiran-2-ylmethyl)-9H-carbazole

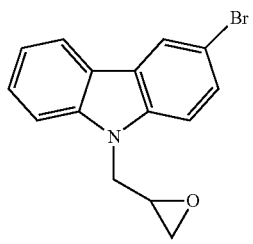 [SMILES: Brc1ccc2c(c1)c1ccccc1n2CC1CO1]

The title compound of Example 36, step 1 was prepared using a procedure analogous to that described in representative procedure 1.

$^1$H NMR (CDCl$_3$, 400 MHz) δ=2.52 (dd, J=4.6, 2.6 Hz, 1H) 2.80 (t, J=4.3 Hz, 1H) 3.33 (td, J=5.3, 2.2 Hz, 1H) 4.34 (dd, J=15.9, 4.9 Hz, 1H) 4.64 (dd, J=15.9, 2.9 Hz, 1H) 7.26 (t, J=7.3 Hz, 1H) 7.35 (d, J=8.7 Hz, 1H) 7.58-7.42 (m, 3H) 8.02 (d, J=5.1 Hz, 1H) 8.19 (d, J=1.7 Hz, 1H).

Step 2

The title compound was prepared from 3-bromo-9-(oxiran-2-ylmethyl)-9H-carbazole using a procedure similar to that described in representative procedure 2

$^1$H NMR (CDCl$_3$, 400 MHz) δ=2.13 (d, J=3.0 Hz, 1H) 3.21 (dd, J=13.0, 6.5 Hz, 1H) 3.35 (dd, J=13.0, 3.2 Hz, 1H) 3.72 (s, 3H) 4.03 (s, br, 1H) 4.50-4.36 (m, 31-1) 6.15 (t, J=2.3 Hz, 1H) 6.24 (dd, J=8.0, 2.2 Hz, 1H) 6.32 (dd, J=8.2, 2.3 Hz, 1H) 7.08 (t, J=8.1 Hz, 1H) 7.30-7.24 (m, 1H) 7.36 (d, J=8.7 Hz, 1H) 7.51-7.44 (m, 2H) 7.53 (dd, J=8.7, 1.9 Hz, 1H) 8.05 (d, J=7.9 Hz, 1H) 8.21 (d, J=1.9 Hz, 1H)

$^{13}$C NMR (CDCl$_3$, 400 MHz) δ=161.0, 149.4, 141.2, 139.6, 130.4, 128.8, 126.9, 125.0, 123.3, 122.2, 120.8, 120.1, 112.4, 110.7, 109.4, 106.7, 103.8, 99.7, 69.6, 55.3, 48.0, 47.4.

ESI m/z: 425.0 [(M+H$^+$), C22H21BrN2O2 (M) requires 421.1].

Example 37

N-(5-(3-(3-(3,6-dibromo-9H-carbazol-9-yl)-2-hydroxypropylamino)phenoxy)pentyl)-2-(7-(dimethylamino)-2-oxo-2H-chromen-4-yl)acetamide

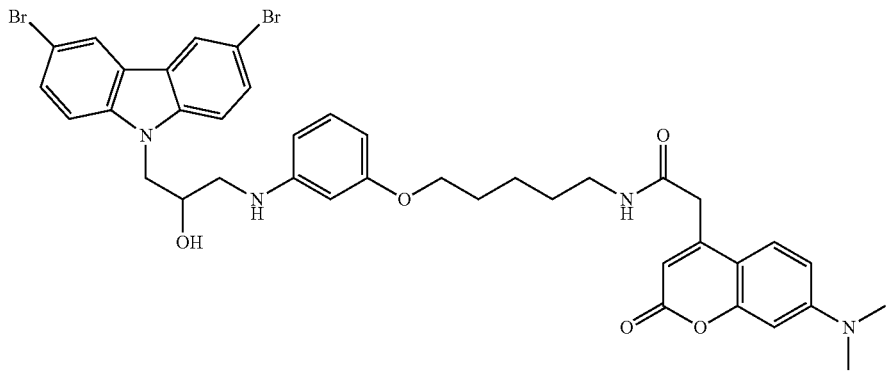 [SMILES: CN(C)c1ccc2c(CC(=O)NCCCCCOc3cccc(NCC(O)Cn4c5ccc(Br)cc5c5cc(Br)ccc54)c3)cc(=O)oc2c1]

The coumarin was attached to Example 62 Compound using a known procedure (Alexander, M. D., Burkart, M. D., Leonard, M. S., Portonovo, P., Liang, B., Ding, X., Joullie, M. M., Gulledge, B. M., Aggen, J. B., Chamberlin, A. R., Sandler, J., Fenical, W., Cui, J., Gharpure, S. J., Polosukhin, A., Zhang, H-R., Evans, P. A., Richardson, A. D., Harper, M. K., Ireland, C. M., Vong, B. G., Brady, T. P., Theodorakis, E. A., and La Clair, J. J. *ChemBioChem,* 2006, 7, 409-416.

Example 39

N-(2-(3-(3,6-dibromo-9H-carbazol-9-yl)-2-hydroxypropoxy)ethyl)-acetamide

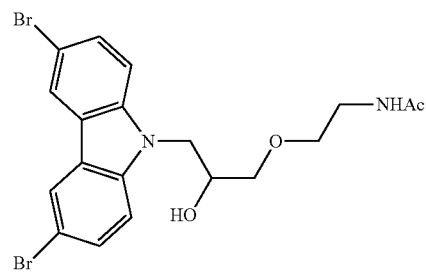 [SMILES: CC(=O)NCCOCC(O)Cn1c2ccc(Br)cc2c2cc(Br)ccc21]

Step 1. 2-(2-(3-(3,6-dibromo-9H-carbazol-9-yl)-2-hydroxypropoxy)ethyl)isoindoline-1,3-dione

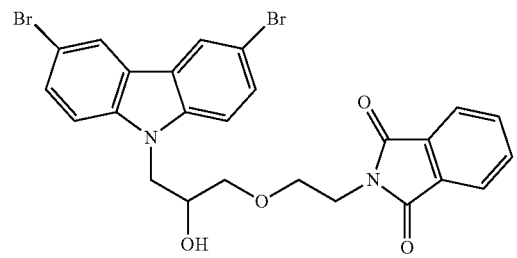 [SMILES: O=C1c2ccccc2C(=O)N1CCOCC(O)Cn1c2ccc(Br)cc2c2cc(Br)ccc21]

Sodium hydride dispersion (31.6 mg, 0.79 mmol) was added to a solution of N-(2-hydroxyethyl)-phthalimide (153.7 mg, 0.80 mmol) in anhydrous THF (1.2 ml, 0.67 M). The suspension is stirred for 15 minutes before the addition of carbazole epoxide 2-A. The reaction was stirred at room temperature for five minutes and then at 60° C. for 1 hour. The cooled reaction was diluted with EtOAc and washed with water. The aqueous layer was extracted and the combined organics were filtered over a celite pad. The Crude product was used without further purification. Yield=44%

¹H NMR (CDCl₃, 500 MHz) ☐ 8.12 (s, 2H), 7.85 (s, 2H), 7.72 (m, 2H), 7.55 (d, 2H, J=8.5 Hz), 7.33 (d, 2H, J=8.7 Hz), 4.64 (d, 1H, J=16.1 Hz), 4.27 (d, 1H), 3.88 (m, 4H), 3.31 (bs, 1H), 2.80 (m, 1H), 2.48 (m, 1H), 2.04 (s, 1H).

MS (ESI), m/z: 614.9 [(M+HCOO)⁻; C25H20Br2N2O4 (M) requires 570].

Step 2. 1-(2-aminoethoxy)-3-(3,6-dibromo-9H-carbazol-9-yl)propan-2-ol

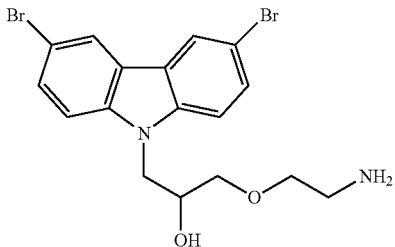 [SMILES: NCCOCC(O)Cn1c2ccc(Br)cc2c2cc(Br)ccc21]

Hydrazine hydrate (400 ul, 8.22 mmol) was added to a solution of the phthalimide prepared in step 1 above (53 mg, 0.093 mmol) in ethanol (2.0 ml, 0.046 M). The reaction was stirred overnight, condensed and purified in 5-10% MeOH/DCM.

¹H NMR (CDCl₃, 500 MHz) ☐ 8.11 (s, 2H), 7.53 (dd, 2H, J=8.7, 1.8 Hz), 7.38 (d, 2H, J=8.5 Hz), 4.37 (dm, 5H), 4.05 (t, 1H, J=6.8 Hz), 2.84 (m, 2H), 2.62 (m, 1H)

MS (ESI), m/z: 440.9 [(M+1)⁺; C17H18Br2N2O2 (M) requires 440.0].

Step 3

The title compound of Example 39 was prepared as follows. Triethylamine (33.5 ul, 0.26 mmol) and acetic anhydride (17 ul, 0.18 mmol) were added to a solution of amine XIII (71 mg, 0.16 mmol) in THF (3.0 ml, 0.053 M). The reaction was stirred overnight. The reaction mixture was diluted with EtOAc, washed with water, dried over Na₂SO₄, filtered and condensed. The crude mixture was subjected to flash chromatography (5% MeOH/CH₂Cl₂).

¹H NMR (CDCl₃, 500 MHz) ☐ 8.13 (d, 2H, J=1.7 Hz, 7.55 (dd, 2H, J=8.7, 1.8 Hz), 7.34 (d, 2H, 9.1 Hz), 5.78 (bs, 1H), 4.35 (ddd, 3H, J=6.2, 6.8 Hz), 4.22 (m, 1H), 3.46 (m, 4H), 3.33 (dd, 1H, J=9.7, 5.4 Hz), 2.80 (bs, 1H), 1.98 (s, 3H)

MS (ESI), m/z: 482.9 [(M+1)⁺; C19H20Br2N2O3 (M) requires 482.0]

Example 40

1-(3,6-dibromo-9H-carbazol-9-yl)-3-(pyridin-3-ylamino)propan-2-ol

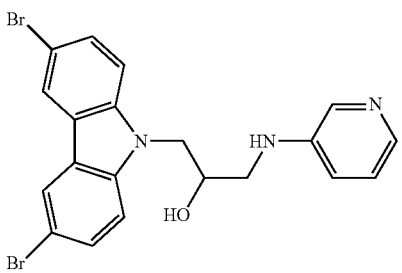 [SMILES: OC(CNc1cccnc1)Cn1c2ccc(Br)cc2c2cc(Br)ccc21]

Step 1. 5-((3,6-dibromo-9H-carbazol-9-yl)methyl)-3-(pyridin-3-yl)oxazolidin-2-one

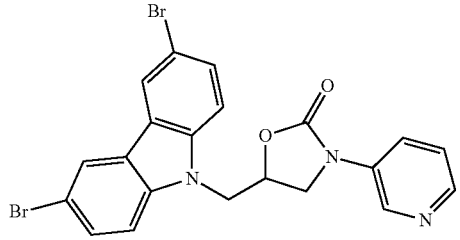 [SMILES: O=C1OC(Cn2c3ccc(Br)cc3c3cc(Br)ccc32)CN1c1cccnc1]

A mixture of the corresponding N—H oxazolidinone (0.0390 g, 0.0920 mmol), 3-iodopyridine (0.0419 g, 0.204 mmol), CuI (0.0018 g, 0.00920 mmol), and K₂CO₃ (0.0116 g, 0.0837 mmol) in 0.5 mL of DMSO was heated at 130° C. for 12 hours in a sealed vial. The reaction mixture was cooled and diluted with 20 mL EtOAc and washed with water 2×10 mL and brine 2×10 mL. The organic layer was dried over anhydrous Na₂SO₄ and evaporated to afford the crude product (0.0383 g white solid, yield 83.7%), which was used without further purification.

¹H NMR (CDCl₃, 400 MHz) δ=3.82 (dd, J=9.1, 6.6 Hz, 1H) 4.12 (dd, J=10.0, 7.9 Hz, 1H) 4.72-4.55 (m, 2H) 5.15 (td, J=11.8, 5.4 Hz, 1H) 7.27 (dd, J=8.3, 4.9 Hz, 1H) 7.34 (d, J=8.7 Hz, 2H) 7.59 (dd, J=8.7, 1.9 Hz, 2H) 8.03 (ddd, J=8.5, 2.6, 1.2 Hz, 1H) 8.14 (d, J=1.9 Hz, 2H) 8.37 (d, J=4.2 Hz, 1H) 8.44 (s, 1H)

ESI m/z: 543.9 [(M+HCOO⁻); C21H15Br2N3O2 (M) requires 499].

Step 2

The title compound of Example 40 was prepared as follows. LiOH.H₂O (0.0097 g, 0.231 mmol) was added to 5-((3,6-dibromo-9H-carbazol-9-yl)methyl)-3-(pyridin-3-yl)oxazolidin-2-one (0.0116 g, 0.0231 mmol) in a mixture of 265 μL THF and 29 μL H₂O (v/v=9:1). The mixture was stirred at room temperature for 7 days. The reaction mixture purified by silica gel chromatography using CHCl₃/MeOH as elute to afford 0.0087 g white solid as product, yield 79.3%.

¹H NMR (CDCl₃, 600 MHz) δ=3.15 (dd, J=12.6, 6.2 Hz, 1H) 3.30 (d, J=11.8 Hz, 1H) 4.45-4.33 (m, 31-1) 6.81 (d, J=7.4 Hz, 1H) 7.02 (s, br, 1H) 7.32 (d, J=8.7 Hz, 2H) 7.52 (dd, J=8.7, 1.8 Hz, 2H) 7.83 (s, br, 2H) 8.11 (d, J=1.6 Hz, 2H)

¹³C NMR (CDCl₃, 400 MHz) δ=139.8, 139.5, 136.2, 130.0, 129.5, 124.1, 123.8, 123.5, 119.7, 112.8, 110.9, 69.0, 47.6, 47.3

ESI m/z: 517.9 [(M+HCOO⁻); C20H17Br2N3O (M) requires 473].

Example 41

1-(3,6-dibromo-9H-carbazol-9-yl)-3-(pyridin-4-ylamino)propan-2-ol

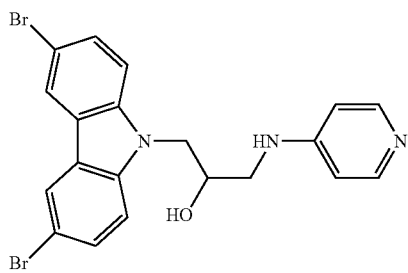 [SMILES: OC(CNc1ccncc1)Cn1c2ccc(Br)cc2c2cc(Br)ccc21]

Step 1. 5-((3,6-dibromo-9H-carbazol-9-yl)methyl)-3-(pyridin-4-yl)oxazolidin-2-one

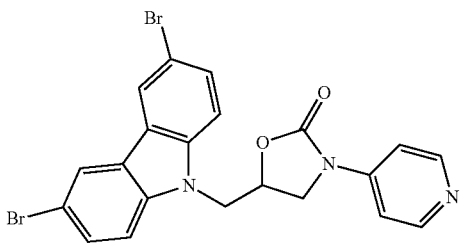 [SMILES: O=C1OC(Cn2c3ccc(Br)cc3c3cc(Br)ccc32)CN1c1ccncc1]

A mixture of the corresponding N—H oxazolidinone (0.0195 g, 0.0460 mmol), 4-iodopyridine (0.0209 g, 0.102 mmol), CuI (0.0009 g, 0.00460 mmol), and $K_2CO_3$ (0.0058 g, 0.0418 mmol) in 0.5 mL of DMSO was at 130° C. for 12 hours in a sealed vial. The reaction mixture was cooled and diluted with 20 mL EtOAc and washed with brine (3×10 mL). The organic layer was dried over anhydrous $Na_2SO_4$ and evaporated to afford the crude product, which was further triturated from $CH_2Cl_2$ suspension by hexane to afford 0.0187 g white solid as product, yield 74.6%.

$^1$H NMR (CDCl$_3$, 400 MHz) δ=3.77 (dd, J=9.4, 6.8 Hz, 1H) 4.08 (t, J=9.0 Hz, 1H) 4.64 (d, J=4.6 Hz, 2H) 5.23-5.10 (m, 1H) 7.34 (d, J=8.7 Hz, 2H) 7.37 (s, br, 2H) 7.61 (dd, J=8.6, 1.8 Hz, 2H) 8.16 (d, J=1.8 Hz, 2H) 8.55 (s, br, 2H).

ESI m/z: 544.0 [(M+HCOO$^-$); C21H15Br2N3O2 (M) requires 499].

Step 2

The title compound of Example 41 was prepared as follows. LiOH.H$_2$O (0.0157 g, 0.373 mmol) was added to 5-((3,6-dibromo-9H-carbazol-9-yl)methyl)-3-(pyridin-4-yl)oxazolidin-2-one (0.0187 g, 0.0373 mmol) in a mixture of 428 μL THF and 48 μL H$_2$O (v/v=9:1). The mixture was stirred at room temperature for 3 days. The reaction mixture was diluted with 30 mL EtOAc and washed with brine 3×30 mL. The organic layer was dried over anhydrous Na$_2$SO$_4$ and evaporated to afford the crude product, which did not require purification (0.0013 g white solid, 7.3%).

$^1$H NMR (d$_6$-Acetone, 400 MHz) δ=3.33 (dd, J=13.1, 6.4 Hz, 1H) 3.49 (dd, J=13.2, 4.4 Hz, 1H) 4.41 (td, J=7.6, 4.1 Hz, 1H) 4.51 (dd, J=15.0, 7.6 Hz, 1H) 4.61 (dd, J=14.8, 3.4 Hz, 1H) 6.61 (s, 2H) 7.56 (d, J=8.6 Hz, 2H) 7.62 (d, J=8.7 Hz, 2H) 8.10 (s, br, 2H) 8.37 (s, 2H)

$^{13}$C NMR (d$_6$-Acetone, 400 MHz) δ=179.0, 149.6, 140.4, 129.0, 123.8, 123.3, 112.1, 111.8, 107.8, 68.8, 47.6, 46.4

ESI m/z: 517.9 [(M+HCOO$^-$); C20H17Br2N3O (M) requires 473].

Example 42

1-(2,8-dimethyl-3,4-dihydro-1H-pyrido[4,3-b]indol-5(2H)-yl)-3-(phenylamino)propan-2-ol

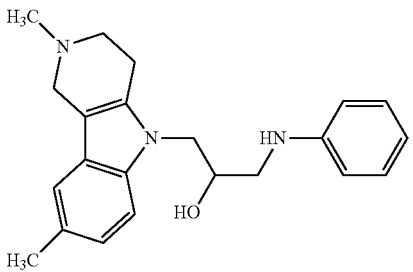 [SMILES: Cc1ccc2c(c1)c1c(n2CC(O)CNc2ccccc2)CCN(C)C1]

Example 42 was synthesized using a similar synthetic procedure analogous to Representative Procedure 2.

Example 43

N-(3-(3,6-dibromo-9H-carbazol-9-yl)-2,2-difluoropropyl)-3-methoxyaniline

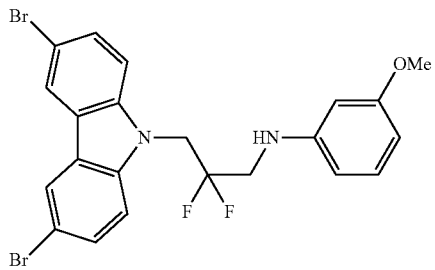 [SMILES: COc1cccc(NCC(F)(F)Cn2c3ccc(Br)cc3c3cc(Br)ccc32)c1]

Step 1. N-(3-(3,6-dibromo-9H-carbazol-9-yl)-2-oxopropyl)-N-(3-methoxyphenyl)-4-nitrobenzenesulfonamide

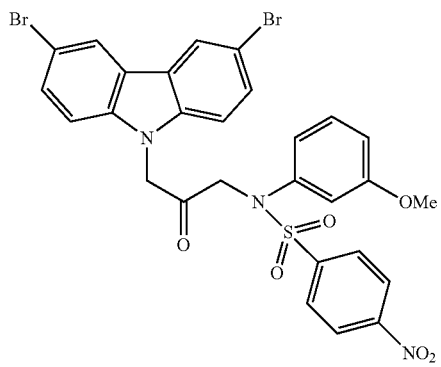

The nosylate of the title compound of Example 62 (prepared according to the procedures described herein) was oxidized with Dess-Martin periodinane using a procedure similar to that described in Example 103. Quantitative yield.

$^1$H NMR (CDCl$_3$, 500 MHz) δ 8.24 (d, 2H, J=8.9 Hz), 8.14 (s, 2H), 7.68 (d, 2H, J=9.1 Hz), 7.53 (d, 2H, J=8.6 Hz), 7.18 (t, 1H, J=8.7 Hz), 7.05 (t, 2H, J=8.1 Hz), 6.87 (dd, 1H, J=8.3, 2.5 Hz) 5.21, (s, 2H), 4.30 (s, 2H), 2.48 (s, 3H).

MS (ESI), m/z: 683.9 [(M−1)$^-$; C28H21Br2N3O6S (M) require 685.0].

Step 2. N-(3-(3,6-dibromo-9H-carbazol-9-yl)-2,2-difluoropropyl)-N-(3-methoxyphenyl)-4-nitrobenzenesulfonamide

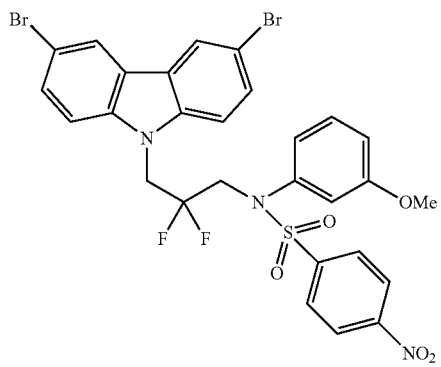 [SMILES: COc1cccc(N(CC(F)(F)Cn2c3ccc(Br)cc3c3cc(Br)ccc32)S(=O)(=O)c2ccc([N+](=O)[O-])cc2)c1]

The title compound of Example 43, step 2 was prepared from the ketone prepared in step 1 above using a procedure similar to that described in Example 103. Yield was quantitative and crude product was used without additional purification.

$^1$H NMR (CDCl$_3$, 500 MHz) δ 8.31 (d, 2H, J=8.9 Hz), 8.11 (s, 2H), 7.77 (d, 2H, J=8.9 Hz), 7.55 (dd, 2H, J=8.7, 1.8 Hz), 7.25 (m, 3H), 6.92 (dd, 1H, J=8.3, 2.0 Hz), 6.73 (m, 1H) 6.61, (d, 1H, J=7.7 Hz), 4.78 (t, 2H, T=14.7 Hz), 4.18 (t, 2H, J=11.2 Hz), 3.78 (s, 3H).

MS (ESI), m/z: 751.9 [(M+HCOO)$^-$; C28H21Br2F2N3O5S (M) requires 707.0].

Step 3

The title compound of Example 43 was prepared as follows. The nosyl group on N-(3-(3,6-dibromo-9H-carbazol-9-yl)-2,2-difluoropropyl)-N-(3-methoxyphenyl)-4-nitrobenzenesulfonamide was removed using the procedure described in Representative Procedure 5.

$^1$H NMR (CDCl$_3$, 400 MHz) δ 8.11 (d, 2H, J=1.6 Hz), 7.49 (dd, 2H, J=8.7, 2.0 Hz), 7.32 (d, 2H, J=8.9 Hz), 7.11 (t, 1H, J=8.2 Hz) 6.39 (dd, 1H, J=8.2, 2.3 Hz), 4.68 (t, 2H, J=13.2 Hz), 3.89 (t, 1H, J=7.0 Hz), 3.74 (s, 3H), 3.47 (m, 2H)

MS (ESI), m/z: 566.9 [(M+HCOO)$^-$; C22H18Br2F2N2O (M) requires 522.0].

Example 45

1-(3,6-dibromo-9H-carbazol-9-yl)-3-(phenylamino)propan-2-ol

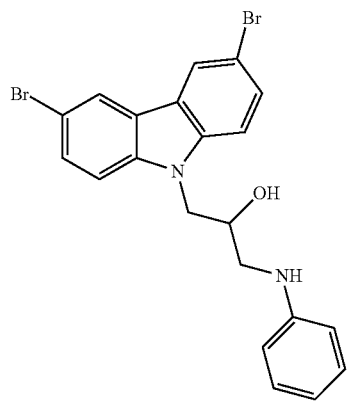 [SMILES: OC(CNc1ccccc1)Cn1c2ccc(Br)cc2c2cc(Br)ccc21]

Purchased from ChemBridge Corporation

Example 46

1-(3,6-dibromo-9H-carbazol-9-yl)-3-(o-tolylamino)propan-2-ol

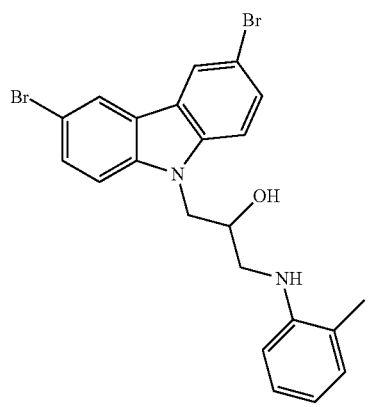 [SMILES: Cc1ccccc1NCC(O)Cn1c2ccc(Br)cc2c2cc(Br)ccc21]

Purchased from ChemBridge Corporation

Example 47

1-(3,6-dibromo-9H-carbazol-9-yl)-3-(m-tolylamino)propan-2-ol

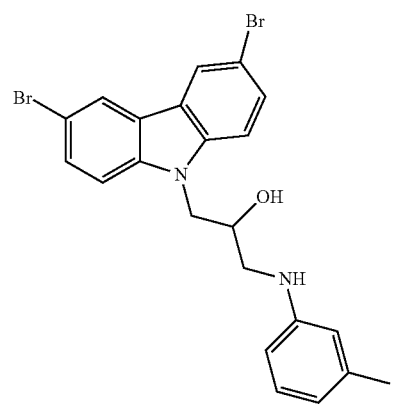 [SMILES: Cc1cccc(NCC(O)Cn2c3ccc(Br)cc3c3cc(Br)ccc32)c1]

Purchased from ChemBridge Corporation

Example 48

1-(3,6-dibromo-9H-carbazol-9-yl)-3-(2-methoxyphenylamino)propan-2-ol

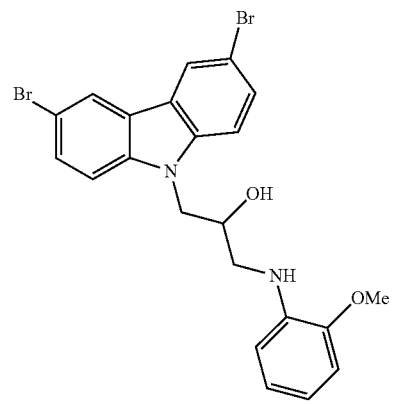 [SMILES: COc1ccccc1NCC(O)Cn1c2ccc(Br)cc2c2cc(Br)ccc21]

Purchased from ChemBridge Corporation

Example 50

1-(4-bromophenylamino)-3-(3,6-dichloro-9H-carbazol-9-yl)propan-2-ol

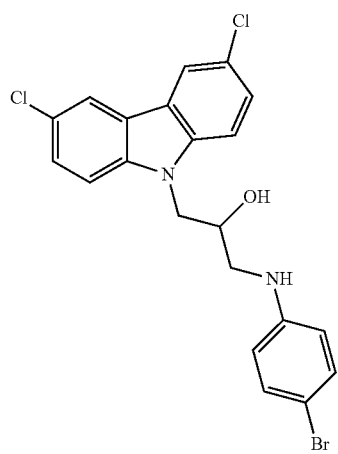 [SMILES: OC(CNc1ccc(Br)cc1)Cn1c2ccc(Cl)cc2c2cc(Cl)ccc21]

Purchased from ChemBridge Corporation

Example 51

1-(4-bromophenylamino)-3-(3,6-dibromo-9H-carbazol-9-yl)propan-2-ol

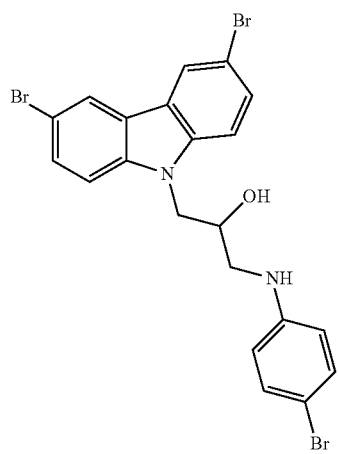

Purchased from ChemBridge Corporation

Example 52

1-(3,6-dibromo-9H-carbazol-9-yl)-3-(4-ethoxyphenylamino)propan-2-ol

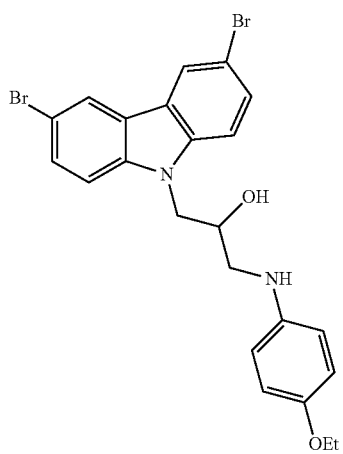 [SMILES: CCOc1ccc(NCC(O)Cn2c3ccc(Br)cc3c3cc(Br)ccc32)cc1]

Purchased from ChemBridge Corporation

Example 53

1-(4-chlorophenylamino)-3-(3,6-dibromo-9H-carbazol-9-yl)propan-2-ol

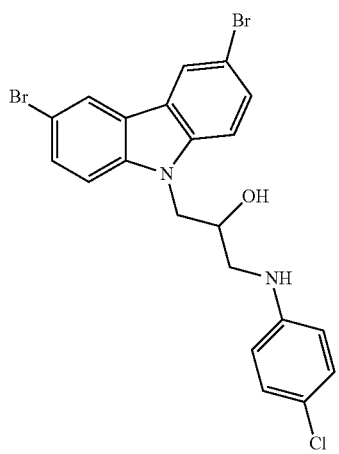

Purchased from ChemBridge Corporation

Example 54

1-(3,6-dibromo-9H-carbazol-9-yl)-3-(phenethylamino)propan-2-ol

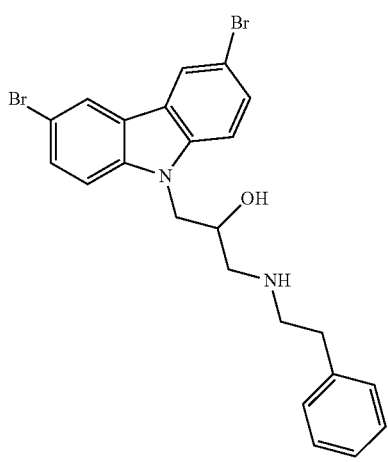 [SMILES: OC(CNCCc1ccccc1)Cn1c2ccc(Br)cc2c2cc(Br)ccc21]

Purchased from ChemBridge Corporation

Example 55

1-(3,6-dibromo-9H-carbazol-9-yl)-3-(2-hydroxyethylamino)propan-2-ol

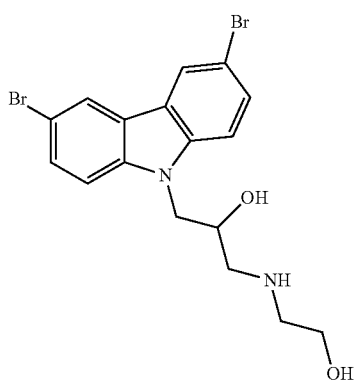 [SMILES: OCCNCC(O)Cn1c2ccc(Br)cc2c2cc(Br)ccc21]

Purchased from ChemBridge Corporation

Example 56

1-(3,6-dibromo-9H-carbazol-9-yl)-3-(2,4-dimethoxyphenylamino)propan-2-ol

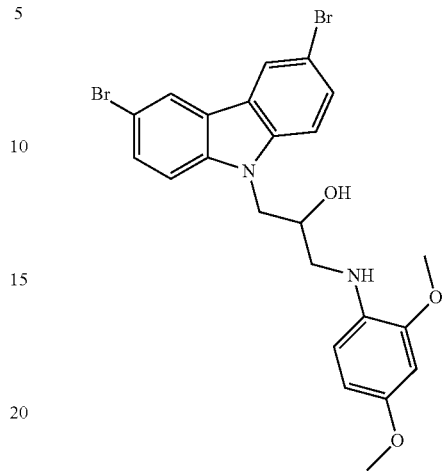

Purchased from ChemBridge Corporation

Example 57

1-(3,6-dibromo-9H-carbazol-9-yl)-3-(2,3-dimethylphenylamino)propan-2-ol

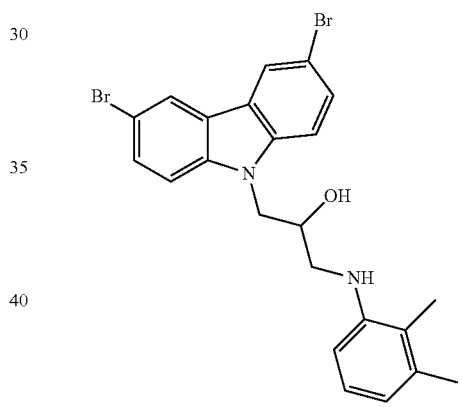

Purchased from ChemDiv, Inc.

Example 58

1-(2-chlorophenylamino)-3-(3,6-dibromo-9H-carbazol-9-yl)propan-2-ol

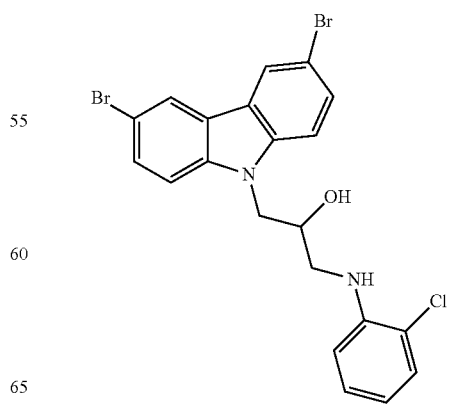

Purchased from ChemDiv, Inc.

Example 59

1-(tert-butylamino)-3-(3,6-dibromo-9H-carbazol-9-yl)propan-2-ol

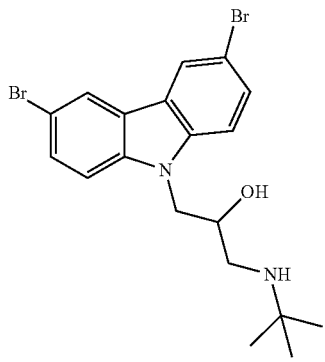 [SMILES: CC(C)(C)NCC(O)Cn1c2ccc(Br)cc2c2cc(Br)ccc21]

Purchased from ChemDiv, Inc.

Example 60

1-(3,6-dibromo-9H-carbazol-9-yl)-3-(isopropylamino)propan-2-ol

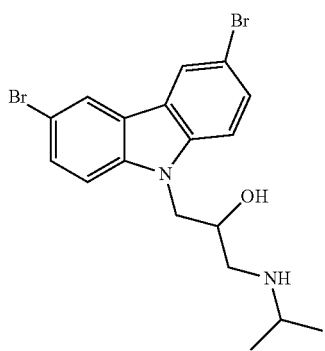 [SMILES: CC(C)NCC(O)Cn1c2ccc(Br)cc2c2cc(Br)ccc21]

Purchased from ChemDiv, Inc.

Example 61

1-(3,6-dibromo-9H-carbazol-9-yl)-3-(4-methoxyphenylamino)propan-2-ol

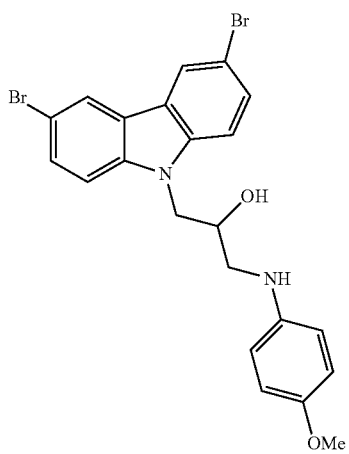 [SMILES: COc1ccc(NCC(O)Cn2c3ccc(Br)cc3c3cc(Br)ccc32)cc1]

Purchased from ChemDiv, Inc.

Example 62

1-(3,6-dibromo-9H-carbazol-9-yl)-3-(3-methoxyphenylamino)propan-2-ol

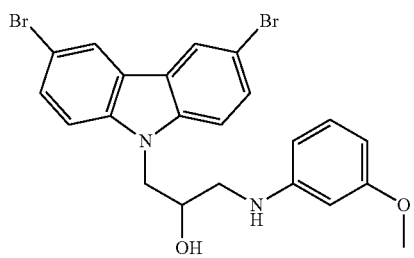 [SMILES: COc1cccc(NCC(O)Cn2c3ccc(Br)cc3c3cc(Br)ccc32)c1]

Purchased from ChemDiv, Inc.

Example 63

1-(3,6-dibromo-9H-carbazol-9-yl)-3-(m-tolylamino)propan-2-ol

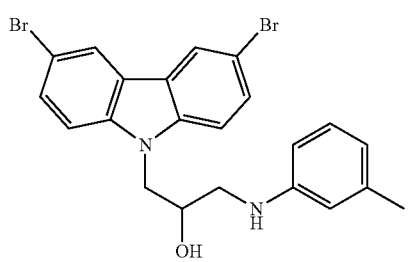 [SMILES: Cc1cccc(NCC(O)Cn2c3ccc(Br)cc3c3cc(Br)ccc32)c1]

Purchased from ChemDiv, Inc.

Example 64

1-(3,6-dibromo-9H-carbazol-9-yl)-3-(3,5-dimethylphenylamino)propan-2-ol

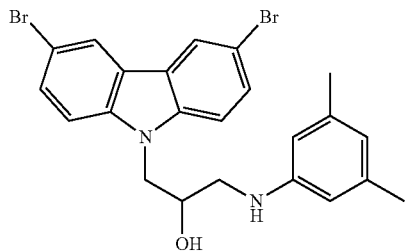 [SMILES: Cc1cc(C)cc(NCC(O)Cn2c3ccc(Br)cc3c3cc(Br)ccc32)c1]

Purchased from ChemDiv, Inc.

Example 65

1-(3,6-dibromo-9H-carbazol-9-yl)-3-(3,4-dimethylphenylamino)propan-2-ol

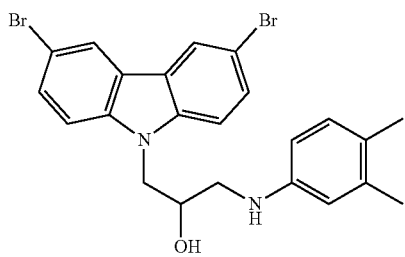 [SMILES: Cc1ccc(NCC(O)Cn2c3ccc(Br)cc3c3cc(Br)ccc32)cc1C]

Purchased from ChemDiv, Inc.

Example 66

1-(3,6-dibromo-9H-carbazol-9-yl)-3-(3,4-dimethylphenylamino)propan-2-ol

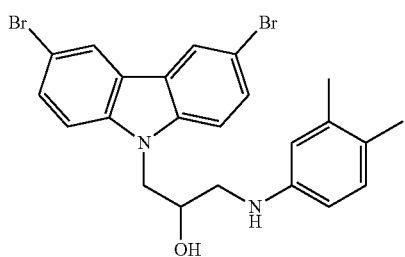 [SMILES: Cc1ccc(NCC(O)Cn2c3ccc(Br)cc3c3cc(Br)ccc32)cc1C]

Purchased from ChemDiv, Inc.

Example 67

1-(3,6-dibromo-9H-carbazol-9-yl)-3-(2,5-dimethylphenylamino)propan-2-ol

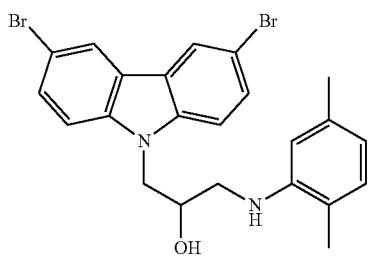 [SMILES: Cc1ccc(C)c(NCC(O)Cn2c3ccc(Br)cc3c3cc(Br)ccc32)c1]

Purchased from ChemDiv, Inc.

Example 68

1-(4-bromophenylamino)-3-(2,3-dimethyl-1H-indol-1-yl)propan-2-ol

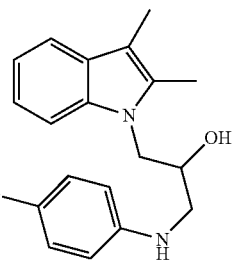

Purchased from ChemBridge Corporation

Example 69

1-(2,3-dimethyl-1H-indol-1-yl)-3-(4-methoxyphenylamino)propan-2-ol

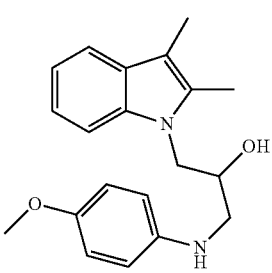 [SMILES: COc1ccc(NCC(O)Cn2c(C)c(C)c3ccccc32)cc1]

Purchased from ChemBridge Corporation

Example 70

1-(2,3-dimethyl-1H-indol-1-yl)-3-(4-ethoxyphenylamino)propan-2-ol

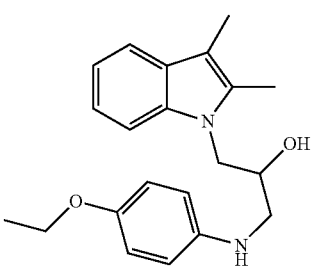 [SMILES: CCOc1ccc(NCC(O)Cn2c(C)c(C)c3ccccc32)cc1]

Purchased from ChemBridge Corporation

Example 71

1-(2,3-dimethyl-1H-indol-1-yl)-3-(p-tolylamino)propan-2-ol

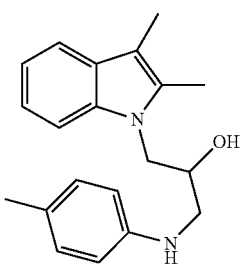 [SMILES: Cc1ccc(NCC(O)Cn2c(C)c(C)c3ccccc32)cc1]

Purchased from ChemBridge Corporation

Example 72

1-(2,3-dimethyl-1H-indol-1-yl)-3-(phenylamino)propan-2-ol oxalate

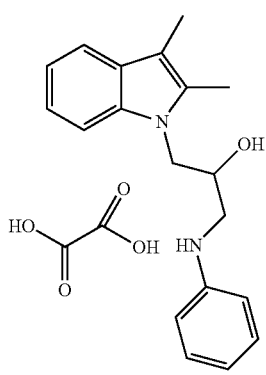

Purchased from ChemBridge Corporation

Example 73

1-(1H-indol-1-yl)-3-(4-methoxyphenylamino)propan-2-ol hydrochloride

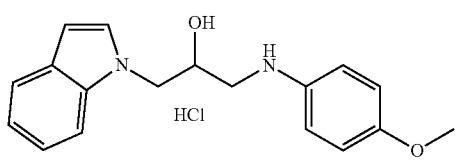 [SMILES: COc1ccc(NCC(O)Cn2ccc3ccccc32)cc1 ; Cl]

Purchased from ChemBridge Corporation

Example 74

1-(1H-indol-1-yl)-3-(phenylamino)propan-2-ol oxalate

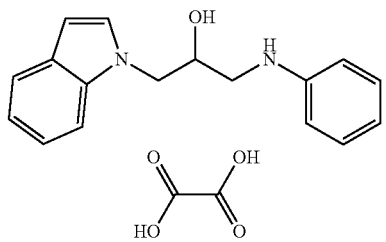 [SMILES: OC(CNc1ccccc1)Cn1ccc2ccccc21 ; O=C(O)C(=O)O]

Purchased from ChemBridge Corporation

Example 75

1-(3,4-dihydro-1H-carbazol-9(2H)-yl)-3-(m-tolylamino)propan-2-ol

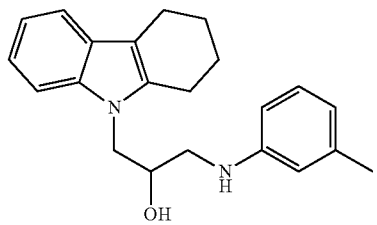 [SMILES: Cc1cccc(NCC(O)Cn2c3c(c4ccccc42)CCCC3)c1]

Purchased from ChemBridge Corporation

Example 76

1-(9H-carbazol-9-yl)-3-(phenylamino)propan-2-ol

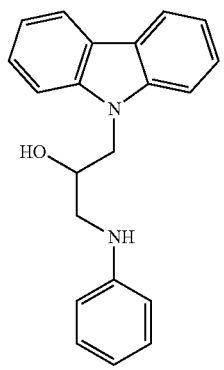 [SMILES: OC(CNc1ccccc1)Cn1c2ccccc2c2ccccc21]

Purchased from ChemBridge Corporation

Example 77

1-(3,6-dichloro-9H-carbazol-9-yl)-3-(phenylamino)propan-2-ol

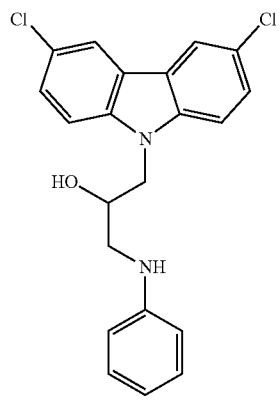 [SMILES: OC(CNc1ccccc1)Cn1c2ccc(Cl)cc2c2cc(Cl)ccc21]

Purchased from ChemBridge Corporation

Example 78

1-(9H-carbazol-9-yl)-3-(p-tolylamino)propan-2-ol

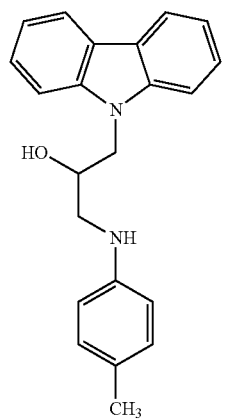 [SMILES: Cc1ccc(NCC(O)Cn2c3ccccc3c3ccccc32)cc1]

Purchased from ChemBridge Corporation

Example 79

1-(3,6-dichloro-9H-carbazol-9-yl)-3-(p-tolylamino)propan-2-ol

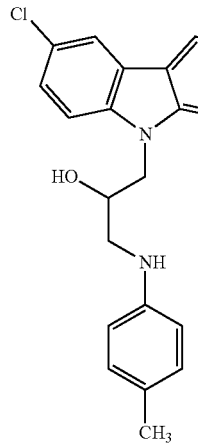

Purchased from ChemBridge Corporation

Example 80

1-(3,6-dibromo-9H-carbazol-9-yl)-3-(p-tolylamino)propan-2-ol

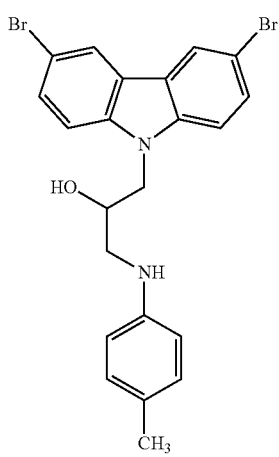 [SMILES: Cc1ccc(NCC(O)Cn2c3ccc(Br)cc3c3cc(Br)ccc32)cc1]

Purchased from ChemBridge Corporation

Example 81

N-(4-(3-(9H-carbazol-9-yl)-2-hydroxypropoxy)phenyl)acetamide

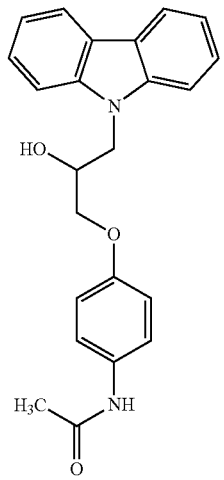 [SMILES: CC(=O)Nc1ccc(OCC(O)Cn2c3ccccc3c3ccccc32)cc1]

Purchased from ChemBridge Corporation

Example 82

1-(9H-carbazol-9-yl)-3-phenoxypropan-2-ol

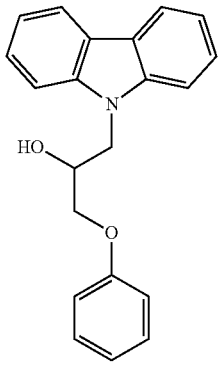 [SMILES: OC(COc1ccccc1)Cn1c2ccccc2c2ccccc21]

Purchased from ChemBridge Corporation

Example 83

1-(9H-carbazol-9-yl)-3-(4-methoxyphenylamino)propan-2-ol

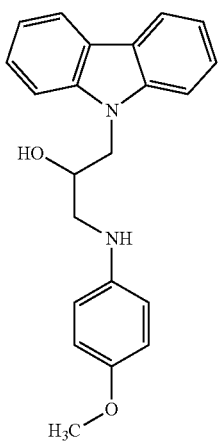 [SMILES: COc1ccc(NCC(O)Cn2c3ccccc3c3ccccc32)cc1]

Purchased from ChemBridge Corporation

Example 84

1-(benzylamino)-3-(9H-carbazol-9-yl)propan-2-ol

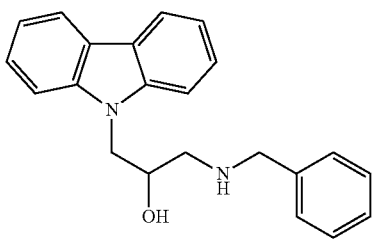 [SMILES: OC(CNCc1ccccc1)Cn1c2ccccc2c2ccccc21]

Purchased from ChemBridge Corporation

Example 85 methyl 4-(3-(9H-carbazol-9-yl)-2-hydroxypropoxy)benzoate

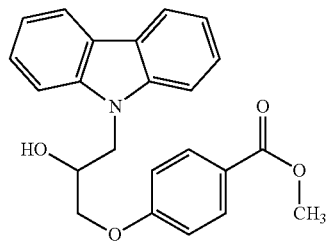 [SMILES: COC(=O)c1ccc(OCC(O)Cn2c3ccccc3c3ccccc32)cc1]

Purchased from ChemBridge Corporation

Example 86

1-(9H-carbazol-9-yl)-3-(4-methoxyphenoxy)propan-2-ol

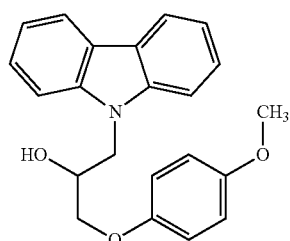

Purchased from ChemBridge Corporation

Example 87

1-amino-3-(3,6-dibromo-9H-carbazol-9-yl)propan-2-ol

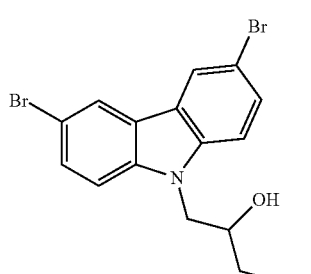

Purchased from ChemBridge Corporation

Example 88a (S)-1-(3,6-dibromo-9H-carbazol-9-yl)-3-phenoxypropan-2-ol

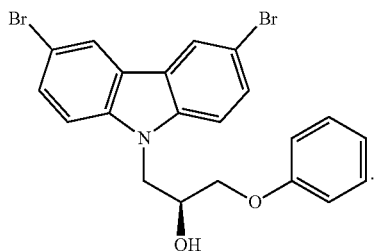 [SMILES: O[C@H](COc1ccccc1)Cn1c2ccc(Br)cc2c2cc(Br)ccc21]

Example 88b (R)-1-(3,6-dibromo-9H-carbazol-9-yl)-3-phenoxypropan-2-ol

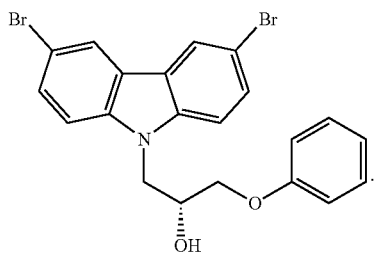 [SMILES: O[C@@H](COc1ccccc1)Cn1c2ccc(Br)cc2c2cc(Br)ccc21]

The title compounds of Examples 88a and 88b were prepared according to the procedure described in Example 3b except using the appropriate commercially available optically active phenoxymethyl oxirane as the epoxide starting material.

Example 89

3,6-dibromo-9-(2-fluoro-3-phenoxypropyl)-9H-carbazole

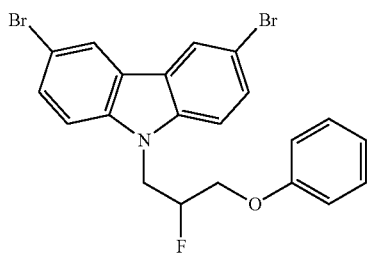 [SMILES: FC(COc1ccccc1)Cn1c2ccc(Br)cc2c2cc(Br)ccc21]

The title compound of Example 89 was prepared according to the procedure described in Representative Procedure 4 except using the title compound of Example 3b as the starting material. The crude mixture was purified in 100% DCM (+0.2% TEA). Isolated yield=97%.

$^1$H NMR (CDCl$_3$, 400 MHz) δ 8.13 (d, 2H, J=1.7 Hz), 7.51 (dd, 2H, J=8.7, 1.9 Hz), 7.29-7.35 (m, 4H), 7.01 (t, 1H, J=7.5 Hz), 6.91 (d, 1H, J=7.8 Hz), 5.16 (dddd, 1H, J=4.5, 5.4, 9.7, 46.0 Hz), 4.59-4.79 (m, 2H), 4.03-4.17 (m, 2H).

MS (ESI), m/z: 519.9 [(M+HCOO)$^-$; C21H16Br2FNO (M) requires 475.0].

Example 90

1-(3,6-dibromo-9H-carbazol-9-yl)-3-(3-methoxyphenylamino)-2-methylpropan-2-ol

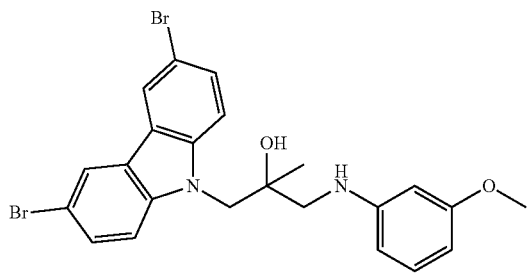 [SMILES: COc1cccc(NCC(C)(O)Cn2c3ccc(Br)cc3c3cc(Br)ccc32)c1]

Step 1. Chlorohydrin-19

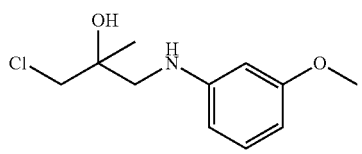

m-Anisidine (0.18 mL, 1.62 mmol) was added to 2-chloromethyl-2-methyl oxirane (0.154 mL, 1.62 mmol) in acetic acid (2 mL) and the mixture was heated to 75° C. Upon completion the reaction was neutralized with saturated sodium bicarbonate to pH 7, then extracted 3× with EtOAc, washed with brine and dried with MgSO$_4$ filtered, and concentrated in vacuo. The crude residue was purified by chromatography (SiO$_2$, 0-25% EtOAc/Hexane) to afford the desired alcohol (332 mg, 89%).

$^1$H NMR (CDCl$_3$, 400 MHz) δ 7.08 (t, 1H, J=8.1 Hz), 6.29 (m, 2H), 6.23 (t, 1H, J=2.3 Hz), 3.95 (s, NH), 3.77 (s, 3H), 3.60 (dd, 2H, J=35.1, 11.0 Hz), 3.25 (dd, 2H, J=44.8, 13.0 Hz), 2.31 (apparent d, OH), 1.36 (s, 31-1) ESI m/z 230.1 ([M+H]$^+$).

Step 2. Epoxide-20

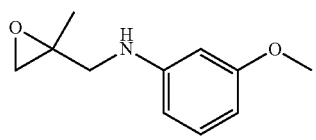

Chlorohydrin-19 (0.166 g, 0.722 mmol) was dissolved in dioxane (1 mL) and added to a solution of KOH (0.168 mgs, 3.0 mmol). The reaction was followed by TLC (20% EtOAc/Hexane) until the starting material was consumed and the less polar product was obtained. After aqueous workup, the crude product was used without purification.

$^1$H NMR (CDCl$_3$, 400 MHz) δ 7.07 (t, 1H, J=8.1 Hz), 6.27 (dd, 1H, J=8.2, 0.8 Hz), 6.22 (dd, 1H, J=8.2, 0.8 Hz), 6.16 (t, 1H, J=2.3 Hz), 3.83 (s, NH), 3.32 (br s, 2H), 2.82 (d, 1H, J=4.5 Hz), 2.63 (d, 1H, J=4.5 Hz).

Reference: Chemistry of Heterocyclic Compounds volume 41, No 4, 2005, pg 426.

Step 3

The title compound of Example 90 was prepared in 83% yield using 3,6-dibromocarbazole, sodium hydride (NaH), and epoxide 20. See, e.g., the procedure described in Example 21, step 4.

$^1$H NMR (CDCl$_3$, 400 MHz): δ 8.14 (s, 2H), 7.53 (d, 2H, J=8.9 Hz), 7.42 (d, 2H, J=8.4 Hz), 7.09 (t, 1H, J=8.4 Hz), 6.33 (d, 1H, J=6.3 Hz), 6.27 (d, 1H, J=6.3 Hz), 6.18 (s, 1H), 4.41 (d, 1H, J=15.3 Hz), 4.32 (d, 1H, J=15.3 Hz) 3.74 (s, NH), 3.49 (s, 3H), 3.28 (d, 1H, 12.4 Hz), 3.22 (d, 1H, 12.4 Hz), 2.03 (s, OH), 1.33 (s, 3H) ESI m/z 518.9 ([M+H]$^+$).

$^{13}$C NMR (CDCl$_3$, 100 MHz) δ 161.0, 149.8, 140.6 (2C), 130.4 (2C), 129.4 (2C), 123.8 (2C), 123.2 (2C), 112.8, 111.8 (2C), 106.9, 103.8, 99.8, 75.0, 55.4, 52.5, 51.5, 25.1

ESI m/z 516.9 ([M+H]$^+$, C$_{23}$H$_{22}$Br$_2$N$_2$O$_2$ requires 516.04

Example 91

1-(2,8-dimethyl-3,4-dihydro-1H-pyrido[4,3-b]indol-5(2H)-yl)-3-(3-methoxyphenylamino)propan-2-ol

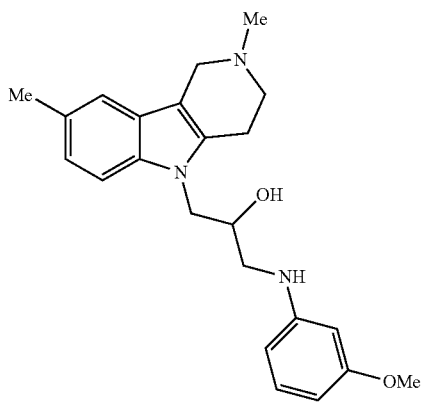 [SMILES: COc1cccc(NCC(O)Cn2c3c(c4cc(C)ccc42)CN(C)CC3)c1]

Following a literature procedure (Zoidis, G; Kolocouris, N; Naesens, L; De Clercq, E. *Bioorg. Med. Chem.* 2009, 17, 1534-1541), the title compound of Example 18 (0.015 g, 0.034 mmol) was dissolved in anhydrous THF (0.34 mL) and cooled to 0° C. A solution of LAH (0.10 mL, 1.0 M in THF) was added dropwise, and the reaction was stirred for 2 h at 0° C. MeOH was added to quench the remaining LAH and after 45 min, the mixture was partitioned between EtOAc/H$_2$O. The organic layer was separated and the aqueous layer was extracted with EtOAc (3×), and the combined organic layers were washed with satd. aq. NaCl, dried over Na$_2$SO$_4$, filtered, and concentrated. The crude residue was purified by column chromatography (SiO$_2$, 0-20% MeOH/Acetone+1% Et$_3$N), followed by PTLC (10% MeOH/Acetone+1% Et$_3$N) to afford the desired product (0.6 mg, 5%).

$^1$H NMR (CDCl$_3$, 500 MHz) δ=7.14 (m, 2H), 7.04 (dd, 1H, J=8.0, 8.0 Hz), 6.98 (d, 1H, J=8.5 Hz), 6.27 (d, 1H, J=8.0 Hz), 6.18 (d, 1H, J=8.0 Hz), 6.12 (s, 1H), 4.14 (m, 1H), 4.10 (m, 1H), 4.01 (m, 1H), 3.72 (s, 3H), 3.20 (m, 1H), 3.06 (m, 1H), 2.72 (s, 3H), 2.41 (s, 3H).

ESI m/z 380.2 ([M+H]$^+$, C$_{23}$H$_{30}$N$_3$O$_2$ requires 380.2).

Example 92

1-(4-azidophenylamino)-3-(3,6-dibromo-9H-carbazol-9-yl)propan-2-ol

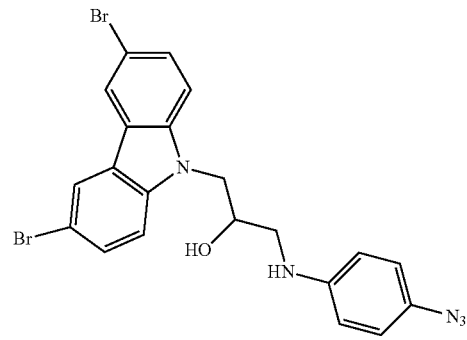 [SMILES: [N-]=[N+]=Nc1ccc(NCC(O)Cn2c3ccc(Br)cc3c3cc(Br)ccc32)cc1]

4-Azidoaniline (0.038 g, 0.283 mmol) was added to a solution of 3,6-dibromo-9-(oxiran-2-ylmethyl)-9H-carbazole (0.100 g, 0.262 mmol) in THF (0.10 mL). LiBr (0.001 g, 0.013 mmol) was added and the reaction was stirred at room temperature for 3 days. The reaction was purified directly by chromatography (SiO$_2$, 0-25% EtOAc/Hexane) to afford the desired product (31 mg, 23%).

$^1$H NMR (d$_6$-acetone, 500 MHz) δ=8.36 (d, 2H, J=2.0 Hz), 7.61 (m, 2H), 7.55 (m, 2H), 6.85 (m, 2H), 6.74 (m, 2H), 5.19 (br s, 1H), 4.61 (dd, 1H, J=4.0, 15.0 Hz), 4.56 (br s, 1H), 4.50 (dd, 1H, J=8.0, 15.0 Hz), 4.39 (m, 1H), 3.39 (dd, 1H, J=4.5, 13.0 Hz), 3.25 (dd, 1H, J=6.5, 13.0 Hz).

$^{13}$C NMR (acetone-d$_6$, 100 MHz) δ=147.7, 141.1, 129.8 (2C), 128.9, 124.5, 124.11 (2C), 120.7 (2C), 114.9 (2C), 112.8 (2C), 112.6, 111.9, 69.6, 48.5, 48.4.

ESI m/z 513.9 ([M+H]$^+$, C$_{21}$H$_{18}$Br$_2$N$_5$O requires 514.0).

Example 93

1-(3-azido-6-bromo-9H-carbazol-9-yl)-3-(3-methoxyphenylamino)propan-2-ol

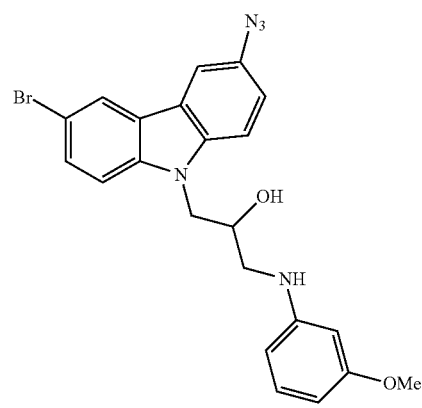 [SMILES: COc1cccc(NCC(O)Cn2c3ccc(Br)cc3c3cc(N=[N+]=[N-])ccc32)c1]

Step 1. 3-azido-6-bromo-9H-carbazole

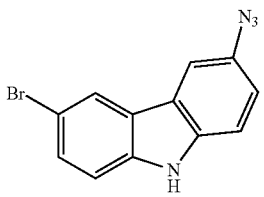 [SMILES: [N-]=[N+]=Nc1ccc2[nH]c3ccc(Br)cc3c2c1]

3,6-Dibromocarbazole (0.500 g, 1.538 mmol), NaN₃ (0.120 g, 1.846 mmol), CuI (0.029 g, 0.154 mmol), L-proline (0.053 g, 0.461 mmol) and NaOH (0.019 g, 0.461 mmol) were dissolved in 7:3 EtOH/H₂O (3.0 mL) and heated to 95° C. under a N₂ atmosphere for 24 h. The completed reaction was partitioned between EtOAc/H2O (3×) and the combined organics were washed with satd. aq. NaCl, dried over Na₂SO₄, filtered, and concentrated. The crude residue was purified by chromatography (SiO₂, 0-15% EtOAc/toluene), followed by HPLC (Phenomenex SiO₂ Luna 10µ, 250×21.2 mm column, 50% EtOAc/Hexane, 21 mL/min, retention time=48 min) to afford the desired product.

¹H NMR (CDCl₃, 500 MHz) δ 8.14 (s, 1H), 8.08 (br s, 1H), 7.64 (s, 1H), 7.50 (d, 1H, J=8.5 Hz), 7.38 (d, 1H, J=9.0 Hz), 7.29 (d, 1H, J=8.5 Hz), 7.10 (d, 1H, J=9.0 Hz).

ESI m/z 285.0 ([M−H]⁻, $C_{12}H_6BrN_4$ requires 285.0).

Step 2

The title compound of Example 93 was synthesized from 3-azido-6-bromo-9H-carbazole in 46% yield using a procedure analogous to that described in Example 90, step 3.

¹H NMR (CDCl₃, 500 MHz) δ 8.14 (d, 1H, J=1.5 Hz), 7.64 (d, 1H, J=2.0 Hz), 7.52 (dd, 1H, J=1.5, 8.5 Hz), 7.40 (d, 1H, J=9.0 Hz), 7.31 (d, 1H, J=8.5 Hz), 7.12 (dd, 1H, J=2.0, 8.5 Hz), 7.07 (dd, 1H, J=8.0, 8.0 Hz), 6.31 (dd, 1H, J=2.0, 8.0 Hz), 6.21 (dd, 1H, J=1.5, 8.0 Hz), 6.13 (dd, 1H, J=2.0, 2.5 Hz), 4.39-4.35 (m, 3H), 3.71 (s, 3H), 3.31 (dd, 1H, J=3.5, 13.0 Hz), 3.16 (dd, 1H, J=7.0, 13.0 Hz), 2.17 (br s, 1H).

ESI m/z 466.0 ([M+H]⁺, $C_{22}H_{21}BrN_5O_2$ requires 466.1).

Example 94

1-(3,6-dibromo-9H-carbazol-9-yl)-3-(4-methoxyphenoxy)propan-2-ol

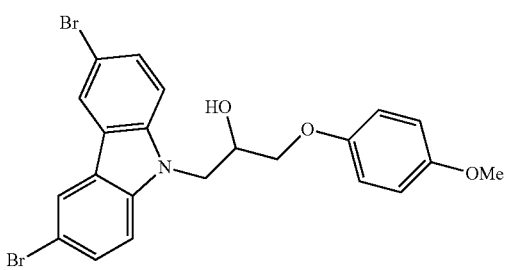 [SMILES: COc1ccc(OCC(O)Cn2c3ccc(Br)cc3c3cc(Br)ccc32)cc1]

The title compound of Example 93 was synthesized from dibromocarbazole and (p-methoxyphenyl)-glycidyl ether in 47% yield using a procedure analogous to those described in Example 90, step 3 and Example 93, step 2.

¹H NMR (CDCl₃, 500 MHz) δ 8.12 (d, 2H, J=2.0 Hz), 7.50 (dd, 2H, J=2.0, 8.5 Hz), 7.34 (d, 2H, J=8.5 Hz), 6.81 (m, 2H), 6.79 (m, 2H), 4.56 (m, 1H), 4.42 (m, 3H), 3.93 (dd, 1H, J=4.5, 9.5 Hz), 3.81 (dd, 1H, J=4.5, 9.5 Hz), 3.76 (s, 3H), 2.39 (d, 1H, J=6.0 Hz).

¹³C NMR (acetone-d₆, 100 MHz) δ 155.2, 153.8, 141.2 (2C), 129.8 (2C), 124.5 (2C), 124.0 (2C), 116.4 (2C), 115.5 (2C), 112.9 (2C), 112.5 (2C), 71.1, 69.8, 55.9, 47.4.

ESI m/z 547.9 ([M+CO₂H]⁺, $C_{23}H_{20}Br_2NO_5$ requires 548.0).

Example 95

1-(3,6-dichloro-9H-carbazol-9-yl)-3-(phenylsulfonyl)propan-2-ol

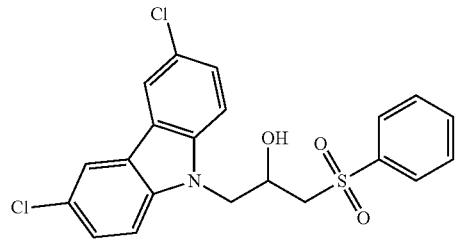 [SMILES: O=S(=O)(CC(O)Cn1c2ccc(Cl)cc2c2cc(Cl)ccc21)c1ccccc1]

Step 1. 1-(3,6-dichloro-9H-carbazol-9-yl)-3-(phenylthio)propan-2-ol

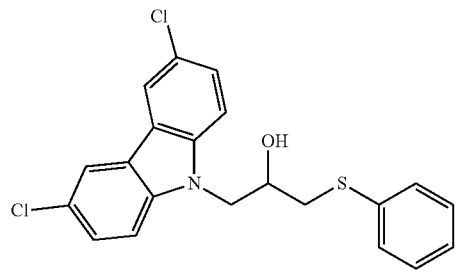 [SMILES: OC(CSc1ccccc1)Cn1c2ccc(Cl)cc2c2cc(Cl)ccc21]

The title compound of Example 95, step 1 was prepared using a procedure analogous to that described in Example 3a (white solid, 0.0293 g, yield 99.0%).

¹H NMR (CDCl₃, 400 MHz) δ=2.55 (s, 1H) 2.97 (dd, J=13.8, 7.2 Hz, 1H) 3.09 (dd, J=13.9, 5.2 Hz, 1H) 4.20-4.06 (m, 1H) 4.28 (dd, J=15.0, 7.0 Hz, 1H) 4.41 (dd, J=15.0, 4.1 Hz, 1H) 7.46-7.14 (m, 9H) 7.93 (d, J=1.8 Hz, 2H)

¹³C NMR (CDCl₃, 400 MHz) δ=139.7, 134.5, 130.3, 129.5, 127.3, 126.8, 125.4, 123.3, 120.4, 110.6, 69.3, 48.2, 39.4

ESI m/z: 446.0, 436.0 [(M+HCOO⁻), (M+Cl⁻); C21H17Cl2NOS (M) requires 401.0].

Step 2

The title compound of Example 95 was prepared as follows. To a solution of 1-(3,6-dichloro-9H-carbazol-9-yl)-3-(phenylthio)propan-2-ol (0.0081 g, 0.0201 mmol) in 0.2 mL CH₂Cl₂, a solution of mCPBA (77%, 0.0113 g, 0.0503 mmol) in 0.2 mL CH₂Cl₂ was added dropwise. The mixture was sealed and stirred at rt overnight. The crude was diluted with 30 mL EtOAc and washed with saturated NaHCO₃ (3×30 mL) and brine 1×30 mL. The organic layer was dried over anhydrous Na₂SO₄ and evaporated to afford the crude product, which was subjected to silica gel chromatography using Hexanes/EtOAc to afford white solid as product (0.0080 g, yield 91.3%).

¹H NMR (CDCl₃, 400 MHz) δ=3.17 (dd, J=14.2, 3.0 Hz, 1H) 3.28 (dd, J=14.3, 8.3 Hz, 1H) 3.29 (d, J=2.9 Hz, 1H) 4.39 (d, J=6.3 Hz, 2H) 4.67 (dtt, J=8.7, 5.9, 3.0 Hz, 1H) 7.31 (d, J=8.7 Hz, 2H) 7.40 (dd, J=8.7, 2.0 Hz, 2H) 7.52 (t, J=7.9 Hz, 2H) 7.66 (t, J=7.5 Hz, 1H) 7.80 (d, J=7.3 Hz, 2H) 7.96 (d, J=2.0 Hz, 2H).

¹³C NMR (CDCl₃, 400 MHz) δ=139.6, 138.8, 134.5, 129.8, 128.0, 127.0, 125.7, 123.5, 120.5, 110.5, 65.8, 60.0, 48.5

ESI m/z: 477.9 [(M+HCOO⁻); C21H17Cl2NO3S (M) requires 433.0].

Example 96

3,6-dibromo-9-(2-fluoro-3-(phenylsulfonyl)propyl)-9H-carbazole

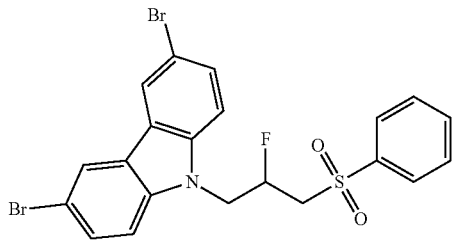

Step 1. 3,6-dibromo-9-(2-fluoro-3-(phenylthio)propyl)-9H-carbazole

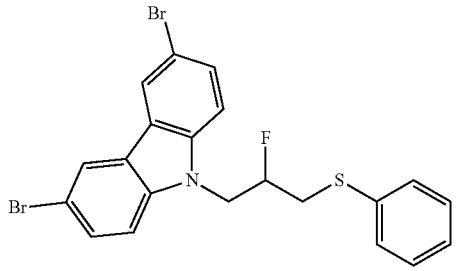 [SMILES: FC(CSc1ccccc1)Cn1c2ccc(Br)cc2c2cc(Br)ccc21]

The title compound of Example 96, step 1 was prepared by fluorination of the title compound of Example 31 using a procedure similar to that described in Representative Procedure 4.

¹H NMR (CDCl₃, 400 MHz) δ=3.09 (ddd, J=14.2, 11.3, 8.4 Hz, 1H) 3.37-3.23 (m, 1H) 4.53 (ddd, J=20.8, 15.9, 6.7 Hz, 1H) 4.66 (ddd, J=26.6, 15.9, 2.8 Hz, 1H) 5.04-4.81 (m, 1H) 7.36-7.27 (m, 5H) 7.42 (dt, J=3.2, 2.0 Hz, 2H) 7.54 (dd, J=8.7, 1.9 Hz, 2H) 8.13 (d, J=1.9 Hz, 2H)

¹³C NMR (CDCl₃, 400 MHz) δ=139.8, 134.3, 129.6, 129.5, 127.6, 123.9, 123.4, 112.9, 110.91 (d, J=2.1 Hz, 1C) 92.2, 90.4, 46.16 (d, J=22.8 Hz, 1C) 35.63 (d, J=23.3 Hz, 1C)

Step 2

The title compound of Example 96 was prepared as follows. To a solution of 3,6-dibromo-9-(2-fluoro-3-(phenylthio)propyl)-9H-carbazole (0.0143 g, 0.0290 mmol) in 0.5 mL CH₂Cl₂, a solution of mCPBA (77%, 0.0162 g, 0.0725 mmol) in 0.5 mL CH₂Cl₂ was added dropwise. The mixture was sealed and stirred at rt overnight. The crude was diluted with 30 mL EtOAc and washed with saturated NaHCO₃ 3×30 mL and brine 1×30 mL. The organic layer was dried over anhydrous Na₂SO₄ and evaporated to afford the crude product, which was subjected to silica gel chromatography using Hexanes/EtOAc as elute to afford white solid as product (0.0114 g, yield 74.8%).

¹H NMR (CDCl₃, 400 MHz) δ=3.61-3.40 (m, 2H) 4.56 (ddd, J=22.4, 16.0, 6.6 Hz, 1H) 4.72 (dd, J=26.8, 15.9 Hz, 1H) 5.38 (dd, J=47.1, 5.9 Hz, 1H) 7.34 (d, J=8.7 Hz, 2H) 7.63-7.53 (m, 4H) 7.68 (t, J=7.4 Hz, 1H) 7.90 (d, J=8.0 Hz, 2H) 8.12 (s, J=2.0 Hz, 2H)

¹³C NMR (CDCl₃, 400 MHz) δ=139.8, 134.7, 129.84, 129.79, 128.2, 124.1, 123.5, 113.3, 110.91, 110.89, 88.1, 86.3, 58.4, 58.1, 47.3, 47.1

ESI m/z: 557.9 [(M+Cl⁻); C21H16Br2FNO2S (M) requires 522.9].

Example 97a (S)-1-(3,6-dibromo-9H-carbazol-9-yl)-3-(phenylsulfonyl) propan-2-ol

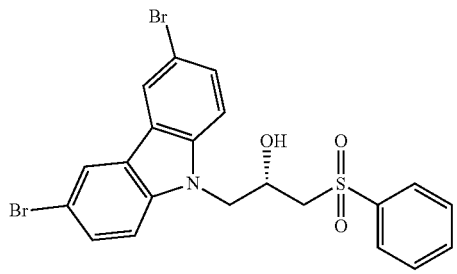 [SMILES: O=S(=O)(C[C@@H](O)Cn1c2ccc(Br)cc2c2cc(Br)ccc21)c1ccccc1]

Example 97b (R)-1-(3,6-dibromo-9H-carbazol-9-yl)-3-(phenylsulfonyl) propan-2-ol

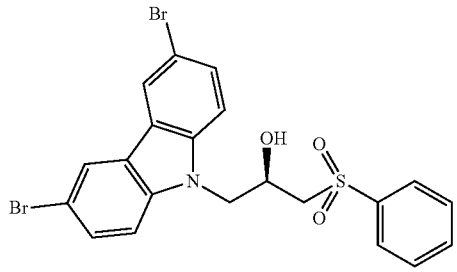 [SMILES: O=S(=O)(C[C@H](O)Cn1c2ccc(Br)cc2c2cc(Br)ccc21)c1ccccc1]

The title compounds of Examples 97a and 97b were prepared from (S)- or (R)-3,6-dibromo-9-(oxiran-2-ylmethyl)-9H-carbazole using a procedure similar to that described in Example 3d.

Preparation of (S)-3,6-dibromo-9-(oxiran-2-ylm-ethyl)-9H-carbazole[(S)-epoxide A]

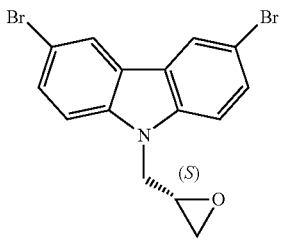

To a solution of 3,6-dibromocarbazole (0.2194 g, 0.675 mmol) and triphenylphosphine (0.1770 g, 0.675 mmol) in THF (5.4 mL) was added S-(−)-glycidol (44.8 μL, 0.0500 g, 0.675 mmol). The reaction mixture was cooled in an ice bath and diethyl azodicarboxylate (106.3 μL, 0.1175 g, 0.675 mmol) was added. The reaction mixture was allowed to warm to room temperature and stir overnight. THF was removed under vacuum and the residue was dissolved in 30 mL EtOAc and washed with brine (3×30 mL). The organic layer was dried over anhydrous $Na_2SO_4$ and evaporated to afford the crude product, which was subjected to silica gel chromatography using Hexanes/EtOAc to afford white solid as product (0.0514 g, yield 20.0%).

Example 98

1-(3,6-dicyclopropyl-9H-carbazol-9-yl)-3-(phenylamino)propan-2-ol

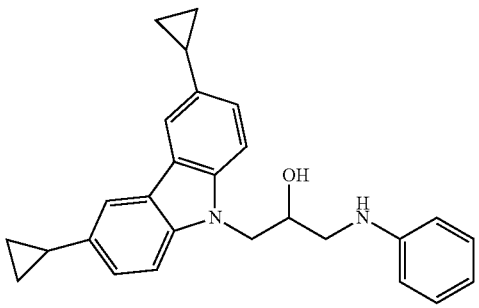 [SMILES: OC(CNc1ccccc1)Cn1c2ccc(C3CC3)cc2c2cc(C3CC3)ccc21]

Step 1. tert-butyl 3,6-dibromo-9H-carbazole-9-carboxylate

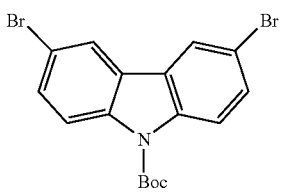 [SMILES: CC(C)(C)OC(=O)n1c2ccc(Br)cc2c2cc(Br)ccc21]

A solution of 3,6-dibromocarbazole (0.8288 g, 2.55 mmol) in 20 mL THF was added to a suspension of NaH (60%, 0.1122 g, 2.81 mmol) in 10 mL THF at −78° C. After stirring for 1 h, a solution of $(Boc)_2O$ anhydride (0.6122 g, 2.81 mmol) in 20 mL THF was added dropwise into the mixture. The reaction was allowed to warm to room temperature and stir overnight. THF was removed under vacuum and the residue was dissolved in 30 mL EtOAc and washed with 1M HCl (2×30 mL) and brine (1×30 mL). The organic layer was dried over anhydrous $Na_2SO_4$ and evaporated and the crude product was subjected to silica gel chromatography using Hexanes/EtOAc to afford white solid as product (0.9890 g, yield 91.7%).

$^1$H NMR ($CDCl_3$, 400 MHz) δ=1.75 (s, 9H) 7.58 (dd, J=8.9, 2.0 Hz, 1H) 8.05 (d, J=1.8 Hz, 1H) 8.16 (d, J=8.9 Hz, 1H).

$^{13}$C NMR ($CDCl_3$, 400 MHz) δ=150.5, 137.5, 130.5, 126.3, 122.6, 117.9, 116.4, 84.9, 28.5.

Step 2. tert-butyl 3,6-dicyclopropyl-9H-carbazole-9-carboxylate

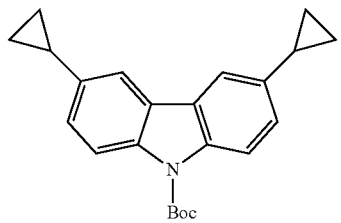 [SMILES: CC(C)(C)OC(=O)n1c2ccc(C3CC3)cc2c2cc(C3CC3)ccc21]

Following a literature procedure (Petit, S; Duroc, Y; Larue, V; Giglione, C; Leon, C; Soulama, C; Denis, A; Dardel, F; Meinnel, T; Artaud, I. *ChemMedChem* 2009, 4, 261-275), tert-butyl 3,6-dibromo-9H-carbazole-9-carboxylate (0.0200 g, 0.0470 mmol), cyclopropyl boronic acid (0.0202 g, 0.235 mmol), palladium acetate (10 mol %, 0.0011 g, 0.00470 mmol), potassium phosphate tribasic (0.0350 g, 0.165 mmol), tricyclohexylphosphine (0.0026 g, 0.00941 mmol), water (12.2 μL) and a stir bar were combined in a sealed vial. The vial was sparged with $N_2$ and charged with 0.22 mL degassed toluene. The mixture was stirred at 100° C. for 65 h. The crude reaction mixture was diluted with 10 mL EtOAc and washed with brine (3×10 mL). The organic layer was dried over anhydrous $Na_2SO_4$ and evaporated to afford the crude product, which was used as is without further purification.

$^1$H NMR ($CDCl_3$, 400 MHz) δ=0.82-0.76 (m, 4H) 1.02 (ddd, J=8.4, 6.4, 4.4 Hz, 4H) 1.74 (s, 9H) 2.11-2.01 (m, 2H) 7.19 (dd, J=8.6, 1.9 Hz, 2H) 7.65 (d, J=1.7 Hz, 2H) 8.14 (d, J=8.5 Hz, 2H)

Step 3. 3,6-dicyclopropyl-9H-carbazole

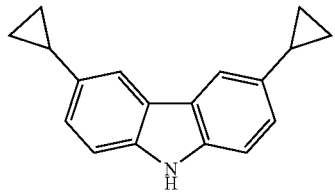 [SMILES: c1cc2[nH]c3ccc(C4CC4)cc3c2cc1C1CC1]

To a solution of the corresponding N-Boc carbazole (0.0163 g, 0.0469 mmol) in 1 mL $CH_2Cl_2$, TFA (144.8 μL, 1.876 mmol) was added dropwise. The mixture was sealed and stirred at rt for 6 h. $CH_2Cl_2$ and TFA were removed under vacuum. The residue was diluted with 30 mL EtOAc and washed with saturated $NaHCO_3$ 3×30 mL. The organic layer was dried over anhydrous $Na_2SO_4$ and evaporated to afford the crude product, which was subjected to silica gel chromatography using Hexanes/EtOAc as elute to afford white solid as product (0.0139 g).

¹H NMR (CDCl₃, 400 MHz) δ=0.77 (dt, J=6.4, 4.5 Hz, 4H) 0.99 (ddd, J=8.4, 6.2, 4.4 Hz, 4H) 2.13-2.03 (m, 2H) 7.16 (dd, J=8.4, 1.7 Hz, 2H) 7.28 (d, J=8.4 Hz, 2H) 7.76 (d, J=1.1 Hz, 2H) 7.83 (s, br, 1H).

Step 4. 3,6-dicyclopropyl-9-(oxiran-2-ylmethyl)-9H-carbazole

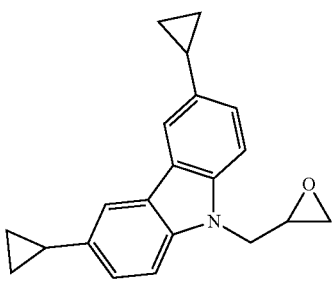 [SMILES: c1cc2c(cc1C1CC1)c1cc(C3CC3)ccc1n2CC1CO1]

The title compound of Example 98, step 4 was prepared from 3,6-dicyclopropyl-9H-carbazole using a procedure similar to that described in Representative Procedure 1.

¹H NMR (CDCl₃, 400 MHz) δ=0.81-0.74 (m, 4H) 1.03-0.96 (m, 4H) 2.09 (ddd, J=14.4, 8.9, 5.6 Hz, 2H) 2.53 (dd, J=4.8, 2.6 Hz, 1H) 2.77 (t, J=4.3 Hz, 1H) 3.30 (dt, J=7.4, 3.9 Hz, 1H) 4.35 (dd, J=15.8, 4.6 Hz, 1H) 4.54 (dd, J=15.8, 3.4 Hz, 1H) 7.22 (dd, J=8.4, 1.7 Hz, 2H) 7.31 (d, J=8.4 Hz, 2H) 7.78 (d, J=1.1 Hz, 2H).

Step 5

The title compound of Example 98 was prepared from 3,6-dicyclopropyl-9-(oxiran-2-ylmethyl)-9H-carbazole using a procedure similar to that described in Representative Procedure 2.

¹H NMR (CDCl₃, 600 MHz) δ=0.79-0.75 (m, 4H) 0.99 (td, J=6.2, 4.6 Hz, 4H) 2.08 (ddd, J=13.6, 8.5, 5.1 Hz, 2H) 3.21 (dd, J=12.9, 5.6 Hz, 1H) 3.35 (d, J=13.8 Hz, 1H) 4.39 (s, J=23.7 Hz, 3H) 6.62 (d, J=8.4 Hz, 2H) 6.75 (t, J=7.3 Hz, 1H) 7.17 (t, J=7.9 Hz, 2H) 7.20 (dd, J=8.4, 1.1 Hz, 2H) 7.32 (d, J=8.4 Hz, 2H) 7.78 (s, 2H)

¹³C NMR (CDCl₃, 500 MHz) δ=148.2, 139.8, 134.9, 129.6, 124.8, 123.2, 118.5, 117.5, 113.7, 108.8, 69.8, 48.0, 47.6, 15.7, 9.1

ESI m/z: 441.2 [(M+HCOO⁻); C27H28N2O (M) requires 396.2].

Example 99

1-(3,6-diiodo-9H-carbazol-9-yl)-3-(phenylamino)propan-2-ol

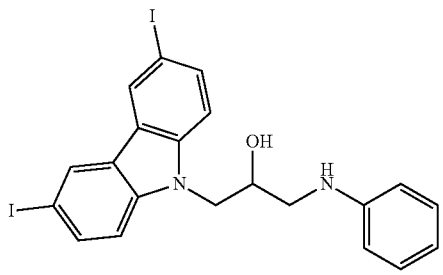 [SMILES: OC(CNc1ccccc1)Cn1c2ccc(I)cc2c2cc(I)ccc21]

Step 1.
3,6-diiodo-9-(oxiran-2-ylmethyl)-9H-carbazole

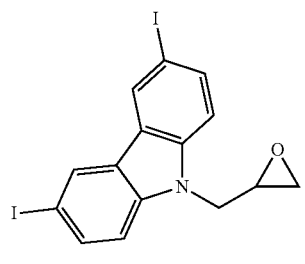 [SMILES: Ic1ccc2c(c1)c1cc(I)ccc1n2CC1CO1]

The title compound of Example 99, step 1 was prepared from 3,6-diiodo carbazole (Maegawa, Y; Goto, Y; Inagaki, S; Shimada, T. *Tetrahedron Lett.* 2006, 47, 6957-6960) using a procedure similar to that described in Representative Procedure 1.

¹H NMR (CDCl₃, 400 MHz) δ=2.48 (dd, J=4.6, 2.6 Hz, 1H) 2.80 (t, J=4.3 Hz, 1H) 3.37-3.24 (m, 1H) 4.28 (dd, J=16.0, 5.1 Hz, 1H) 4.64 (dd, J=15.9, 2.7 Hz, 1H) 7.24 (d, J=8.6 Hz, 2H) 7.73 (dd, J=8.6, 1.6 Hz, 2H) 8.33 (d, J=1.7 Hz, 2H)

¹³C NMR (CDCl₃, 500 MHz) δ=140.0, 135.0, 129.5, 124.3, 111.3, 82.6, 50.6, 45.2, 44.9

Step 2

The title compound of Example 99 was prepared from 3,6-diiodo-9-(oxiran-2-ylmethyl)-9H-carbazole using a procedure similar to that described in Representative Procedure 1.

¹H NMR (CDCl₃, 400 MHz) δ=2.92 (s, br, 1H) 3.19 (dd, J=12.8, 6.1 Hz, 1H) 3.33 (d, J=10.9 Hz, 1H) 4.49-4.29 (m, 3H) 6.63 (d, J=8.3 Hz, 2H) 6.78 (t, J=7.3 Hz, 1H) 7.20 (t, J=7.7 Hz, 2H) 7.28 (d, J=2.5 Hz, 2H) 7.72 (d, J=8.6 Hz, 2H) 8.35 (s, 2H).

¹³C NMR (CDCl₃, 400 MHz) δ=147.9, 140.1, 135.1, 129.65, 129.63, 124.4, 118.9, 113.7, 111.5, 82.6, 69.6, 48.0, 47.3

ESI m/z: 613.0 [(M+HCOO⁻); C21H18I2N2O (M) requires 568.0].

Example 100

1-(3,6-diethynyl-9H-carbazol-9-yl)-3-(3-methoxyphenylamino)propan-2-ol

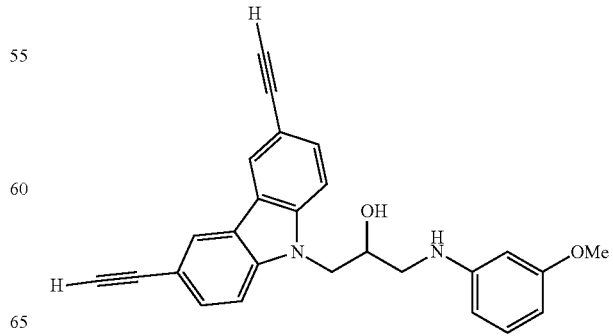

Step 1. 1-(3,6-bis((triisopropylsilyl)ethynyl)-9H-carbazol-9-yl)-3-(3-methoxyphenylamino)propan-2-ol

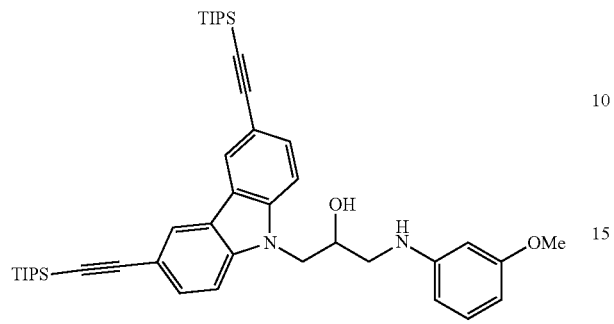

The title compound of Example 62 (0.0112 g, 0.0222 mmol), bis(benzonitrile)dichloropalladium (3 mol %, 0.0003 g, 0.0007 mmol), [(tBu)₃PH]BF₄ (6.2 mol %, 0.0004 g, 0.0014 mmol), copper(I) iodide (2 mol %, 0.0001 g, 0.0004 mmol), DABCO (0.0060 g, 0.0533 mmol) were combined under an $N_2$ atmosphere. Degassed dioxane (0.1 mL) was added, and the resulting solution was stirred at room temperature for 10 min. Trimethylsilylacetylene (11.8 µL, 0.0533 mmoL) was added into the mixture via microsyringe. The mixture was then stirred at rt overnight. The crude reaction mixture was diluted with 10 mL EtOAc and washed with brine (3×10 mL). The organic layer was dried over anhydrous $Na_2SO_4$ and evaporated to afford the crude product, which was subjected to silica gel chromatography using Hexanes/EtOAc to afford colorless oil as product (0.0152 g, yield 96.8%).

$^1$H NMR (CDCl₃, 400 MHz) δ=1.22-1.13 (m, 42H) 2.24 (s, br, 1H) 3.17 (dd, J=12.6, 6.7 Hz, 1H) 3.31 (d, J=12.1 Hz, 1H) 3.71 (s, 3H) 4.48-4.31 (m, 3H) 6.12 (t, J=2.1 Hz, 1H) 6.22 (dd, J=8.0, 1.8 Hz, 1H) 6.31 (dd, J=8.1, 2.1 Hz, 1H) 7.07 (t, J=8.1 Hz, 1H) 7.37 (d, J=8.5 Hz, 2H) 7.58 (dd, J=8.5, 1.5 Hz, 2H) 8.22 (d, J=1.4 Hz, 2H)

$^{13}$C NMR (CDCl₃, 400 MHz) δ=171.5, 161.0, 149.3, 140.9, 130.6, 130.4, 124.9, 122.7, 115.1, 109.3, 108.2, 106.7, 103.9, 99.7, 88.7, 69.5, 55.3, 47.4, 19.0, 11.6

Step 2

The title compound of Example 100 was prepared as follows. To a solution of 1-(3,6-bis((triisopropylsilyl)ethynyl)-9H-carbazol-9-yl)-3-(3-methoxyphenylamino)propan-2-ol (0.0152 g, 0.0215 mmol) in 200 µL anhydrous THF, a solution of TBAF in THF (1 M, 64.5 µL, 0.0645 mmol) and acetic acid (2.5 µL, 0.0430 mmol) were added. The mixture was sealed and stirred under $N_2$ atmosphere at rt for 27 h until TLC showed the complete disappearance of starting material. The crude was diluted with 10 mL EtOAc and washed with saturated NaHCO₃ (3×10) mL. The organic layer was dried over anhydrous $Na_2SO_4$ and evaporated to afford the crude product, which was subjected to silica gel chromatography using Hexanes/EtOAc to afford white solid as product (0.0061 g, yield 71.9%).

$^1$H NMR (CDCl₃, 400 MHz) δ=2.24 (s, br, 1H) 3.09 (s, 2H) 3.20 (s, br, 1H) 3.32 (s, br, 1H) 3.72 (s, 3H) 4.48-4.27 (m, 3H) 6.14 (s, 1H) 6.23 (dd, J=8.0, 1.4 Hz, 1H) 6.32 (dd, J=8.2, 1.8 Hz, 1H) 7.08 (t, J=8.1 Hz, 1H) 7.40 (d, J=8.5 Hz, 2H) 7.59 (dd, J=8.5, 1.4 Hz, 2H) 8.21 (d, J=1.1 Hz, 2H)

$^{13}$C NMR (CDCl₃, 500 MHz) δ=161.1, 149.3, 141.2, 130.7, 130.4, 125.0, 122.7, 113.6, 109.6, 106.7, 103.8, 99.8, 84.7, 76.0, 69.6, 55.3, 48.0, 47.4

ESI m/z: 439.1 [(M+HCOO⁻); C26H22N2O2 (M) requires 394.2].

Example 101

9-(2-hydroxy-3-(3-methoxyphenylamino)propyl)-9H-carbazole-3,6-dicarbonitrile

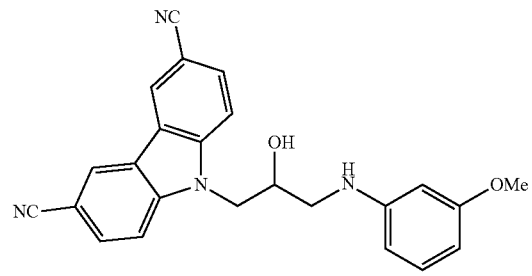 [SMILES: COc1cccc(NCC(O)Cn2c3ccc(C#N)cc3c3cc(C#N)ccc32)c1]

Following a literature procedure (Weissman, S. A; Zewge, D; Chen, C. *J. Org. Chem.* 2005, 70, 1508-1510), the title compound of Example 62 (0.0252 g, 0.05 mmol), potassium hexacyanoferrate(II) trihydrate (0.0106 g, 0.025 mmol), sodium bicarbonate (0.0106 g, 0.1 mmol) and palladium acetate (1 mol %, 0.0001 g) were combined under a $N_2$ atmosphere. Anhydrous dimethylacetamide (0.1 mL) was added, and the reaction mixture was stirred at 120° C. overnight. The crude reaction mixture was diluted with 10 mL EtOAc and washed with water (2×10 mL) and brine (1×30 mL). The organic layer was dried over anhydrous $Na_2SO_4$ and evaporated to afford the crude product, which was subjected to silica gel chromatography using Hexanes/EtOAc to afford white solid as product (0.0110 g, yield 54.6%).

$^1$H NMR (d₆-acetone, 400 MHz) δ=2.81 (s, 1H) 3.36-3.28 (m, 1H) 3.50-3.43 (m, 1H) 3.71 (s, 3H) 4.44 (s, br, 1H) 4.66 (dd, J=15.0, 8.5 Hz, 1H) 4.77 (dd, J=15.1, 3.4 Hz, 1H) 5.16 (t, J=5.8 Hz, 1H) 6.22 (dd, J=8.1, 2.1 Hz, 1H) 6.27 (t, J=2.0 Hz, 1H) 6.31 (dd, J=8.1, 1.2 Hz, 1H) 7.01 (t, J=8.1 Hz, 1H) 7.84 (dd, J=8.6, 1.2 Hz, 2H) 7.91 (d, J=8.6 Hz, 2H) 8.74 (s, 2H)

$^{13}$C NMR (d₆-acetone, 500 MHz) δ=161.3, 150.4, 143.9, 130.02, 129.95, 126.0, 122.4, 119.8, 112.0, 106.0, 103.3, 102.5, 98.9, 69.0, 54.5, 48.0, 47.7

ESI m/z: 441.1 [(M+HCOO⁻); C24H20N4O2 (M) requires 396.2).

Example 102

N-(3-(3,6-dibromo-9H-carbazol-9-yl)-2-fluoropropyl)aniline

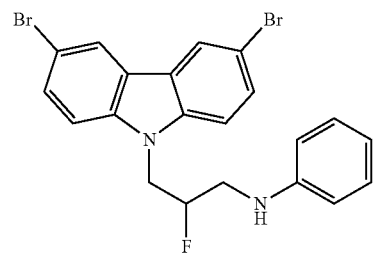 [SMILES: FC(CNc1ccccc1)Cn1c2ccc(Br)cc2c2cc(Br)ccc21]

Step 1. N-(3-(3,6-dibromo-9H-carbazol-9-yl)-2-fluoropropyl)-4-nitro-N-phenylbenzenesulfonamide

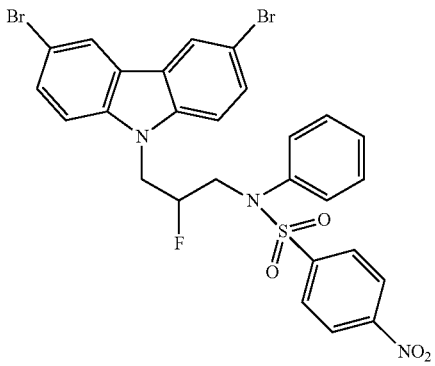 [SMILES: O=[N+]([O-])c1ccc(S(=O)(=O)N(CC(F)Cn2c3ccc(Br)cc3c3cc(Br)ccc32)c2ccccc2)cc1]

The title compound of Example 102, step 1 was prepared from epoxide 2-A and Ns-aniline using procedures similar to those described in representative procedures 3 and 4. The crude mixture was purified in 40% EtOAc/hexanes (+0.1% TEA). The isolated yield was 60%.

$^1$H NMR ((CD$_3$)$_2$CO)$_3$, 400 MHz) δ 8.37 (m, 2H), 7.90 (m, 2H), 7.68 (m, 1H), 7.53-7.60 (m, 6H), 7.32-7.40 (m, 5H), 5.03 (dm, 1H), 4.71-4.93 (m, 2H), 4.27-4.41 (m, 2H).

MS (ESI), m/z: 703.9 [(M+HCOO)$^-$; C27H20Br2FN3O4S (M) requires 659.0]

Step 2

The title compound of Example 102 was prepared as follows. Cesium carbonate (11.5 mg, 0.036 mmol), the nosylate prepared in step 1 above (7.9 mg, 0.012 mmol), THF (0.7 ml, 0.017 M) and benezenthiol (3.8 ul, 0.037 mmol) were combined and stirred overnight. The crude reaction mixture was diluted with EtOAc, washed with water and brine. The organic layer was dried over Na$_2$SO$_4$, filtered and condensed. Chromatographic purification on SiO$_2$ (20% EtOAc/hexanes (0.2% TEA)) provided 74% (4.2 mg).

$^1$H NMR (CDCl$_3$, 500 MHz) δ=8.16 (s, 2H), 7.56 (d, 2H, J=8.5 Hz), 7.31 (d, 2H, J=8.5 Hz), 7.21 (t, 2H, J=7.4 Hz), 6.80 (t, 1H, J=7.3 Hz), 6.62 (d, 2H, J=8.5 Hz), 5.11 (dddd, 1H, J=5.4, 5.4, 10.4, 47.4 Hz), 4.52-4.68 (m, 2H), 3.94 (t, 1H, J=6.02 Hz), 3.30-3.51, (dm, 2H).

MS (ESI), m/z: 475.0 [(M+1)–; C21H17Br2FN2 (M) requires 474.0].

Example 103

3,6-dibromo-9-(2,2-difluoro-3-phenoxypropyl)-9H-carbazole

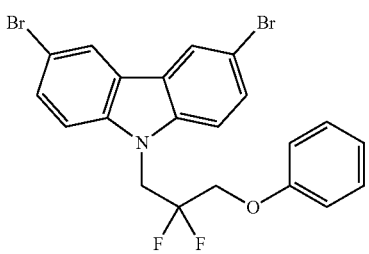 [SMILES: FC(F)(COc1ccccc1)Cn1c2ccc(Br)cc2c2cc(Br)ccc21]

Step 1. 1-(3,6-dibromo-9H-carbazol-9-yl)-3-phenoxypropan-2-one

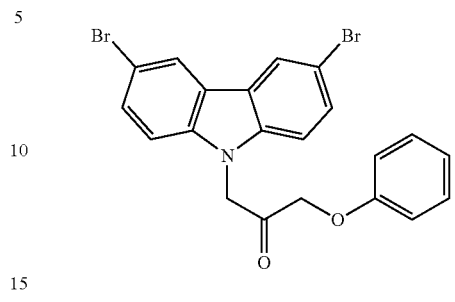

Dess-Martin periodinane (58.2 mg, 0.137 mmol) was charged to a solution of the title compound of Example 3b (45.0 mg, 0.095 mmol) in dichloromethane (1.0 ml, 0.095 M). After two hours the reaction mixture was diluted with EtOAc and washed with saturated sodium thiosulfate solution, water and brine. The organic layer was dried over Na$_2$SO$_4$, filtered and condensed. The crude product was used without additional purification. Yield=74%

$^1$H NMR (CDCl$_3$, 400 MHz) δ 8.15 (d, 2H, J=1.9 Hz), 7.52 (dd, 2H, J=8.6, 1.9 Hz) 7.35 (m, 2H), 7.08 (t, 1H, J=7.3 Hz), 7.04 (d, 2H, J=8.9 Hz), 6.91 (m, 2H), 5.29 (s, 2H), 4.68 (m, 2H)

MS (ESI), m/z: 469.9 [(M−1)$^-$; C21H15Br2NO2 (M) requires 570.9].

Step 2

The title compound of Example 103 was prepared as follows. Diethylaminosulfur trifluoride (39 ul, 0.30 mmol) was added dropwise to a solution of 1-(3,6-dibromo-9H-carbazol-9-yl)-3-phenoxypropan-2-one (33.3 mg, 0.070 mmol) in anhydrous dichloromethane (1.5 ml, 0.047M). The reaction was quenched with saturated sodium bicarbonate solution, and then extracting three times with dichloromethane. The organic layer is dried over Na$_2$SO$_4$, filtered and condensed. The crude mixture was purified on SiO2 (10% EtOAc/hexanes+0.2% TEA. Isolated yield was 69%.

$^1$H NMR (CDCl$_3$, 400 MHz) δ 8.09 (d, 2H, J=1.9 Hz), 7.48 (dd, 2H, J=8.7, 1.8 Hz) 7.30-7.4 (m, 4H), 7.06 (t, 1H, J=7.3 Hz), 6.91 (d, 2H, J=7.9 Hz), 4.79 (t, 2H, J=12.4 Hz), 4.07 (t, 2H, J=11.1 Hz).

MS (ESI), m/z: 537.9 [(M+HCOO)$^-$; C21H15Br2F2NO (M) requires 492.9].

Example 104

N-(3-(3,6-dibromo-9H-carbazol-9-yl)-2-fluoropropyl)-4-methoxyaniline

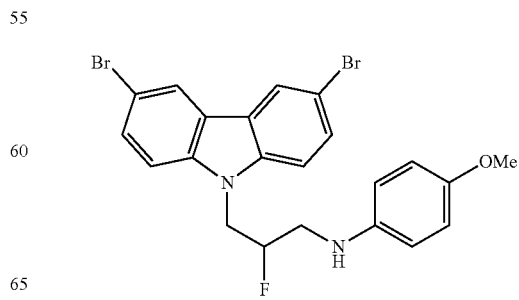

Step 1. N-(3-(3,6-dibromo-9H-carbazol-9-yl)-2-hydroxypropyl)-N-(4-methoxyphenyl)-4-nitrobenzenesulfonamide

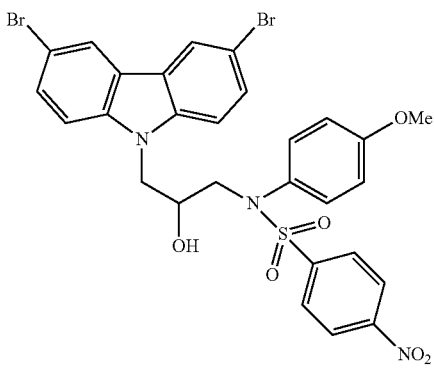 [SMILES: COc1ccc(N(CC(O)Cn2c3ccc(Br)cc3c3cc(Br)ccc32)S(=O)(=O)c2ccc([N+](=O)[O-])cc2)cc1]

The title compound of Example 104, step 1 was prepared from epoxide 2-A and Ns-anisidine according to Representative Procedure 3. Yield=71%

$^1$H NMR (CDCl$_3$, 400 MHz) δ 8.29 (d, 2H, J=8.7 Hz), 8.11 (d, 2H, J=1.9 Hz), 7.71 (, 2H, J=8.6 Hz), 7.52 (dd, 2H, J=8.6, 1.9 Hz), 7.23 (d, 2H, J=8.9 Hz), 6.94 (d, 2H, J=8.9 Hz), 6.82 (d, 2H, J=8.9 Hz), 4.44 (dd, 1H, J=14.8, 3.8 Hz), 4.30 (m, 1H), 4.21 (bs, 1H), 3.81 (s, 3H), 3.69 (m, 21-1).

MS (ESI), m/z: 732.0 [(M+HCOO$^-$); C28H23Br2N3O6S (M) requires 687.0]

Step 2. N-(3-(3,6-dibromo-9H-carbazol-9-yl)-2-fluoropropyl)-N-(4-methoxyphenyl)-4-nitrobenzenesulfonamide

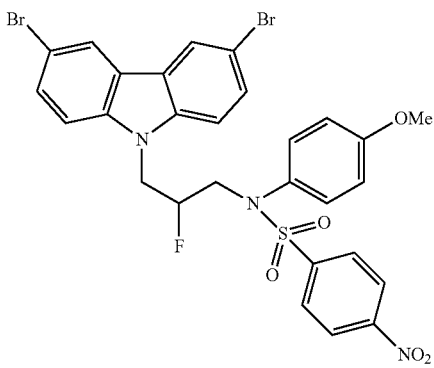

The title compound of Example 104, step 2 was prepared from the nosylate prepared in step 1 above according to General Procedure 4. Yield=61.5%

$^1$H NMR (CDCl$_3$, 400 MHz) δ 8.27 (m, 2H), 8.09 (m, 2H), 7.71 (d, 2H, J=7.41 Hz), 7.53 (m, 2H), 7.19 (m, 2H), 6.95 (d, 2H, J=8.8 Hz), 6.82 (d, 2H, J=8.8 Hz), 4.92 (dm, 1H, J$_d$=48.3 Hz), 4.55 (m, 2H), 3.88 (m, 2H), 3.79 (s, 3H).

MS (ESI), m/z: 734.0 (M+HCOO)$^-$; C28H22Br2FN3O5S (M) requires 689.0]

Step 3

The title compound of Example 104 was prepared according to Representative Procedure 5. Isolated yield 70%.

$^1$H NMR (CDCl$_3$, 400 MHz) δ 8.14 (m, 2H0, 7.53 (dt, 2H, J=8.8, 1.6 Hz), 7.30 (d, 2H, 8.6 Hz), 6.78 (d, 2H, J=7.9 Hz), 6.57 (d, 2H, J=7.9 Hz), 5.07 (dddd, 1H, J=4.7, 6.1, 9.4, 47.7), 4.58 (m, 2H), 3.75 (s, 3H), 3.32 (m, 2H).

MS (ESI), m/z: 549.0 [(M+HCOO)$^-$; C22H19Br2FN2O (M) requires 505.0).

Example 105

N-(2-bromo-3-(3,6-dibromo-9H-carbazol-9-yl)propyl)-N-(4-methoxyphenyl)-4-nitrobenzenesulfonamide

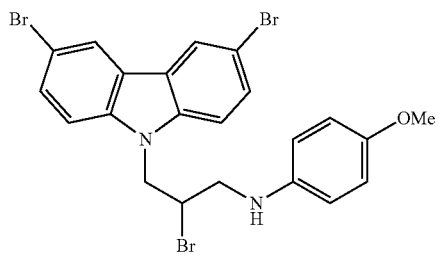 [SMILES: COc1ccc(NCC(Br)Cn2c3ccc(Br)cc3c3cc(Br)ccc32)cc1]

Step 1. N-(2-bromo-3-(3,6-dibromo-9H-carbazol-9-yl)propyl)-N-(4-methoxyphenyl)-4-nitrobenzenesulfonamide

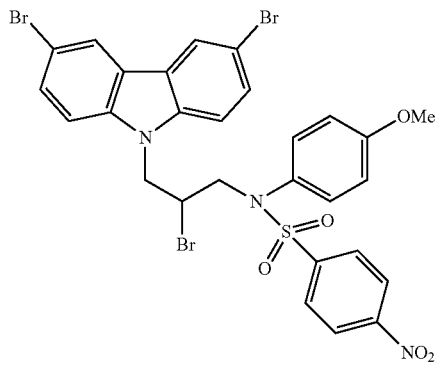 [SMILES: COc1ccc(N(CC(Br)Cn2c3ccc(Br)cc3c3cc(Br)ccc32)S(=O)(=O)c2ccc([N+](=O)[O-])cc2)cc1]

A solution of the title compound Example 104 (20.5 mg, 0.030 mmol) in anhydrous dichloromethane (1.0 ml, 0.03 M) was cooled in an ice bath before the addition of BBr$_3$ (7 ul, 0.074 mmol). After 1 h the reaction was diluted with EtOAc, washed twice with water, saturated sodium bicarbonate solution and brine. The organic layer was dried over Na$_2$SO$_4$, filtered and condensed. The crude mixture was purified in 100% CH$_2$Cl$_2$ (+0.2% TEA). Isolated yield=56%

$^1$H NMR (CDCl$_3$, 500 MHz) δ 8.26 (d, 2H, J=8.9 Hz), 8.12 (d, 2H, J=1.7 Hz), 7.60 (d, 2H, J=8.8 Hz) 7.53 (dd, 2H, J=8.7, 1.9 Hz), 7.18 (d, 2H, J=8.7 Hz), 6.89 (d, 2H, J=8.9 Hz) 6.81 (d, 2H, J=9.0 Hz), 4.86 (dd, 1H, J=15.6, 5.4 Hz), 4.57 (m, 1H), 4.44 (m, 1H), 3.92 (m, 2H), 3.82 (s, 3H)

MS (ESI), m/z: 747.9 [(M−1)$^-$; C28H22Br3N3O5S (M) requires 748.9]

Step 2

The title compound of Example 105 was prepared from the nosylate prepared in step 1 above according to Representative Procedure 5. Isolated yield=43% in approximately 90% purity.

$^1$H NMR (CDCl$_3$, 400 MHz) δ 8.14 (d, 2H, J=1.7 Hz), 7.51 (dd, 2H, J=8.6, 1.9 Hz), 7.28 (d, 2H, J=8.7 Hz), 6.71 (d, 2H, J=8.9 Hz), 6.41 (d, 2H, J=8.8 Hz), 4.84 (m, 1H), 4.63 (m, 3H), 3.82 (m, 1H), 3.73 (s, 3H)

MS (ESI), m/z: 564.8 [(M+1)$^+$; C22H19Br3N2O requires 563.9].

The title compounds of Examples 106-109 can be prepared using the methods described herein and/or using conventional synthesis methods.

Example 106

Ethyl 2-(4-(3-(3,6-dibromo-9H-carbazol-9-yl)-2-fluoropropylamino)phenoxy)acetate

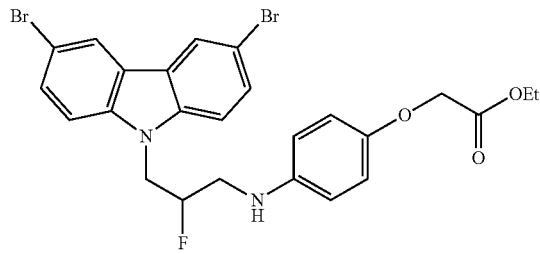 [SMILES: CCOC(=O)COc1ccc(NCC(F)Cn2c3ccc(Br)cc3c3cc(Br)ccc32)cc1]

Example 107

N-(3-(3,6-dibromo-9H-carbazol-9-yl)-2-fluoropropyl)-4-(2-(2-methoxyethoxy)ethoxy)aniline

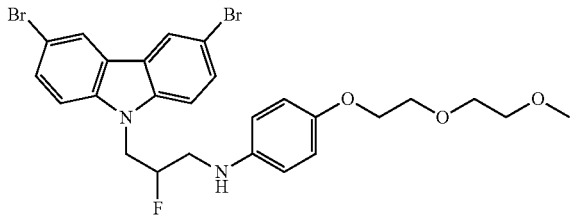 [SMILES: COCCOCCOc1ccc(NCC(F)Cn2c3ccc(Br)cc3c3cc(Br)ccc32)cc1]

Example 108

Example 109

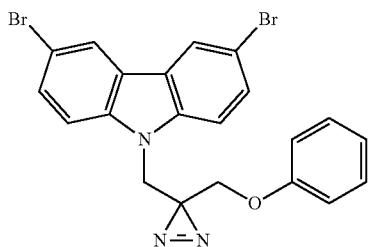

Compounds were tested in vivo for dose-responsive neurotrophic efficacy. The results are shown in Table 1.

TABLE 1

| | In Vivo Activity | |
|---|---|---|
| Test Material | (X10$^{-06}$) BrdU+ cells/mm$^3$ dentate gyrus | SEM: (standard error of the mean) |
| Vehicle | 14.5 | 1.08 |
| FGF-2: (fibroblast growth factor 2) | 28.4 | 2.12 |
| Example 1a | 29.8 | 2.0 |
| Example 1b | 18.3 | 0.8 |
| Example 2 | 24.4 | 1.4 |
| Example 3a | 30.9 | 3 |
| Example 3b | 29.6 | 1.3 |
| Example 3c | 16.1 | 1.74 |
| Example 3d | 27.1 | 1.34 |
| Example 4 | 23.7 | 0.6 |
| Example 5 | 21.5 | 2.18 |
| Example 6a | 38 | 2.4 |
| Example 6b | 25.5 | (one animal tested) |
| Example 7a | 18.4 | 1.8 |
| Example 7b | 23.4 | 1.31 |
| Example 8 | 23.2 | 0.8 |
| Example 9 | 16.2 | 1.7 |
| Example 10 | 27 | 1.3 |
| Example 11 | 15.1 | 0.6 |
| Example 12 | 21.7 | 2.9 |
| Example 13 | 28.5 | 2.6 |
| Example 14 | 17.8 | 1.9 |
| Example 15 | 15.1 | 0.9 |
| Example 16 | 17.1 | 0.9 |
| Example 17 | 20.8 | 0.3 |
| Example 19 | 15 | 0.5 |
| Example 20 | 23.2 | 0.48 |
| Example 21 | 27.6 | 3.4 |
| Example 22 | 27.3 | 1.8 |
| Example 23 | 21.5 | 2.2 |
| Example 25 | 16.8 | 1.3 |
| Example 26 | 15.6 | 1 |
| Example 28 | 21 | 0.6 |

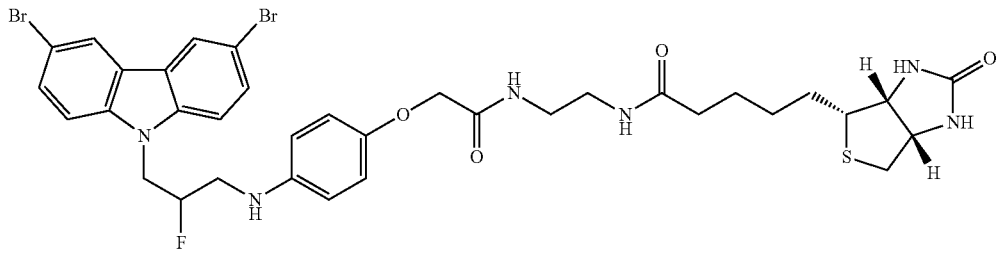 [SMILES: O=C(CCCC[C@H]1SC[C@H]2NC(=O)N[C@H]21)NCCNC(=O)COc1ccc(NCC(F)Cn2c3ccc(Br)cc3c3cc(Br)ccc32)cc1]

TABLE 1-continued

In Vivo Activity

| Test Material | (X10$^{-06}$) BrdU+ cells/mm$^3$ dentate gyrus | SEM: (standard error of the mean) |
|---|---|---|
| Example 29 | 17.6 | 2.3 |
| Example 30 | 13.4 | 1.2 |
| Example 31 | 14.7 | 1 |
| Example 32 | 16 | 0.4 |
| Example 33 | 14 | 0.2 |
| Example 36 | 19 | 2.54 |
| Example 39 | 23.4 | 1.1 |
| Example 40 | 14.4 | 1.5 |
| Example 41 | 16 | 1.1 |
| Example 43 | 21.3 | 2.6 |
| Example 45 | 30 | 1.42 |
| Example 88a | 16.2 | 1 |
| Example 88b | 30.6 | 3.66 |
| Example 89 | 23.4 | 0.26 |
| Example 90 | 33.3 | 3.3 |
| Example 91 | 18.3 | 2.9 |
| Example 92 | 29 | 1.6 |
| Example 93 | 20.1 | 2.5 |
| Example 94 | 23.9 | 2.43 |
| Example 95 | 21.5 | 1.2 |
| Example 96 | 34.2 | 4.29 |
| Example 97a | 32.4 | 3.84 |
| Example 97b | 26.3 | 1.55 |
| Example 101 | 25.8 | 2.6 |
| Example 102 | 27.6 | 2.7 |
| Example 103 | 16.8 | 1.13 |
| Example 104 | 25.1 | 2 |
| [structure: 3,6-dibromo-9H-carbazole substituted with -CH$_2$-CH(OH)-CH$_2$-NH$_2$ at N] | 25.4 | 2.4 |
| Example 109 | 23.7 | 0.75 |

Compounds were evaluated for pro-neurogenic efficacy/neuroprotection in our standard in vivo assay at 10 μM concentration in four 12 week old adult male C57/B16 mice.

The (+) (dextrorotatory) enantiomer of 1-(3,6-Dibromo-9H-carbazol-9-yl)-3-(3-methoxyphenylamino)-propan-2-ol as described herein exhibited high activity.

The (−) (levorotatory) enantiomer of 1-(3,6-Dibromo-9H-carbazol-9-yl)-3-(3-methoxyphenylamino)-propan-2-ol as described herein exhibited low activity.

Identification of Pro-Neurogenic or Neuroprotective Compounds:

In an effort to identify compounds that might stimulate the birth of new neurons, or protect newborn neurons from cell death, a library of 1,000 compounds was screened using an in vivo assay. In the initial screen, compounds were randomly pooled into groups of ten and administered intracerebroventricularly at a constant rate over seven days into the left lateral ventricle of living mice via Alzet osmotic mini-pumps. Compounds were administered at a concentration of 10 μM for each molecule, making a total solute concentration of 100 μM. After seven days of infusion at a constant rate of 0.5 μL/hour, a total of 84 μL of volume will have left the pump (0.00084 μMoles) and entered the cerebrospinal fluid. The average volume of a brain from a 12 week old male, C57/B6 mouse in our study is 500 mm$^3$. The maximal amount of drug was estimated that could potentially be present in the brain, taking the extreme and unlikely scenario of 100% absorbance of the drug into brain tissue and 0% clearance throughout the seven day infusion period. Under these conditions, at the end of one week of infusion each compound would be present at 1.7 μMolar concentration. Since the actual amount of chemical compound in the brain is likely to be only a fraction of this predicted level, it is reasonable to estimate that compounds were administered at mid to low-nanomolar concentrations.

Figure 2:
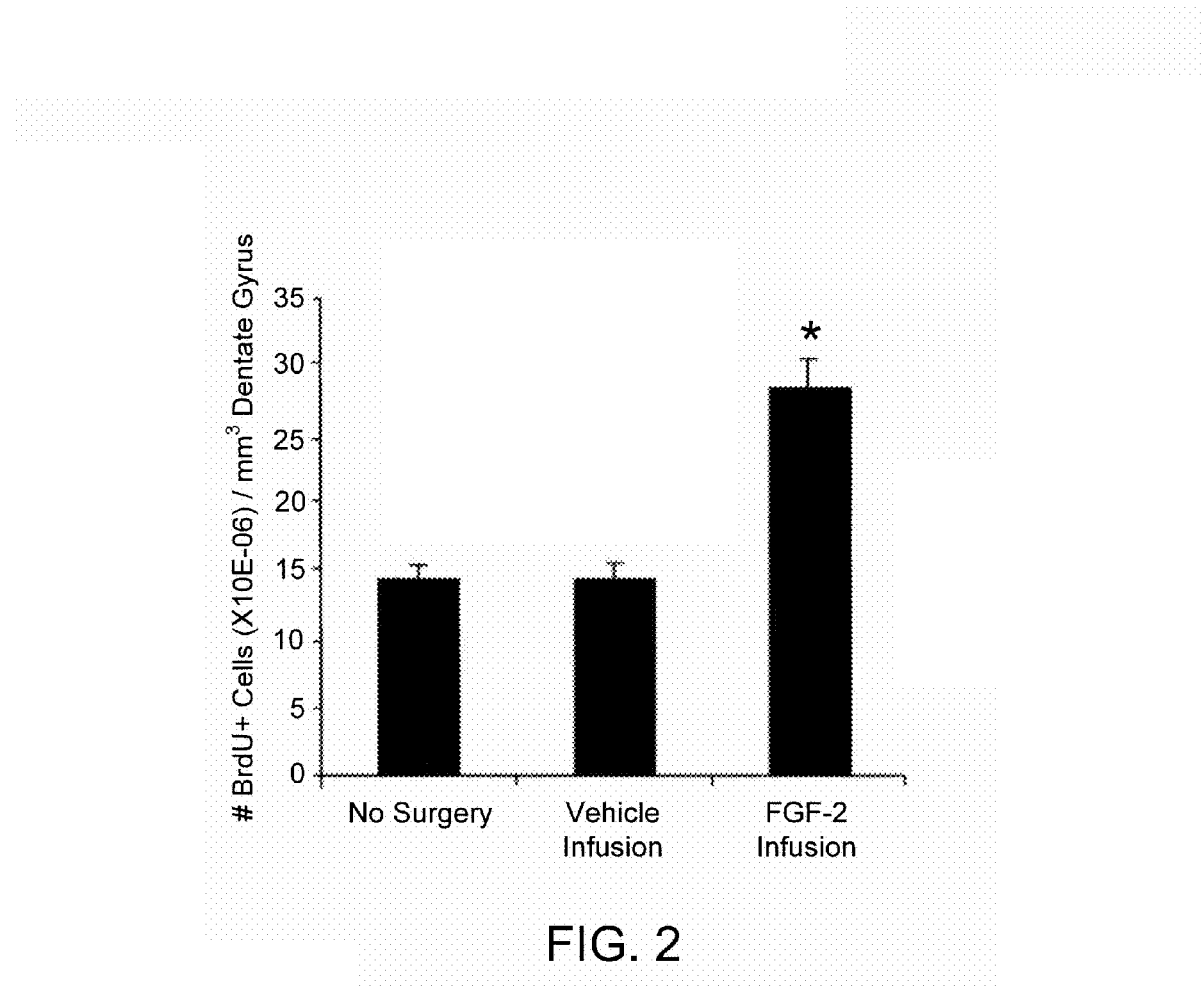
FIG. 2: Surgical placement of cannula and pumps did not affect hippocampal neurogenesis or survival of newborn neurons on the contralateral side of the brain. Mice infused with vehicle (artificial cerebrospinal fluid) over seven days by means of surgically implanted Alzet osmotic minipumps (Vehicle Infusion, n=5) displayed no difference in hippocampal neural precursor cell proliferation, as assessed by BrdU incorporation normalized for dentate gyrus volume, from mice treated identically except not having undergone surgery (No Surgery, n=4). When Alzet osmotic minipumps were loaded with fibroblast growth factor 2 (FGF-2; 10 mg/mL) (n=5), however, hippocampal neural precursor cell proliferation roughly doubled with respect to both of the other two groups (*, p<0.001, Student's t test).

During compound infusion, animals were intraperitoneally (IP) injected daily with the thymidine analog, bromodeoxyuridine (BrdU), as a means of scoring the birth and survival of proliferating neural precursor cells in the hippocampus. Because both social interaction and voluntary exercise are known to stimulate hippocampal neurogenesis, mice were housed individually without access to running wheels throughout the screening period. Following the week-long period of compound administration, animals were perfused and sacrificed. Dissected brain tissue was fixed, embedded, sectioned, stained with antibodies to BrdU, and evaluated by light microcopy as a means of quantifying neurogenesis and survival of newborn neural precursor cells localized to the subgranular layer of the dentate gyrus on the brain hemisphere contralateral to the side of mini-pump cannulation. Every fifth section throughout the entire rostral-caudal extent of the hippocampus was analyzed, and the total number of BrdU+ cells was normalized against the measured volume of the dentate gyrus. Because both increased proliferation and survival of newborn neurons are important screening parameters, the screen was conducted over seven days in order to cast a wide net to detect molecules that might augment either process. The choice of parameters for the screen was based on pulse-chase experiments with a single injection of BrdU, under identical conditions to those used in our screen, which revealed that 40% of newborn cells in the dentate gyrus die within the first five days of their birth (FIG. 1). Intracranial infusions of either fibroblast growth factor 2 (FGF-2) or artificial cerebral spinal fluid (aCSF) vehicle via the same, week-long protocol were employed as positive and negative controls. There was no difference in the number of BrdU-labeled cells in the dentate gyrus between mice subjected to surgical pump implantation and infusion with vehicle, and mice having had no surgery (FIG. 2). This confirmed the validity of the in vivo approach to assess the ability of intracerebroventricularly infused compounds to enhance hippocampal neurogenesis in the contralateral hemisphere.

Figure 3:
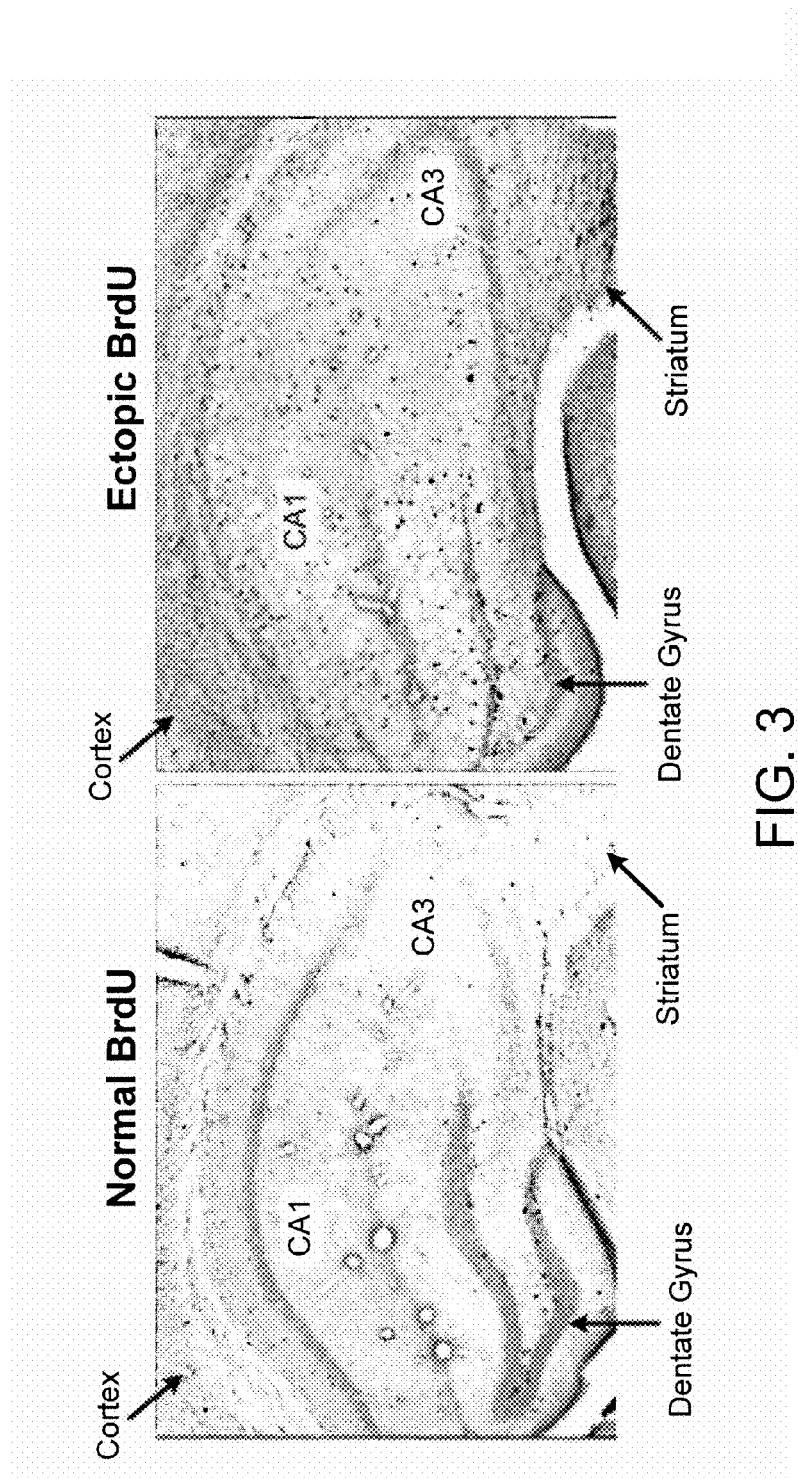
FIG. 3: Ectopic incorporation of BrdU served to eliminate molecules from further consideration. Immunohistochemical staining of BrdU in the hippocampal field should normally be restricted to the SGZ of the dentate gyrus, as shown on the left. The in vivo neurogenic screen employed was designed to detect small molecules that selectively stimulated BrdU incorporation into replicating cells of the SGZ. Infrequently, some compounds exhibited non-specific BrdU incorporation in ectopic regions, such as CA3, CA1, cortex, and striatum, as shown on the right. Any molecules that demonstrated ectopic incorporation of BrdU were eliminated from the study.

We considered it to be important that stimulation of neurogenesis triggered by any compound be localized to the exact region of the brain known to produce new neurons at an enhanced level in response to healthy activities such as wheel running, access to an enriched environment, or access to social interaction. For this reason attention was focused solely on compound pools that stimulated BrdU incorporation only in the subgranular zone of the dentate gyrus. Prominent nonspecific incorporation of BrdU in ectopic regions, such as CA3, CA1, cortex, or striatum, was presumed to reflect pathological inflammation, as proliferating cells incorporate BrdU in DNA synthesis, or to indicate other forms of toxicity, as cells also incorporate BrdU during DNA repair. Any compound pools yielding ectopic BrdU incorporation were eliminated from the screen. For an example, see FIG. 3.

Figure 4:
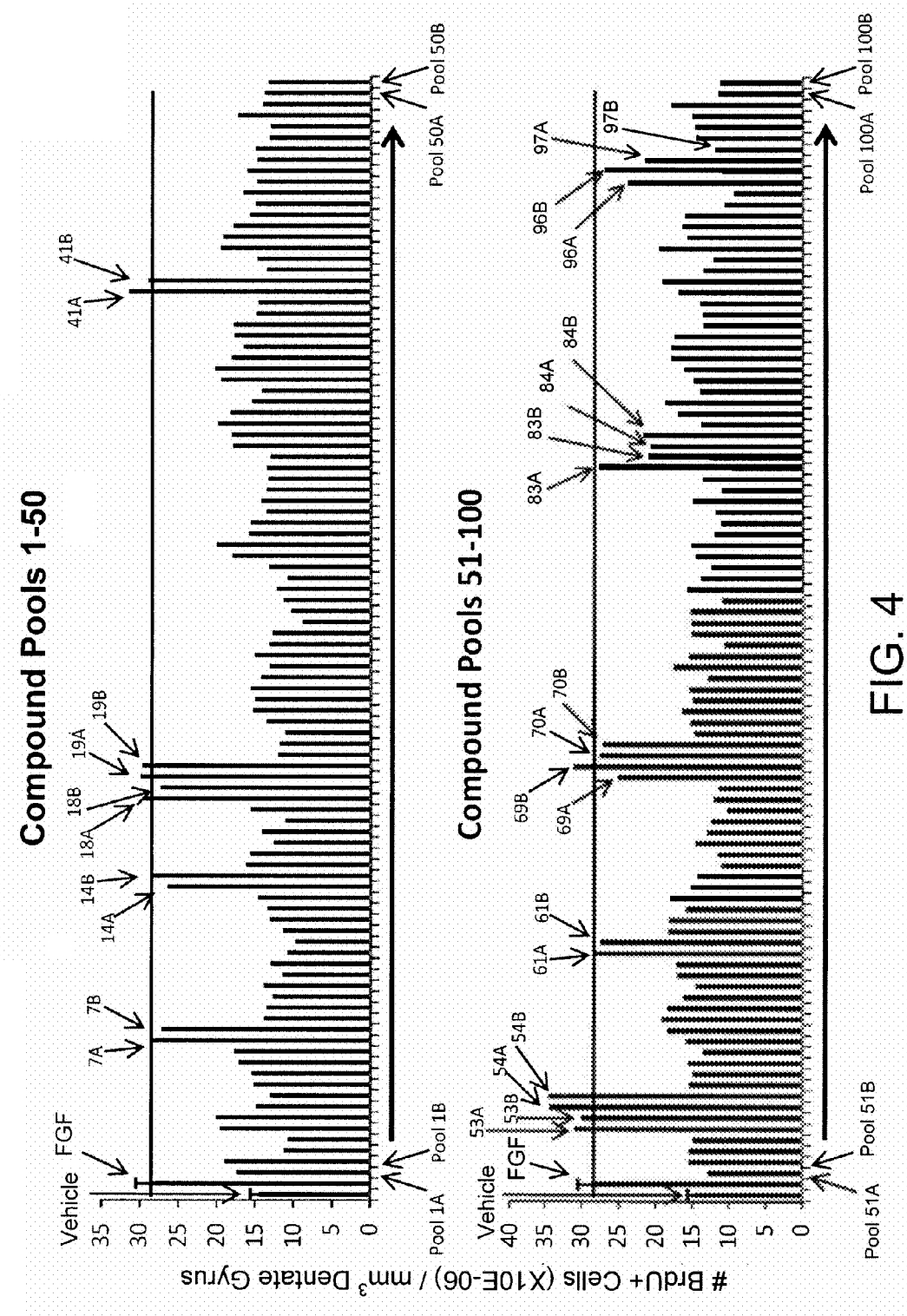
FIG. 4: Screening of 100 pools of 10 compounds identified 10 pools with pro-neurogenic efficacy. The total number of BrdU-labeled cells in the dentate gyms subgranular zone (SGZ) approximately doubled following seven day infusion with fibroblast growth factor 2 (FGF-2; 10 mg/mL) (n=5) relative to mice infused with vehicle (artificial cerebrospinal fluid (aCSF) (n=5). Each pool of ten compounds was tested for pro-neurogenic efficacy over a 7 day period in two independent mice at 10 µM concentration for each individual compound. Pools 7, 14, 18, 19, 41, 53, 54, 61, 69 and 70 displayed comparable stimulation of neural precursor cell proliferation as FGF-2 infusion. The majority of pools displayed no effect on hippocampal neural precursor cell proliferation.

Each of the 100 pools was tested on two independent mice. As shown in FIG. 4, ten of the 100 test pools were observed to enhance dentate gyrus-specific neurogenesis to an extent roughly equivalent to FGF-2. Each pool that scored positive in the initial two test animals was subsequently re-evaluated in two additional mice, and all ten pools were found to exert their pro-neurogenic effect with statistical significance (FIG.

Figure 6A:
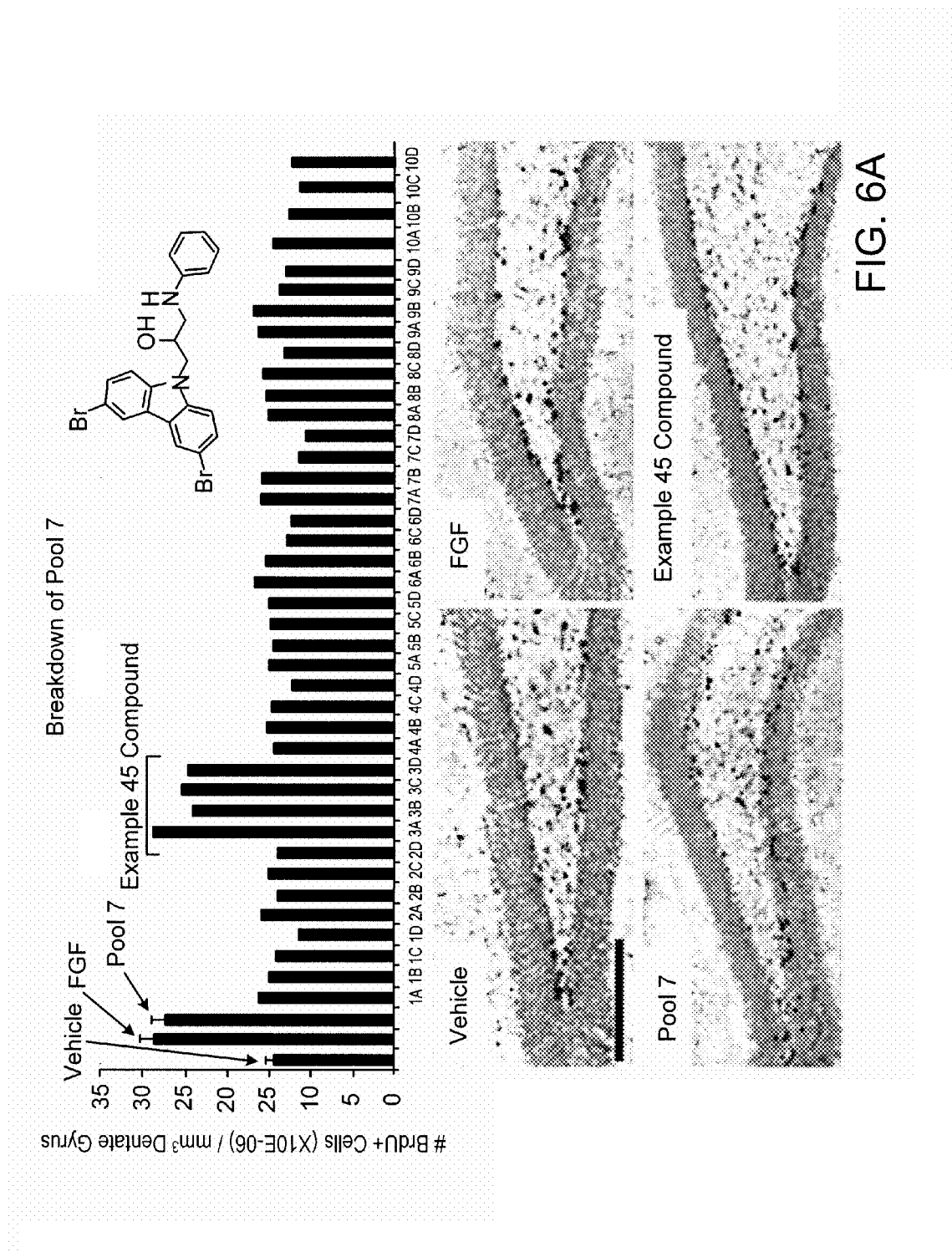
FIG. 6: Pro-neurogenic pools were broken down to identify individual pro-neurogenic compounds. (a) In vivo evaluation of the ten individual compounds that composed pool #7 revealed that compound #3 stimulated either the proliferation or survival of neural precursor cells in the SGZ, whereas the remaining individual components of pool #7 did not. In this document this molecule is referred to as 'Example 45 Compound.' Each compound was infused at two different concentrations (100 μM (A and B) and 10 μM (C and D)) in two mice each. Example 45 Compound showed either pro-neurogenic or neuroprotective activity at both concentrations. Below the graphs are typical results of BrdU incorporation in the SGZ, which is notably greater in animals infused with either Pool #7 or Example 45 Compound. (b) Molecular formulas and weights of individual pro-neurogenic compounds identified through the in vivo screen. (c) Re-supplied compounds were evaluated in three mice per compound at 10 μM concentration to verify that the pro-neurogenic or neuroprotective effect on neural stem cells was not an artifact of storage conditions in the UTSWMC chemical compound library. Re-supplied compounds were verified to be 99% pure by mass spectrometry and shown to retain either pro-proliferative or neuroprotective properties in vivo in neural stem cells. All compounds significantly (*, $P<0.001$, Student's t test) stimulated neural precursor cell proliferation in the hippocampal dentate gyrus SGZ relative to vehicle control.
Figure 6C:
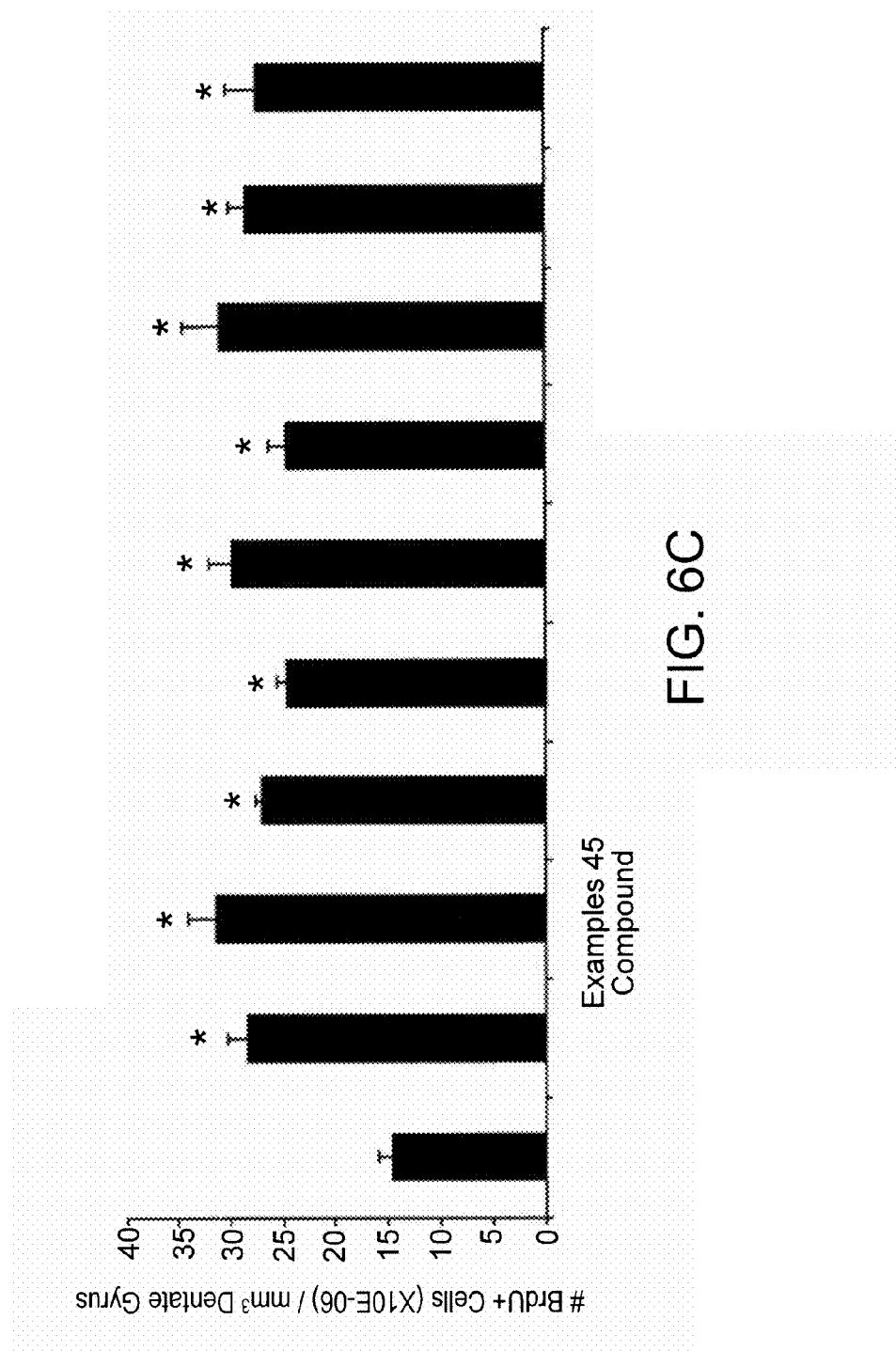

5). In order to identify single, pro-neurogenic compounds, positive pools were broken down into their ten component molecules, each of which was infused individually at two concentrations (10 μM and 100 μM) in two mice per concentration. FIG. 6A shows the results of break-down assays on pool #7, wherein it was discovered that neurogenesis was selectively stimulated by one of the constituent chemicals of the pool (compound #3), chemicals in the pool demonstrating no effect. We designate this molecule as Example 45 Compound. In breaking down the ten positive pools, eight pools yielded a single pro-neurogenic compound (FIG. 6B). To ensure that the pro-proliferative or neuroprotective effect on neural stem cells was not an artifact of storage conditions in the UTSWMC chemical compound library, re-supplied compounds were verified to by 99% pure by mass spectrometry, evaluated in 4 mice each at 10 μM concentration, and shown to retain either pro-proliferative or neuroprotective properties in neural stem cells (FIG. 6C).

Figure 7:
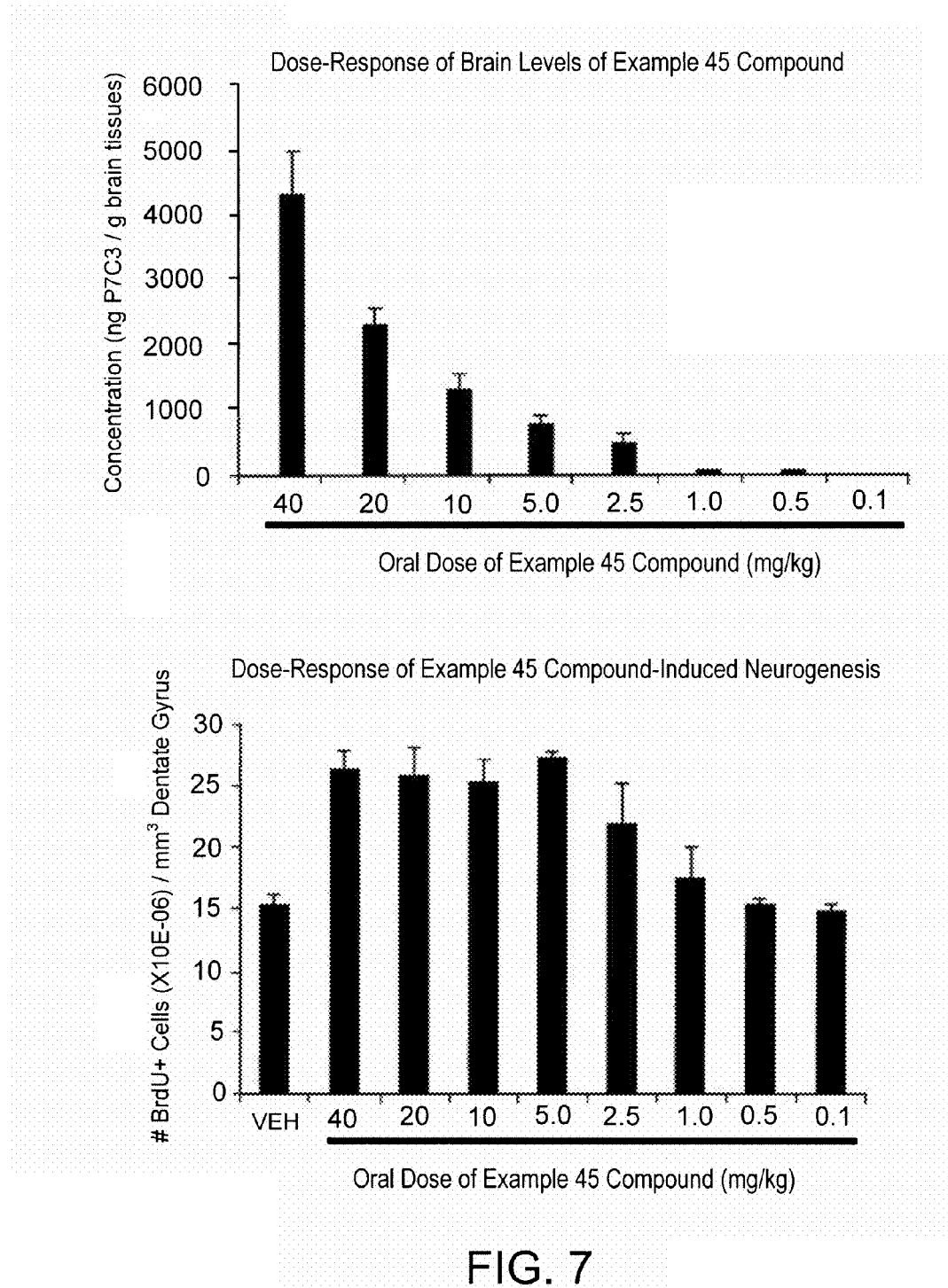
FIG. 7: Neurogenic efficacy of orally administered Example 45 Compound was dose-related. The graph on the left shows that the concentration of Example 45 Compound in brain tissue of mice that were administered compound by daily oral gavage for 7 consecutive days correlated with the dose of Example 45 Compound administered. The graph on the right shows that pro-neurogenic or neuroprotective efficacy of Example 45 Compound was roughly double that of vehicle control at doses ranging from 5 to 40 mg/kg. At decreasing dosage of Example 45 Compound the amount of neurogenesis decreased accordingly, until it reached levels no greater than vehicle control at compound doses below 1.0 mg/kg. Results shown are the average obtained from analysis of 5 adult wild type male mice at each dose.

Pharmacokinetic analysis of Example 45 Compound in plasma and whole brain tissue was undertaken after single IV, IP and oral gavage administrations. Example 45 Compound was noted to be orally bioavailable, readily able to cross the blood-brain barrier, and endowed with a plasma terminal half life of 6.7 hours after IP delivery. These favorable pharmacological properties facilitated a dose response experiment wherein daily oral administration of Example 45 Compound to adult mice was monitored for both brain levels of the chemical and pro-neurogenic efficacy (FIG. 7). Maximal, pro-neurogenic efficacy was observed at oral doses of 5 mg/kg and above, and graded reductions in efficacy were observed at doses of 2.5 and 1 mg/kg. Liquid chromatography-mass spectrometry analysis of the brain levels of Example 45 Compound in the dose ranges of 1, 2.5 and 5 mg/kg revealed corresponding compound concentrations of 213 nM (101 ng/g brain tissue), 1.13 μM (534 ng/g brain tissue) and 1.35 μM (640 ng/g brain tissue) five hours after dosing.

Figure 8:
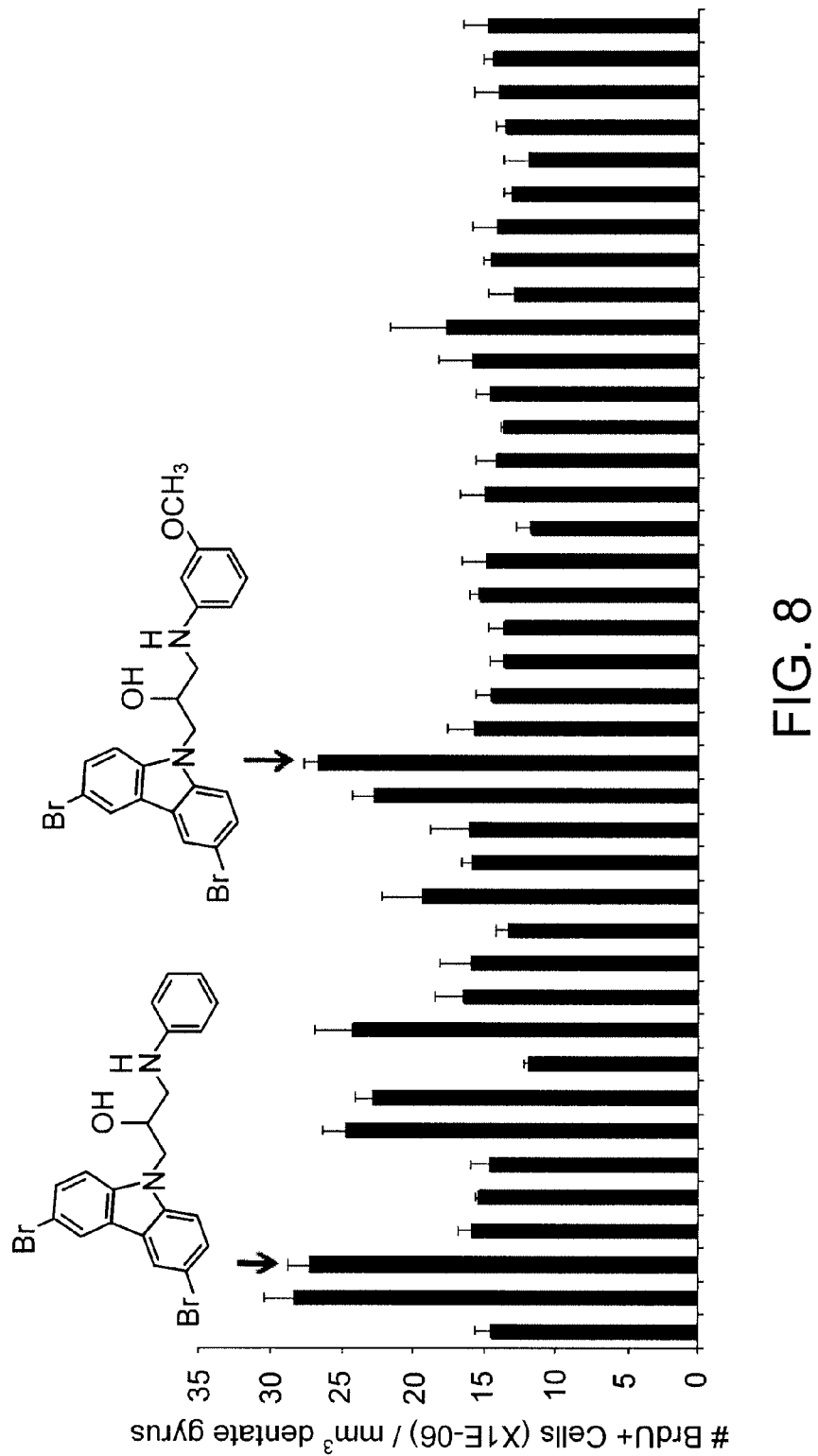
FIG. 8: Analysis of molecules related structurally to Example 45 Compound revealed a region of the compound that could be chemically modified without loss of in vivo activity. An in vivo SAR study was conducted using 37 chemical analogs of Example 45 Compound (labeled on the graph as P7C3A1-41), each evaluated in 4 or 5 adult C57/B6 male mice. Some analogs revealed activity comparable to the parent compound, whereas others showed significantly diminished activity, or evidence of pro-neurogenic effect intermediate between vehicle and FGF controls. This exercise enabled identification of regions of the parent compound that might be amenable to chemical modification without loss of activity. As an example, Example 62 Compound retained robust activity with the aniline ring of Example 45 Compound substituted by an anisidine. This derivative compound was exploited to yield a fluorescent derivative by attaching a coumarin moiety to the N-phenyl ring.
Figure 9A:
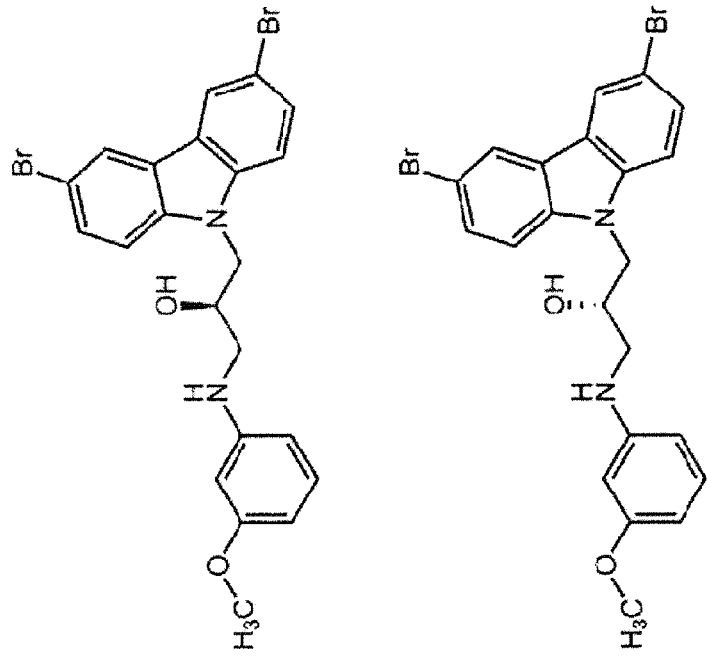
FIG. 9: Activity of Example 62 Compound is enantiomer-specific. (a) (+) and (−) enantiomers of Example 62 Compound were prepared. (b) Evaluation of Example 62 Compound enantiomers showed that in vivo pro-neurogenic or neuroprotective efficacy was fully retained by the (+) enantiomer in a dose-dependent manner, while the (−) enantiomer showed diminished activity. Each enantiomer was evaluated at each dose in between 3 and 5 three month old adult wild type male C57/B6 mice.
Figure 9A:
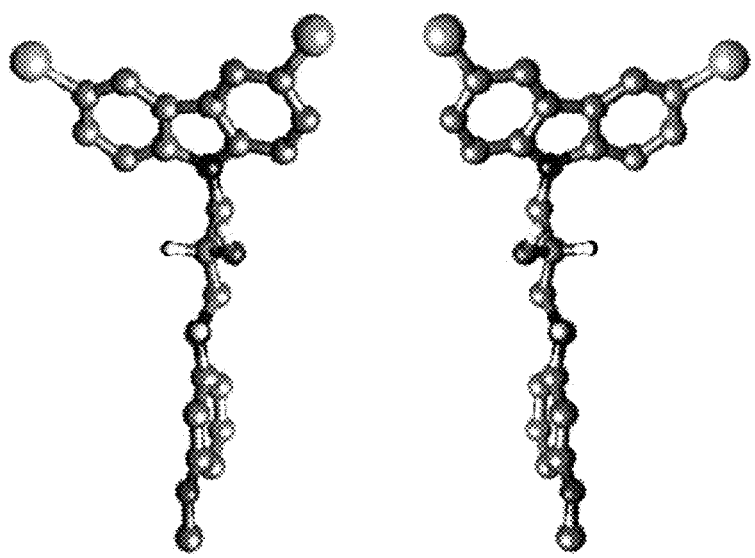

Enantiomer Selective Activity of Example 45 Compound Derivative 62:

In order to further study Example 45 Compound, an in vivo structure activity relationship (SAR) study was conducted using 37 chemical derivatives of the compound for pro-neurogenic activity via direct administration into the brain of adult mice via Alzet minipumps. Compounds were administered for one week at 10 uM into 4 mice per compound, along with daily IP injections of BrdU. Following compound administration, animals were perfused, sacrificed and subjected to sectioning, staining and light microscopy in order to monitor hippocampal neurogenesis localized to the sub-granular layer of the dentate gyrus. Roughly 10% of the variant compounds retained pro-neurogenic activity indistinguishable from the parent compound. An approximately equal number of compounds yielded slightly diminished activity, yet the majority of variants were of significantly diminished activity. (FIG. 8). A variant of Example 45 Compound having a methoxy substitution on the aniline ring (Example 62 Compound) was re-tested for pro-neurogenic activity via direct administration into the brain of adult mice via Alzet minipumps. The compound was administered for one week at 10 μM into 4 mice which were injected daily with BrdU. Following compound administration, animals were perfused, sacrificed and subjected to sectioning, staining and light microscopy in order to monitor hippocampal neurogenesis localized to the subgranular layer of the dentate gyrus. The methoxy derivative exhibited activity comparable to Example 45 Compound. Subsequently, the (+) and (−) enantiomers of Example 62 Compound were prepared (FIG. 9A).

Figure 9B:
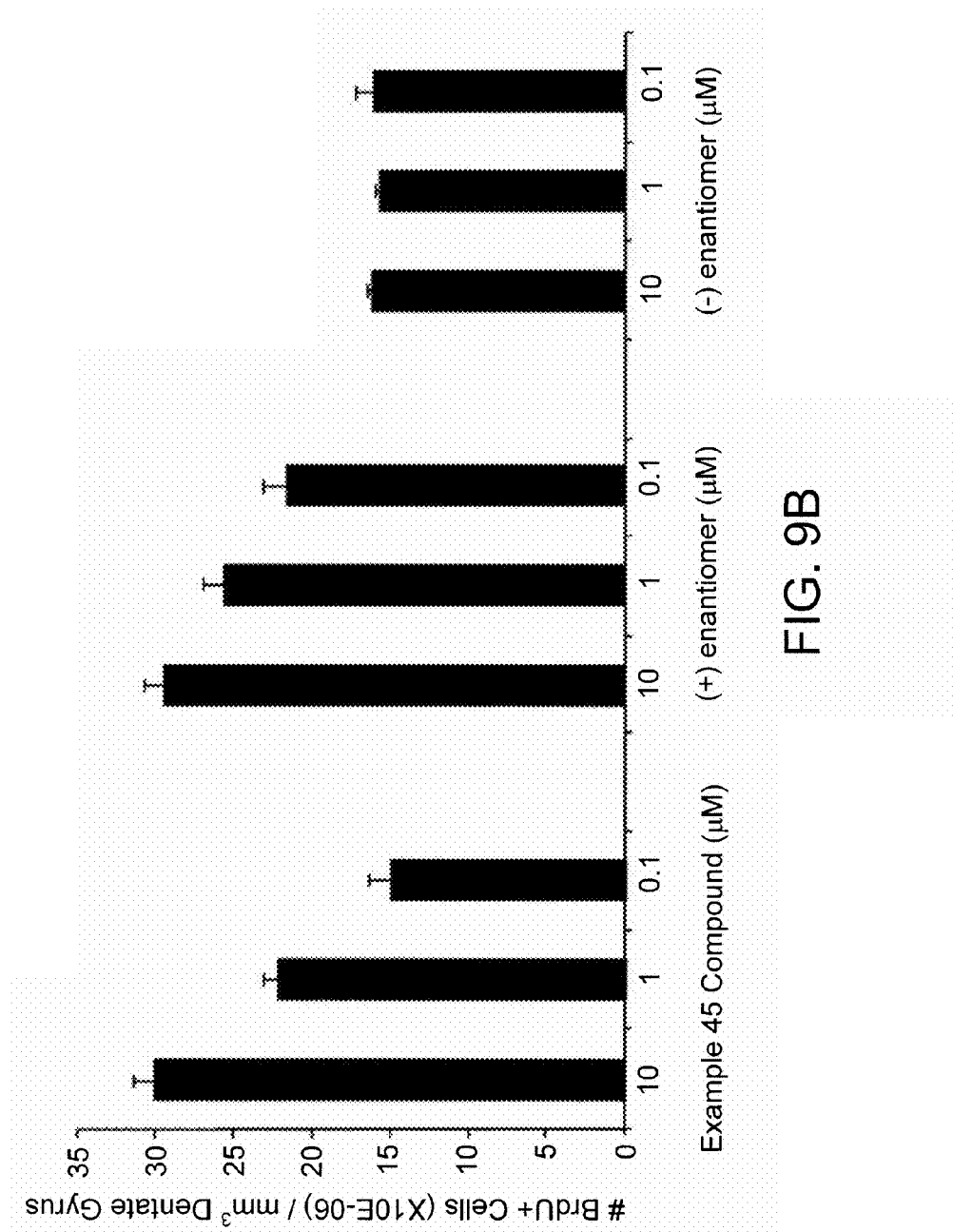

The two enantiomers were evaluated in the in vivo neurogenesis assay. The (+)-enantiomer of Example 62 Compound retained potent pro-neurogenic activity, and the (−) enantiomer displayed diminished activity (FIG. 9B).

Figure 10A:
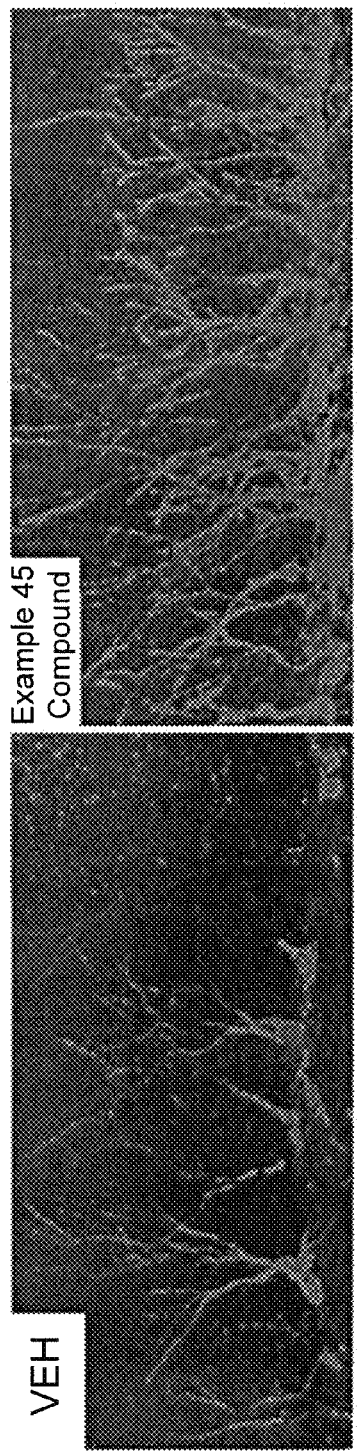
FIG. 10: Example 45 Compound enhances the survival of newborn neurons in the dentate gyrus. (a) Immunohistochemical staining for doublecortin (DCX), an antigen specifically and transiently expressed in proliferating hippocampal neural precursor cells when they become irreversibly committed to neuronal differentiation, was substantially increased in newborn neurons in mice that were administered Example 45 Compound (20 mg/kg) daily for 30 days by oral gavage, relative to that seen in mice that received vehicle only. These results are representative of 10 sections each from 5 mice in each group, and demonstrate that Example 45 Compound specifically promoted hippocampal neurogenesis. (b) Example 45 Compound enhances hippocampal neurogenesis by promoting survival of newborn neurons. Three month old wild type C57/B6 male mice were exposed to orally-delivered Example 45 Compound or vehicle for 30 days (n=5 animals/group), administered a single pulse of BrdU via IP injection (150 mg/kg), and then sacrificed 1 hour, 1 day, 5 days or 30 days later for immunohistochemical detection of BrdU incorporation into cells localized in the subgranular layer of the dentate gyrus. No significant differences were observed between groups at the 1 hour or 1 day time points, though at one day there was a trend towards increased BrdU+ cells in the Example 45 Compound-treated group. At the 5 day time point, by which time 40% of newborn neurons normally die, animals that received Example 45 Compound showed a statistically significant (*, $P<0.001$, Student's t test) 25% increase in BrdU+ cells compared to the vehicle-only control group. This difference between groups progressed with time such that mice that received a daily oral dose of Example 45 Compound for 30 days, starting 24 hours after the pulse administration of BrdU, exhibited a 5-fold increase in the abundance of BrdU+ cells in the dentate gyrus relative to vehicle-only controls. In this longer-term trial, BrdU+ cells were observed both in the SGZ and the granular layer of the dentate gyrus.

Example 45 Compound Enhances the Survival of Newborn Neurons:

The nature of the cells produced in the subgranular zone of the dentate gyrus was investigated when Example 45 Compound was administered as follows. Animals were exposed to oral administration of Example 45 Compound for 30 days. Brain tissue was then prepared for immunohistochemical staining with an antibody to doublecortin (DCX), a microtubule-associated protein that serves as a marker of neurogenesis in the dentate gyrus by virtue of transient expression in newly formed neurons, but not glial cells, between the timing of their birth and final maturation (Brown et al., 2003). As shown in FIG. 10A, the relative abundance of doublecortin-positive neurons increased dramatically as a function of exposure to prolonged administration of Example 45 Compound. Although this observation does not rule out the possibility that the compound might also enhance the formation of glial cells, it clearly shows that Example 45 Compound enhanced the formation of cells destined to become neurons.

Figure 10B:
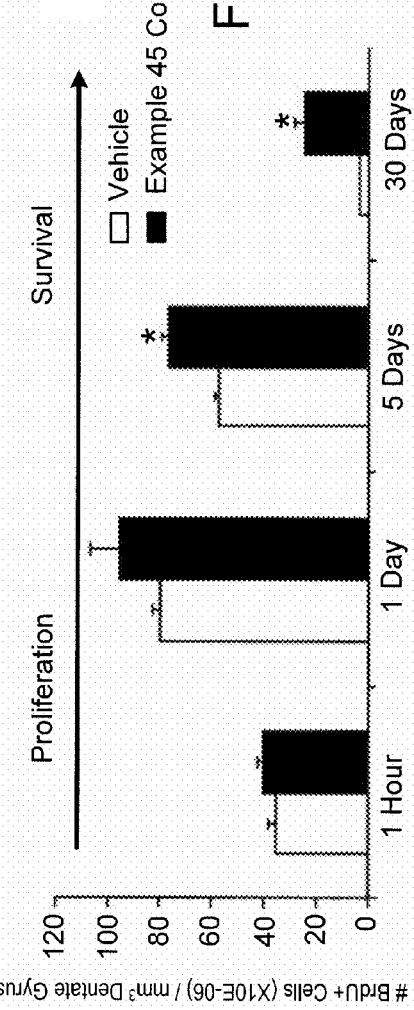
Figure 10B:
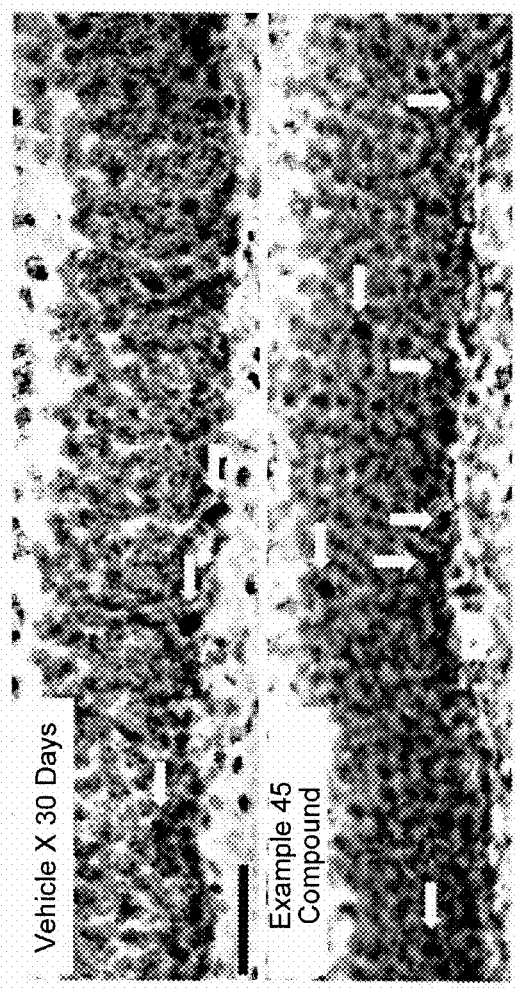

Example 45 Compound-mediated neurogenesis was next investigated to see whether it was attributable to increased cell proliferation or protection of newborn cells from cell death during the time between their birth and eventual incorporation into the granular layer of the dentate gyrus. This was accomplished by comparing the ability of Example 45 Compound to enhance either short- or long-term increases in the incorporation of BrdU in the dentate gyrus (FIG. 10B). Animals exposed to orally-delivered Example 45 Compound or vehicle for 30 days were administered a single pulse of BrdU via IP injection. Short-term effects on neuron birth were monitored by sacrificing animals one hour post-BrdU injection, followed by fixation of the tissue, sectioning and immunohistochemical detection of BrdU incorporation into cells localized in the subgranular layer of the dentate gyrus. Example 45 Compound administration did not lead to an elevation in the level of BrdU-positive cells relative to vehicle in this short-term assay. At one day after BrdU administration both groups still showed no statistically significant differences in number of BrdU+ cells in the dentate gyrus. By contrast, at the 5 day time point, by which time 40% of newborn cells in our assay normally die (FIG. 1), animals that received Example 45 Compound showed a statistically significant, 25% increase in BrdU+ cells compared to the vehicle-only control group. This difference between groups progressed with time such that mice that received a daily oral dose of Example 45 Compound for 30 days starting 24 hours after the pulse treatment of BrdU exhibited a 5-fold increase in the abundance of BrdU-positive cells in the dentate gyrus relative to vehicle-only controls. Notably, in this longer-term trial, BrdU-positive cells were observed not only along the subgranular layer of the dentate gyrus where new neurons are known to be born, but also within the granular layer itself. We hypothesize that these cells represent mature neurons that have migrated into the granular layer, completed the differentiation process, and incorporated themselves into the dentate gyrus as properly wired neurons. Observations supportive of this interpretation will be presented in a subsequent section of this document. In summary, these experiments give evidence that Example 45 Compound enhances the formation of neurons in the mature hippocampus, and that its mode of action would appear to take place at some point subsequent to their birth.

Figure 11:
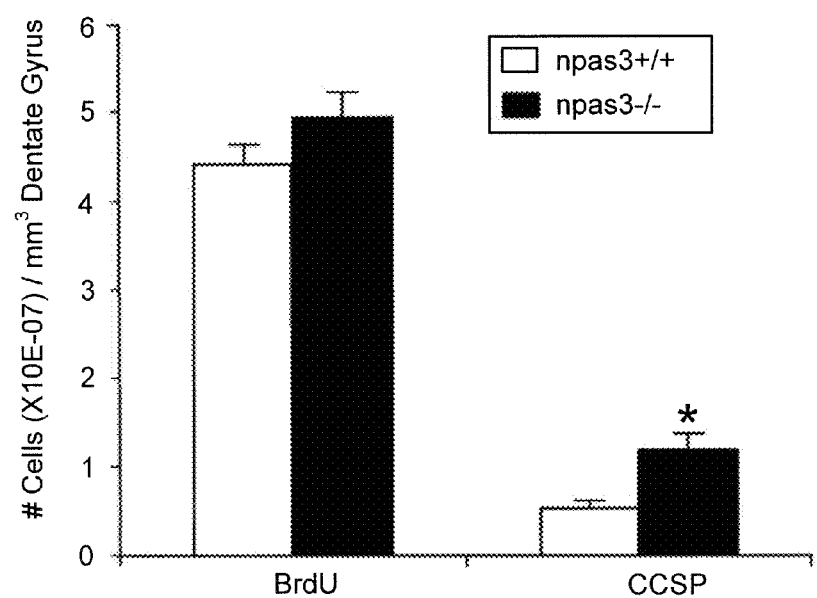
FIG. 11: Quantification of short term (1 hour pulse) BrdU incorporation and cleaved-caspase 3 (CCSP3) formation in the dentate gyrus showed that NPAS3-deficient mice have the same rate of proliferation of newborn cells in the dentate as wild type littermates (BrdU), but roughly twice the level of programmed cell death (CCSP3) (*, $P<0.01$, Student's t test). Three 6 week old male mice (NPAS3-deficient or wild type littermates) in each group were evaluated.

Example 45 Compound Normalizes Apoptosis and Ameliorates Morphological and Electrophysiological Deficits in the Dentate Gyrus of NPAS3-Deficient Mice:

Mice lacking both copies of the gene encoding neuronal PAS domain protein 3 (NPAS3) suffer a profound impairment in adult neurogenesis (Pieper et al., 2005). By evaluating BrdU incorporation in a short-term assay of neurogenesis by sacrificing animals 1 hours after BrdU pulse, it was observed that NPAS3-deficient animals have no detectable deficit in the birth of neurons in the subgranular layer of the dentate gyrus (FIG. 11). This is in contrast to our earlier observations of profoundly diminished BrdU labeling in the dentate gyrus of NPAS3-deficient animals when BrdU is administered for a longer period of time (12 days) (Pieper et al., 2005). Knowing that the NPAS3 transcription factor is required for proper expression of the fibroblast growth factor receptor 1 (FGFR1) in the hippocampus (Pieper et al., 2005), it is possible that impediments in growth factor signaling might impair the trophic environment critical for the survival of newborn neurons in the dentate gyrus. As an initial test of this hypothesis, brain tissue prepared from NPAS3-deficient animals was compared with that of wild type littermates for the presence of cleaved caspase 3 (CCSP3)-positive cells in the subgranular layer of the dentate gyrus. A statistically significant, 2-fold increase in CCSP3-positive (apoptotic) cells was observed in the dentate gyrus of NPAS3-deficient animals (FIG. 11). This enhanced rate of programmed cell death is likely to account, at least in part, for the nearly complete elimination of adult neurogenesis in mice lacking the NPAS3 transcription factor (Pieper et al., 2005).

Figure 12A:
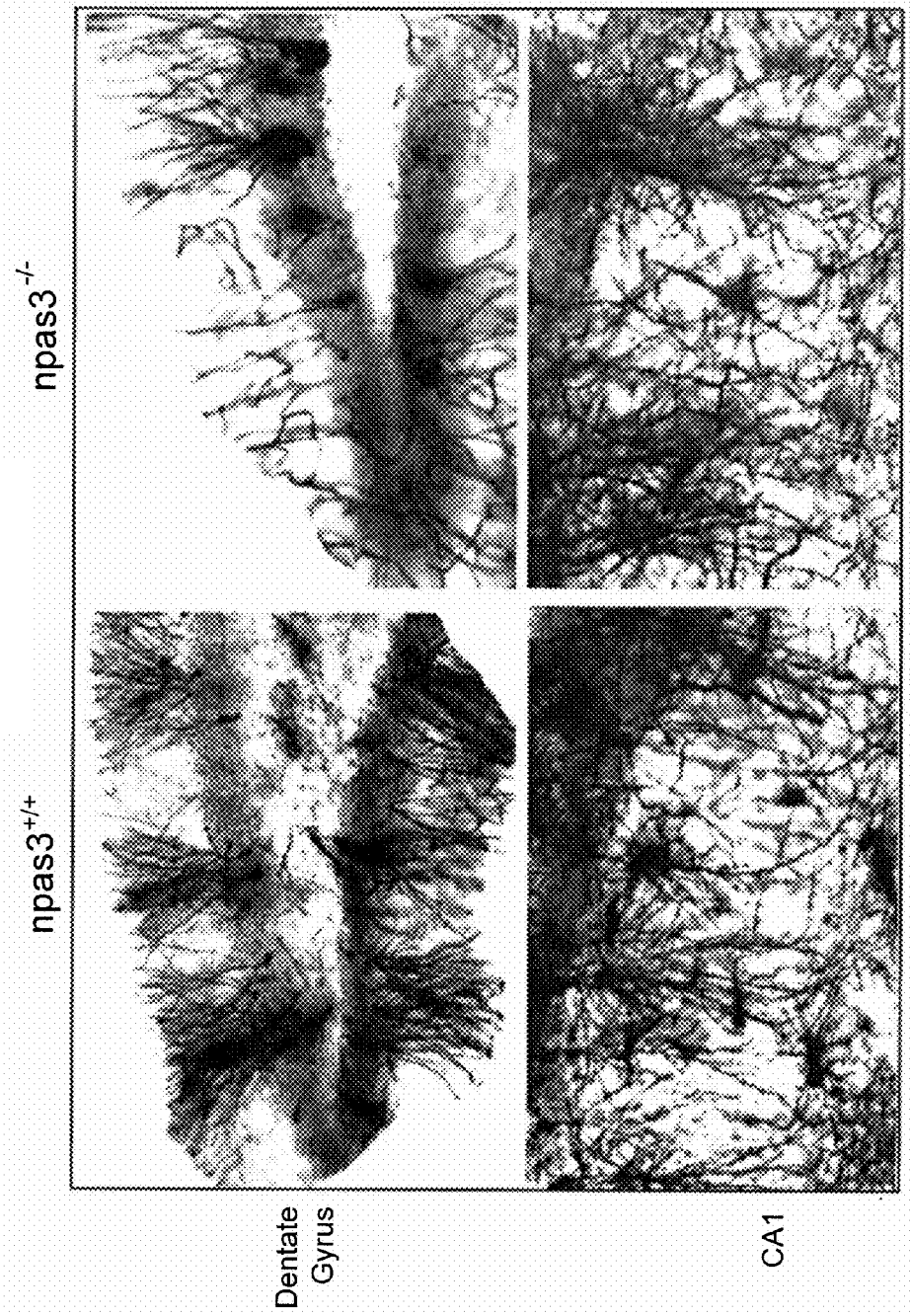
FIG. 12: Granule cell neurons in the dentate gyrus of NPAS3-deficient mice displayed morphological deficits in dendritic branching and spine density. (a) Golgi-Cox staining of the dentate gyrus illustrates that dendritic arborization of dentate gyrus granule cell neurons in npas3$^{-/-}$ mice is substantially less developed than in wild type littermates. Results shown are representative of 15 sections from five 12-14 week old adult male mice of each genotype. (b) In addition to obviously reduced dendritic length and branching, granular neurons in the dentate gyrus of npas3$^{-/-}$ mice also exhibited significantly reduced spine density relative to wild type littermates (*, $P<0.00001$, Student's t test). These genotype-specific differences were not exhibited by neurons in the CA1 region of the hippocampus.
Figure 12B:
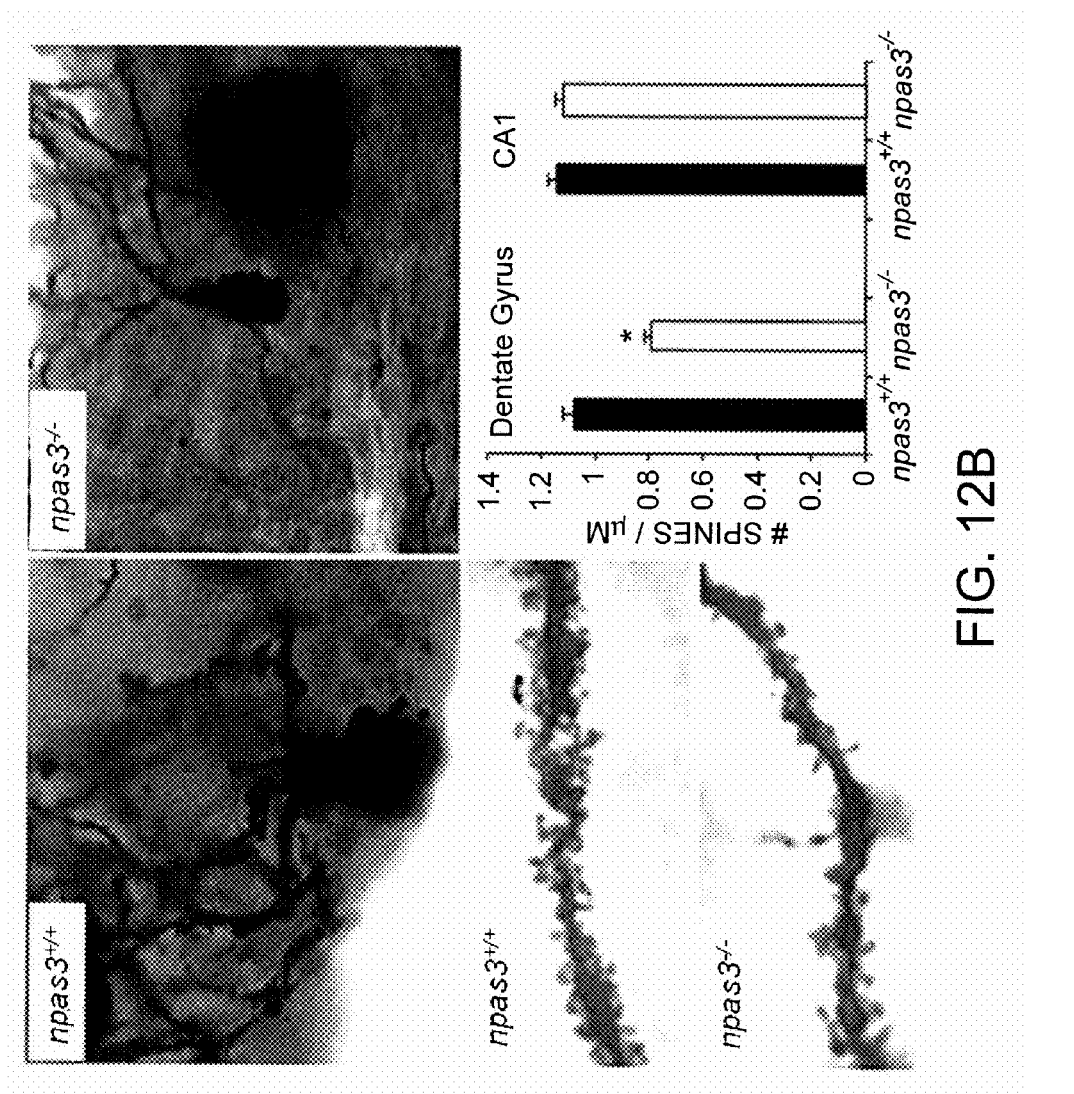
Figure 13A:
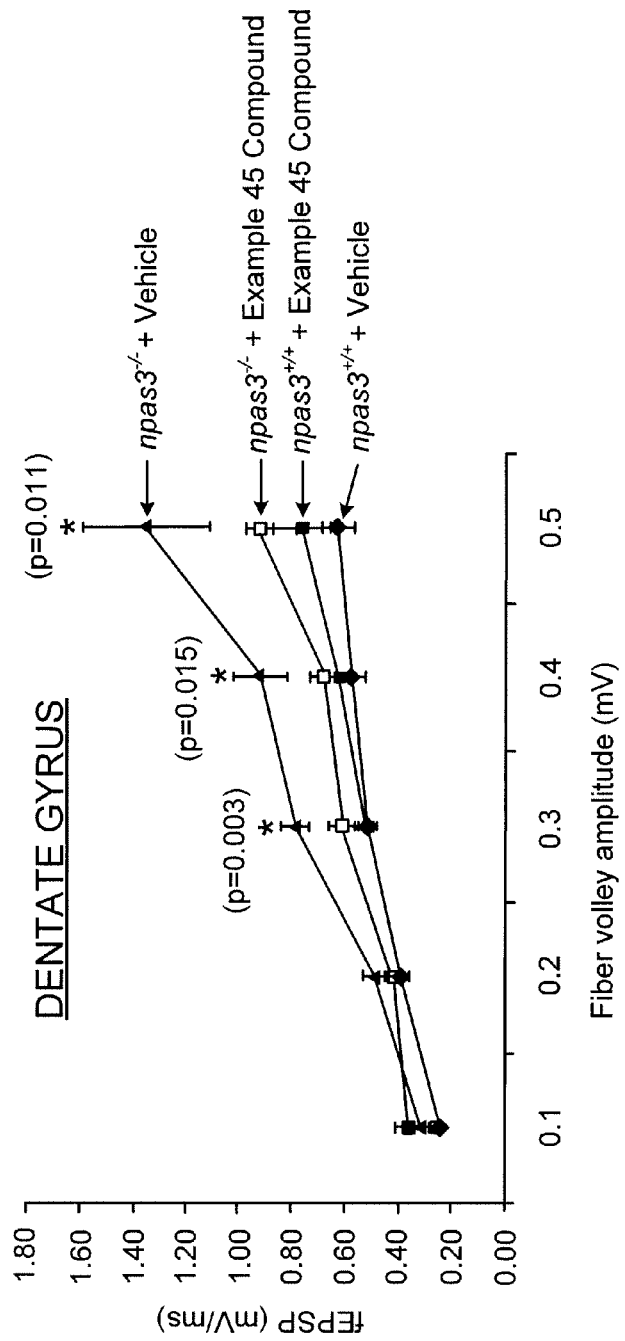
FIG. 13: In hippocampal slice preparation from npas3$^{-/-}$ mice, synaptic transmission was increased both in the outer molecular layer of the dentate gyrus (a) and the CA1 region of the hippocampus (b) relative to hippocampal slices from wild type mice. Extended treatment with Example 45 Compound normalized synaptic responses in the dentate gyrus but not the CA1 region of npas3⁻/⁻ mice. Extended treatment with Example 45 Compound did not affect wild-type responses. Data are presented as the mean±SEM. Each group consisted of 1 or 2 slice preparation from each of 5 mice.

In addition to this quantitative deficit in adult neurogenesis, we have observed abnormalities in both the morphology and electrophysiology of granular neurons of the dentate gyrus of NPAS3-deficient animals. Relative to wild type animals, Golgi-Cox staining revealed severe attenuation in dendritic branching and spine density of dentate gyrus granular neurons of NPAS3-deficient animals (FIGS. 12a and 12b). By contrast, no genotype-dependent differences in these measures were observed in pyramidal cells of the CA1 region of the hippocampus. Equivalently specific deficits were observed by electrophysiologic recordings of NPAS3-deficient animals compared with wild type littermates (FIGS. 13a and 13b). Whole field recordings of excitatory postsynaptic potentials (fEPSP) revealed significant deficits in NPAS3-deficient animals, relative to wild type littermates. In the dentate gyrus, stimulating and recording electrodes were positioned in the outer molecular layer, which is innervated by axons of the perforant pathway originating from the entorhinal cortex. In the CA1 region of the hippocampus, stimulation and recording electrodes were positioned in the stratum radiatum, which is innervated by the Schaffer collateral axons of CA3 pyramidal cells. Stimulus intensity was increased in 5 μA increments, the slope of the decreasing part of field potentials was measured, and fEPSP was quantified relative to the amplitude of the fiber volley, which represents firing of action potentials in pre-synaptic axons. This analysis revealed aberrant hyper-excitability of synaptic transmission in npas3$^{-/-}$ mice both in the outer molecular layer of the dentate gyrus and in the CA1 region (FIGS. 13a and 13b).

Figure 14:
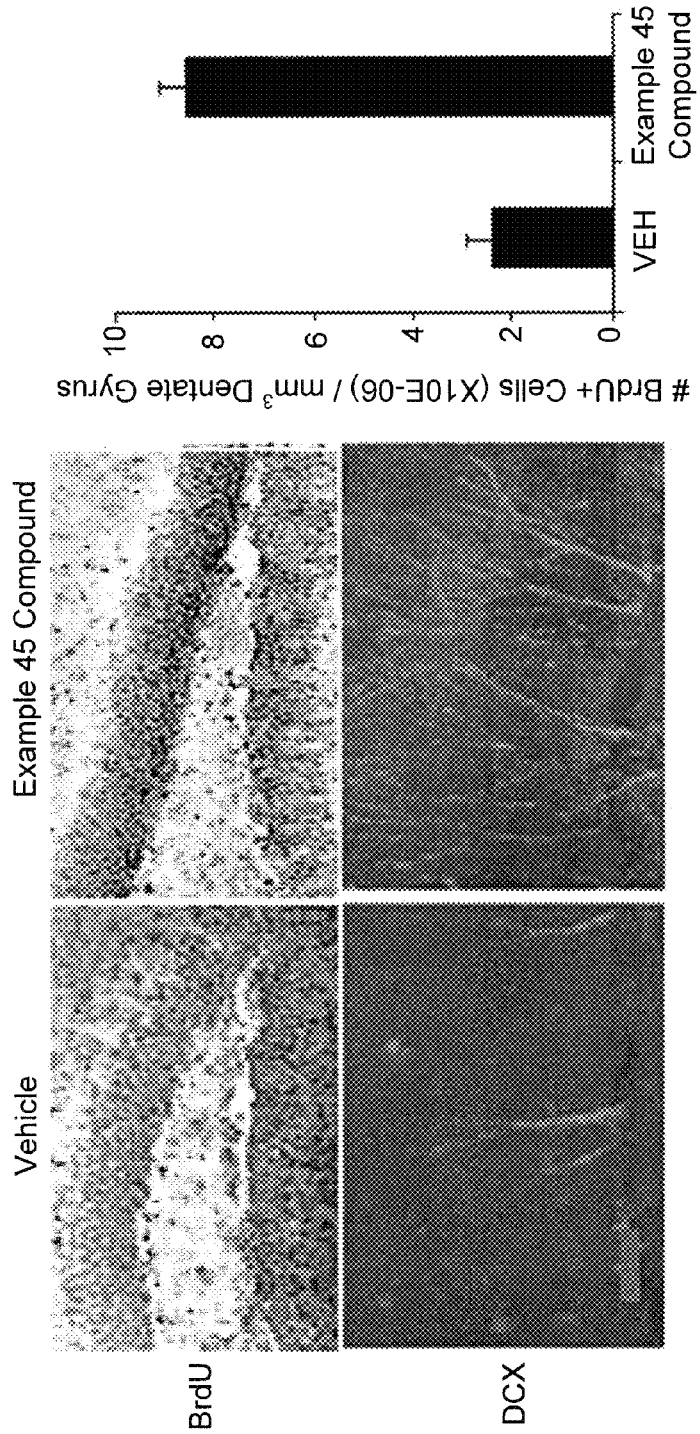
FIG. 14: Example 45 Compound has pro-neurogenic or neuroprotective efficacy in the dentate gyrus of NPAS3-deficient animals. Six 12 week old npas3⁻/⁻ mice were orally administered vehicle or Example 45 Compound (20 mg/kg/d) for 12 days, and also injected daily with BrdU (50 mg/kg). At the end of day 12, mice were sacrificed and tissue was stained for BrdU and doublecortin (DCX). BrdU staining showed that Example 45 Compound increased the magnitude of neurogenesis in npas3⁻/⁻ mice by roughly 4-fold, as graphically represented above (*, $P<0.001$, Student's t test). DCX staining shows that Example 45 Compound also promoted more extensive process formation in differentiating neurons of the adult dentate gyrus in npas3⁻/⁻ mice.

Armed with these genotype- and region-specific deficits in both neuron morphology and electrophysiological activity, we set out to test whether prolonged administration of Example 45 Compound might favorably repair either deficit in NPAS3-deficient animals. Before embarking on this effort, we first confirmed that Example 45 Compound was capable of enhancing hippocampal neurogenesis in NPAS3-deficient mice, by demonstrating that Example 45 Compound enhances both BrdU incorporation as well as expression of doublecortin in newborn neurons in the dentate gyrus of npas3$^{-/-}$ mice (FIG. 14). Knowing that formation of the dentate gyrus initiates in the late pre-natal mouse embryo around embryonic day 14 (Stanfield and Cowan, 1988), we sought to expose animals to Example 45 Compound for as extended a period of time as possible in order to give the compound the best possible chance for exhibiting favorable effects. Following oral gavage of pregnant female mice, 14 day embryos were recovered, dissected and processed by acetonitrile:water extraction so that Example 45 Compound levels could be measured in the embryonic brain. Daily administration of 20 mg/kg of Example 45 Compound to pregnant females yielded appreciable levels of the compound in the brain tissue of developing embryos. It was similarly observed that oral administration of the compound to lactating females led to delivery of Example 45 Compound to the brain tissue of weanling pups. In both cases, LC/MS-based quantitation of Example 45 Compound revealed levels of compound accumulation at or above the 1.35 μM limit required to support adult neurogenesis (FIG. 7). Finally, it was observed that daily IP administration of Example 45 Compound to weaned pups at 20 mg/kg was sufficient to yield brain levels of Example 45 Compound at or above the level required to enhance adult neurogenesis.

Figure 15:
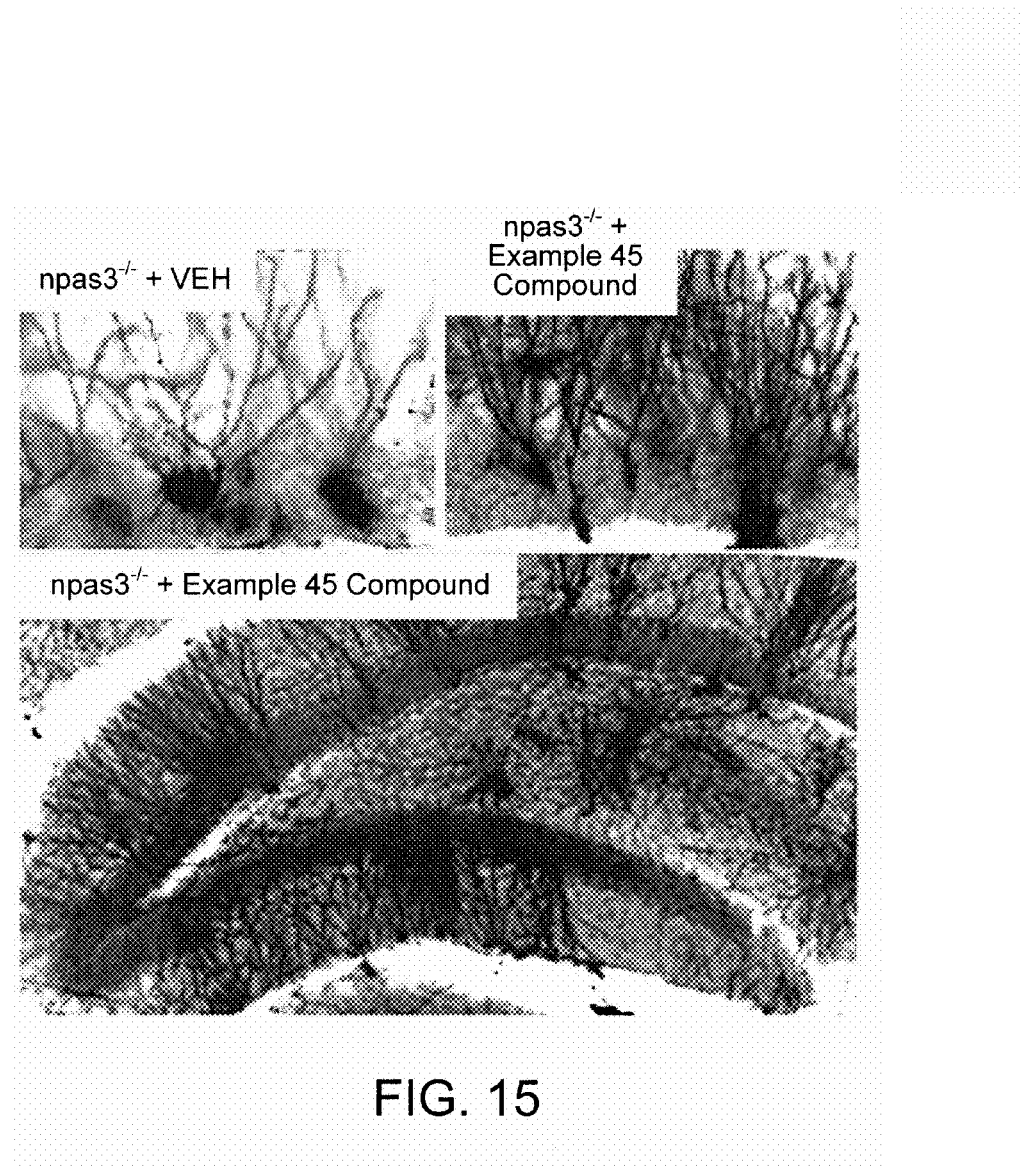
FIG. 15: Golgi-Cox staining of neurons in the dentate gyrus shows that extended daily treatment of npas3⁻/⁻ mice with Example 45 Compound (20 mg/kg/d) enhanced dendritic arborization. Hi-power micrographs are shown on top, and a lower power micrograph illustrating the entire dentate gyrus is shown below.

Female mice heterozygous at the NPAS3 locus were mated to heterozygous males. Two weeks post-mating, females were given a daily oral gavage of either 20 mg/kg of Example 45 Compound or vehicle-only formula. Dosing was continued throughout the last trimester of pregnancy, as well as the two week post-natal period of lactation. Following weaning, pups were given a daily IP dose of either 20 mg/kg Example 45 Compound or vehicle control. At about 7 weeks of age, mice were switched to oral gavage delivery of the same dose of Example 45 Compound. When mice were 3 months of age they were sacrificed and brain tissue was dissected and subjected to either Golgi-Cox staining or electrophysiological recording. As shown in FIG. 15, prolonged exposure to Example 45 Compound robustly repaired morphological deficits in the dendritic branching of granular neurons of the dentate gyrus in NPAS3-deficient mice. Moreover, as shown in FIG. 13A, the electrophysiological deficit in the dentate gyrus of NPAS3-deficient mice was also corrected following prolonged exposure of mice to Example 45 Compound. The corresponding electrophysiological deficit in CA1 region of the hippocampus, however, was not affected (FIG. 13B), underscoring the specificity of Example 45 Compound to improving functioning of the dentate gyrus in this animal model.

Figure 16:
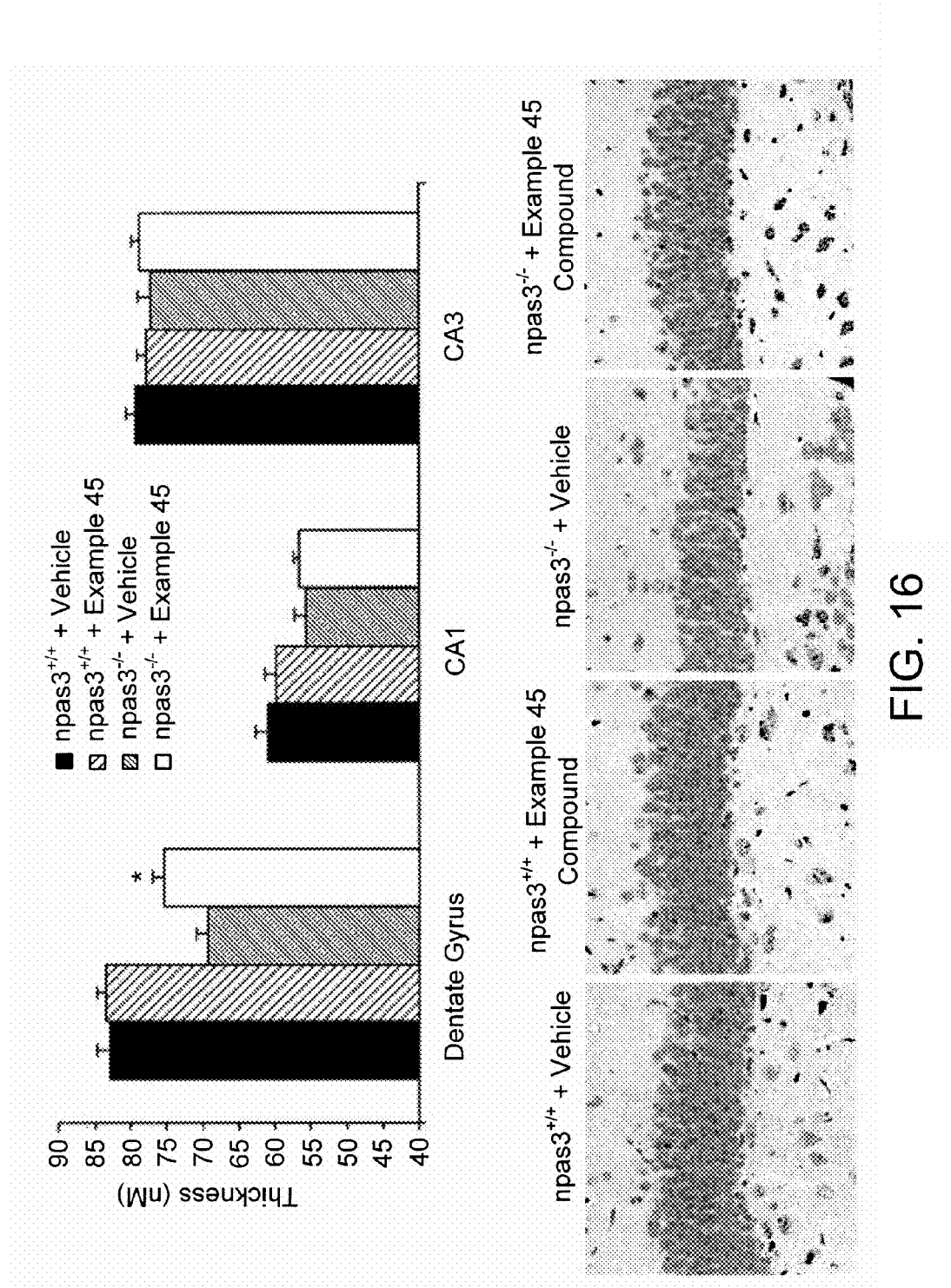
FIG. 16: Measured thickness of hippocampal subfields in npas3⁻/⁻ and wild type littermate mice that were treated with Example 45 Compound (20 mg/kg/d) or vehicle every day from embryonic day 14 until 3 months, of age demonstrated that Example 45 Compound selectively increased the thickness of the dentate gyrus granular cell layer to a level approaching wild type thickness (*, $P<0.01$, Student's t test), without affecting thickness of the pyramidal cell layers of CA1 or CA3 regions.

It is also notable that, relative to vehicle-only controls, administration of Example 45 Compound did not affect any aspect of the health of mothers, embryos, weanlings or young adult mice. Gross histology of brain tissue was normal in both compound- and vehicle-treated animals, and there was no evidence of neuronal cell loss or degenerative changes (cytoplasmic eosinophilia, vacuolization or nuclear pyknosis). The only morphological change, other than normalization of dendritic arborization of granular neurons of the dentate gyrus, was a compound-dependent increase in the thickness of the granular layer of the dentate gyrus itself (FIG. 16). The thickness of the granular layer of the dentate gyrus is roughly 40% less in NPAS3-deficient animals than wild type littermates. Prolonged administration of Example 45 Compound through late embryonic development, early post-natal development, and two months post-weaning significantly corrected this deficit without affecting the thickness of other hippocampal layers in NPAS3-deficient mice (FIG. 16).

Figure 17:
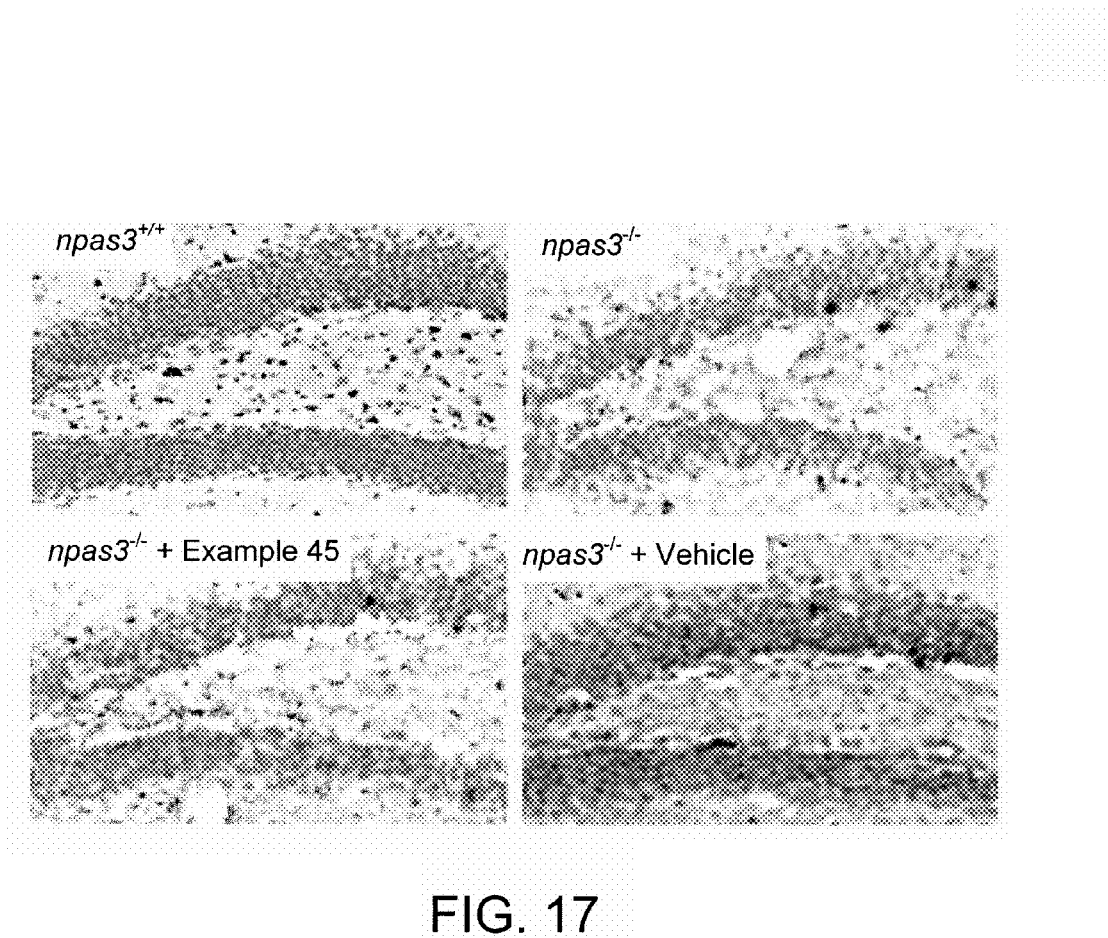
FIG. 17: Immunohistochemical detection of cleaved caspase 3 (CCSP3), a marker of apoptosis, showed elevated levels of programmed cell death in the dentate gyrus of NPAS3-deficient animals. Apoptosis in NPAS3-deficient animals was inhibited by treatment with Example 45 Compound (20 mg/kg/d, p.o., for 12 days), whereas analogous treatment with vehicle alone had no effect. Images shown are representative of 10-12 sections evaluated per animal, with 3-5 eight-week-old male NPAS3-deficient mice per group.

Recognizing that the reduced thickness of the granular layer of the dentate gyrus in NPAS3-deficient animals could be attributed to elevated levels of apoptosis of newborn hippocampal neural precursor cells, we examined the effect of Example 45 Compound treatment on apoptosis in the hippocampus of NPAS3-deficient animals through immunohistochemical staining of cleaved caspase 3 (CCSP3). As shown in FIG. 17, 12 days of treatment with orally delivered Example 45 Compound (20 mg/kg) to adult NPAS3-deficient animals significantly reduced CCSP3 staining in the dentate gyrus, whereas vehicle-treatment had not effect. We thereby propose that Example 45 Compound facilitated repair of the granular layer of the dentate gyrus in NPAS3-deficient mice by ameliorating a genotype-specific exacerbation of programmed cell death.

Figure 18:
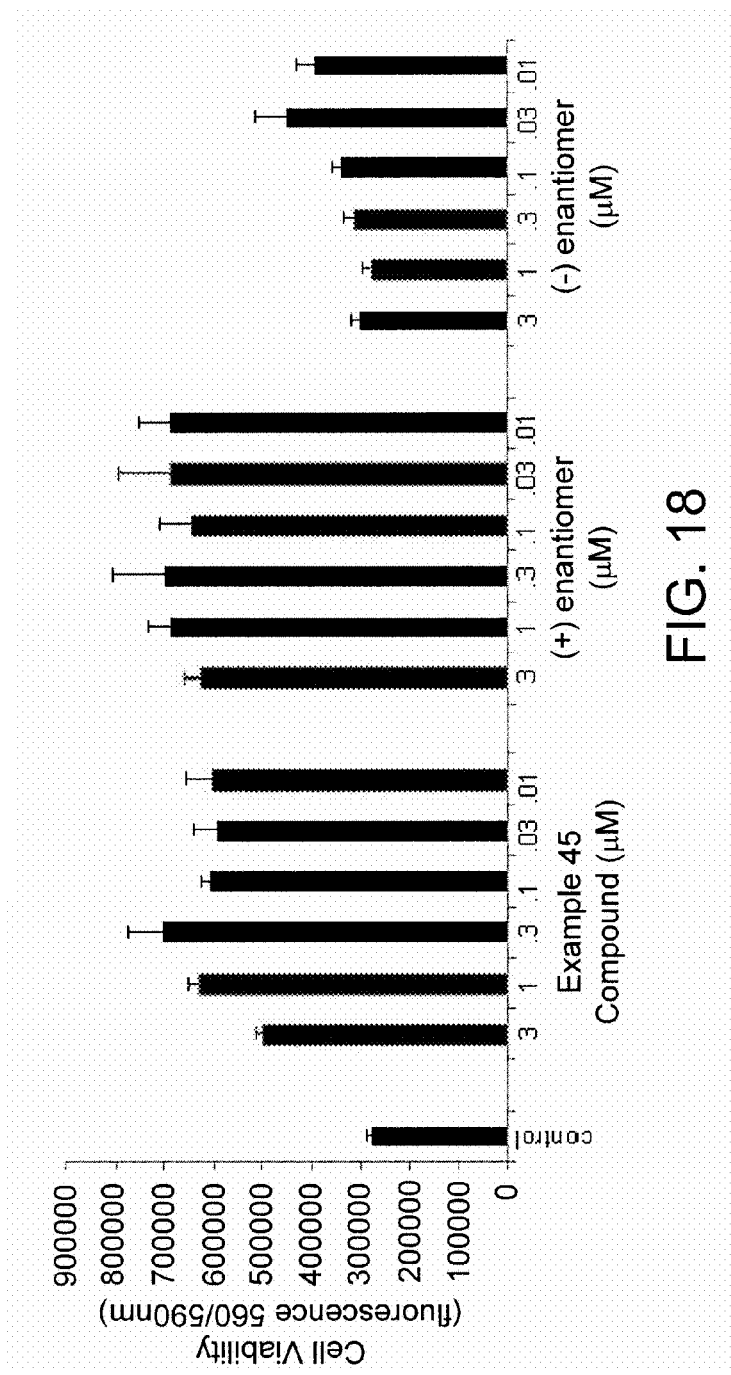
FIG. 18: Cell viability assay after exposure of cultured primary cortical neurons to $A\beta_{(25-35)}$ for 48 hours shows that Example 45 Compound protected neurons from cell death compared to vehicle-treated (control) samples. Observed protection was afforded with the (+) enantiomer of Example 62 Compound, but less so with the (−) enantiomer. Data are presented as the mean±SEM.
Figure 19:
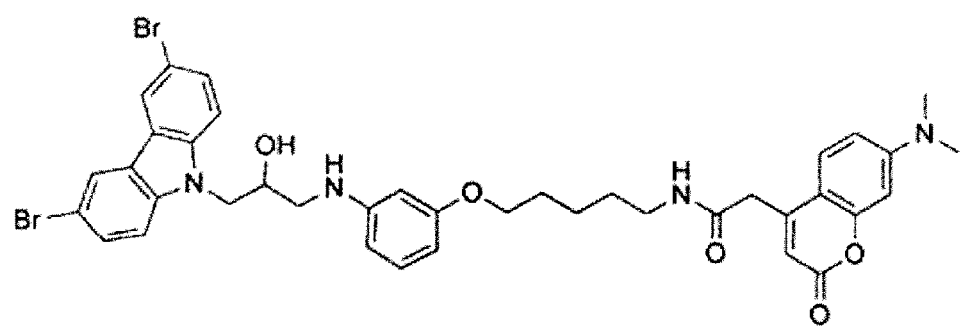
FIG. 19: Chemical structure of FASDP.
Figure 20:
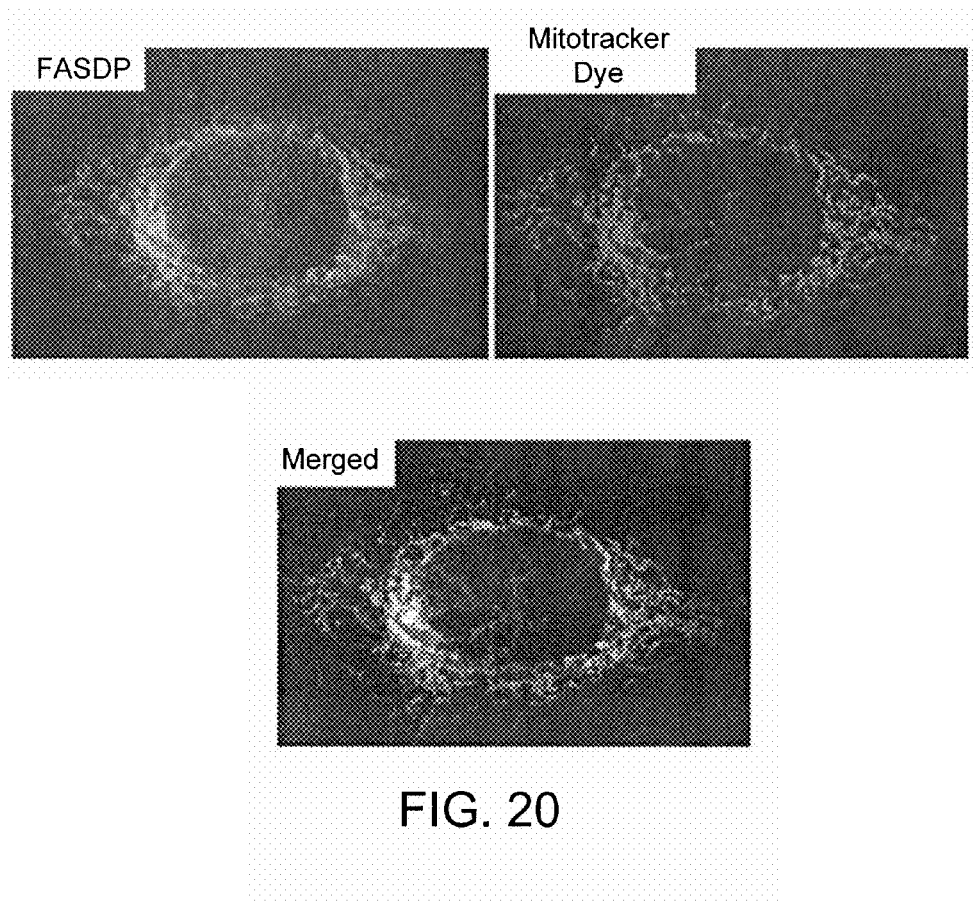
FIG. 20: Fluorescently-labeled Example 62 Compound, termed FASDP, was exposed to cultured U2OS osteoblast cells and observed to localize with a distribution that overlapped with that of Mitotracker dye. This observation indicated that the site of action of Example 45 Compound is localized in mitochondria.

Example 45 Compound Protects Cultured Cortical Neurons from Beta-Amyloid Toxicity:

Apoptosis is implicated in numerous neurodegenerative disorders, and we wondered if Example 45 Compound might protect mature neurons from programmed cell death. Cultured primary cortical neurons have been shown to undergo apoptosis following exposure to β-amyloid peptide (Loo et al., 1993). Accordingly, we investigated whether Example 45 Compound might protect cultured neurons from this paradigm of cell death. Cortical neurons from embryonic day 18 rats were allowed to mature for 1 week, exposed to 25 μM A$β_{(25-35)}$ peptide fragment for 48 hours, and then assayed for cell viability by light microscopic visualization as well as the cell titer blue viability assay (Promega), which utilizes the indicator dye resazurin to measure the metabolic activity of cultured cells. As shown in FIG. 18, Example 45 Compound protected cultured primary cortical neurons from A $β_{(25-35)}$-mediated toxicity. Dose response testing revealed that Example 45 Compound did not lose maximal neuroprotective activity even when diluted to low nanomolar levels. Importantly, when the (+) and (−) enantiomers of the methoxy derivative of Example 45 Compound (Example 62 Compound) were tested, neuroprotective activity was observed with the same (+) enantiomer of Example 62 Compound that also retained pro-neurogenic activity in living mice, while the (−) enantiomer again displayed diminished activity Example 45 Compound Acts in Mitochondria to Protect Mitochondrial Integrity:

In order to investigate its cellular site of action, example 62 compound was modified by attaching a coumarin moiety to the N-phenyl ring according to established methods (Alexander et al., 2006), yielding a fluorescent derivative designated FASDP (fluorescent, anisidine substituted derivative of Example 45 Compound) (FIG. 19). FASDP was confirmed to retain pro-neurogenic activity in adult mice in our standard assay, and cultured osteoblast cells were exposed to FASDP and visualized by fluorescence optics in a light microscope. As shown in FIG. 20, FASDP labeled cells in a punctuate pattern that overlapped with mitochondria as visualized by Mitotracker dye. These observations are consistent with the hypothesis that the activity and molecular target of Example 45 Compound may reside within mitochondria.

Figure 21A:
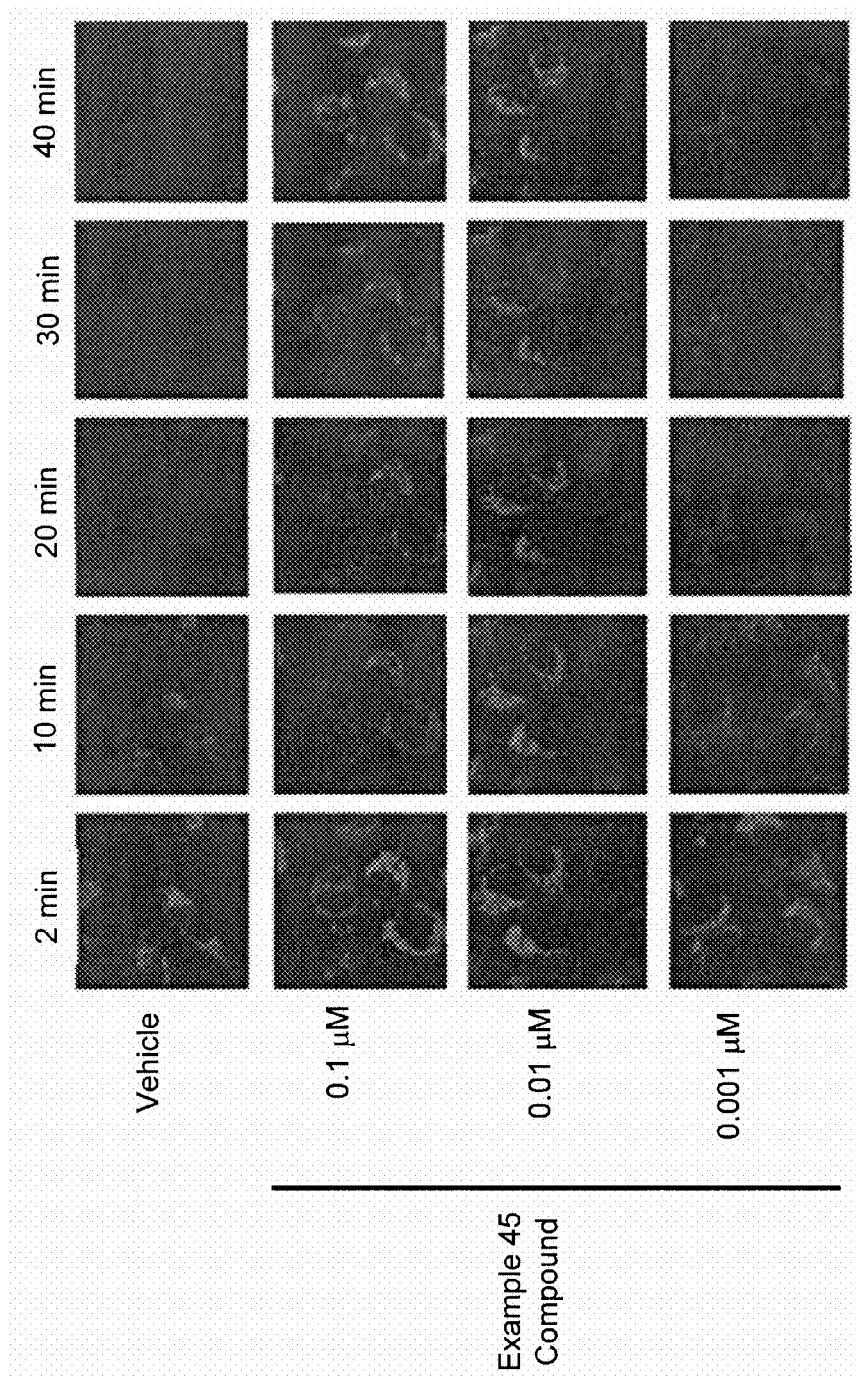
FIG. 21: Example 45 Compound acts mechanistically in the mitochondria. (a) Example 45 Compound preserved mitochondrial membrane potential following exposure to the calcium ionophore A23187 in a dose dependent manner as judged by fluorescent imaging of TMRM dye, a cell-permeant, cationic red-orange fluorescent dye that is readily sequestered by intact mitochondria. (b) The protective effect of Example 62 Compound was enantiomeric specific, with the (+) enantiomer retaining activity more so than the (−) enantiomer.
Figure 21B:
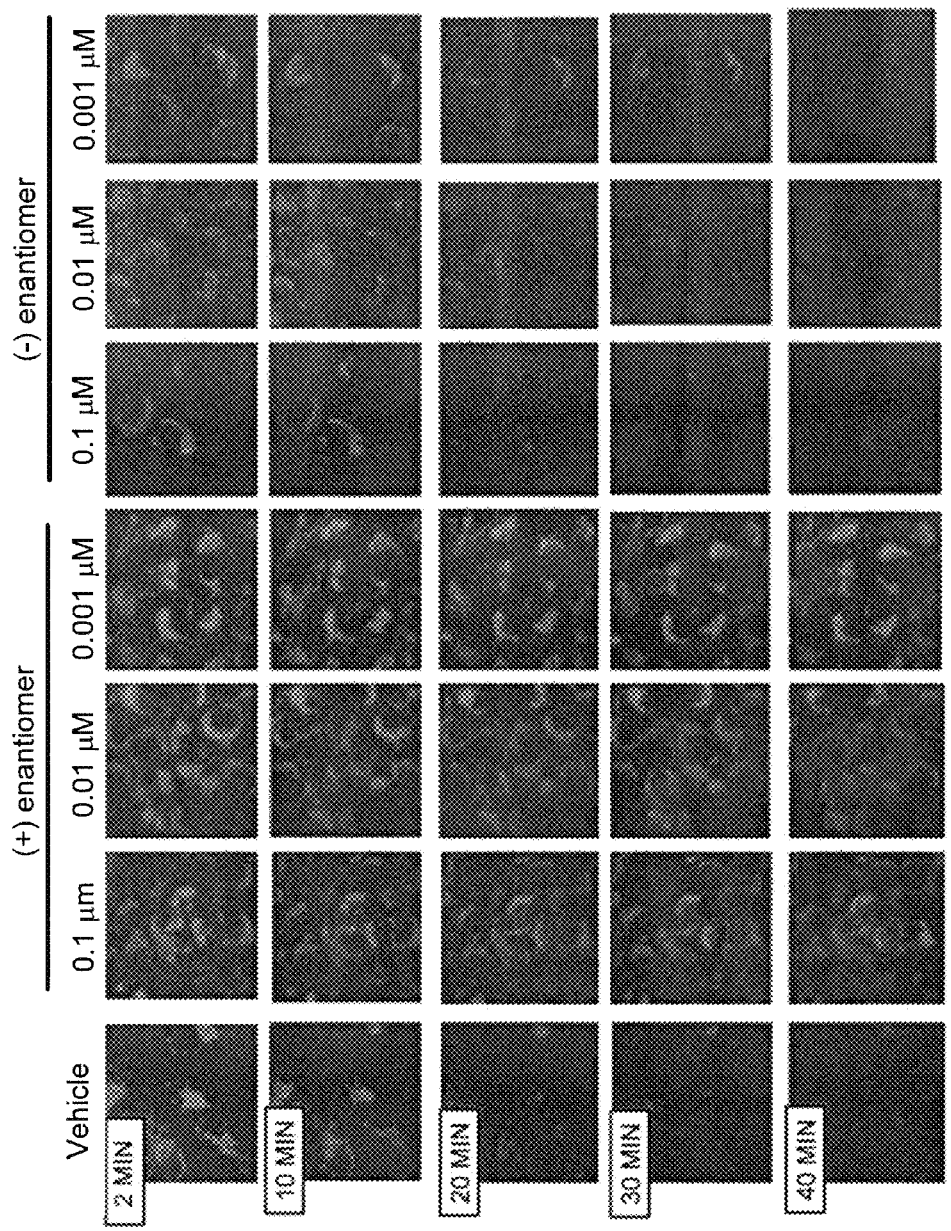

Extensive evidence pioneered by the laboratory of Xiaodong Wang has shown that an intrinsic pathway leading to programmed cell death emanates from mitochondria (Liu et al., 1996; Yang et al., 1997). With the help of the Wang lab, assays were established to test whether Example 45 Compound might protect mitochondria from calcium-induced dissolution (Distelmaier et al., 2008). Tetramethylrhodamine methyl ester (TMRM) is a cell-permeant, cationic red-orange fluorescent dye that is readily sequestered by active mitochondria. When loaded with TMRM dye, vehicle-only treated cells released the dye within 15 minutes of exposure to the calcium ionophore A23187. By contrast, dye release was prevented in cells exposed to as little as 10 ng of Example 45 Compound (FIG. 21A). As with in vivo neurogenesis assay, as well as the in vitro protection from $Aβ_{(25-35)}$-mediated toxicity of cultured cortical neurons, preservation of mitochondrial membrane potential in this assay was observed only with the (+) enantiomer of Example 62 Compound (FIG. 21B).

Figure 22A:
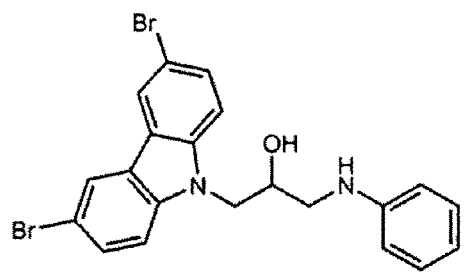
FIG. 22: Example 45 Compound as compared to a known drug. (a) Both Example 45 Compound and the Dimebon anti-histamine enhanced hippocampal neurogenesis (b), protected cultured cortical neurons from $A\beta_{(25-35)}$-mediated cell death (c), and protected mitochondria from dissolution following toxic exposure to the calcium ionophore A23187 (d). In the in vivo assay of neurogenesis the Example 45 Compound exhibited a higher ceiling of efficacy than the Dimebon anti-histamine. In all three assays, the Example 45 Compound performed with greater relative potency than the Dimebon anti-histamine.
Figure 22A:
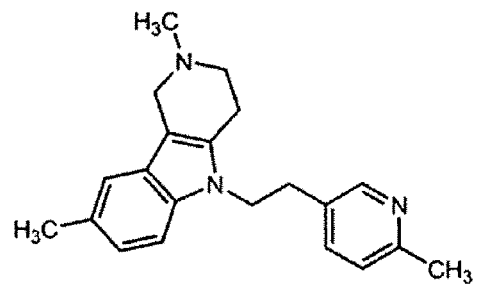
Figure 22B:
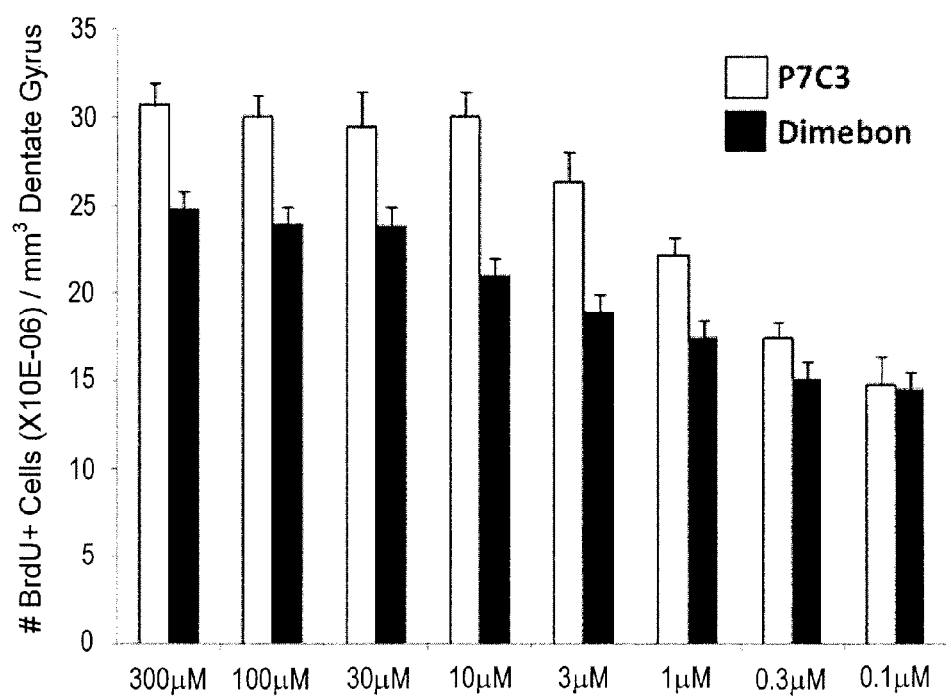
Figure 22C:
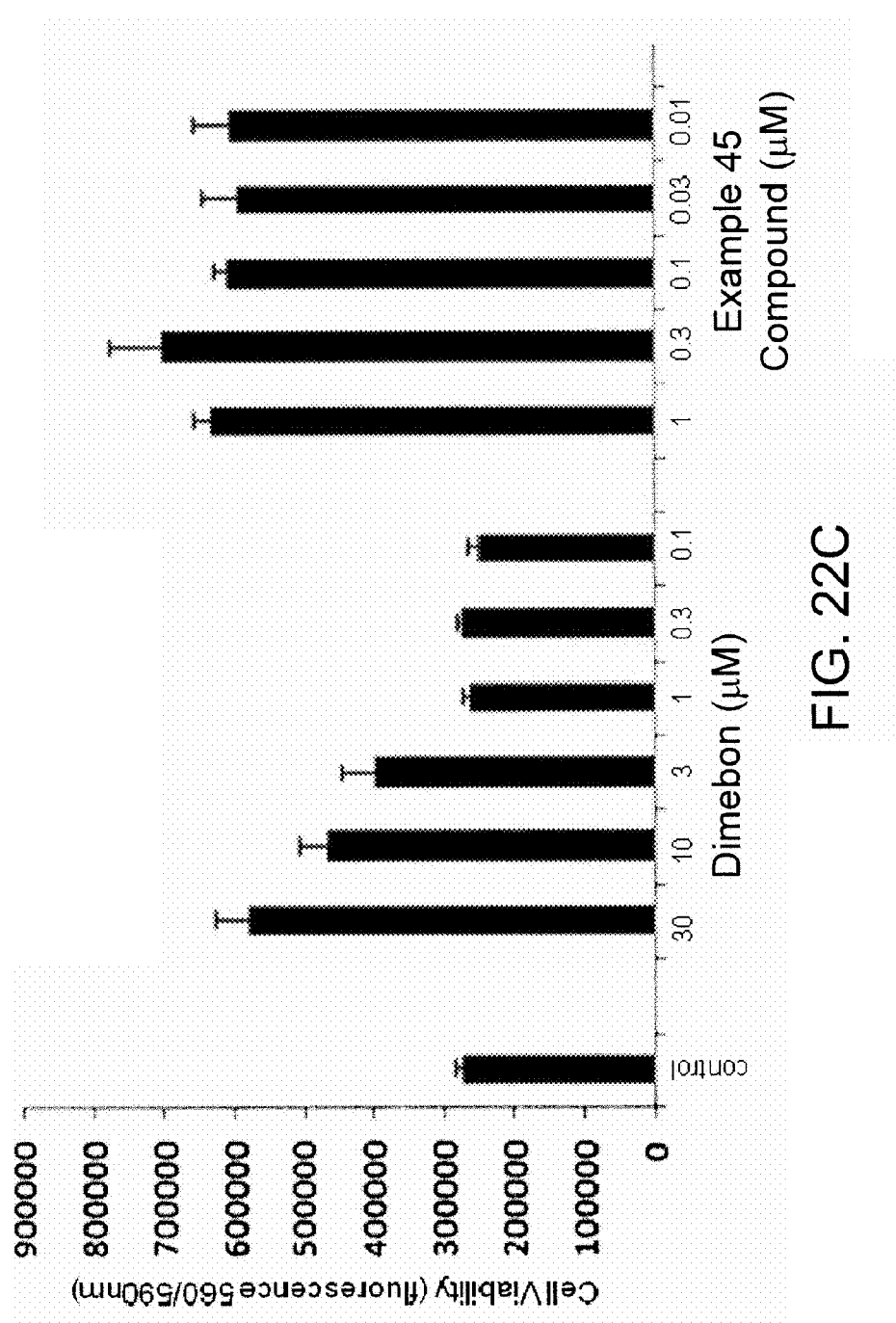
Figure 22D:
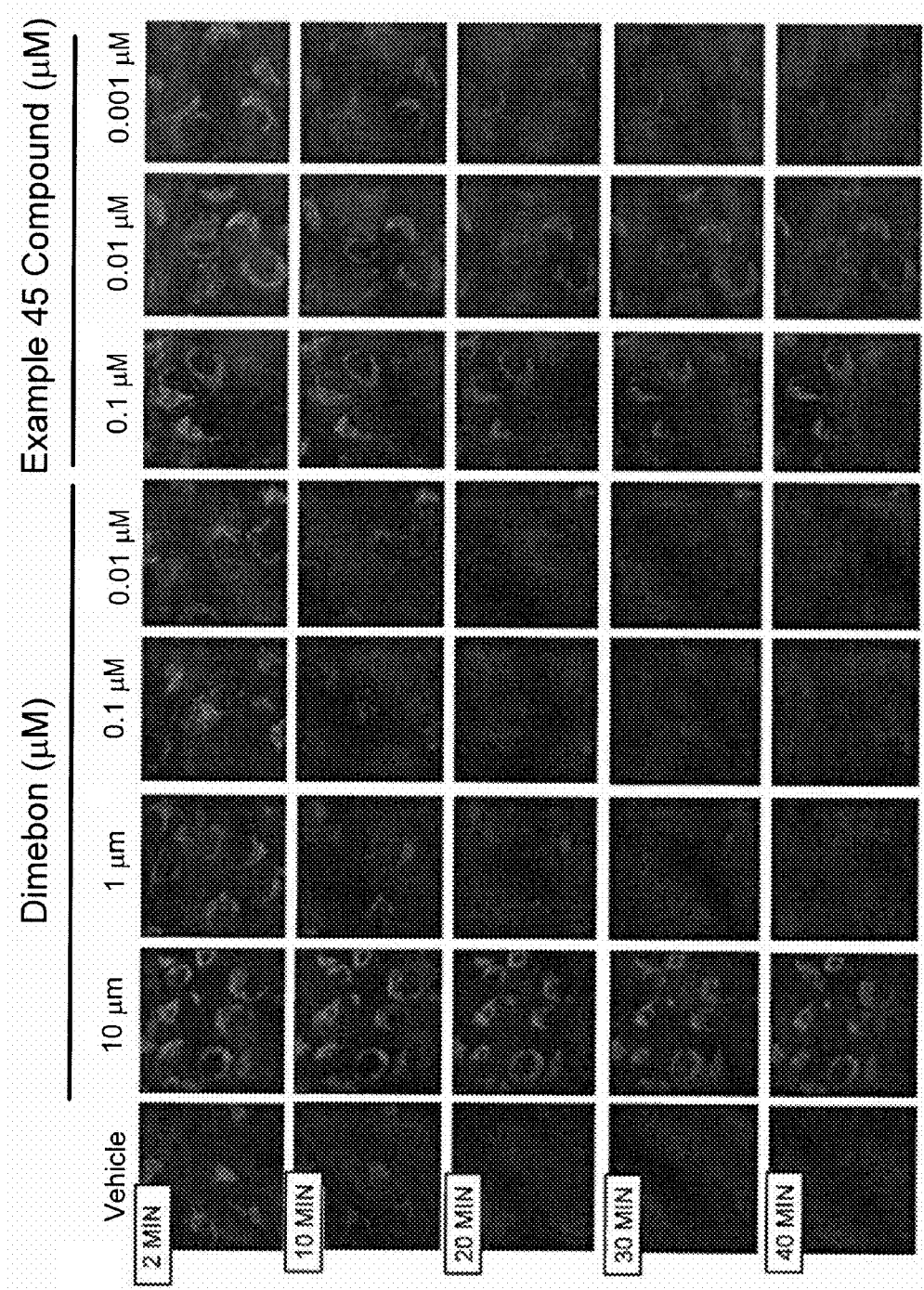

Comparison of Example 45 Compound and Dimebon:

A chemical compound sharing structural similarity to Example 45 Compound is 2,3,4,5-Tetrahydro-2,8-dimethyl-5-(2-(6-methyl-3-pyridyl)ethyl)-1H-pyrido(4,3-b)indole (FIG. 22A). An anti-histamine, trade named Dimebon, was anecdotally noticed over the decades to ameliorate symptoms of dementia (O'Brien, 2008; Burns and Jacoby 2008). More recently, an American biotechnology company designated Medivation initiated clinical trials to formally test whether Dimebon might improve the symptoms of patients suffering from Alzheimer's disease. The results of FDA-sponsored, phase 2 clinical trials in Alzheimer's disease were recently published, reporting favorable response rates (Doody et al., 2008). Example 45 Compound and Dimebon were compared in three functional assays. The in vivo test for effects on hippocampal neurogenesis revealed activity for both compounds, with Example 45 Compound exhibiting between 10- and 30-fold higher level of potency and a ceiling of efficacy roughly 40% higher than the anti-histamine drug (FIG. 22b). Dimebon has previously been reported to protect cortical neurons from $Aβ_{(25-35)}$-mediated toxicity (Bachurin et al., 2001). As shown in FIG. 22C, Dimebon only afforded protection at doses of 3 μM. Example 45 Compound did not lose neuroprotective activity even when diluted to low nanomolar levels. Dimebon has also been implicated in protecting mitochondria (Bachurin et al., 2003). We therefore compared Dimebon with Example 45 Compound in the calcium-induced mitochondrial dissolution assay. Both compounds were observed to be active, and it was again observed that the relative potency of Example 45 Compound was superior to Dimebon (FIG. 22D). Protection of mitochondrial membrane permeability was lost for Example 45 Compound between the 10 and 1 nM doses, whereas that of Dimebon was lost between 10 and 1 μM.

Example 45 Compound and Dimebon were tested for binding to the H1 histamine receptor. While Dimebon displayed high affinity for this receptor (IC50<100 nM), both enantiomers of Example 45 Compound display low H1 affinity (IC50>10 μM).

Effect of Example 45 Compound on Aged Rats

Figure 23A:
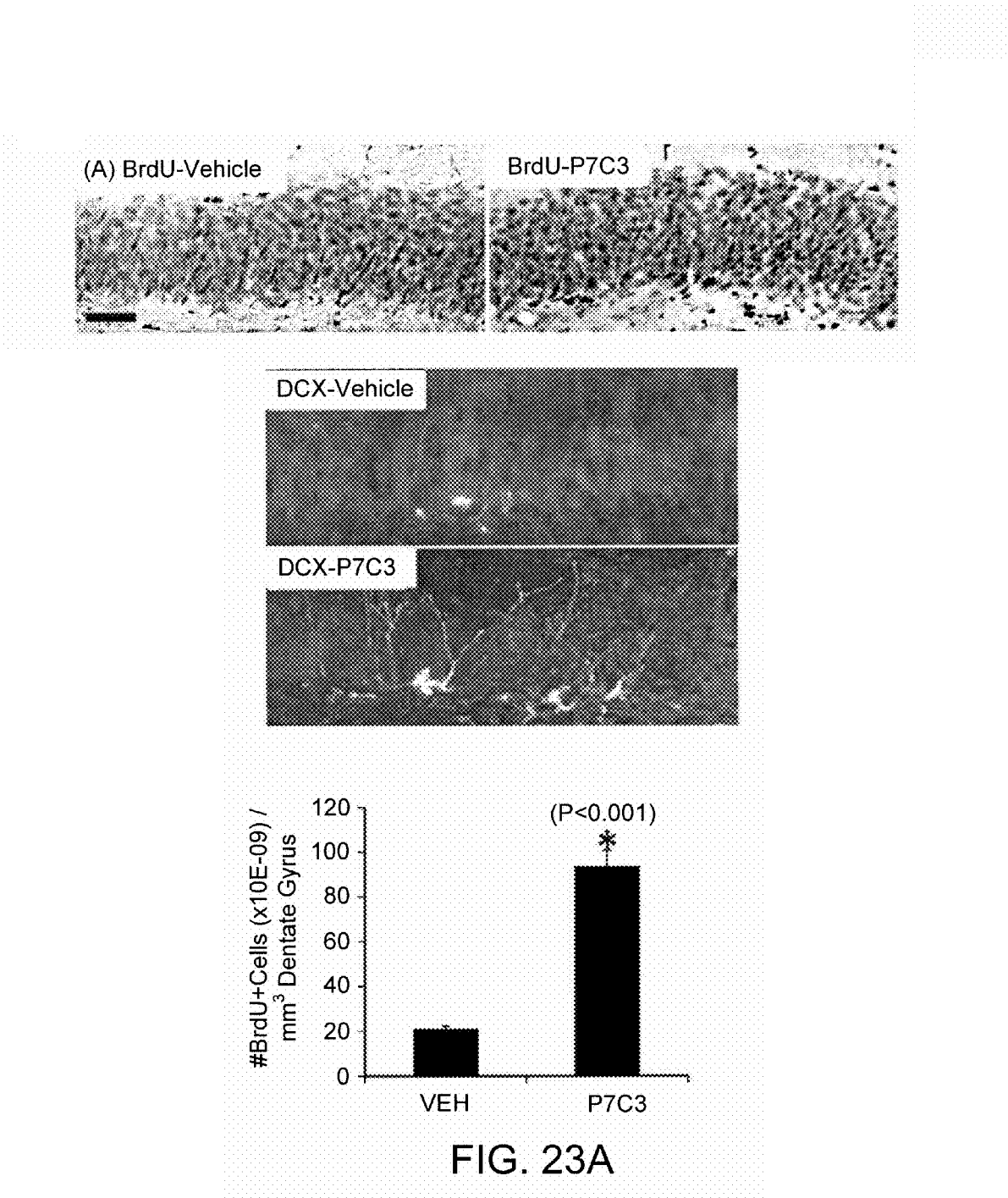
FIG. 23: Effect of Example 45 Compound in aged rats. (a) Example 45 Compound (20 mg/kg/d, i.p.) and BrdU (50 mg/kg, i.p.) were administered daily for 7 days to 12-18 month old Fisher 344 rats (n=4 in each group). P7C3 promoted neural precursor cell proliferation by roughly 5 fold compared to vehicle. (*$p<0.001$, Students t test). DCX staining demonstrates that P7C3 specifically promoted neuronal differentiation and dendritic branching. These micrographs were taken at the same magnification. Scale bar=50 mm. Data are expressed as mean+/−SEM. (b) Latency to find the hidden platform in the Morris water maze task, as well as (c) swim spend in aged rats treated with P7C3 or vehicle both before and after 2 months of treatment did not differ between groups. Data are expressed as mean+/−SEM. (d) Quantification of food intake and (e) fasting blood glucose levels in aged rats did not differ with respect to whether rats received P7C3 or vehicle. Data are expressed as mean+/−SEM.
Figure 24A:
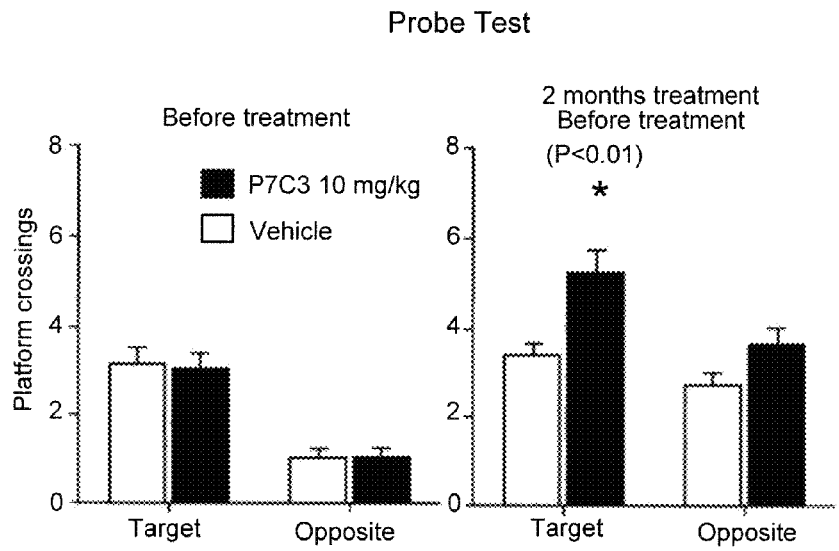
FIG. 24: Example 45 Compound Enhances Hippocampal Neurogenesis, Ameliorates Cognitive Decline, and Prevents Weight Loss in Terminally Aged Rats (a) Prior to treatment, both groups (n=23 for each group) showed similar frequency of crossings through the goal platform. After 2 months of treatment, however, Example 45 Compound-treated rats displayed a statistically significant increase of crossings through the goal platform area relative to vehicle treated rats. (b) Example 45 Compound-treated rats displayed significantly enhanced hippocampal neurogenesis, as assessed by BrdU incorporation, relative to vehicle treated rats. Many more of the BrdU-labeled cells were noted to have migrated into the granular layer in Example 45 Compound-treated rats in comparison to vehicle treated animals, consistent with their functional incorporation into the dentate gyrus as properly wired neurons. The scale bar represents 50 mM. (c) Relative to vehicle-treated animals, Example 45 Compound-treated rats displayed significantly lower number of cleaved caspase 3-positive cells in the dentate gyrus, indicating that P7C3 was capable of inhibiting apoptosis in the aged rat brain. The scale bar represents 50 mM. (d) Relative to vehicle-treated animals, Example 45 Compound-treated rats were observed to maintain stable body weight as a function of terminal aging. In all graphs data are expressed as mean±SEM.

We turned to aged Fisher rats as a means of performing behavioral tests capable of assessing the potential benefits of Example 45 Compound on hippocampus-dependent learning. It is well established that normal rodent aging is associated with attenuation of hippocampal neurogenesis (Kuhn et al., 1996, Driscoll et al., 2006). Reduced neurogenesis in aged rats is likely related to increased neuronal apoptosis in the aged rat brain (Martin et al., 2002; Kim et al., 2010). These changes have been hypothesized to contribute to cognitive decline as a function of terminal aging. We first evaluated whether Example 45 Compound would enhance hippocampal neurogenesis in aged rats as it does in adult mice. Rats were injected with a daily, IP dose of either 10 mg/kg of Example 45 Compound or vehicle, coinjected with a daily dose of BrdU, and then sacrificed after 7 days for immunohistochemistry. As shown in FIG. 23A, compound-treated animals revealed a 500% increase in BrdU labeling in the dentate gyrus relative to vehicle-treated controls. Immunohistochemical staining with antibodies to doublecortin likewise revealed a robust, compound-specific enrichment in this marker of newborn neurons. Having observed proneurogenic efficacy of Example 45 Compound in this short term assay, we then tested whether prolonged administration of Example 45 Compound might ameliorate age-related decline in cognition by subjecting 18-month-old rats to daily administration of either 10 mg/kg of Example 45 Compound or vehicle only for 2 months. Animals of both groups were further subjected to weekly IP administration of BrdU (50 mg/kg) for later immunohistochemical measurements of hippocampal neurogenesis. As a control, both Example 45 Compound- and vehicle-treated groups were confirmed to display equal ability to physically participate in the task, and learn the task, as shown by decreased latency times to find the hidden platform over the 5 day training period, both before and after 2 months of treatment (FIG. 23B). Moreover, neither swim speed (FIG. 23C) nor locomotor activity (FIG. 23D) varied with age or treatment paradigm. After 2 months of compound or vehicle administration, cognitive ability was assessed blind to treatment group by removing the goal platform. Animals of the Example 45 Compound-treated group retained a statistically significant improvement in ability to navigate to the region of the missing platform, as evidenced by performance in the probe test. As shown in FIG. 24A, when the platform was removed from the maze, rats treated with Example 45 Compound crossed the precise location previously containing the platform significantly more often than vehicle-treated rats. Furthermore, Example 45 Compound-treated rats spent a higher percentage of time in the general goal area, defined as the quadrant previously containing the platform, than vehicle-treated rats (35.5%±2.2% for Example 45 Compound treated, 28.1%±2.6% for vehicle treated, Student's t Test, p<0.02).

Figure 24B:
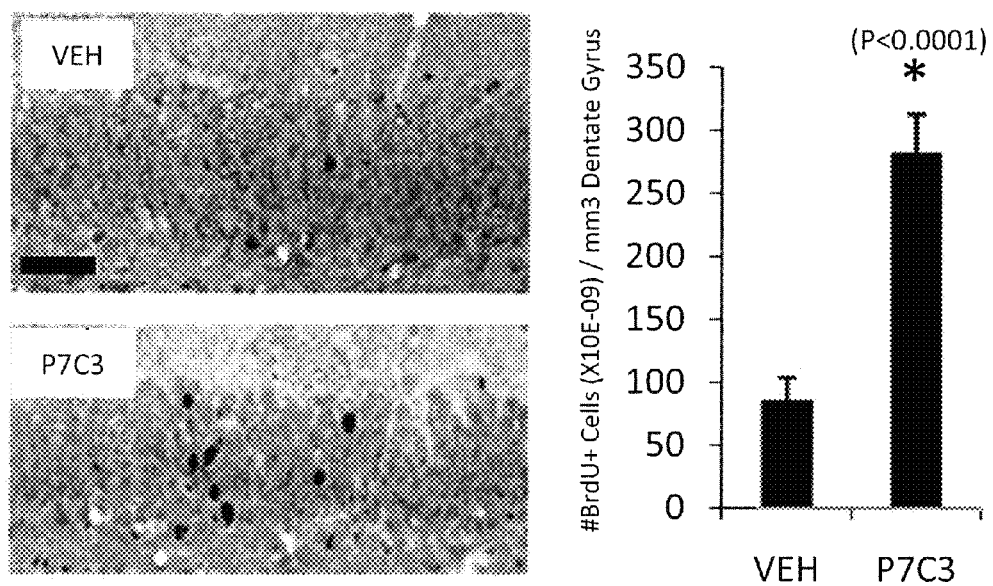
Figure 24C:
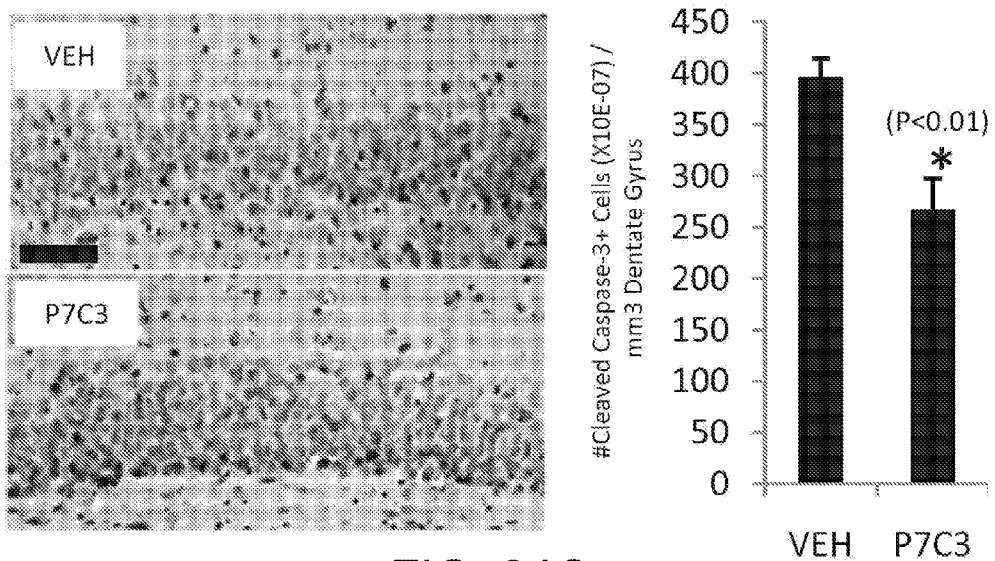
Figure 24D:
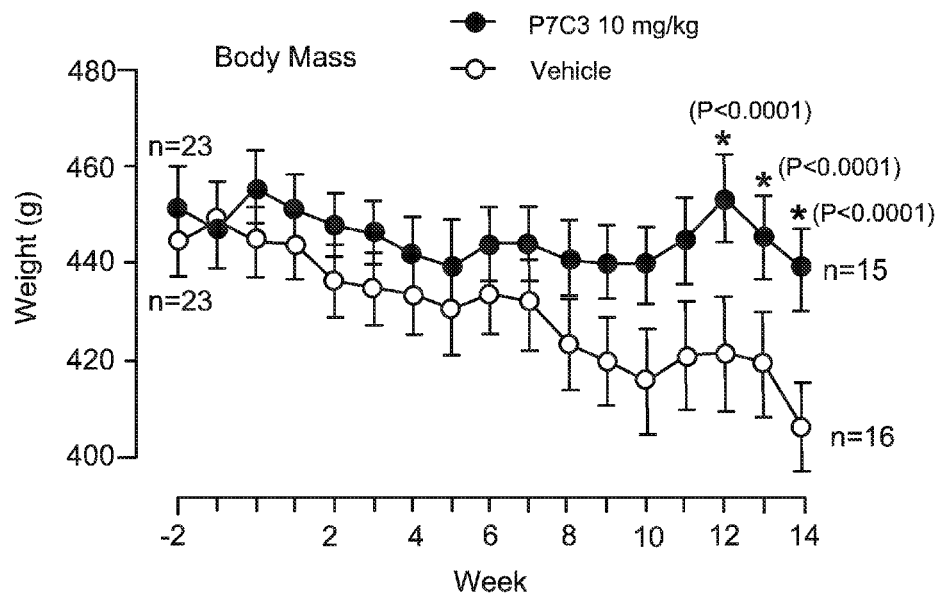
Figure 25A:
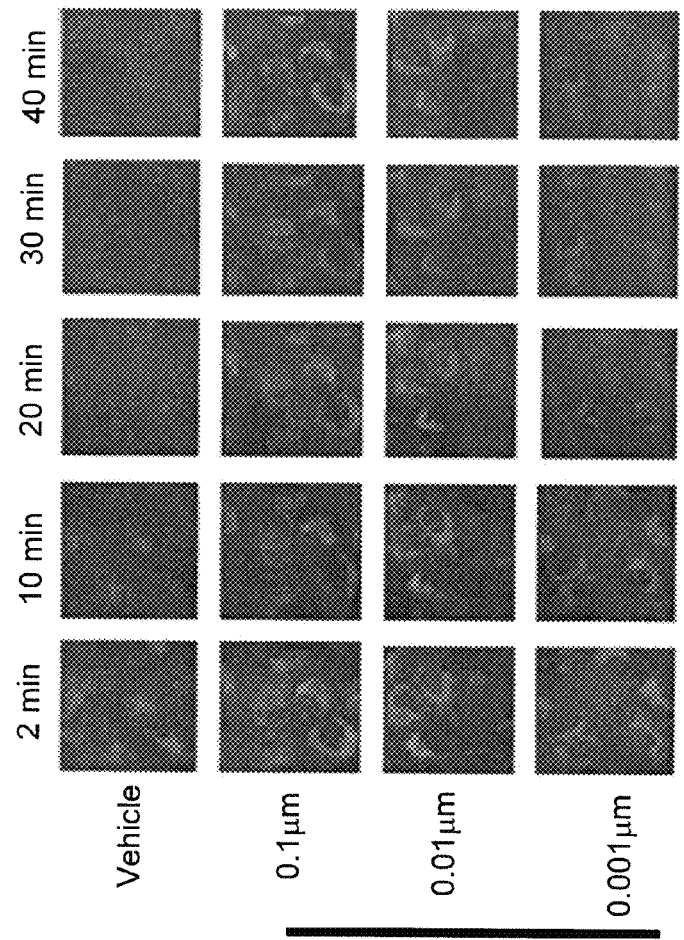
FIG. 25 Example 45 Compound Preserves Mitochondrial Membrane Potential in Parallel to Proneurogenic Activity U2OS cells were loaded with tetramethylrhodamine methyl ester (TMRM) dye and then exposed to the calcium ionophore A23187 either in the presence or absence of test compounds. Example 45 Compound (A) preserved mitochondrial membrane potential following exposure to the calcium ionophore A23187 in a dose-dependent manner. The protective effect of P7C3 was enantiomeric specific. The (R)-enantiomer of another compound (B) blocked dye release at levels as low as 1 nM, whereas the (S)-enantiomer (C) failed to block dye release even at the highest drug dose tested (100 nM). A proneurogenic (D) exhibited dye release protection at all doses tested, yet compounds devoid of proneurogenic activity (E and F) failed to preserve mitochondrial membrane potential at any test dose. Each compound was evaluated in triplicate with similar results.
Figure 25A:
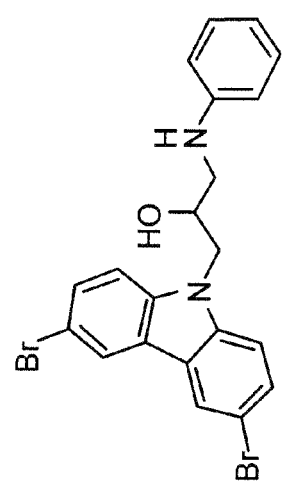
Figure 25B:
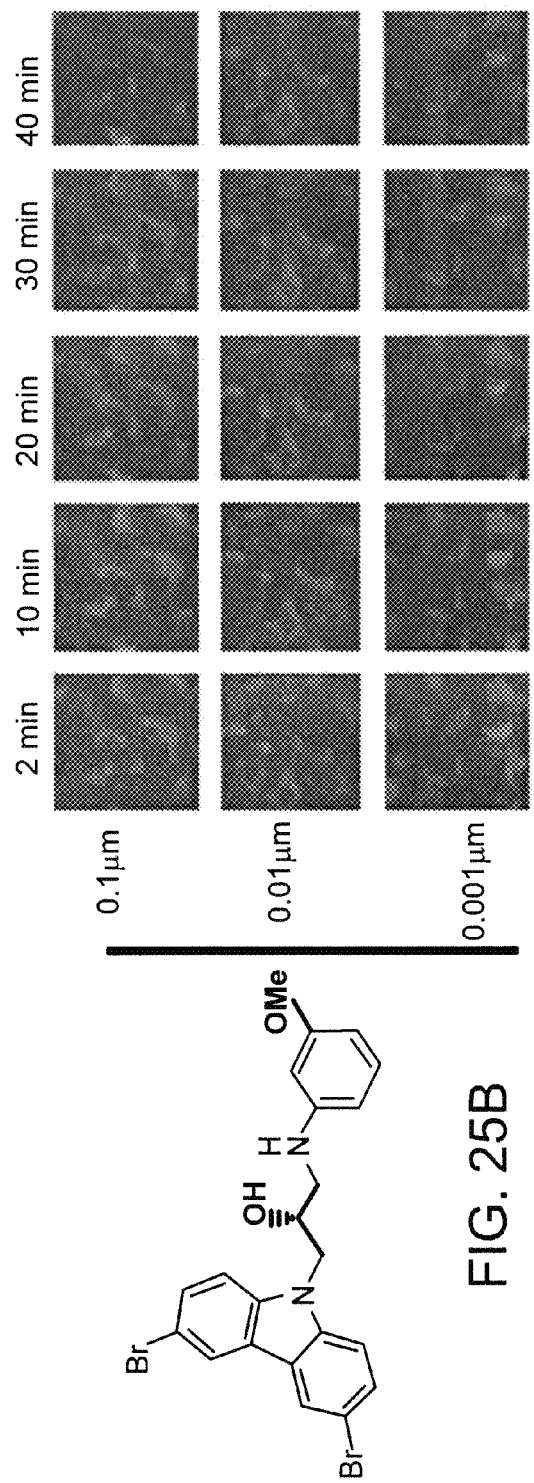
Figure 25C:
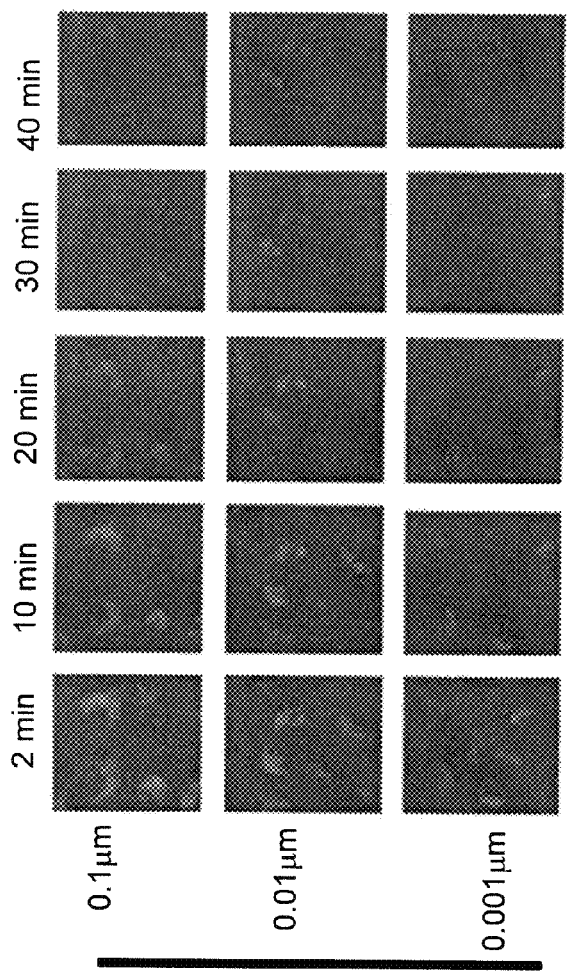
Figure 25D:
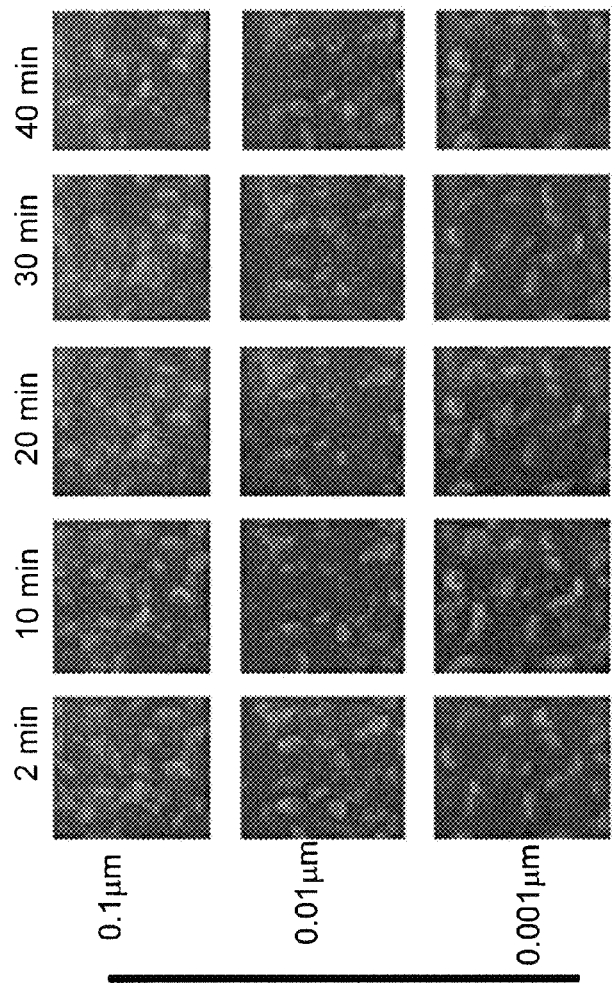
Figure 25D:
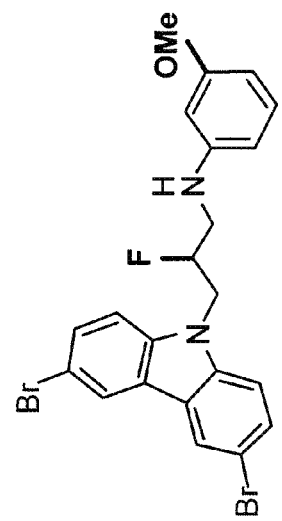
Figure 25E:
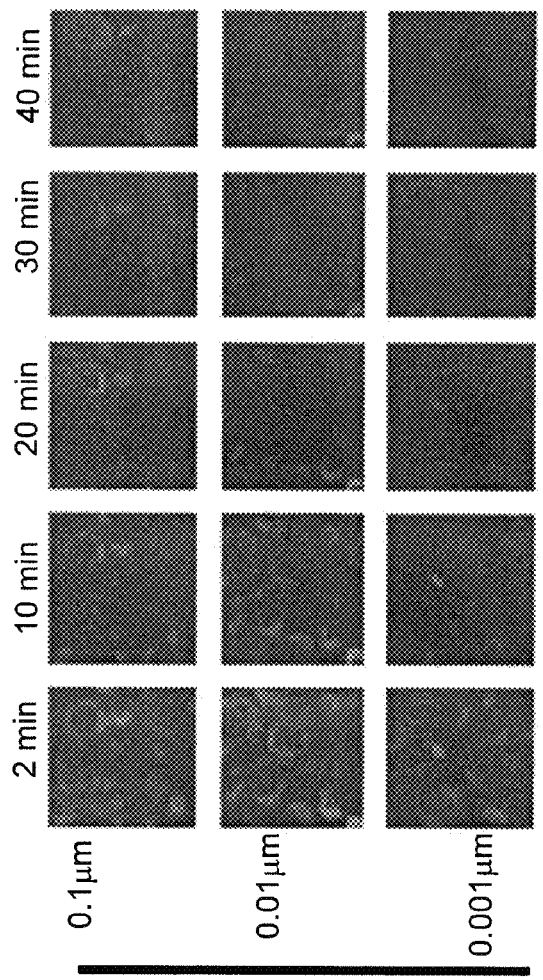
Figure 25E:
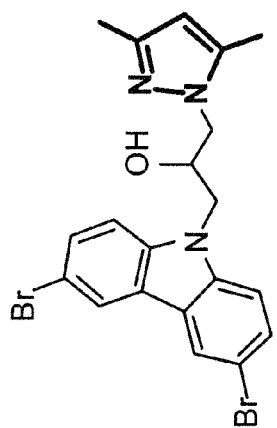
Figure 25F:
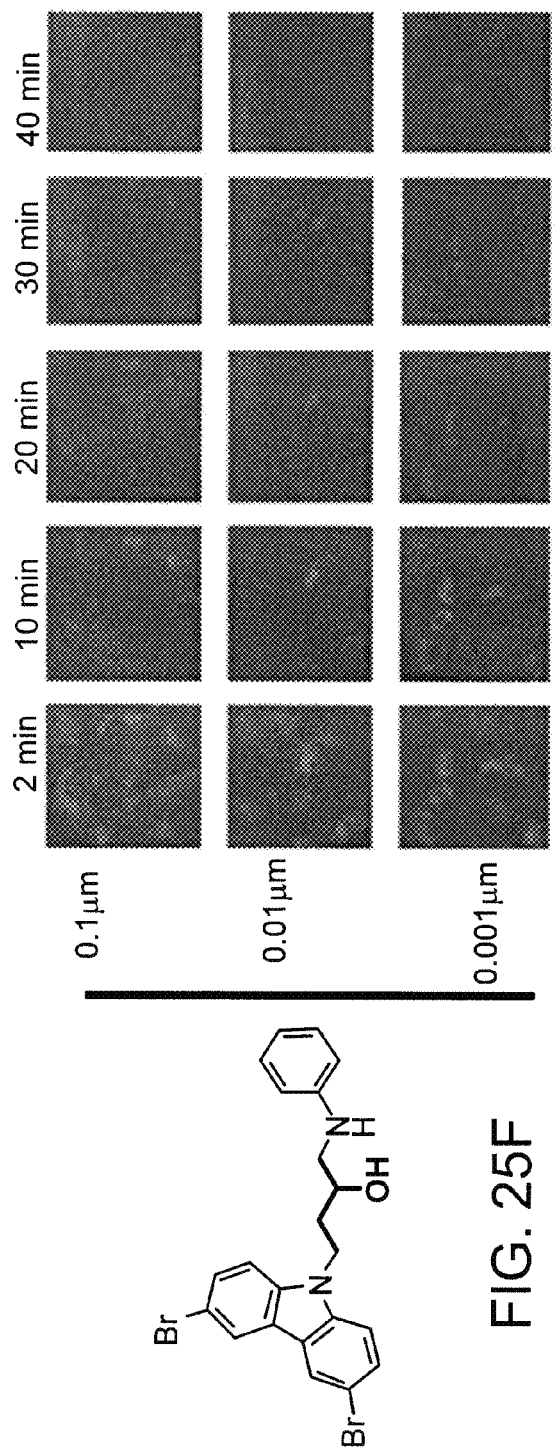
Figure 26:
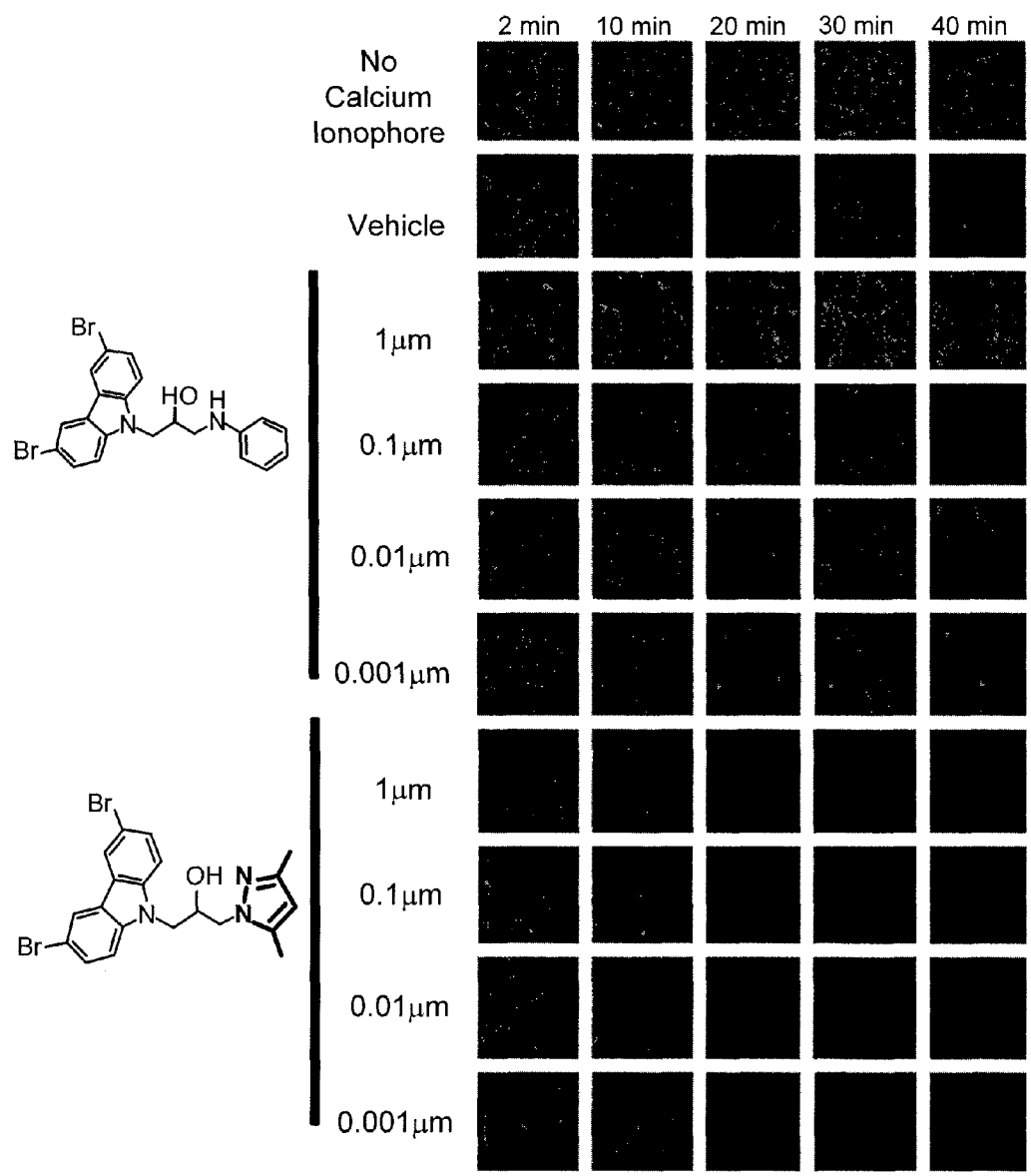
FIG. 26: Example 45 Compound Preserves Mitochondrial Membrane Potential in Cultured Primary Cortical Neurons. Cortical neurons cultures from rats on embryonic day 14 were loaded with tetramethylrhodamine methyl ester (TMRM) dye after 6 days of maturation. The top panels (no calcium ionophore) show that the dye alone did not affect the health of neurons. The remaining panels are from cells that were exposed to the calcium ionophore A23187 at time zero. With vehicle-alone, cortical neuron mitochondrial membrane potential was rapidly lost after exposure to the ionophore. Escalating doses of Example 45 Compound (A) preserved mitochondrial membrane potential following exposure to the calcium ionophore A23187 in a dose dependent manner, with full protection achieved at 1 mM. The inactive compound (B) failed to preserve mitochondrial membrane potential at any dose. Results shown are representative of 10 fields analyzed in each of 2 experimental runs for all conditions.

After behavioral testing, animals were sacrificed for immunohistochemical detection of BrdU and CCSP3. As shown in FIG. 24B, the dentate gyrus of rats exposed to Example 45 Compound showed a 3-fold higher level of BrdU-positive neurons than that of the vehicle group. Moreover, Example 45 Compound-treated animals showed a statistically significant reduction in the number of CCSP3-positive cells relative to vehicle controls (FIG. 24C). Unexpectedly, administration of Example 45 Compound helped rats maintain stable body weight with aging, in contrast to vehicle-treated rats, whose weight declined steadily with age (FIG. 24D). Example 45 Compound-mediated effects on body weight were independent of food intake (FIG. 23E), and treatment of aged rats with Example 45 Compound had no effect on postfasting blood glucose levels (FIG. 23E). It will be of interest to determine whether Example 45 Compound-mediated preservation of body weight in aged rats operates via central or peripheral modes of action.

Example 45 Compound Protects Mitochondria

Knowing that P7C3 ameliorates the death of newborn neurons in the dentate gyrus in living mice, we wondered whether its function might relate to mitochondrial integrity. Assays were established to test whether P7C3 might protect cultured U2OS cells from calcium-induced mitochondrial dissolution (Distelmaier et al., 2008).

Tetramethylrhodamine methylester (TMRM) dye is sequestered by active mitochondria, and, when loaded with TMRM, vehicle-treated cells released the dye within 15 min of exposure to the calcium ionophor A23187. By contrast, dye release was fully prevented in cells exposed to as little as 10 nM of P7C3 (FIG. 25). Compound known to be inactive in vivo were also inactive in this assay (FIG. 25). Preservation of mitochondrial membrane potential in this assay was observed for the R-enantiomer of one compound (B), but not the S-enantiomer (C). Finally, protection of mitochondrial membrane permeability was observed at an enhanced level for a compound variant, which also exhibited a high level of proneurogenic activity (FIG. 25). Example 45 Compound, but not an inactive compound, was also capable of preserving mitochondrial integrity in cultured primary cortical neurons (FIG. 25).

Example Compound 45 Normalizes Elevated Levels of Hippocampal Apoptosis in npas3$^{-/-}$ Mice Recognizing that reduced thickness of the npas3$^{-/-}$ dentate gyrus granular layer could be attributed to increased apoptosis of proliferating neural precursor cells, we examined the effect of Example 45 Compound treatment on apoptosis in the hippocampus of npas3$^{-/-}$ mice through immunohistochemical staining of CCSP3. After 12 days of orally delivered Example 45 Compound (20 mg/kg) to adult npas3–/– mice, a statistically significant reduction in CCSP3 staining was observed in the dentate gyrus. We thereby propose that Example 45 Compound facilitates repair of the granular layer of the dentate gyrus in npas3$^{-/-}$ mice by overcoming a genotype-specific enhancement in apoptosis.

Other Embodiments

This application claims the benefit of U.S. Provisional Application No. 61/143,755, which is incorporated herein by reference in its entirety. The disclosure of U.S. Provisional Application No. 61/143,755 includes, but is not limited to:

methods for promoting postnatal mammalian neurotrophism in a patient determined to be in need thereof, comprising administering to the patient an effective amount of a neurotrophic carbazole compound of formula 1:

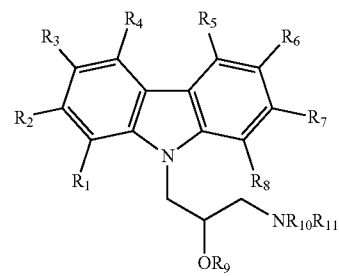

wherein:

$R_1$-$R_8$ are each independently selected hydrogen, heteroatom, heteroatom functional group, and optionally-substituted, optionally heteroatom lower (C1-C6) alkyl;

$R_9$ is hydrogen or optionally-substituted, optionally heteroatom lower (C1-C6) alkyl; and $R_{10}$ and $R_{11}$ are each independently selected hydrogen, optionally-substituted, optionally heteroatom C1-C6 alkyl, optionally-substituted, optionally heteroatom C2-C6 alkenyl, optionally-substituted, optionally heteroatom C2-C6 alkynyl, and optionally-substituted, optionally heteroatom C6-C14 aryl, including tautomers, stereoisomers and pharmaceutically-acceptable salts thereof.

Unless otherwise noted, all structures depicted herein encompass interconvertable tautomers as if each were separately depicted.

The invention encompasses all alternative combinations of particular embodiments:
wherein $R_1$-$R_8$ are each independently selected hydrogen and halide;
wherein $R_1$, $R_2$, $R_4$, $R_5$, $R_7$ and $R_8$ are hydrogen, and $R_3$ and $R_6$ are halide, such as Cl, Br, I and F;
wherein $R_9$ is hydrogen;
wherein $R_{10}$ is hydrogen and $R_{11}$ is optionally-substituted, optionally heteroatom C6-C14 aryl;
wherein $R_{10}$ and $R_{11}$ are joined to form a 5-7 membered, optionally substituted heterocyclic ring;
wherein $R_{10}$ and $R_{11}$ are joined to form an optionally substituted pyrrolidine or a piperidine;
wherein $R_{10}$ is hydrogen and $R_{11}$ is substituted phenyl, such as halide- or C1-C6 alkoxy-phenyl, including para-, meta-, or ortho positions;
wherein $R_{10}$ is hydrogen and $R_{11}$ is napthyl;
wherein the compound has a formula of Table 1 (herein) or Table 2 (herein);
wherein the compound has formula 2:

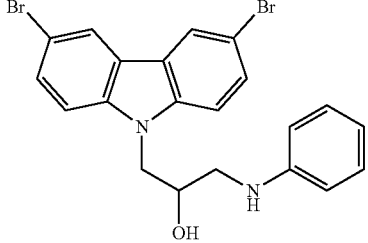 [SMILES: OC(CNc1ccccc1)Cn1c2ccc(Br)cc2c2cc(Br)ccc21]

wherein (a) at least one of $R_1$-$R_8$ is heteroatom, optionally-substituted, or optionally heteroatom lower (C1-C6) alkyl, and at least one of $R_1$-$R_4$ or at least one of $R_5$-$R_8$ is different; or (b) $R_9$ is optionally-substituted, optionally heteroatom lower (C1-C6) alkyl;
further comprising the step of detecting a resultant neurotrophism, particularly neurogenesis; and/or
further comprising the antecedent step of determining that the patient has aberrant neurotrophism, particularly aberrant neurogenesis, particularly aberrant hippocampal neurogenesis, or a disease or disorder associated therewith, particularly by detecting and/or diagnosing the same.

The invention also provides novel pharmaceutical, particularly novel neurogenic, compositions in unit dosage comprising a disclosed neurotrophic carbazole not previously known or suggested to provide pharmacological, particularly neurogenic, activity, or a pharmaceutically-acceptable salt thereof, and a pharmaceutically acceptable excipient.

The invention also provides disclosed novel neurotrophic carbazoles and pharmaceutically-acceptable salts thereof.

U.S. Provisional Application No. 61/143,755 further discloses:

The term "heteroatom" as used herein generally means any atom other than carbon, hydrogen or oxygen. Preferred heteroatoms include oxygen (O), phosphorus (P), sulfur (S), nitrogen (N), silicon (S), arsenic (As), selenium (Se), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulthydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2$—$CH_2$—$CH_2$—$CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5, 6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR"R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO2R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR'—C(O)NR"R'", —NR'—SO$_2$NR"R'", —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$NR'R", —NR"SO$_2$R, perfluoro(C1-C4)alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed; Academic Press: New York, 1996; p. 203.

Two of the substituents on adjacent atoms of the aryl or heteroaryl ring may optionally be replaced with a substituent of the formula -T-C(O)—(CH$_2$)q-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1-C6)alkyl.

What is claimed is:

1. A compound having formula (IIIa) or a pharmaceutically acceptable salt thereof:

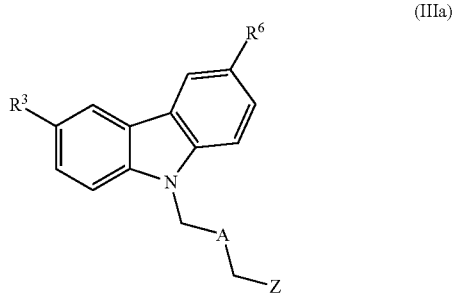

(IIIa)

wherein:
R$^3$ and R$^6$ are each independently selected from halo, C$_1$-C$_6$ alkyl, C$_2$-C$_6$ alkynyl, cyclopropyl, —N$_3$, and cyano;

A is CR$^{A1}$R$^{A2}$, wherein R$^{A1}$ is selected from hydrogen, halo, C$_1$-C$_3$ alkyl, and OR$^9$, and R$^{A2}$ is selected from halo, C$_1$-C$_3$ alkyl, and OR$^9$;

Z is selected from —NHR$^{10}$; —N(CH$_3$)R$^{11}$; —OR$^{12}$; and —S(O)$_n$R$^{13}$, wherein n is 0, 1, or 2;

R$^9$ is hydrogen or C$_1$-C$_3$ alkyl that is optionally substituted with hydroxyl or C$_1$-C$_3$ alkoxy;

R$^{10}$, R$^{11}$, R$^{12}$ and R$^{13}$ are each independently selected from:
(a) C$_6$-C$_{10}$ aryl that is optionally substituted with 1 to 4 R$^b$; or
(b) heteroaryl containing from 6-14 ring atoms, wherein from 1-6 of the ring atoms are independently selected from N, NH, N(C$_1$-C$_3$ alkyl), O, and S; and wherein said heteroaryl is optionally substituted with from 1 to 4 R$^b$;

R$^b$ at each occurrence is independently selected from the substituents delineated in (aa) through (dd) below:
(aa) C$_1$-C$_6$ alkyl; C$_1$-C$_6$ haloalkoxy; C$_1$-C$_6$ thioalkoxy; C$_1$-C$_6$ thiohaloalkoxy; —O—(CH$_2$)$_{1-3}$—[O(CH$_2$)$_{1-3}$]$_{1-3}$—H; C$_1$-C$_6$ alkyl, C$_1$-C$_6$ haloalkyl, —NH(C$_1$-C$_6$alkyl), —N(C$_1$-C$_6$alkyl)$_2$, —NHC(O)(C$_1$-C$_6$ alkyl);
(bb) halo; hydroxyl; cyano; nitro; —NH$_2$; azido; sulfhydryl; C$_2$-C$_6$ alkenyl; C$_2$-C$_6$ alkynyl; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$;
(cc) C$_3$-C$_6$ cycloalkyl or heterocyclyl containing from 5 to 6 ring atoms, wherein from 1 to 2 of the ring atoms of the heterocyclyl is independently selected from N, NH, N(C$_1$-C$_6$ alkyl), NC(O)(C$_1$-C$_6$ alkyl), O, and S; and
(dd) phenyl or heteroaryl containing from 5 to 6 ring atoms, wherein from 1 to 2 of the ring atoms of the heteroaryl is independently selected from N, NH, N(C$_1$-C$_3$ alkyl), O, and S; wherein each of said phenyl and heteroaryl is optionally substituted with from 1 to 3 substituents independently selected from halo; hydroxyl; cyano; nitro; —NH$_2$; —NH(C$_1$-C$_6$ alkyl), —N(C$_1$-C$_6$ alkyl)$_2$, —NHC(O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl;

wherein when R3 and R6 are both halo, one of R$^{A1}$ and R$^{A2}$ is OH and the other is hydrogen, Z is —NHR$^{10}$, and R$^{10}$ is C$_6$-C$_{10}$ aryl that is optionally substituted with 1 to 4 R$^b$, then R$^{10}$ is unsubstituted phenyl or phenyl substituted with 1 R$^b$.

2. A pharmaceutical composition comprising the compound or salt of claim 1 and a pharmaceutically acceptable carrier.

3. A compound having formula (IIIb) or a pharmaceutically acceptable salt thereof:

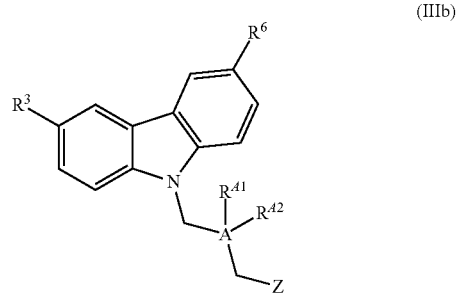

(IIIb)

wherein
- $R^3$ and $R^6$ are each independently selected from halo, $CH_3$, ethynyl, cyclopropyl, —$N_3$, and cyano;
- $R^{A1}$ and $R^{A2}$ are each independently selected from hydrogen, halo, $CH_3$, and $OR^9$, wherein one of $R^{A1}$ and $R^{A2}$ is halo or $OR^9$;
- Z is selected from —$NHR^{10}$; —$N(CH_3)R^{11}$; —$OR^{12}$; and —$S(O)_nR^{13}$, wherein n is 0, 1, or 2;
- $R^9$ is hydrogen or $C_1$-$C_3$ alkyl that is optionally substituted with hydroxyl or $C_1$-$C_3$ alkoxy;
- $R^{10}$, $R^{11}$, $R^{12}$ and $R^{13}$ are each independently $C_6$-$C_{10}$ aryl that is optionally substituted with 1 to 4 $R^b$;
- $R^b$ at each occurrence is independently selected from the substituents delineated in (aa) through (dd) below:
  - (aa) $C_1$-$C_6$ alkoxy; $C_1$-$C_6$ haloalkoxy; $C_1$-$C_6$ thioalkoxy; $C_1$-$C_6$ thiohaloalkoxy; —O—$(CH_2)_{1-3}$—$[O(CH_2)_{1-3}]_{1-3}$—H; $C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl);
  - (bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;
  - (cc) $C_3$-$C_6$ cycloalkyl or heterocyclyl containing from 5 to 6 ring atoms, wherein from 1 to 2 of the ring atoms of the heterocyclyl is independently selected from N, NH, N($C_1$-$C_6$ alkyl), NC(O)($C_1$-$C_6$ alkyl), O, and S; and
  - (dd) phenyl or heteroaryl containing from 5 to 6 ring atoms, wherein from 1 to 2 of the ring atoms of the heteroaryl is independently selected from N, NH, N($C_1$-$C_3$ alkyl), O, and S; wherein each of said phenyl and heteroaryl is optionally substituted with from 1 to 3 substituents independently selected from halo; hydroxyl; cyano; nitro; —$NH_2$; —NH($C_1$-$C_6$ alkyl), —N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

wherein when R3 and R6 are both halo, one of $R^{A1}$ and $R^{A2}$ is OH and the other is hydrogen, and Z is —$NHR^{10}$, then $R^{10}$ is unsubstituted phenyl or phenyl substituted with 1 $R^b$.

4. A pharmaceutical composition comprising the compound or salt of claim 3 and a pharmaceutically acceptable carrier.

5. A compound having formula (IIId) or a pharmaceutically acceptable salt thereof:

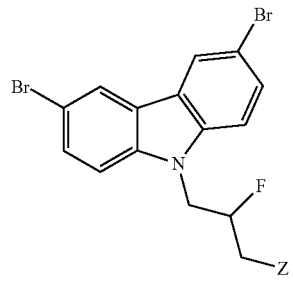

(IIId)

wherein
- Z is selected from —$NHR^{10}$; —$N(CH_3)R^{11}$; —$OR^{12}$; and —$S(O)_nR^{13}$, wherein n is 0, 1, or 2;
- $R^{10}$, $R^{11}$, $R^{12}$ and $R^{13}$ are each independently $C_6$-$C_{10}$ aryl that is optionally substituted with 1 to 4 $R^b$;
- $R^b$ at each occurrence is independently selected from the substituents delineated in (aa) through (dd) below:
  - (aa) $C_1$-$C_6$ alkoxy; $C_1$-$C_6$ haloalkoxy; $C_1$-$C_6$ thioalkoxy; $C_1$-$C_6$ thiohaloalkoxy; —O—$(CH_2)_{1-3}$—$[O(CH_2)_{1-3}]_{1-3}$—H; $C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl);
  - (bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;
  - (cc) $C_3$-$C_6$ cycloalkyl or heterocyclyl containing from 5 to 6 ring atoms, wherein from 1 to 2 of the ring atoms of the heterocyclyl is independently selected from N, NH, N($C_1$-$C_6$ alkyl), NC(O)($C_1$-$C_6$ alkyl), O, and S; and
  - (dd) phenyl or heteroaryl containing from 5 to 6 ring atoms, wherein from 1 to 2 of the ring atoms of the heteroaryl is independently selected from N, NH, N($C_1$-$C_3$ alkyl), O, and S; wherein each of said phenyl and heteroaryl is optionally substituted with from 1 to 3 substituents independently selected from halo; hydroxyl; cyano; nitro; —$NH_2$; —NH($C_1$-$C_6$ alkyl), —N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl.

6. A pharmaceutical composition comprising the compound or salt of claim 5 and a pharmaceutically acceptable carrier.

7. The compound of claim 1, selected from:
- 1-(3,6-dibromo-9H-carbazol-9-yl)-3-(phenylthio)propan-2-ol;
- N-(3-(3,6-dibromo-9H-carbazol-9-yl)-2-fluoropropyl)-3-methoxyaniline;
- N-(3-(3,6-dibromo-9H-carbazol-9-yl)-2-methoxypropyl)-3-methoxyaniline;
- 1-(3,6-Dimethyl-9H-carbazol-9-yl)-3-(3-methoxyphenylamino)propan-2-ol;
- 1-(3-Bromo-6-methyl-9H-carbazol-9-yl)-3-(3-methoxyphenylamino)-propan-2-ol;
- 1-(3,6-Dichloro-9H-carbazol-9-yl)-3-(3-methoxyphenylamino)propan-2-ol;
- 1-(3,6-Dibromo-9H-pyrido[3,4-b]indol-9-yl)-3-(phenylamino)propan-2-ol;
- 1-(3-Azidophenylamino)-3-(3,6-dibromo-9H-carbazol-9-yl)propan-2-ol;
- 1,3-Bis(3,6-dibromo-9H-carbazol-9-yl)propan-2-ol;
- 1-(9H-Carbazol-9-yl)-3-(3,6-dibromo-9H-carbazol-9-yl)propan-2-ol;
- 1-(3,6-dibromo-9H-carbazol-9-yl)-3-(pyridin-2-ylamino)propan-2-ol;
- 1-(3,6-dibromo-9H-carbazol-9-yl)-3-((3-methoxyphenyl)(methyl)-amino)propan-2-ol;
- 1-(3,6-dibromo-9H-carbazol-9-yl)-3-(pyrimidin-2-ylamino)propan-2-ol;
- N-(3-(3,6-dibromo-9H-carbazol-9-yl)-2-fluoropropyl)-3-methoxy-N-methylaniline;
- 1-(3,6-dibromo-9H-carbazol-9-yl)-3-(3-ethoxyphenylamino)propan-2-ol;
- 1-(3,6-dibromo-9H-carbazol-9-yl)-3-(phenylsulfinyl)propan-2-ol;
- 1-(3,6-dibromo-9H-carbazol-9-yl)-3-(phenylsulfonyl)propan-2-ol;

1-(3-bromo-9H-carbazol-9-yl)-3-(3-methoxyphenylamino)propan-2-ol;
1-(3,6-dibromo-9H-carbazol-9-yl)-3-phenoxypropan-2-ol;
1-(3,6-dibromo-9H-carbazol-9-yl)-3-(pyridin-3-ylamino)propan-2-ol;
1-(3,6-dibromo-9H-carbazol-9-yl)-3-(pyridin-4-ylamino)propan-2-ol;
N-(3-(3,6-dibromo-9H-carbazol-9-yl)-2,2-difluoropropyl)-3-methoxyaniline;
1-(3,6-dibromo-9H-carbazol-9-yl)-3-phenoxypropan-2-ol;
(S)-1-(3,6-dibromo-9H-carbazol-9-yl)-3-phenoxypropan-2-ol;
(R)-1-(3,6-dibromo-9H-carbazol-9-yl)-3-phenoxypropan-2-ol;
3,6-dibromo-9-(2-fluoro-3-phenoxypropyl)-9H-carbazole;
1-(3,6-dibromo-9H-carbazol-9-yl)-3-(3-methoxyphenylamino)-2-methylpropan-2-ol;
1-(4-azidophenylamino)-3-(3,6-dibromo-9H-carbazol-9-yl)propan-2-ol;
1-(3-azido-6-bromo-9H-carbazol-9-yl)-3-(3-methoxyphenylamino)propan-2-ol;
1-(3,6-dibromo-9H-carbazol-9-yl)-3-(4-methoxyphenoxy)propan-2-ol;
1-(3,6-dichloro-9H-carbazol-9-yl)-3-(phenylsulfonyl)propan-2-ol;
3,6-dibromo-9-(2-fluoro-3-(phenylsulfonyl)propyl)-9H-carbazole;
(S)-1-(3,6-dibromo-9H-carbazol-9-yl)-3-(phenylsulfonyl)propan-2-ol;
(R)-1-(3,6-dibromo-9H-carbazol-9-yl)-3-(phenylsulfonyl)propan-2-ol;
1-(3,6-dicyclopropyl-9H-carbazol-9-yl)-3-(phenylamino)propan-2-ol;
1-(3,6-diiodo-9H-carbazol-9-yl)-3-(phenylamino)propan-2-ol;
1-(3,6-diethynyl-9H-carbazol-9-yl)-3-(3-methoxyphenylamino)propan-2-ol;
9-(2-hydroxy-3-(3-methoxyphenylamino)propyl)-9H-carbazole-3,6-dicarbonitrile;
N-(3-(3,6-dibromo-9H-carbazol-9-yl)-2-fluoropropyl)aniline;
3,6-dibromo-9-(2,2-difluoro-3-phenoxypropyl)-9H-carbazole;
N-(3-(3,6-dibromo-9H-carbazol-9-yl)-2-fluoropropyl)-4-methoxyaniline;
N-(2-bromo-3-(3,6-dibromo-9H-carbazol-9-yl)propyl)-N-(4-methoxyphenyl)-4-nitrobenzenesulfonamide;
Ethyl 2-(4-(3-(3,6-dibromo-9H-carbazol-9-yl)-2-fluoropropylamino)phenoxy)acetate; and
N-(3-(3,6-dibromo-9H-carbazol-9-yl)-2-fluoropropyl)-4-(2-(2-methoxyethoxy)ethoxy)aniline;
or a pharmaceutically acceptable salt thereof.

8. The compound claim 1, selected from:
1-(3,6-dibromo-9H-carbazol-9-yl)-3-(phenylthio)propan-2-ol;
1-(3,6-dibromo-9H-carbazol-9-yl)-3-phenoxypropan-2-ol;
1-(3,6-dibromo-9H-carbazol-9-yl)-3-(phenylsulfinyl)propan-2-ol;
1-(3,6-dibromo-9H-carbazol-9-yl)-3-(phenylsulfonyl)propan-2-ol;
N-(3-(3,6-dibromo-9H-carbazol-9-yl)-2-fluoropropyl)-3-methoxyaniline;
N-(3-(3,6-dibromo-9H-carbazol-9-yl)-2-fluoropropyl)-3-methoxy-N-methylaniline;
N-(3-(3,6-dibromo-9H-carbazol-9-yl)-2-methoxypropyl)-3-methoxyaniline;
1-(3-bromo-6-methyl-9H-carbazol-9-yl)-3-(3-methoxyphenylamino)-propan-2-ol;
1-(3,6-dibromo-9H-carbazol-9-yl)-3-(pyridin-2-ylamino)propan-2-ol;
(R)-1-(3,6-dibromo-9H-carbazol-9-yl)-3-phenoxypropan-2-ol;
3,6-dibromo-9-(2-fluoro-3-phenoxypropyl)-9H-carbazole;
1-(3,6-dibromo-9H-carbazol-9-yl)-3-(3-methoxyphenylamino)-2-methylpropan-2-ol;
1-(4-azidophenylamino)-3-(3,6-dibromo-9H-carbazol-9-yl)propan-2-ol;
3,6-dibromo-9-(2-fluoro-3-(phenylsulfonyl)propyl)-9H-carbazole;
(S)-1-(3,6-dibromo-9H-carbazol-9-yl)-3-(phenylsulfonyl)propan-2-ol;
(R)-1-(3,6-dibromo-9H-carbazol-9-yl)-3-(phenylsulfonyl)propan-2-ol;
9-(2-hydroxy-3-(3-methoxyphenylamino)propyl)-9H-carbazole-3,6-dicarbonitrile;
N-(3-(3,6-dibromo-9H-carbazol-9-yl)-2-fluoropropyl)aniline; and
N-(3-(3,6-dibromo-9H-carbazol-9-yl)-2-fluoropropyl)-4-methoxyaniline;
or a pharmaceutically acceptable salt thereof.

9. The compound of claim 1, selected from:
N-(3-(3,6-dibromo-9H-carbazol-9-yl)-2-fluoropropyl)-3-methoxyaniline;
N-(3-(3,6-dibromo-9H-carbazol-9-yl)-2-fluoropropyl)-3-methoxy-N-methylaniline;
3,6-dibromo-9-(2-fluoro-3-phenoxypropyl)-9H-carbazole;
3,6-dibromo-9-(2-fluoro-3-(phenylsulfonyl)propyl)-9H-carbazole;
N-(3-(3,6-dibromo-9H-carbazol-9-yl)-2-fluoropropyl)aniline; and
N-(3-(3,6-dibromo-9H-carbazol-9-yl)-2-fluoropropyl)-4-methoxyaniline;
or a pharmaceutically acceptable salt thereof.

10. The compound of claim 1, wherein the compound is N-(3-(3,6-dibromo-9H-carbazol-9-yl)-2-fluoropropyl)-3-methoxyaniline.

* * * * *

UNITED STATES PATENT AND TRADEMARK OFFICE
CERTIFICATE OF CORRECTION

Page 1 of 1

PATENT NO. : 8,362,277 B2
APPLICATION NO. : 12/832056
DATED : January 29, 2013
INVENTOR(S) : Steven L. McKnight et al.

Figure 5:
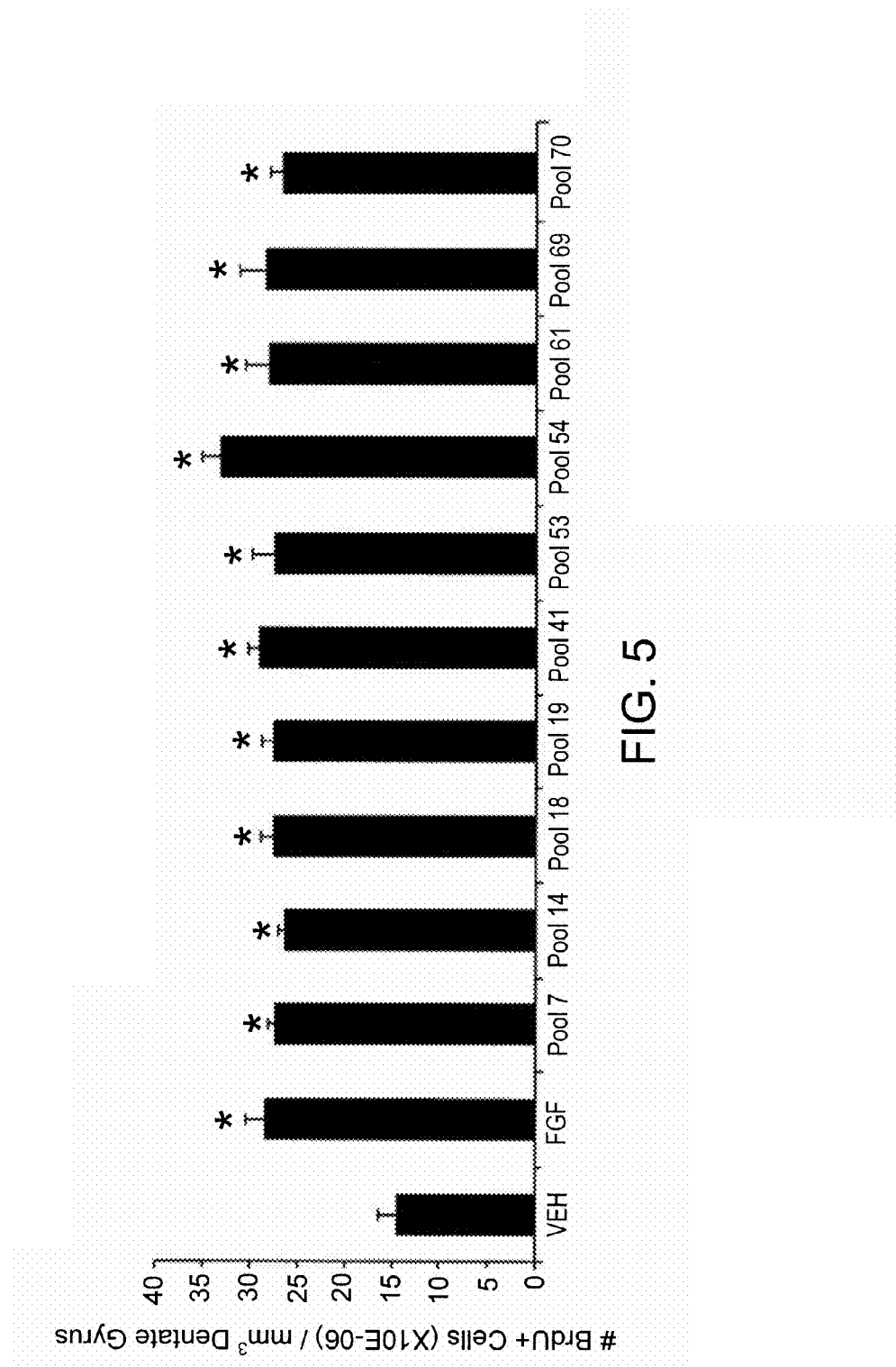
FIG. 5: Re-evaluation of positive pools verified statistical significance of enhanced BrdU-incorporation. Subsequent to their initial identification, pools 7, 14, 18, 19, 41, 53, 54, 61, 69, and 70 were re-evaluated in 2 additional mice each. Results shown are average with SEM of all 4 mice evaluated for each compound. All pools significantly (*, P<0.001, Student's t test) stimulated neural precursor cell proliferation in the hippocampal dentate gyrus SGZ relative to vehicle control.

It is certified that error appears in the above-identified patent and that said Letters Patent is hereby corrected as shown below:

In the drawings:

In the Y axis in FIG. 2; FIG. 4, upper and lower panels; FIG. 5; FIG. 6A, upper panel; FIG. 6C; FIG. 7, lower panel; FIG. 8; FIG. 9B; FIG. 10B, upper panel; FIG. 14, right panel; and FIG. 22B, replace the phrase "# BrdU+ Cells (X10E-06) / mm3" with --Relative # BrdU+ Cells / Volume--.

In the Y axis in FIG. 11, replace the phrase "# Cells (X10E-07) / mm3" with --Relative # Cells / Volume--.

In the Y axis in FIG. 23A, bottom panel and FIG. 24B, right panel, replace the phrase "#BrdU+ Cells (X10E-09) / mm3" with --Relative # BrdU+ Cells / Volume--.

In the Y axis in FIG. 24C, right panel, replace the phrase "#Cleaved Caspase-3+ Cells (X10E-07)/mm3" with --# Cleaved Caspase-3+ Cells / Volume--.

In the specification:

In column 45, line 45; column 45, line 52; column 45, line 58; column 45, line 63; and column 46, line 1, replace "mm3" between "BrdU+ cells/" and "dentate" with --volume--.

In Table 1 at column 164, lines 22-23 and column 165, lines 4-5, replace "BrdU+ cells/mm3" with --Relative BrdU+ cells/volume--.

Signed and Sealed this
Eighth Day of April, 2014

Michelle K. Lee
*Deputy Director of the United States Patent and Trademark Office*